US007364866B2

(12) United States Patent
Lowery et al.

(10) Patent No.: US 7,364,866 B2
(45) Date of Patent: Apr. 29, 2008

(54) DROSOPHILA G PROTEIN COUPLED RECEPTORS, NUCLEIC ACIDS, AND METHODS RELATED TO THE SAME

(75) Inventors: David E. Lowery, Portage, MI (US); Valdin G. Smith, Kalamazoo, MI (US); Teresa M. Kubiak, Richland, MI (US); Martha J. Larsen, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 509 days.

(21) Appl. No.: 10/213,821

(22) Filed: Aug. 6, 2002

(65) Prior Publication Data

US 2003/0180297 A1    Sep. 25, 2003

Related U.S. Application Data

(63) Continuation-in-part of application No. 09/693,746, filed on Oct. 20, 2000, now Pat. No. 6,835,546, which is a continuation-in-part of application No. 09/425,676, filed on Oct. 22, 1999, now abandoned.

(51) Int. Cl.
*G01N 33/53* (2006.01)
*C12N 5/06* (2006.01)
*C12N 5/00* (2006.01)
*C07K 1/00* (2006.01)
*C07K 5/00* (2006.01)

(52) U.S. Cl. .................. 435/7.2; 435/348; 435/325; 530/350; 530/328

(58) Field of Classification Search .................. None
See application file for complete search history.

(56) References Cited

U.S. PATENT DOCUMENTS

| | | | |
|---|---|---|---|
| 4,343,940 A | 8/1982 | Kreighbaum et al. | 544/283 |
| 4,399,216 A | 8/1983 | Axel et al. | 435/6 |
| 4,447,608 A | 5/1984 | Jones et al. | 544/287 |
| 4,683,195 A | 7/1987 | Mullis et al. | 435/6 |
| 4,683,202 A | 7/1987 | Mullis | 435/91 |
| 4,757,072 A | 7/1988 | Kabbe et al. | 514/257 |
| 4,879,236 A | 11/1989 | Smith et al. | 435/235 |
| 5,217,999 A | 6/1993 | Levitzki et al. | 514/613 |
| 5,302,606 A | 4/1994 | Spada et al. | 514/357 |
| 5,316,553 A | 5/1994 | Kaul et al. | 8/639 |
| 5,330,992 A | 7/1994 | Eissenstat et al. | 514/312 |
| 5,585,277 A | 12/1996 | Bowie et al. | 436/518 |
| 5,753,615 A | 5/1998 | Thorpe et al. | 514/14 |
| 5,880,141 A | 3/1999 | Tang et al. | 514/339 |
| 6,703,491 B1 | 3/2004 | Homburger et al. | |

FOREIGN PATENT DOCUMENTS

| | | |
|---|---|---|
| WO | WO01/70980 | 9/2001 |
| WO | WO01/70981 | 9/2001 |
| WO | WO01/71042 | 9/2001 |

OTHER PUBLICATIONS

Wells. 1990. Biochemistry 29:8509-8517.*
Ngo et al. 1994. in The Protein Folding Problem and Tertiary Structure Prediction. pp. 492-495.*
Schoneberg et al. 2004. Pharmacology and Therapeutics 104:173-206.*
Li et al. 1991. EMBO J. 10:3221-3229.*
Garcynski, et al., "Characterization of a functional neuropeptide F receptor from *Drosophila melanogaster*," Peptides (2002) 23:773-780.
Holmes, et al., "Cloning and transcriptional expression of leucokinin-like peptide receptor from the Southern cattle tick, *Boophilus microplus* (*Acari:Ixodidae*)," Insect Mol. Biol. (2000) 9:457-465.
Kramer, et al., "Identification of an allatostatin from the tobacco hornworm *Manduca sexta*," Proc. Natl. Acad. Sci. USA (1991) 88:9458-9462.
Kubiak, et al., "Cloning and functional expression of the first *Drosophila melanogaster* sulfakinin receptor DSK-R1," Biochem. Biophys. Res. Comm. (2002) 291:313-320.
Larsen, et al., "Type A allatostatinsfrom *Drosophila melanogaster* and *Diplotera punctata* activate two *Drosophila* allatostatin receptors, DAR-1 and DAR-2, expressed in CHO cells," Biochem. Biophys. Res. Comm. (2001) 286:895-901.
Nichols, "Isolation and expression of the *Drosophila drosufakinin* neural peptide gene product DSK-I,"0 Mol. Cell. Neurosci. (1992) 3:342-347.
O'Donnell, et al., "Hormonally controlled chloride movement across *Drosophila* tubules is via ion channels in stellate cells," Am. J. Physiol. (1998) 43:R1039-R1049.
Price et al. "*Drosophila melanogaster* flatline encodes a myotropin orthologue to *Manduca sexta* allatostatin," Peptides (2002) 23:787-794.
Siviter, et al., "Expression and functional characterization of a *Drosophila* neuropeptide precursor with homology to mammalian preprotachykinin A," J. Biol. Chem. (2000) 275:23273-23280.
Staubli, et al., "Molecular identification of the insect adipokinetic hormone receptors," Proc. Natl. Acad. SCi. USA (2002) 99:3446-3451.

(Continued)

*Primary Examiner*—Elizabeth Kemmerer
*Assistant Examiner*—Shulamith H Shafer
(74) *Attorney, Agent, or Firm*—Pepper Hamilton, LLP

(57) ABSTRACT

The present invention provides *Drosophila melanogaster* GPCR (DmGPCR) polypeptides and polynucleotides which identify and encode such a DmGPCR. In addition, the invention provides expression vectors, host cells, and methods for its production. The invention also provides methods for the identification of homologs in other species and of DmGPCR agonists/antagonists useful as potential insecticides. The invention further provides methods for binding a DmGPCR, methods for identifying modulators of DmGPCR expression and activity, methods for controlling a population of insects with a DmGPCR antibody, a DmGPCR antisense polynucleotide, a DmGPCR binding partner or modulator, and methods of preventing or treating a disease or condition associated with an ectoparasite. Specifically, this invention discloses the matching of the orphan *Drosophila* drotachykinin, droleucokinin, and drostatin-C receptors with their cognate peptide ligands.

5 Claims, No Drawings

OTHER PUBLICATIONS

Williamson, et al., "Molecular cloning, genomic organization, and expression of a C-type (*Manduca sexta*-type) allatostatin preprohormone from *Drosophila melanogaster*," Biochem. Biophys. Res. Comm. (2001) 282-124-130.

Stapleton, et al., "A *Drosophila* full-length cDNA resource," Genome Biol. (2002) 3:1-8.

Cazzamali, et al., "Molecular cloning and functional expression of a *Drosophila corazonin* receptor," Biochem. Biophys. Res. Comm. (2002) 298:31-36.

Mertens, et al., " Characterization of the short neuropeptide F receptor from *Drosophila melanogaster*," Biochem. Biophys. Res. Comm. (2002) 1140-1148.

Park et al., "Identification of G protein-coupled receptors for *Drosophila* PRXamide peptides, CCAP, corazonin, and AKH supports a theory of ligand-receptor coevolution," Proc. Natl. Acad. Sci. USA (2002) 99:11423-11428.

Kreikenkamp et al., "Functional annotation of two orphan G-protein-coupled receptors, drostar1 and -2, from *Drosophila melanogaster* and their ligands by reverse pharmacology," J. Biol. Chem. (2002) 277:39937-39943.

Radford, et al., "Systematic G-protein-coupled receptor analysis in *Drosophila melanogaster* identifies a leucokinin receptor with novel roles," J. Biol. Chem. (2002) 277:38810-38817.

Cazzamali et al., "Molecular cloning and functional expression of the first insect FMRFamid receptor," PNAS (2002) 99(19):12073-12078.

Howard et al., "Orphan G-protein-coupled receptors and natural ligand discovery," Trends Pharmacol Sci (2001) 22(3):132-140.

Mickle et al., "Genotype-phenotype relationships in cystic fibrosis," Med Clin North Am (2000) 84(3):597-607.

Skolnick et al., "From genes to protein structure and function: novel applications of computational approaches in the genomic era," Tends Biotechnol (2000) 18(1):34-9.

Voet et al. *Biochemistry*, John Wiley & Sons, New York (1990), pp. 126-129 and pp. 228-234.

Yan et al., "Two-amino acid molecular switch in an epithelial morphogen that regulates binding to two distinct receptors," Science (2000) 290(5491):523-527.

Allen et al., "Modulation of CD4 by Suramin", Clin. Exp. Immunol., 1993, vol. 91, pp. 141-156.

Altschul et al., "Gapped BLAST and PSI-BLAST: a new generation of protein database search programs," Nucl. Acids Res., 1997, 25(17), 3389-3402.

Altschul et al., "Basic Local Alignment Search Tool," J. Mol. Biol., 1990, 215, 403-410.

Anafi et al., "Tyrphostin-Induced Inhibition of p210[ber-abl] Tyrosine Kinase Activity Induces K562 to Differentiate", Blood, 1993, vol. 82, No. 12, pp. 3524-3529.

Anderson, W. F., "Human gene therapy," Science, 1992, 256, 808-813.

Aukrust et al., "Enhanced Levels of Soluble and Membrane-Bound CD40 Ligand in Patients with Unstable Angina. Possible Reflection of T Lymphocyte and Platelet Involvement in the Pathogenesis of Acute Coronary Syndromes", Circulation, 1999, vol. 100, pp. 614-620.

Ausubel, et al. (Eds.), "Chapter 6, Screening of recombinant DNA libraries," Current Protocols in Molecular Biology, 1994, John Wiley & Sons, 6.0.1-6.4.10.

Baindur et al.,"Selective fluorescent ligands for pharmacological receptors," Drug Dev. Res., 1994, 33, 373-398.

Baker et al., "Induction of Acetylcholine Receptor Clustering by Native Polystyrene Beads. Implication of an Endogenous Muscle-derived Signalling System", J. Cell Sci., 1992, vol. 102, pp. 543-555.

Benoist et al., "In vivo sequence requirements of the SV40 early promoter region," Nature, 1981, 290, 304-310.

Bertino, Cancer Res., "Toward Improved Selectivity in Cancer Chemotherapy: The Richard and Hinda Rosenthal Foundation Award Lecture", 1979, vol. 3, pp. 293-304.

Bilder et al., "Tyrphostins Inhibit PDGF-induced DNA Synthesis and Associated Early Events in Smooth Muscle Cells", Amer. Physiol. Soc., 1991, pp. 6363-6143:C721-C730.

Birgul, N. et al., "Reverse physiology in *Drosphila*: Identification of a novel allatostatin-like neuropeptide and its cognate receptor structurally related to the mammalian somatostatin/galanin/opioid receptor family", The EMBO Journal, 1999, 18(21), 5892-5900.

Bohm, S. K., et al., "Regulatory mechanisms that modulate signalling by G-protein coupled receptors," Biochem. J., 1997, 322, 1-18.

Bossé, R., et al., "Development of nonseparation binding and functional assays for G protein-coupled receptors for high throughput screening: Pharmacological characterization of the immobilized CCR5 receptor on FlashPlate®," J. Biomolecular Screening, 1998, 3(4), 285-292.

Boulton, T. G., et al., "ERKs: A family of protein-serine/threonine kinases that are activated and tyrosine phosphorylated in response to insulin and NGF," Cell, 1991, 65, 663-675.

Bryckaert, M., et al., "Inhibition of platelet-derived growth factor-induced mitogenesis and tyrosine kinase activity in cultured bond marrow fibroblasts by tyrphostins," Experimental Cell Research, 1992, 199, 255-261.

Burke, T. R., et al., "Bicyclic compounds as ring-constrained inhibitors of protein-tyrosine kinase p56[kk]," J. Med. Chem., 1993, 36(4), 425-432.

Burke, T.R., et al., "Arylamides of hydroxylated isoquinolines as protein-tyrosine kinaseinhibitors,"BioOrganic Med. Chem. Ltrs., 1992, 2(12), 1771-1774.

Capecchi, M. R., "Altering the genome by homologous recombination," Science, 1989, 244, 1288-1292.

Chambers, R. C., et al., "Thrombin stimulates fibroblast procollagen production via proteolytic activation of protease-activated receptor 1," Biochem J., 1998, 333, 121-127.

Choo, Y., et al., "Promoter-specific activation of gene expression directed by bacteriophage-selected zinc fingers," J. Mol. Biol., 1997, 273, 525-532.

Cicala, C., et al., "Bronchoconstrictor effect of thrombin and thrombin receptor activating peptide in guinea-pigs in vivo," Br. J. Pharmacol, 1999, 126, 478-484.

Cirino, G., et al., "Thrombin functions as an inflammatory mediator through activation of its receptor," J. Exp. Med., 1996, 183, 821-827.

Colotta, F., et al., "Expression of monocyte chemotactic protein-1 by monocytes and endothelial cells exposed to thrombin," Am. J. Pathol, 1994, 144, 975-985.

Cosman, D., et al., "High Level Stable Expression of Human Interleukin-2 receptors in Mouse Cells Generates only Low Affinity Interleukin-2 Binding Sites," Mol. Immunol., 1986, 23(9), 935-941.

Cosman, D., et al., "Cloning, sequence and expression of human interleukin-2 receptor," Nature, 1984, 312, 768-771.

Curtin, N. J., et al., "Inhibition of the growth of human hepatocellular carcinoma in vitro and in athymic mice by a quinazoline inhibitor of thymidylate synthase, CB3717," J. Cancer, 1986, 53, 361-368.

Dayoff, in *Atlas of Protein Sequence and Structure*, 1972, National Biochemical Research Foundation, Washington, D.C., 5, 124.

DiCuccio, M. N., et al., "A functional tethered ligand thrombin receptor is present on human hematopoietic progenitor cells," Exp. Hematol, 1996, 24, 914-918.

Dolle, R. E., et al., "5,7-dimethoxy-3-(4-pyridinyl)quinoline is a potent and selective inhibitor of human vascular β-type platelet-derived growth factor receptor tyrosine kinase," J. Med. Chem., 1994, 37, 2627-2629.

Dong, Z., et al. "Activation of tumoricidal properties in macrophages by lipopolysaccharide requirements protein-tyrosine kinase activity," J. Leukocyte Biology, 1993, 53, 53-60.

Dong, Z., et al. "Protein tyrosine kinase inhibitors decrease induction of nitric oxide synthase activity in lipopolysaccharide-responsive and lipopolysaccharide-nonresponsive murine macrophages," J. Immunol., 1993, 151(5), 2717-2724.

Donovan, F. M., et al., "Thrombin induces apoptosis in cultured neurons and astrocytes via a pathway requiring tyrosin kinase and RhoA activities," J. Neurosci, 1997, 17(14), 5316-5326.

Dooley, C. T., et al., "Binding and in vitro activities of peptides with high affinity for the nociceptin/orphanin FQ receptor, ORL1," *J. Pharmacology and Experimental Therapeutics*, 1997, 283(2), 735-741.

Dunlop, J., et al., "Characterization of 5-HT$_{1A}$ receptor functional coupling in cells expressing the human 5-HT$_{1A}$ receptor as assessed with the cytosensor microphysiometer," *J. Pharmacological and Toxicological Methods*, 1998, 40(1), 47-55.

Fernandes, D. J., et al., "Biochemical and antitumor effects of 5,8-dideazaisopteroylglutamate, a unique quinazoline inhibitor of thymidylate synthase," *Cancer Research*, 1983, 43, 1117-1123.

Ferris, J. P., et al., "Synthesis of Quinazoline Nucleosides from Ribose and Anthranilonitrile. Application of Phase-Transfer Catalysis in Nucleoside Synthesis," *J. Org. Chem.*, 1979, 44(2), 173-178.

Fields, S., et al., "A novel genetic system to detect protein-protein interactions," *Nature*, 1989, 340, 245-246.

Fields, S., et al., "The two-hybrid system: an assay for protein-protein interactions," *Trends in Genetics*, 1994, 10, 286-292.

Foote, J., et al., "Antibody framework residues affecting the conformation of the hypervariable loops," *J. Mol. Biol.*, 1992, 224, 487-499.

Frandsen, E. K., et al., "A simple ultrasensitive method for the assay of cyclic AMP and CMP in tissues," *Life Sciences*, 1976, 529-542.

Fry, D. W., et al., "A specific inhibitor of the epidermal growth factor receptor tyrosine kinase," *Science*, 1994, 265, 1093-1095.

Gazit, A., et al., "Tyrphostins I: Synthesis and biological activity of protein tyrosine kinase inhibitors," *J. Med. Chem.*, 1989, 32, 2344-2352.

Gazit, A., et al., "Tyrphostins. 3. Structure-activity relationship studies of α-substituted benzylidenemalononitrile 5-S-aryltyrphostins," *J. Med. Chem.*, 1993, 36, 3556-3564.

George, S. E., et al., "Evaluation of a CRE-directed luciferase reporter gene assay as an alternative to measuring cAMP accumulation," *J. Biomolecular Screening*, 1997, 2(4), 235-240.

Gerhardt, C. C., et al., "Functional characteristics of heterologously expressed 5-HT receptors," *Eur. J. Pharmacology*, 1997, 334, 1-23.

Gill, J. S., et al., "Thrombin induced inhibition of neurite outgrowth from dorsal root ganglion neurons," *Brain Res.*, 1998, 797, 321-327.

Grabham, P., et al., Thrombin receptor activation stimulates astrocyte proliferation and reversal of stellation by distinct pathways: involvement of tyrosine phosphorylation, *J. Neurochem*, 1995, 64, 583-591.

Greisman, H. A., et al., "A general strategy for selecting high-affinity zinc finger proteins for diverse DNA target sites," *Science*, 1997, 275, 657-661.

Guerrero, F. D., "Transcriptional Expression of a Putative Tachykinin-like Peptide Receptor Gene From Stable Fly[1]," *Peptides*, 1997, 18(1), 1-5.

Hauck, R. W., et al., "α-thrombin stimulates contraction of human bronchial rings by activation of protease-activated receptors," *Am J. Physiol*, 1999, 277, L22-L29.

Hauser, F., et al., "Molecular Cloning, Genomic Organization, and Developmental Regulation of a Novel Receptor from *Drosophila melanogaster* Structurally Related to Members of the Thyroid-stimulating Hormone, Follicle-stimulating Hormone, Luteinizing Hormone/ Choriogonadotropin Receptor Family from Mammals," *The J. of Biological Chemistry*, 1997, 272(2), 1002-1010.

Hauser, F. et al., "Molecular Cloning, Genomic Organization, and Developmental Regulation of a Novel Receptor from *Drosophila melanogaster* Structurally Related to Gonadotropin-Releasing Hormone Receptors from Vertebrates", *Biochem. Biophys. Res. Comm.*, 1998, 249, 822-828.

Henikoff, S., et al., "Amino acid substitution matrices from protein blocks," *Proc. Natl. Acad. Sci. USA*, 1992, 89, 10915-10919.

Hodgson, J., "Receptor screening and the search for new pharmaceuticals," *Bio/Technology*, 1992, 10, 973-980.

Hoffman, M., et al., "Thrombin enhances monocyte secretion of tumor necrosis factor and interleukin-1 beta by two distinct mechanisms," *Blood Cells Mol Dis*, 1995, 21, 156-167.

Jackman, A. L., et al., "ICID1694, a quinazoline antifolate thymidylate synthase inhibitor that is a potent inhibitor of L1210 tumor cell growth in vitro and in vivo: A new agent for clinical study," *Cancer Research*, 1981, 51, 5579-5586.

Jayawickreme, C. K., et al., Gene expression systems in the development of high-throughput screens, *Current Opinion in Biotechnology*, 1997, 8, 629-634.

Jones, P. T., et al., "Replacing the compementarity-determining regions in a human antibody with those from a mouse," *Nature*, 1986, 321, 522-525.

Jones, T. R., et al., "Quinazoline Antifolates Inhibiting Thymidylate Synthase: Variation of the Amino Acid," *J. Med Chem.*, 1986, 29, 1114-1118.

Kanterman, R. Y., et al., "Transfected D$_2$ dopamine receptors mediate the potentiation of arachidonic acid release in chinese hamster ovary cells," *Molecular Pharmacology*, 1991, 39, 364-369.

Karlin, S., et al., "Applications and statistics for multiple high-scoring segments in molecular sequences," *Proc. Natl. Acad. Sci. USA*, 1993, 90, 5873-5787.

Kaur, G., et al., " Tyrphostin induced growth inhibition: corelation with effect on p210$^{ber-abl}$ autokinase activity in K562 chronic myelogenous leukemia," *Anti-Cancer Drugs*, 1994, 5, 213-222.

Kettleborough, C. A., et al., "Humanization of a mouse monoclonal antibody by CDR-grafting: the importance of framework residues on loop conformation," *Protein Engin.*, 1991, 4(7), 773-783.

Kim, J., et al., "Design of TATA box-binding protein/zinc finger fusions for targeted regulation of gene expression," *Proc. Natl. Acad. Sci. USA*, 1997, 94, 3616-3620.

King, M. J., et al., "Site-specific dephosphorylation and deactivation of the human insulin receptor tyrosine kinase by particulate and soluble phosphotyrosyl protein phosphatases," *Biochem. J.*, 1991, 275, 413-418.

Kowal, D., et al., "A [$^{35}$S]GTPγS binding assessment of metabotropic glutamate receptor standards in chinese hamster ovary cell lines expressing the human metabotropic receptor subtypes 2 and 4," *Neurophramacology*, 1998, 37, 179-187.

Kuntzweiler, T. A., et al., "Rapid assessment of ligand actions with nicotinic acetylcholine receptors using calcium dynamics and FLIPR," *Drug Development Research*, 1998, 44(1), 14-20.

Lajiness et al., "D2 dopamine receptor stimulation of mitogenesis in transfected chinese hamster ovary cells: relationship to dopamine stimulation of tyrosine phosphorylations", *J. Pharm. Exp. Ther.*, 1993, vol. 267, No. 3, 1573-1581.

Lehninger, "Chapter 4, The amino acid building blocks of proteins," *Biochemistry*, 2nd Ed., 1975, Worth Publishers, Inc., New York, New York, 71-77.

Lemus, et al., "Studies of extended quinone methides. Synthesis and physical studies of purine-like monofunctional and bifunctional imidazo[4,5-g]quinazoline reductive alkylating agents," *J. Org. Chem.*, 1989, 54, 3611-3618.

Lenz, C. et al., "Molecular Cloning and Genomic Organization of a Second Probable Allastatin Receptor from *Drosophila melanogaster*", *Biochem. Biophys. Res. Comm.*, 2000, 273, 571-577.

Lenz, C. et al., *Drosophila melanogaster* allatostatin G-protein receptor mRNA, complete cds, GenBank Accession No. AF253526, Jul. 14, 2000.

Lenz, C. et al., "Molecular Cloning and Genomic Organization of an Allatostatin Preprohormone from *Drosophila melanogaster*", *Biochem. Biophys. Res. Comm.*, 2000, 273, 1126-1131.

Levitzki, A., "Tyrphostins: tyrosine kinase blockers as novel antiproliferative agents and dissectors of signal transduction," *The FASEB J.*, 1992, 6, 3275-3282.

Ley, K., et al., "Synthesen unter verwendung von benzofuroxan," *Synthesis*, 1975, 415-522 (English abstract).

Li, X-J., et al. "Cloning, heterologous expression and developmental regulation of a *Drosophila* receptor for tachykinin-like peptides," *The EMBO Journal*, 1991, 10(11), 3221-3229.

Li, X-J., et al., "Cloning, Functional Expression, and Developmental Regulation of a Neuropeptide Y Receptor from *Drosophila melanogaster*," *The J. of Biological Chemistry*, 1992, 267(1), 9-12.

Li, X.-J. et al., *D. melanogaster* neuropeptide receptor mRNA, complete cds, GenBank Accessin No. M81490, Apr. 26, 1993.

Lin, A. H., et al., "The oxazolidinone eperezolid binds to the 50S ribosomal subunit and competes with binding of chloramphenicol and lincomycin," *Antimicrobial Agents and Chemotherapy*, 1997, 41(10), 2127-2131.

Liu, Q., et al. "Design of polydactyl zinc-finger proteins for unique addressing within complex genomes," *Proc. Natl. Acad. Sci. USA*, 1997, 94, 5525-5530.

Luckow, V. A., et al., "High Level Expression of Nonfused Foreign Genes with Autographa californica Nuclear Polyhedrosis Virus Expression Vectors," *Virology*, 1989, 170, 31-39.

Luckow, V. A., et al., "Trends in the development of baculovirus expression vectors," *Bio/Technology*, 1988, 6, 47-55.

Lyall, R. M., et al., "Tyrphostins inhibit epidermal growth factor (EGF)-receptor tyrosine kinase activity in living cells and EGF-stimulated cell preliferation," *J. Biol. Chem.*, 1989, 264, 14503-14509.

Maguire, M. P., et al., "A new series of PDGF receptor tyrosine kinase inhibitors: 3-substituted quinoline derivatives," *J. Med. Chem.*, 1994, 37, 2129-2131.

Maxwell, R. J., et al., "$^{19}$F nuclear magnetic resonance imaging of drug distribution in vivo: The disposition of an antifolate anticancer drug in mice," *Magnetic Resonance in Medicine*, 1991, 17, 189-196.

McColl, D. J., et al., "Structure-based design of an RNA-binding zinc finger", *Proc. Natl. Acad. Sci. (USA)*, 1997, vol. 96, 9521-9526.

Mini, E., et al., "Cytotoxic effects of folate antagonists against methotrexate-resistant human leukemic lymphoblast CCRF-CEM cell lines," *Cancer Res.*, 1985, 45, 325-330.

Monnier, D., et al. "NKD, a Developmentally Regulated Tachykinin Receptor in *Drosophila,*" *The J. of Biological Chemistry*, 1992, 267(2), 1298-1302.

Monnier, D. et al., *Drosophila melanogaster* tachykinin receptor (NKD) mRNA, complete cds, GenBank Accession No. M77168, Apr. 26, 1993.

Morris, R., et al., "Thrombin receptor expression in rheumatoid and osteoarthritic synovial tissue", *Ann. Rheum. Dis.*, 1996, vol. 55, 841-843.

Morrison, et al., "Genetically engineered antibody molecules," Dixon, F.J., et al. (Eds.), *Adv. Immunol.*, 1989, 44, 65-92.

Murphy, A. J., et al., "From DNA to drugs: the orphan G-protein coupled receptors," *Cur. Opinion Drug Disc. Dev.*, 1998, 1(2), 192-199.

Myers, P., "Will combinatorial chemistry deliver real medicines," *Curr. Opin. Biotechnology*, 1997, 8, 701-707.

Nachman & Homan, in *Insect Neuropeptides; Chemistry, Biology and Action*, Menn, Kelly & Massler, Eds., 1991, 194-214, American Chemical Society, Washington, DC.

Nakayama, G.R., "Microplate assays for high-throughput screening," *Cur. Opinion Drug Disc. Dev.*, 1998, 1, 85-91.

Naldini, A., et al., "Thrombin modulation of natural killer activity in human peripheral lymphocytes," *Cell Immunol*, 1996, 172, 35-42.

Nambu et al., "Isolation and Characterization of a *Drosophila* Neuropeptide Gene", *Neuron*, 1988, 1, 55-61.

Nichols, R. et al., "Identification and Characterization of a *Drosophila* Homologue to the Vertebrate Neuropeptide Cholecystokinin", *J. Biol. Chem.*, 1988, 263, 12167-12170.

Okayama, H., et al., "A cDNA cloning vector that permits expression of cDNA inserts in mammalian cells," *Mol. Cell. Biol.*, 1983, 3(2), 280-289.

Padlan, E. A., "A possible procedure for reducing the immunogenicity of antibody variable domains while preserving their ligand-binding properties," *Molecular Immunol.*, 1991, 28(4/5), 489-498.

Pausch, M. H., "G-protein-coupled receptors in *Saccharomyces cerevisiae*: high-throughput screening assays for drug discovery," *Trends in Biotechnology*, 1997, 15, 487-494.

Peterson, G., et al. "Genistein and biochanin A inhibit the growth of human prostate cancer cells but not epidermal growth factor receptor tyrosine autophosphorylation," *The Prostate*, 1993, 22, 335-345.

Phillips, S. D., et al., "Quino[1,2-c]quinazolines. I. Synthesis of quino[1,2-c]quinazolinium derivatives and the related indazolo[2,3-a]quinoline derivatives as analogs of the antitumor benzo[c]phenanthridine alkaloids," *J. Heterocyclic Chem.*, 1980, 17(19), 1489-1596.

Pillemer, G., et al., "Insulin dependence of murine lymphoid T-cell leukemia," *Int. J. Cancer*, 1992, 50, 80-85.

Pindon, A., et al., "Thrombin-induced reversal if astricyte stellation is mediated by activation of protein kinase C β-1," *Eur. J. Biochem.*, 1998, 255, 766-774.

Posner, I., et al., "Kinetics of inhibition by tyrphostins of the tyrosine kinase activity of the epidermal growth factor receptor and analysis," *Molecular Pharmacology*, 1993, 45, 673-683.

Reece, P. A., et al., "Pharmacokinetics of trimetrexate administered by five-day continuous infusion to patients with advanced cancer," *Cancer Research*, 1977, 47(11), 2996-2999.

Rendu, F., et al., "Inhibition of platelet activation by tyrosine kinase inhibitors," *Biol. Pharmacology*, 1992, 44(5), 881-888.

Riechmann, L., et al., "Reshaping human antibodies for therapy," *Nature*, 1988, 332, 323-327.

Rogers, M. V., "Light on high-throughput screening: fluorescence-based assay technologies," *Drug Discovery Today*, 1997, 2(4), 156-160.

Sauro, M. D., et al., "Tyrphostin attenuates platelet-derived growth factor-induced contraction in aortic smooth muscle through inhibition of protein tyrosine kinase(s)," *J. Pharm. And Experimental Therapeutics*, 1993, 267(3), 1119-1125.

Schroeder, K. S., et al. "FLIPR: A new instrument for accurate, high throughput optical screening," *J. Biomolecular Screening*,1996, 1, 75-80.

Sculier, J. P., et al. "Role of an intensive care unit (ICU) in a medical oncology department," No. 257, *Cancer Immunol. And Immunother.*, 1986, 23, A65.

Segal, D. J., et al., "Toward controlling gene expression at will: Selection and design of zinc finger domains recognizing each of the 5'-GNN-3' DNA target sequences," *Proc. Natl. Acad. Sci. USA*, 1999, 96, 2758-2763.

Sikora, E., et al., "Quinazoline CB 3717 and CB 3703 inhibition of folate retention and metabolism in ehrlich ascites carcinoma cells and some organs of the host-mouse," *Cancer Letters*, 1984, 23, 289-295.

Sikora, E., et al. "Development of an assay for the estimation of $N^{10}$-propargyl-5,8-dideazafolic acid polyglutamates in tumor cells," *Analytical Biochemistry*, 1988, 172, 344-355.

Sim, L. J., et al., "Identification of opioid receptor-like (ORL1) peptide-stimulated [$^{35}$S]GTPγS binding in rat brain," *Neuroreport*, 1996, 7, 729-733.

Smith, T. F., et al., "Comparison of biosequences," *Adv. Appl. Math.*, 1981, 2, 482-489.

Smith-Swintosky, V. L., et al., "Protease-activated receptor-2 (PAR-2_is present in the rat hippocampus and is associated with neurodegeneration," *J. Neurocham*, 1997, 69, 1890-1896.

Stables, J., et al., "A bioluminescent assay for agonist activity at potentially any G-protein-coupled receptor," *Analytical Biochemistry*, 1997, 252, 115-126.

Stratowa, C., et al., "Use of a luciferase reporter system for characterizing G-protein linked receptors," *Current Opinion in Biotechnology*, 1995, 6, 574-581.

Strosberg, et al., "Functional expression of receptors in microorganisms," *Trends in Pharmacological Sciences*, 1992, 13, 95-98.

Strosberg, A. D., et al., "Structure/function relationship of proteins belonging to the family of receptors coupled to GTP-binding proteins,," *Eur. J. Biochem.*, 1991, 196, 1-10.

Suidan, H. A., et al., "The thrombin receptor in the nervous system," *Semin Thromb Hemost*, 1996, 22(2), 125-133.

Sutherland, E. W., et al., "Some aspects of the biological role of adenosine 3',5'-monophosphate (cyclic AMP)," *Circulation*, 1968, 37, 279-306.

Sweetnam, P. M., et al., "The role of receptor binding in drug discovery," *J. Natural Products*, 1993, 56(4), 441-455.

Tempest, P. R., et al.,"Reshaping a human monoclonal antibody to inhibit human respiratory syncytial virus infection in vivo," *Bio/Technology*, 1991, 9, 266-271.

Torfs, H. et al., "Characterization of a receptor for insect tachykinin-like peptide agonists by functional expression in a stable *Drosophila* Schneider 2 Cell Line", *J. Neurochem.*, 2000, 74, 2182-2189.

Trejo, J., et al., "The cloned thrombin receptor is necessary and sufficient for activation of mitogen-activated protein kinase and mitogenesis in mouse lung fibroblasts," *J. Biol. Chem.*, 1996, 271, 21536-21541.

Turgeon, V. L., et al., "Thrombin perturbs neurite outgrowth and induces apoptotic cell death in enriched chick spinal motoneuron cultures through caspase activation," *J. Neurosci*, 1998, 18(17), 6882-6891.

Ubl, J. J., et al., "Characteristics of thrombin-induced calcium signals in rat astrocytes," *Glia*, 1997, 21, 361-369.

Vanden Broeck, "G-protein-coupled receptors in insect cells", *Int. Rev. Cytology*, 1996, 164, 189-268.

Verhoeyen, M., et al., "reshaping human antibodies: Grafting an antilysozyme activity," *Science*, 1988, 239, 1534-1536.

Wieboldt, R., et al., "Immunoaffinity ultrafiltration with ion spray HPLC/MS for screening small-molecule libraries," *Anal. Chem.*, 1997, 69(9), 1683-1691.

Williams, M., "Receptor binding in the drug discovery process," *Medicinal Research Reviews*, 1991, 11(2), 147-184.

Wolbring, G., et al., "Inhibition of GTP-utilizing enyzmes by tyrphostins," *J. Biol. Chem.*, 1994, 269(36), 22470-22472.

Wu, H., et al., "Building zinc fingers by selection: toward a therapeutic application," *Proc. Natl. Acad. Sci. USA*, 1995, 92, 344-348.

Yoneda, T., et al., "The antiproliferative effects of tyrosine kinase inhibitors tyrphostins on a human squamous cell carcinoma in vitro and in nude mice," *Cancer Research*, 1991, 51, 4430-4435.

Adams, M.D., et al., "The genome sequence of *Drosophila melanogaster*," *EMBL/GenBank/DDBJ*, XP-002176201, Mar. 21, 2000, 3 pages.

Alcedo, J., et al., "The *Drosophila* smoothened gene encodes a seven-pass membrane protein, a putative receptor for the hedgehog signal," *Cell*, XP-002166694, Jul. 26, 1996, 86, 221-232.

Celniker, S.E., et al., "*Drosophila melanogaster*, chromosome X, region 17C-17E," *EMBL*, XP-002176202, Oct. 22, 1999, 2 pages.

Celniker, S.E., et al., "*Drosophila melanogaster*, chromosome 2R, region 42A8-42A16, P1 clones DS06954 and DS05325," *EMBL*, XP-002176200, Mar. 24, 1999, 2 pages.

Celniker, et al., "*Drosophila melanogaster*, chromosome 3R, region 83D-83D, BAC clone BACR26C09," *EMBL*, XP-002176198, Sep. 17, 1999, 2 pages.

Muzny, D.M., et al., "*Drosophila melanogaster* clone RPC198-10L1," *EMBL*, XP-002166695, Aug. 23, 1999, 3 pages.

Muzny, D.M., et al., "*Drosophila melanogaster* clone RPC198-23M20," *EMBL*, xP-002176199, Aug. 23, 1999, 3 pages.

Nichols, R., "Isolation and structural characterization of *Drosophila* TDVDHVFLRF amide and FMRF amide-containing neural peptides," *Medline*, XP-002166696, 1992, 1 page.

Taghert, P.H., et al., "Interspecific comparison of a *Drosophila* gene encoding FMRF amide-related neuropeptides," *J. Neuroscience, USA.*, 1990, 10(6), 1929-1942.

\* cited by examiner

US 7,364,866 B2

DROSOPHILA G PROTEIN COUPLED RECEPTORS, NUCLEIC ACIDS, AND METHODS RELATED TO THE SAME

CROSS REFERENCE TO RELATED APPLICATIONS

This application is a continuation-in-part of U.S. patent application Ser. No. 09/693,746, filed Oct. 20, 2000, now U.S. Pat. No. 6,835,546 which in turn is a continuation-in-part of U.S. patent application Ser. No. 09/425,676, filed Oct. 22, 1999, now abandoned each of which is hereby incorporated by reference in its entirety.

FIELD OF THE INVENTION

The present invention is directed, in part, to nucleic acid molecules encoding novel *Drosophila melanogaster* G protein coupled receptors (DmGPCRs), novel polypeptides, assays for screening compounds that bind to a DmGPCR and/or modulate the activity of a DmGPCR, methods for binding a DmGPCR, reagents such as antibodies to a DmGPCR, primers, and probes for detection of nucleotide sequences encoding a DmGPCR, kits including the antibodies, primers, and probes of the invention, compositions including DmGPCRs, DmGPCR binding partners, and DmGPCR modulators, and methods for controlling an insect population using a DmGPCR binding partner or modulator.

BACKGROUND OF THE INVENTION

Humans and other life forms are comprised of living cells. Among the mechanisms through which the cells of an organism communicate with each other and obtain information and stimuli from their environment is cell membrane receptor molecules expressed on the cell surface. Many such receptors have been identified, characterized, and sometimes classified into major receptor superfamilies based on structural motifs and signal transduction features. Such families include (but are not limited to) ligand-gated ion channel receptors, voltage-dependent ion channel receptors, receptor tyrosine kinases, receptor protein tyrosine phosphatases, and G protein-coupled receptors. The receptors are a first essential link for translating an extracellular signal into a cellular physiological response.

G protein-coupled receptors (i.e., GPCRs) form a vast superfamily of cell surface receptors which are characterized by an amino-terminal extracellular domain, a carboxy-terminal intracellular domain, and a serpentine structure that passes through the cell membrane seven times. Hence, such receptors are sometimes also referred to as seven transmembrane (7TM) receptors. These seven transmembrane domains define three extracellular loops and three intracellular loops, in addition to the amino- and carboxy-terminal domains. The extracellular portions of the receptor have a role in recognizing and binding one or more extracellular binding partners (e.g., ligands), whereas the intracellular portions have a role in recognizing and communicating with downstream effector molecules.

The GPCRs bind a variety of ligands including calcium ions, hormones, chemokines, neuropeptides, neurotransmitters, nucleotides, lipids, odorants, and even photons. Not surprisingly, GPCRs are important in the normal (and sometimes the aberrant) function of many cell types. See generally Strosberg, *Eur. J. Biochem.*, 1991, 196, 1-10; Bohm et al, *Biochem J.*, 1997, 322, 1-18. When a specific ligand binds to its corresponding receptor, the ligand typically stimulates the receptor to activate a specific heterotrimeric guanine nucleotide-binding regulatory protein (G protein) that is coupled to the intracellular portion or region of the receptor. The G protein, in turn, transmits a signal to an effector molecule within the cell by either stimulating or inhibiting the activity of that effector molecule. These effector molecules include adenylate cyclase, phospholipases, and ion channels. Adenylate cyclase and phospholipases are enzymes that are involved in the production of the second messenger molecules cAMP, inositol triphosphate, and diacyglycerol. It is through this sequence of events that an extracellular ligand stimulus exerts intracellular changes through a G protein-coupled receptor. Each such receptor has its own characteristic primary structure, expression pattern, ligand binding profile, and intracellular effector system.

Because of the vital role of G protein-coupled receptors in the communication between cells and their environment, such receptors are attractive targets for regulation, for example, by activating or antagonizing such receptors. For receptors having a known ligand, the identification of agonists or antagonists may be sought specifically to enhance or inhibit the action of the ligand. For example, some G protein-coupled receptors have roles in disease pathogenesis (e.g., certain chemokine receptors that act as HIV co-receptors may have a role in AIDS pathogenesis), and are attractive targets for therapeutic intervention even in the absence of knowledge of the natural ligand of the receptor. Other receptors are attractive targets for therapeutic intervention by virtue of their expression pattern in tissues or cell types that are themselves attractive targets for therapeutic intervention. Examples of this latter category of receptors include receptors expressed in immune cells, which can be targeted to either inhibit autoimmune responses or to enhance immune responses to fight pathogens or cancer; and receptors expressed in the brain or other neural organs and tissues, which are likely targets in the treatment of schizophrenia, depression, bipolar disease, or other neurological disorders. This latter category of receptor is also useful as a marker for identifying and/or purifying (e.g., via fluorescence-activated cell sorting) cellular subtypes that express the receptor.

Insects are recognized as major pests in agriculture and in human domestic environments. Insects also parasitize animals and humans, being denoted as ectoparasites in such cases, causing morbidity and mortality. Insects also serve as vectors for the transmission of viral and parasitic diseases to plants, animals and humans. Thus, there is a continuing and compelling need to discover new methods for controlling insect populations and for repelling and/or killing pathogenic or pestiferous species. One way to control insect populations by killing or paralyzing insects is through the use of chemical agents, denoted as insecticides, that are selectively toxic to insects and potentially other invertebrates. Currently, insecticides have enormous value for the control of insects that are damaging to agricultural products, including crops and livestock. Insecticides are also used in human domestic situations, for the control of lawn and garden pests as well as insects that are damaging or annoying to humans, including stinging or biting insects, flies and cockroaches. Insecticides also have enormous value for the treatment or prevention of disease states caused by ectoparasites, including fleas, lice, ticks, mites, and biting flies, in livestock animals and pets. However, current chemicals used as insecticide are not optimal. Some have demonstrable toxicity for mammals, while resistance to some of them has arisen in certain target species. Therefore, there exists a need for new selective insecticides that have novel mechanisms of action.

Examples of insect GPCRs that have neuropeptide ligands are known (see, e.g., Li, et al., *EMBO Journal*, 1991, 10, 3221-3229; Li, et al., *J. Biol. Chem.*, 1992, 267, 9-12; Monnier, et al., *J. Biol. Chem.*, 1992, 267, 1298-1302; Vanden Broeck, et al., *Int. Rev. Cytology*, 1996, 164, 189-268; Guerrero, *Peptides*, 1997, 18, 1-5; Hauser, et al., *J. Biol. Chem.*, 1997, 272, 1002-1010; Birgul et al., *EMBO J*, 1999, 18, 5892-5900; Torfs et al., *J. Neurochem.*, 2000, 74, 2182-2189; and Hauser et al., *Biochem. Biophys. Res. Comm.*, 1998, 249, 822-828; Larsen, et al., *Biochem. Biophys. Res. Comm.*, 2001, 286, 895-901; Lenz, et al., *Biochem. Biophys. Res. Comm.*, 2001, 286, 1117-1122; Kubiak et al., *Biochem. Biophys. Res. Comm.*, 2002, 291, 313-320; Staubli et al., *Proc. Natl. Acad. Sci. USA*, 2002, 99, 3446-3451; Garczynski et al., *Peptides*, 2002, 23, 773-780), Holmes et al. *Insect Molecular Biology*, 2000, (5), 457-465. Recent related patent applications: Ebens, Allen James, Jr.; Torpey, Justin; Keegan, Kevin Patrick. Nucleic acids and polypeptides of *Drosophila melanogaster* G protein-coupled receptor and their use as pesticidal and pharmaceutical targets. PCT Int. Appl. (2001), 43 pp. CODEN: PIXXD2 WO 0170981 A2 20010927 CAN 135:268323 AN2001: 713564 CAPLUS. Kravchik, Anibal. *Drosophila* G protein-coupled receptors, genomic DNA and cDNA molecules encoding GPCR proteins, and their uses as insecticidal targets. PCT Int. Appl. (2001), 392 pp. CODEN:PIXXD2 WO 0170980 A2 20010927 CAN135:269068 AN 2001: 713563 CAPLUS.

A large family of peptides generally 4-12 amino acids in length typically found in invertebrate animals (e.g., insects) is a class of neuropeptides known as FMRFamide-related peptides (i.e., FaRPs). The prototypical FMRFamide (FMRFa) peptides are so named because of the "FMRF" consensus amino acid sequence at their C-termini, consisting generally of (F,Y)(M,V,I,L)R(F,Y)NH$_2$. As neuropeptides, these molecules are involved in vital biological processes requiring controlled neuromuscular activity. Although some neurotransmitters and neuromodulators (including neuropeptides) have been shown to function as ligands for receptors, to date there has been no identification of a FaRP neuropeptide as a ligand of a GPCR.

*Drosophila* peptides containing a conserved FXGXR-amide motif are structurally related to mammalian tachykinins and, hence, have been coined drotachykinins (Siviter et al., *J. Biol. Chem.*, 2000, 275(30), 23273-23280). The drotachykinins have potent stimulatory effects on contractions of the insect gut (id.).

Leucokinins are a group of widespread insect hormones that stimulate gut motility and tubule fluid secretion rates. In tubules, their major action is to raise chloride permeability by binding to a receptor on the basolateral membrane. Leucokinin acts by raising intracellular calcium in only the stellate cells (O'Donnell et al., *Am. J. Physiol.*, 1998, 43, R1039-R1049).

The allatostatins are an important group of insect neurohormones controlling diverse functions including the synthesis of juvenile hormones known to play a central role in metamorphosis and reproduction in various insect species. The very first *Drosophila* allatostatin, Ser-Arg-Pro-Tyr-Ser-Phe-Gly-Leu-NH$_2$ (i.e., drostatin-3) (SEQ ID NO: 165), was isolated from *Drosophila* head extracts (Birgul et al., *EMBO J.*, 1999, 18, 5892-5900). Recently, a *Drosophila* allatostatin preprohormone gene has been cloned which encodes four *Drosophila* allatostatins: Val-Glu-Arg-Tyr-Ala-Phe-Gly-Leu-NH$_2$ (drostatin-1) (SEQ ID NO: 163), Leu-Pro-Val-Tyr-Asn-Phe-Gly-Leu-NH$_2$ (drostatin-2) (SEQ ID NO: 164), Ser-Arg-Pro-Tyr-Ser-Phe-Gly-Leu-NH$_2$ (drostatin-3) (SEQ ID NO: 165), and Thr-Thr-Arg-Pro-Gln-Pro-Phe-Asn-Phe-Gly-Leu-NH$_2$ (drostatin-4) (SEQ ID NO: 166) (Lenz et al., *Biochem. Biophys. Res. Comm.*, 2000, 273, 1126-1131). The first *Drosophila* allatostatin receptor was cloned by Birgul et al. and was shown to be functionally activated by drostatin-3 via Gi/Go pathways (Birgul et al., *EMBO J.* 1999, 18, 5892-5900). A second putative *Drosophila* allatostatin receptor (i.e., DARII) has been recently cloned (Lenz et al., *Biochem. Biophys. Res. Comm.*, 2000, 273, 571-577). The DARII receptor cDNA (Accession No. AF253526) codes for a protein that is strongly related to the first *Drosophila* allatostatin receptor. Recently, functional activation of DARII by allatostatins have been shown by us (Larsen, et al., *Biochem. Biophys. Res. Comm.*, 2001, 286, 895-901) and others (Lenz, et al., *Biochem. Biophys. Res. Comm.*, 2001, 286, 1117-1122). Recently, a *Drosophila* allatostatin type C preprohormone gene has been cloned which encodes a *Drosophila* allatostatin-C: Gln-Val-Arg-Tyr-Gln-Cys-Tyr-Phe-Asn-Pro-Ile-Ser-Cys-Phe-OH (Williamson et al., *Biochem. Biophys. Res. Comm.*, 2001, 282, 124-130). The mature peptide should have a pGlu at the N-terminus, formed as a result of the N-terminal Gln cyclization, to yield: pGlu-Val-Arg-Tyr-Gln-Cys-Tyr-Phe-Asn-Pro-Ile-Ser-Cys-Phe-OH (SEQ ID NO: 183), and a disulfide bridge between Cys$^6$ and Cys$^{13}$, similar to the Manduca sexta type C allatostatin, pGlu-Val-Arg-Phe-Gln-Cys-Tyr-Phe-Asn-Pro-Ile-Ser-Cys-Phe-OH (SEQ ID NO: 182)., which differs only at position 4 (Phe$^4$ vs Tyr$^4$) (Kramer et al., *Proc. Natl. Acad. Sci. USA*, 1991, 88, 9458-9462). Nichols at al., showed potent and prolonged inhibition of muscle contraction of the *Drosophila* allatostatin-C and named it a flatline (FLT) peptide (Nichols et al. *Peptides*, 2002, 23, 787-794). To our knowledge, to date no receptors for insect allatostatin type-C have been identified.

The sulfakinins are a family of insect Tyr-sulfated neuropeptides. They show sequence and functional (myotropic effects, stimulation of digestive enzyme release) similarity to the vertebrate peptides gastrin and cholecystokinin. A gene encoding two sulfakinins (also called drosulfakinins), DSKI [Phe-Asp-Asp-Tyr(SO$_3$H)-Gly-His-Met-Arg-Phe-amide] (SEQ ID NO: 160) and DSKII [Gly-Gly-Asp-Asp-Gln-Phe-Asp-Asp-Tyr(SO$_3$H)-Gly-His-Met-Arg-Phe-amide] (SEQ ID NO: 161), has been identified in *Drosophila melanogaster* (Nichols, *Mol. Cell Neuroscience*, 1992, 3, 342-347; Nichols et al., *J. Biol. Chem.*, 1988, 263, 12167-12170). The C-terminal heptapeptide sequence, Asp-Tyr (SO$_3$H)-Gly-His-Met-Arg-Phe-amide (SEQ ID NO: 162), is identical in all sulfakinins identified so far from insects that are widely separated in evolutionary terms. The conservation of the heptapeptide sequence, including the presence of the sulfated Tyr residue, in widely divergent insect taxa presumably reflects functional significance of this myotropic "active core" (Nachman & Holman, in INSECT NEUROPEPTIDES: CHEMISTRY, BIOLOGY AND ACTION, Menn, Kelly & Massler, Eds., American Chemical Society, Washington, D.C., 1991, pp. 194-214). Recently, we identified the *Drosophila* orphan receptor (DmGPCR9) as a drosulfakinin receptor (named DSK-R1) and matched it with its activating peptide, a Met$^5$→Leu modified drosulfakinin-1, Asp-Tyr(SO$_3$H)-Gly-His-Leu-Arg-Phe-amide (SEQ ID NO: 157) (Kubiak et al., *Biochem. Biophys. Res. Comm.*, 2002, 291, 313-320).

SUMMARY OF THE INVENTION

The present invention involves the surprising discovery of novel polypeptides in *Drosophila melanogaster*, designated herein DmGPCRs (*Drosophila melanogaster* G Protein-Coupled Receptors), which exhibit varying degrees of homology to other neuropeptide GPCRs. The present invention provides genes encoding these heretofore unknown G protein-coupled receptors, the DmGPCR polypeptides encoded by the genes; antibodies to the polypeptides; kits employing the polynucleotides and polypeptides, and methods of making and using all of the foregoing. The DmGPCRs may play a role as a key component, for example, in regulating neuropeptide binding and/or signaling. DmGPCRs are thus useful in the search for novel agents that can modify and/or control binding and/or signaling by neuropeptides or other agents. These and other aspects of the invention are described below.

In some embodiments, the invention provides purified and isolated DmGPCR polypeptides comprising the amino acid sequence set forth in any of SEQ ID NOs: 2, 4, 6, 8, 10, 12, 14, 16, 18, 20, 22, or 24, or a fragment thereof comprising an epitope specific to the DmGPCR. By "epitope specific to" is meant a portion of the DmGPCR receptor that is recognizable by an antibody that is specific for the DmGPCR, as defined in detail below. One embodiment of the invention comprises purified and isolated polypeptides comprising the complete amino acid sequences set forth in SEQ ID NOs: 2, 4, 6, 8, 10, 12, 14, 16, 18, 20, 22, or 24, found in Table 4 below. These amino acid sequences were deduced from polynucleotide sequences encoding DmGPCR (SEQ ID NOs: 1, 3, 5, 7, 9, 11, 13, 15, 17, 19, 21, or 23, found in Table 4 below). The term "DmGPCR" as used herein in singular form is intended to encompass each of the ten amino acid sequences exemplified below, encoded by the respective polynucleotide sequences.

Although the sequences provided are particular *Drosophila* sequences, the invention is intended to include within its scope allelic variants, vertebrate, and invertebrate forms of DmGPCR.

In some embodiments, the invention provides purified and isolated polynucleotides (e.g., cDNA, genomic DNA, synthetic DNA, RNA, or combinations thereof, whether single- or double-stranded) that comprise a nucleotide sequence encoding the amino acid sequence of the polypeptides of the invention. Such polynucleotides are useful for recombinantly expressing the receptor and also for detecting expression of the receptor in cells (e.g., using Northern hybridization and in situ hybridization assays). Such polynucleotides also are useful in the design of antisense and other molecules for the suppression or regulation of the expression of DmGPCR in a cultured cell, a tissue, or an animal. Specifically excluded from the definition of polynucleotides of the invention are entire isolated, non-recombinant native chromosomes of host cells. Polynucleotides of the invention may have the sequence of any sequence set forth in SEQ ID NOs: 1, 3, 5, 7, 9, 11, 13, 15, 17, 19, 21, or 23, which correspond to naturally occurring DmGPCR sequences. It will be appreciated that numerous other polynucleotide sequences exist that also encode the DmGPCR having the sequence set forth in any of SEQ ID NOs: 2, 4, 6, 8, 10, 12, 14, 16, 18, 20, 22, or 24 due to the well-known degeneracy of the universal genetic code.

The invention also provides a purified and isolated polynucleotide comprising a nucleotide sequence that encodes a mammalian polypeptide, wherein the polynucleotide hybridizes to a polynucleotide having the sequence set forth in any of SEQ ID NOs: 1, 3, 5, 7, 9, 11, 13, 15, 17, 19, 21, or 23 or the non-coding strand complementary thereto, under the following hybridization conditions:

(a) hybridization for 16 hours at 42° C. in a hybridization solution comprising 50% formamide, 1% SDS, 1 M NaCl, 10% dextran sulfate; and (b) washing 2 times for 30 minutes each at 60° C. in a wash solution comprising 0.1% SSC, 1% SDS.

Hybridization conditions should be such that hybridization occurs only with the genes in the presence of other nucleic acid molecules. Under stringent hybridization conditions only highly complementary nucleic acid sequences hybridize. Such conditions may prevent hybridization of nucleic acids having 1 or 2 mismatches out of 20 contiguous nucleotides.

In some embodiments, the invention provides vectors comprising a polynucleotide of the invention. Such vectors are useful, e.g., for amplifying the polynucleotides in host cells to create useful quantities thereof. In some embodiments, the vector is an expression vector wherein the polynucleotide of the invention is operatively linked to a polynucleotide comprising an expression control sequence. Such vectors are useful for recombinant production of polypeptides of the invention.

In some embodiments, the invention provides host cells that are transformed or transfected (stably or transiently) with polynucleotides of the invention or vectors of the invention. As stated above, such host cells are useful for amplifying the polynucleotides and also for expressing the DmGPCR polypeptide or fragment thereof encoded by the polynucleotide.

In still another embodiment, the invention provides methods for producing a DmGPCR polypeptide (or fragment thereof) comprising the steps of growing a host cell of the invention in a nutrient medium and isolating the polypeptide or variant thereof from the cell or the medium. Because DmGPCR is a seven transmembrane receptor, it will be appreciated that, for some applications, such as certain activity assays, the isolation may involve isolation of cell membranes containing the polypeptide embedded therein, whereas for other applications a more complete isolation may be desired.

It will be appreciated that extracellular epitopes are particularly useful for generating and screening for antibodies and other binding compounds that bind to receptors such as DmGPCR. Thus, in another embodiment, the invention provides a purified and isolated polypeptide comprising at least one extracellular domain (e.g., the N-terminal extracellular domain or one of the three extracellular loops) of DmGPCR such as the N-terminal extracellular domain of DmGPCR. Also included in the invention are purified polypeptides comprising transmembrane domains of DmGPCR, an extracellular loop connecting transmembrane domains of DmGPCR, an intracellular loop connecting transmembrane domains of DmGPCR, the C-terminal cytoplasmic region of DmGPCR, and fusions thereof. Such fragments may be continuous portions of the native receptor. However, it will also be appreciated that knowledge of the DmGPCR gene and protein sequences as provided herein permits recombining of various domains that are not contiguous in the native protein.

In still another embodiment, the invention provides antibodies specific for the DmGPCR of the invention. Antibody specificity is described in greater detail below. However, it should be emphasized that antibodies that can be generated from polypeptides that have previously been described in the literature and that are capable of fortuitously cross-reacting with DmGPCR (e.g., due to the fortuitous existence of a similar epitope in both polypeptides) are considered "cross-reactive" antibodies. Such cross-reactive antibodies are not antibodies that are "specific" for DmGPCR. The determination of whether an antibody is specific for DmGPCR or is cross-reactive with another known receptor is made using any of several assays, such as Western blotting assays, that are well-known in the art. For identifying cells that express DmGPCR and also for modulating DmGPCR-ligand binding activity, antibodies that specifically bind to an extracellular epitope of the DmGPCR may be used.

In one variation, the invention provides monoclonal antibodies. Hybridomas that produce such antibodies also are intended as aspects of the invention.

In another variation, the invention provides a cell-free composition comprising polyclonal antibodies, wherein at least one of the antibodies is an antibody of the invention specific for DmGPCR. Antisera isolated from an animal is an exemplary composition, as is a composition comprising an antibody fraction of an antisera that has been resuspended in water or in another diluent, excipient, or carrier.

In still another related embodiment, the invention provides anti-idiotypic antibodies specific for an antibody that is specific for DmGPCR.

It is well-known that antibodies contain relatively small antigen binding domains that can be isolated chemically or by recombinant techniques. Such domains are useful DmGPCR binding molecules themselves, and also may be fused to toxins or other polypeptides. Thus, in still another embodiment, the invention provides a polypeptide comprising a fragment of a DmGPCR-specific antibody, wherein the fragment and the polypeptide bind to the DmGPCR. By way of non-limiting example, the invention provides polypeptides that are single chain antibodies, CDR-grafted antibodies, and humanized antibodies.

Also within the scope of the invention are compositions comprising polypeptides, polynucleotides, or antibodies of the invention that have been formulated with, e.g., a pharmaceutically acceptable carrier.

The invention also provides methods of using antibodies of the invention. For example, the invention provides methods for modulating ligand binding of a DmGPCR comprising the step of contacting the DmGPCR with an antibody specific for the DmGPCR, under conditions wherein the antibody binds the receptor.

The invention provides methods of inducing an immune response in a subject against a polypeptide comprising a sequence from the group of SEQ ID NOs: 2, 4, 6, 8, 10, 12, 14, 16, 18, 20, 22, and 24, or a homolog or fragment thereof. The methods comprise administering to a subject an amount of the polypeptide sufficient to induce the immune response.

The invention also provides assays to identify compounds that bind a DmGPCR. One such assay comprises the steps of: (a) contacting a composition comprising a DmGPCR with a compound suspected of binding DmGPCR; and (b) measuring binding between the compound and DmGPCR. In one variation, the composition comprises a cell expressing DmGPCR on its surface. In another variation, isolated DmGPCR or cell membranes comprising DmGPCR are employed. The binding may be measured directly, e.g., by using a labeled compound, or may be measured indirectly by several techniques, including measuring intracellular signaling of DmGPCR induced by the compound (or measuring changes in the level of DmGPCR signaling).

The invention also provides methods of binding a DmGPCR with a binding partner. The methods comprise the steps of: (a) contacting a composition comprising a DmGPCR with a binding partner and (b) allowing the binding partner to bind the DmGPCR. For example, the DmGPCR may be DmGPCR5 (SEQ ID NO: 9), DmGPCR7 (SEQ ID NO: 17), or DmGPCR8 (SEQ ID NO: 19). The binding partner may be, for example, a drotachykinin, a leucokinin, or an allatostatin-C. The drotachykinin (DTK) may be, for example, DTK-1 (SEQ ID NO: 169), Met8-DTK-2 (SEQ ID NO: 170), DTK-2 (SEQ ID NO: 171), DTK-3 (SEQ ID NO: 172), DTK-4 (SEQ ID NO: 173), and DTK-5 (SEQ ID NO: 174). The leucokinin (LK) may be, for example, LK-I (SEQ ID NO: 175), LK-V (SEQ ID NO: 176), LK-VI (SEQ ID NO: 177), and LK-VIII (SEQ ID NO: 178), Culekinin (SEQ ID NO: 179), mollusc leucokinin-like peptide, lymnokinin (PSFHSWSa) (SEQ ID NO: 180), and *Drosophila* leucokinin-like peptides DLK-1 (NSVVLGKKQRFHSWGa) (SEQ ID NO: 181), DLK-2 (pGlu-RFHSWGa) (SEQ ID NO: 182) and DLK-2A (QRFHSWGa) (SEQ ID NO: 183). The allatostatin (AST) may be, for example, AST-C (SEQ ID NO: 184), or DST-C (SEQ ID NO: 185).

The invention also provides methods for identifying a modulator of binding between a DmGPCR and a DmGPCR binding partner, comprising the steps of: (a) contacting a DmGPCR binding partner and a composition comprising a DmGPCR in the presence and in the absence of a putative modulator compound; (b) detecting binding between the binding partner and the DmGPCR; and (c) identifying a putative modulator compound or a modulator compound in view of decreased or increased binding between the binding partner and the DmGPCR in the presence of the putative modulator, as compared to binding in the absence of the putative modulator. For example, the DmGPCR may be DmGPCR5 (SEQ ID NO: 9), DmGPCR7 (SEQ ID NO: 17), or DmGPCR8 (SEQ ID NO: 19). The binding partner may be, for example, a drotachykinin, a leucokinin, or an allatostatin. The drotachykinin (DTK) may be, for example, DTK-1 (SEQ ID NO: 169), Met8-DTK-2 (SEQ ID NO: 170), DTK-2 (SEQ ID NO: 171), DTK-3 (SEQ ID NO: 172), DTK-4 (SEQ ID NO: 173), and DTK-5 (SEQ ID NO: 174). The leucokinin (LK) may be, for example, LK-I (SEQ ID NO: 175), LK-V (SEQ ID NO: 176), LK-VI (SEQ ID NO: 177), and LK-VIII (SEQ ID NO: 178), Culekinin (SEQ ID NO: 179), mollusc leucokinin-like peptide, lymnokinin (PSFHSWSa) (SEQ ID NO: 180), and *Drosophila* leucokinin-like peptides DLK-1 (NSVVLGKKQRFHSWGa) (SEQ ID NO: 181), DLK-2 (pGlu-RFHSWGa) (SEQ ID NO: 182), and DLK-2A (QRFHSWGa) (SEQ ID NO: 183). The allatostatin (AST) may be, for example, AST-C (SEQ ID NO: 184), or DST-C (SEQ ID NO: 185). In one variation, the composition comprises a cell expressing DmGPCR on its surface. In another variation, isolated DmGPCR or cell membranes comprising DmGPCR are employed. The binding may be measured directly, e.g., by using a labeled compound, or may be measured indirectly by several techniques, including measuring intracellular signaling of DmGPCR induced by the compound (or measuring changes in the level of DmGPCR signaling). For example, the function may be measured by an agonist induced [$^{35}$S]GTPγS binding assay, by cAMP assay (induction or inhibition of cAMP production), or by measuring intracellular calcium levels using fluorometric imaging plate reader (FLIPR) analysis.

DmGPCR binding partners that stimulate DmGPCR activity are useful as agonists to enhance or prolong DmGPCR signaling and this way to interfere with normally activated receptor signaling pathways. DmGPCR binding partners that block ligand-mediated DmGPCR signaling are useful as DmGPCR antagonists to to interfere with normal DmGPCR signaling and impair receptor-mediated effects. In addition, DmGPCR modulators, as well as DmGPCR polynucleotides and polypeptides, are useful in diagnostic assays for states or conditions in which DmGPCR activity is enhanced or impaired.

In another aspect, the invention provides methods for treating a disease or abnormal condition caused by an ectoparasite by administering to a subject in need of such treatment a substance that modulates the activity or expression of a polypeptide of the ectoparasite selected from the group consisting of SEQ ID NOs: 2, 4, 6, 8, 10, 12, 14, 16, 18, 20, 22, or 24.

Substances useful for treatment of disorders or diseases caused by an ectoparasite may show positive results in one or more in vitro assays for an activity corresponding to treatment of the disease or disorder in question. Substances that modulate the activity of the polypeptides include, but are not limited to, antisense oligonucleotides, agonists and antagonists, and antibodies.

In another aspect, the invention features methods for detection of a polypeptide in a sample as a diagnostic tool for diseases or disorders caused by an ectoparasite, wherein the methods comprise the steps of: (a) contacting the sample with a nucleic acid probe which hybridizes under hybridization assay conditions to a nucleic acid target region encoding a polypeptide selected from the group consisting of SEQ ID NOs: 2, 4, 6, 8, 10, 12, 14, 16, 18, 20, 22, or 24, said probe comprising the nucleic acid sequence encoding the polypeptide, fragments thereof, and/or the complements of the sequences and fragments; and (b) detecting the presence or amount of the probe:target region hybrid as an indication of the condition.

The test samples suitable for nucleic acid probing methods of the present invention include, for example, cells or nucleic acid extracts of cells, or biological fluids. The samples used in the above-described methods will vary based on the assay format, the detection method and the nature of the tissues, cells or extracts to be assayed. Methods for preparing nucleic acid extracts of cells are well-known in the art and can be readily adapted in order to obtain a sample that is compatible with the method utilized.

In some embodiments the present invention provides homologs, such as mammalian homologs, of DmGCPRs. Mammalian homologs of DmGPCR may be expressed in tissues including but not limited to tissues of the nervous system, pancreas (and particularly pancreatic islet tissue), pituitary, skeletal muscle, adipose tissue, liver, gastrointestinal (GI)-tract, and thyroid.

In some embodiments, the present invention provides methods of identifying a mammalian homolog of DmGPCR comprising the steps of screening a nucleic acid database or a nucleic acid library of the mammal with a nucleic acid molecule selected from SEQ ID NOs: 1, 3, 5, 7, 9, 11, 13, 15, 17, 19, 21, and 23, or a portion thereof, and determining whether a portion of the database or library is homologous to the sequence.

Another aspect of the invention provides methods of controlling an insect population by administering a binding partner or a modulator of a DmGPCR polynucleotide or polypeptide to an insect to modify the expression or activity of the DmGPCR. For example, the insect may be selected from the group consisting of a fly, a fruitfly, a tick, a flea, lice, a mite, and a cockroach.

The DmGPCR binding partner may be a drotachykinin (e.g., DTK-1 (SEQ ID NO: 169), Met8-DTK-2 (SEQ ID NO: 170), DTK-2 (SEQ ID NO: 171), DTK-3 (SEQ ID NO: 172), DTK-4 (SEQ ID NO: 173), and DTK-5 (SEQ ID NO: 174)), a leucokinin (e.g., LK-I (SEQ ID NO: 175), LK-V (SEQ ID NO: 176), LK-VI (SEQ ID NO: 177), and LK-VIII (SEQ ID NO: 178), Culekinin (SEQ ID NO: 179), mollusc leucokinin-like peptide, lymnokinin (PSFHSWSa) (SEQ ID NO: 180), DLK-1 (SEQ ID NO: 181), DLK-2 (SEQ ID NO: 182), and DLK-2A (QRFHSWGa) (SEQ ID NO: 183)), or an allatostatin (AST-C (SEQ ID NO: 184 or DST-C SEQ ID NO: 185)). The DmGPCR modulator may be an anti-DmGPCR antibody or a DmGPCR antisense polynucleotide.

Another embodiment of the invention provides methods of preventing or treating a disease or condition caused by an ectoparasite in a host subject by administering to the subject a binding partner or modulator of a DmGPCR polynucleotide or polypeptide to modify the expression or avtivity of the DmGPCR.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

DETAILED DESCRIPTION OF PREFERRED EMBODIMENTS

The present invention provides, inter alia, isolated and purified polynucleotides that encode *D. melanogaster* G protein coupled receptor (DmGPCR) or a portion thereof, vectors containing these polynucleotides, host cells transformed with these vectors, processes of making DmGPCR, methods of using the above polynucleotides and vectors, isolated and purified DmGPCR, methods of screening compounds which modulate DmGPCR activity, and methods of identifying mammalian, vertebrate, or invertebrate homologs of DmGPCR.

Various definitions are made throughout this document. Most words have the meaning that would be attributed to those words by one skilled in the art. Words specifically defined either below or elsewhere in this document have the meaning provided in the context of the present invention as a whole and as are typically understood by those skilled in the art.

It is to be understood that when groups of sequences are set forth, combinations and sub-combinations thereof are also specifically contemplated. For example, with the disclosure of "SEQ ID NOs: 1, 3, 5, 7, 9, 11, 13, 15, 17, 19, 21, or 23", it is to be understood that the present invention includes combinations and subcombinations, including but not limited to, SEQ ID NOs: 1 and 3; 1 and 5; 1, 3, and 5; etc.

"Synthesized" as used herein and understood in the art, refers to polynucleotides produced by purely chemical, as opposed to enzymatic, methods. "Wholly" synthesized DNA sequences are therefore produced entirely by chemical means, and "partially" synthesized DNAs embrace those wherein only portions of the resulting DNA were produced by chemical means.

By the term "region" is meant a physically contiguous portion of the primary structure of a biomolecule. In the case of proteins, a region is defined by a contiguous portion of the amino acid sequence of that protein.

The term "domain" is herein defined as referring to a structural part of a biomolecule that contributes to a known or suspected function of the biomolecule. Domains may be co-extensive with regions or portions thereof; domains may also incorporate a portion of a biomolecule that is distinct from a particular region, in addition to all or part of that region. Examples of GPCR protein domains include, but are not limited to, the extracellular (i.e., N-terminal), transmembrane and cytoplasmic (i.e., C-terminal) domains, which are co-extensive with like-named regions of GPCRs; each of the seven transmembrane segments of a GPCR; and each of the loop segments (both extracellular and intracellular loops) connecting adjacent transmembrane segments.

As used herein, the term "activity" refers to a variety of measurable indicia suggesting or revealing binding, either direct or indirect; affecting a response, i.e., having a measurable effect in response to some exposure or stimulus, including, for example, the affinity of a compound for directly binding a polypeptide or polynucleotide of the invention, or, for example, measurement of amounts of upstream or downstream proteins or other similar functions after some stimulus or event.

As used herein, the term "antibody" is meant to refer to complete, intact antibodies, and Fab, Fab', F(ab')$_2$, F$_v$, and other fragments thereof. Complete, intact antibodies include monoclonal antibodies such as murine monoclonal antibodies, chimeric antibodies, human antibodies, and humanized antibodies.

As used herein, the term "binding" means the physical or chemical interaction between two proteins or compounds or associated proteins or compounds or combinations thereof. Binding includes ionic, non-ionic, hydrogen bonds, van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates.

As used herein, the term "compound" means any identifiable chemical or molecule, including, but not limited to, small molecule, peptide, protein, sugar, nucleotide, or nucleic acid, and such compound can be natural or synthetic.

As used herein, the term "complementary" refers to Watson-Crick basepairing between nucleotide units of a nucleic acid molecule.

As used herein, the term "contacting" means bringing together, either directly or indirectly, a compound into physical proximity to a polypeptide or polynucleotide of the invention. The polypeptide or polynucleotide can be in any number of buffers, salts, solutions etc. Contacting includes, for example, placing the compound into a beaker, microtiter plate, cell culture flask, or a microarray, such as a gene chip, or the like, which contains the nucleic acid molecule, or polypeptide encoding the GPCR or fragment thereof.

As used herein, the phrase "homologous nucleotide sequence," or "homologous amino acid sequence," or variations thereof, refers to sequences characterised by a homology, at the nucleotide level or amino acid level, of at least the specified percentage. Homologous nucleotide sequences include those sequences coding for isoforms of proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a protein of a species other than insects, including, but not limited to, mammals. Homologous nucleotide sequences also include, but are not limited to, naturally occurring allelic variations and mutations of the nucleotide sequences set forth herein. A homologous nucleotide sequence does not, however, include the nucleotide sequence encoding other known GPCRs. Homologous amino acid sequences include those amino acid sequences which encode conservative amino acid substitutions, as well as polypeptides having neuropeptide binding and/or signalling activity. A homologous amino acid sequence does not, however, include the amino acid sequence encoding other known GPCRs. Percent homology can be determined by, for example, the Gap program (Wisconsin Sequence Analysis Package, Version 8 for Unix, Genetics Computer Group, University Research Park, Madison, Wis.), using the default settings, which uses the algorithm of Smith and Waterman (*Adv. Appl. Math.*, 1981, 2, 482-489, which is incorporated herein by reference in its entirety).

As used herein, the term "isolated" nucleic acid molecule refers to a nucleic acid molecule (DNA or RNA) that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

As used herein, the terms "regulates", "modulates", or "modifies" means an increase or decrease in the amount, quality, or effect of a particular activity or protein.

As used herein, the term "enhanced activity" means increased activity. The term "impaired activity" means decreased activity.

As used herein, the term "oligonucleotide" refers to a series of linked nucleotide residues which has a sufficient number of bases to be used in a polymerase chain reaction (PCR). This short sequence is based on (or designed from) a genomic or cDNA sequence and is used to amplify, confirm, or reveal the presence of an identical, similar or complementary DNA or RNA in a particular cell or tissue. Oligonucleotides comprise portions of a DNA sequence having at least about 10 nucleotides and as many as about 50 nucleotides, preferably about 15 to 30 nucleotides. They are chemically synthesized and may be used as probes.

As used herein, the term "probe" refers to nucleic acid sequences of variable length, preferably between at least about 10 and as many as about 6,000 nucleotides, depending on use. They are used in the detection of identical, similar, or complementary nucleic acid sequences. Longer length probes are usually obtained from a natural or recombinant source, are highly specific and much slower to hybridize than oligomers. They may be single- or double-stranded and carefully designed to have specificity in PCR, hybridization membrane-based, or ELISA-like technologies.

"Portion" or "fragment" when referring to a polynucleotide includes a polynucleotide sequence having at least 14, 16, 18, 20, 25, 50, or 75 consecutive nucleotides of the reference polynucleotide from which the fragment or portion is derived. "Portion" or "fragment" when referring to a polypeptide refers to a polypeptide having at least 5, 10, 15, 20, 25, 30, 35, or 40 consecutive amino acids of the reference polypeptide from which the fragment is derived.

The term "preventing" refers to decreasing the probability that an organism contracts or develops an abnormal condition.

The phrase "controlling an insect population" or variants thereof refers to an increase or decrease in the number of insects in the population. For example, methods of controlling an insect population include methods of increasing the number of beneficial insects in a given insect population and methods of decreasing the number of harmful insects in a given insect population.

The term "treating" refers to having a therapeutic effect and at least partially alleviating or abrogating an abnormal condition in the organism.

The term "subject" as used herein refers to insects, vertebrates, invertebrates, and mammals.

The term "therapeutic effect" refers to the inhibition or activation of factors causing or contributing to an abnormal or normal condition. A therapeutic effect relieves to some extent one or more of the symptoms of the abnormal or normal condition. A therapeutic effect can refer to one or more of the following: (a) an increase in the proliferation, growth, and/or differentiation of cells; (b) inhibition (i.e., slowing or stopping) of cell death; (c) inhibition of degeneration; (d) relieving to some extent one or more of the symptoms associated with the condition; and (e) enhancing the function of the affected population of cells. Compounds demonstrating efficacy against abnormal or normal conditions can be identified as described herein.

A condition of an organism to be treated may be abnormal or normal. The term "abnormal condition" refers to a function in the cells or tissues of an organism that deviates from their normal functions in that organism. For example, abnormal condition can relate to cell proliferation, cell differentiation, cell signaling, or cell survival.

The phrase "normal condition" refers to a normal function in the cells or tissue of an organism. For example, a normal condition can relate to cell proliferation, cell differentiation, cell signaling, or cell survival.

The term "administering" relates to a method of incorporating a compound into cells or tissues of an organism. A condition can be prevented, treated, or induced when the cells or tissues of the organism exist within the organism or outside of the organism. Cells existing outside the organism can be maintained or grown in cell culture dishes. For cells harbored within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques and carrier techniques.

The condition can also be prevented, treated, or induced by administering a compound to a group of cells having to modify a signal transduction pathway of a subject organism. The effect of administering a compound on organism function can then be monitored. The subject may be, for example, a mammal, such as a mouse, rat, rabbit, guinea pig, companion animal (such as a dog or cat), livestock animal (such as a chicken, pig, or cow), goat, horse, monkey, ape, or human; a worm; or an insect.

By "amplification" it is meant increased numbers of DNA or RNA in a cell compared with normal cells. "Amplification" as it refers to RNA can be the detectable presence of RNA in cells, since in some normal cells there is no basal expression of RNA. In other normal cells, a basal level of expression exists, therefore in these cases amplification is the detection of at least 1-2-fold, and preferably more, compared to the basal level.

As used herein, the phrase "stringent hybridization conditions" or "stringent conditions" refers to conditions under which a probe, primer, or oligonucleotide will hybridize to its target sequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 to 50 nucleotides) and at least about 60° C. for longer probes, primers or oligonucleotides. Stringent conditions may also be achieved with the addition of destabilizing agents, such as formamide.

The amino acid sequences are presented in the amino to carboxy direction, from left to right. The amino and carboxy groups are not presented in the sequence. The nucleotide sequences are presented by single strand only, in the 5' to 3' direction, from left to right. Nucleotides and amino acids are represented in the manner recommended by the IUPAC-IUB Biochemical Nomenclature Commission, or (for amino acids) by three letters code.

Polynucleotides

Genomic DNA of the invention comprises the protein-coding region for a polypeptide of the invention and is also intended to include allelic variants thereof. It is widely understood that, for many genes, genomic DNA is transcribed into RNA transcripts that undergo one or more splicing events wherein introns (i.e., non-coding regions) of the transcripts are removed, or "spliced out." RNA transcripts that can be spliced by alternative mechanisms, and therefore are subject to removal of different RNA sequences but still encode a DmGPCR polypeptide, are referred to in the art as "splice variants" which are embraced by the invention. Splice variants comprehended by the invention therefore are encoded by the same original genomic DNA sequences but arise from distinct mRNA transcripts. Allelic variants are modified forms of a wild-type gene sequence, the modification resulting from recombination during chromosomal segregation or exposure to conditions which give rise to genetic mutation. Allelic variants, like wild type genes, are naturally occurring sequences (as opposed to non-naturally occurring variants which arise from in vitro manipulation).

The invention also comprehends cDNA that is obtained through reverse transcription of an RNA polynucleotide encoding DmGPCR (conventionally followed by second strand synthesis of a complementary strand to provide a double-stranded DNA).

A DNA sequence encoding a Dm GPCR polypeptide is set out in any of SEQ ID NOs: 1, 3, 5, 7, 9, 11, 13, 15, 17, 19, 21, or 23. A DNA of the invention may comprise a double stranded molecule along with the complementary molecule (the "non-coding strand" or "complement") having a sequence unambiguously deducible from the coding strand according to Watson-Crick base-pairing rules for DNA. Also included in the invention are other polynucleotides encoding any of the particular DmGPCR polypeptides of the invention which differ in sequence from the particular polynucleotides described herein by virtue of the well-known degeneracy of the universal nuclear genetic code.

The invention further embraces species, such as mammalian, homologs of the DmGPCR DNA. Species homologs, sometimes referred to as "orthologs," in general, share at least 35%, at least 40%, at least 45%, at least 50%, at least 60%, at least 65%, at least 70%, at least 75%, at least 80%, at least 85%, at least 90%, at least 95%, at least 98%, or at least 99% homology with DNA of the invention. Generally, percent sequence "homology" with respect to polynucleotides of the invention may be calculated as the percentage of nucleotide bases in the candidate sequence that are identical to nucleotides in the DmGPCR sequence set forth in a particular polynucleotide sequence, after aligning the sequences and introducing gaps, if necessary, to achieve the maximum percent sequence identity.

Another aspect of the present invention is the use of the DmGPCR nucleotide sequences disclosed herein for identifying homologs of the DmGPCR, in other animals, including mammals, vertebrates, and invertebrates. Any of the nucleotide sequences disclosed herein, or any portion thereof, can be used, for example, as probes to screen databases or nucleic acid libraries, such as, for example, genomic or cDNA libraries, to identify homologs, using screening procedures well-known to those skilled in the art.

The polynucleotide sequence information provided by the invention makes possible large-scale expression of the encoded polypeptide by techniques well-known and routinely practiced in the art. Polynucleotides of the invention also permit identification and isolation of polynucleotides encoding related DmGPCR polypeptides, such as allelic variants and species homologs, by well-known techniques including Southern and/or Northern hybridization, and polymerase chain reaction (PCR). Examples of related polynucleotides include genomic sequences, including allelic variants, as well as polynucleotides encoding polypeptides homologous to DmGPCR and structurally related polypeptides sharing one or more biological, immunological, and/or physical properties of DmGPCR. Genes encoding proteins homologous to DmGPCR can also be identified by Southern and/or PCR analysis and are useful in animal models for GPCR disorders. Knowledge of the sequence of a DmGPCR DNA also makes possible through use of Southern hybridization or polymerase chain reaction (PCR) the identification of genomic DNA sequences encoding DmGPCR expression control regulatory sequences such as promoters, operators, enhancers, repressors, and the like. Polynucleotides of the invention are also useful in hybridization assays to detect the capacity of cells to express DmGPCR. Polynucleotides of the invention may also provide a basis for diagnostic methods useful for identifying the presence of an ectoparasite expressing a DmGPCR that underlies a disease state or states, which information is useful both for diagnosis and for selection of therapeutic strategies.

The disclosure herein of a full-length polynucleotide encoding a DmGPCR polypeptide makes readily available to the worker of ordinary skill in the art every possible fragment of the full length polynucleotide. The invention therefore provides fragments of DmGPCR-encoding polynucleotides comprising at least 14, and preferably at least 16, 18, 20, 25, 50, or 75 consecutive nucleotides of a polynucleotide encoding DmGPCR. Fragment polynucleotides of the invention may comprise sequences unique to the DmGPCR-encoding polynucleotide sequence, and therefore hybridize under highly stringent or moderately stringent conditions only (i.e., "specifically") to polynucleotides encoding DmGPCR (or fragments thereof). Polynucleotide fragments of genomic sequences of the invention comprise not only sequences unique to the coding region, but also include fragments of the full-length sequence derived from introns, regulatory regions, and/or other non-translated sequences. Sequences unique to polynucleotides of the invention are recognizable through sequence comparison to other known polynucleotides, and can be identified through use of alignment programs routinely utilized in the art, e.g., those made available in public sequence databases. Such sequences also are recognizable from Southern hybridization analyses to determine the number of fragments of genomic DNA to which a polynucleotide will hybridize. Polynucleotides of the invention can be labeled in a manner that permits their detection, including radioactive, fluorescent, and enzymatic labeling.

Fragment polynucleotides are particularly useful as probes for detection of full-length or fragment DmGPCR polynucleotides. One or more polynucleotides can be included in kits that are used to detect the presence of a polynucleotide encoding DmGPCR, or used to detect variations in a polynucleotide sequence encoding DmGPCR.

The invention also embraces DNAs encoding DmGPCR polypeptides that hybridize under moderately stringent or high stringency conditions to the non-coding strand, or complement, of the polynucleotides in SEQ ID NOs: 1, 3, 5, 7, 9, 11, 13, 15, 17, 19, 21, or 23.

Exemplary highly stringent hybridization conditions are as follows: hybridization at 42° C. in a hybridization solution comprising 50% formamide, 1% SDS, 1 M NaCl, 10% Dextran sulfate, and washing twice for 30 minutes at 60° C. in a wash solution comprising 0.1×SSC and 1% SDS. It is understood in the art that conditions of equivalent stringency can be achieved through variation of temperature and buffer, or salt concentration as described Ausubel et al. (Eds.), PROTOCOLS IN MOLECULAR BIOLOGY, John Wiley & Sons, 1994, pp.6.0.3-6.4.10. Modifications in hybridization conditions can be empirically determined or precisely calculated based on the length and the percentage of guanosine/cytosine (GC) base pairing of the probe. The hybridization conditions can be calculated as described in Sambrook et al. (Eds.), MOLECULAR CLONING: A LABORATORY MANUAL, Cold Spring Harbor Laboratory Press: Cold Spring Harbor, N.Y., 1989, pp. 9.47-9.51.

With the knowledge of the nucleotide sequence information disclosed in the present invention, one skilled in the art can identify and obtain nucleotide sequences which encode DmGPCRs from different sources (i.e., different tissues or different organisms) through a variety of means well-known to the skilled artisan and as disclosed by, for example, Sambrook et al., MOLECULAR CLONING: A LABORATORY MANUAL, Second Edition, Cold Spring Harbor Press, Cold Spring Harbor, N.Y., 1989, which is incorporated herein by reference in its entirety.

For example, DNA that encodes DmGPCR may be obtained by screening of mRNA, cDNA, or genomic DNA with oligonucleotide probes generated from the DmGPCR gene sequence information provided herein. Probes may be labeled with a detectable group, such as a fluorescent group, a radioactive atom or a chemiluminescent group in accordance with procedures known to the skilled artisan and used in conventional hybridization assays, as described by, for example, Sambrook et al.

A nucleic acid molecule comprising any of the DmGPCR nucleotide sequences described above can alternatively be synthesized by use of the polymerase chain reaction (PCR) procedure, with the PCR oligonucleotide primers produced from the nucleotide sequences provided herein. See U.S. Pat. Nos. 4,683,195 to Mullis et al. and 4,683,202 to Mullis. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase-mediated replication of a desired nucleic acid molecule.

A wide variety of alternative cloning and in vitro amplification methodologies are well-known to those skilled in the art. Examples of these techniques are found in, for example, Berger et al., GUIDE TO MOLECULAR CLONING TECHNIQUES, METHODS IN ENZYMOLOGY 152 Academic Press, Inc., San Diego, Calif. (Berger), which is incorporated herein by reference in its entirety.

The nucleic acid molecules of the present invention, and fragments derived therefrom, are useful for screening for restriction fragment length polymorphisms (RFLPs) and for genetic mapping.

Automated sequencing methods can be used to obtain or verify the nucleotide sequence of DmGPCR. The DmGPCR nucleotide sequences of the present invention are believed to be 100% accurate. However, as is known in the art, nucleotide sequences obtained by automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well-known in the art. An error in a sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation.

Expression Constructs and Vectors

Autonomously replicating recombinant expression constructs such as plasmid and viral DNA vectors incorporating polynucleotides of the invention are also provided. Vectors are used herein either to amplify DNA or RNA encoding a DmGPCR and/or to express DNA which encodes a DmGPCR. Vectors of the invention include, but are not limited to, plasmids, phages, cosmids, episomes, viral particles, viruses, and integratable DNA fragments (i.e., fragments integratable into the host genome by homologous recombination). Viral particles may include, but are not limited to, adenoviruses, baculoviruses, parvoviruses, herpesviruses, poxyiruses, adeno-associated viruses, Smeliki Forest viruses, vaccinia viruses, and retroviruses. Examples of expression vectors include, but are not limited to, pcDNA3 (Invitrogen) and pSVL (Pharmacia Biotech). Other expression vectors include, but are not limited to, pSPORT vectors, pGEM vectors (Promega), pPROEXvectors (LTI, Bethesda, Md.), Bluescript vectors (Stratagene), pQE vectors (Qiagen), pSE420 (Invitrogen), and pYES2 (Invitrogen).

Expression constructs wherein DmGPCR-encoding polynucleotides are operatively linked to an endogenous or exogenous expression control DNA sequence and a transcription terminator are also provided. Expression control DNA sequences include promoters, enhancers, operators, and regulatory element binding sites generally, and are typically selected based on the expression systems in which the expression construct is to be utilized. Promoter and enhancer sequences are generally selected for the ability to increase gene expression, while operator sequences are generally selected for the ability to regulate gene expression. Expression constructs of the invention may also include sequences encoding one or more selectable markers that permit identification of host cells bearing the construct. Expression constructs may also include sequences that facilitate, and/or promote, homologous recombination in a host cell. Constructs of the invention may also include sequences necessary for replication in a host cell.

Expression constructs may be utilized for production of an encoded protein, but may also be utilized simply to amplify a DmGPCR-encoding polynucleotide sequence. In some embodiments, the vector is an expression vector wherein the polynucleotide of the invention is operably linked to a polynucleotide comprising an expression control sequence. Some expression vectors are replicable DNA constructs in which a DNA sequence encoding a DmGPCR is operably linked or connected to suitable control sequences capable of effecting the expression of the DmGPCR in a suitable host. DNA regions are operably linked or connected when they are functionally related to each other. For example, a promoter is operably linked or connected to a coding sequence if it controls the transcription of the sequence. Amplification vectors do not require expression control domains but rather need only the ability to replicate in a host, usually conferred by an origin of replication, and a selection gene to facilitate recognition of transformants. The need for control sequences in the expression vector will vary depending upon the host selected and the transformation method chosen. Generally, control sequences include a transcriptional promoter, an optional operator sequence to control transcription, a sequence encoding suitable mRNA ribosomal binding and sequences which control the termination of transcription and translation.

Vectors may contain a promoter that is recognized by the host organism. The promoter sequences of the present invention may be prokaryotic, eukaryotic, or viral. Examples of suitable prokaryotic sequences include the $P_R$ and $P_L$ promoters of bacteriophage lambda (THE BACTERIOPHAGE LAMBDA, Hershey, A. D., Ed., Cold Spring Harbor Press, Cold Spring Harbor, N.Y., 1973, which is incorporated herein by reference in its entirety; LAMBDA II, Hendrix, R. W., Ed., Cold Spring Harbor Press, Cold Spring Harbor, N.Y., 1980, which is incorporated herein by reference in its entirety); the trp, recA, heat shock, and lacZ promoters of *E. coli* and the SV40 early promoter (Benoist et al., *Nature*, 1981, 290, 304-310, which is incorporated herein by reference in its entirety). Additional promoters include, but are not limited to, mouse mammary tumor virus, long terminal repeat of human immunodeficiency virus (HIV), maloney virus, cytomegalovirus immediate early promoter, Epstein Barr virus, Rous sarcoma virus, human actin, human myosin, human hemoglobin, human muscle creatine, and human metallothionein.

Additional regulatory sequences may also be included in the vectors of the invention. Examples of suitable regulatory sequences include, for example, the Shine-Dalgarno sequence of the replicase gene of the phage MS-2 and of the gene cII of bacteriophage lambda. The Shine-Dalgarno sequence may be directly followed by a DNA encoding a DmGPCR, resulting in the expression of the mature DmGPCR protein.

Moreover, suitable expression vectors may include an appropriate marker that allows the screening of the transformed host cells. The transformation of the selected host is carried out using any one of the various techniques well-known to the skilled artisan and described in, for example, Sambrook et al., supra.

An origin of replication can also be provided either by construction of the vector to include an exogenous origin or by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and DmGPCR DNA. An example of a suitable marker is dihydrofolate reductase (DHFR) or thymidine kinase (e.g., U.S. Pat. No. 4,399,216).

Nucleotide sequences encoding a DmGPCR may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra, and are well-known in the art. Methods for construction of mammalian expression vectors are disclosed in, for example, Okayama et al., *Mol. Cell. Biol.,* 1983, 3, 280; Cosman et al., *Mol. Immunol.* 1986, 23, 935; Cosman et al., *Nature,* 1984, 312, 768; EP-A-0367566 and WO 91/18982, each of which is incorporated herein by reference in its entirety.

Host Cells

According to another aspect of the invention, host cells are provided, including prokaryotic and eukaryotic cells, comprising a polynucleotide of the invention (or vector of the invention) in a manner which permits expression of the encoded DmGPCR polypeptide. Polynucleotides of the invention may be introduced into the host cell as part of a circular plasmid, or as linear DNA comprising an isolated protein-coding region or a viral vector. Methods for introducing DNA into the host cell that are well-known and routinely practiced in the art include transformation, transfection, electroporation, nuclear injection, or fusion with carriers such as liposomes, micelles, ghost cells, and protoplasts. Expression systems of the invention include bacterial, yeast, fungal, plant, insect, invertebrate, vertebrate, and mammalian cells systems.

The invention provides host cells that are transformed or transfected (stably or transiently) with polynucleotides of the invention or vectors of the invention. As stated above, such host cells are useful for amplifying the polynucleotides and also for expressing the DmGPCR polypeptide or fragment thereof encoded by the polynucleotide.

According to some aspects of the present invention, transformed host cells having an expression vector comprising any of the nucleic acid molecules described above are provided. Expression of the nucleotide sequence occurs when the expression vector is introduced into an appropriate host cell. Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera *Escherichia, Bacillus, Salmonella, Pseudomonas, Streptomyces,* and *Staphylococcus.*

If an eukaryotic expression vector is employed, then the appropriate host cell would be any eukaryotic cell capable of expressing the cloned sequence. Eukaryotic cells may be cells of higher eukaryotes. Suitable eukaryotic cells include, but are not limited to, non-human mammalian tissue culture cells and human tissue culture cells. Host cells may include, but are not limited to, insect cells, HeLa cells, Chinese hamster ovary cells (CHO cells), African green monkey kidney cells (COS cells), human 293 cells, and murine 3T3 fibroblasts. Propagation of such cells in cell culture has become a routine procedure (see, e.g., TISSUE CULTURE, Academic Press, Kruse and Patterson, eds., 1973, which is incorporated herein by reference in its entirety).

In addition, a yeast host may be employed as a host cell. Examples of yeast cells include, but are not limited to, the genera *Saccharomyces, Pichia,* and *Kluveromyces.* Examples of yeast hosts are *S. cerevisiae* and *P. pastoris.* Yeast vectors can contain an origin of replication sequence from a 2T yeast plasmid, an autonomously replicating sequence (ARS), a promoter region, sequences for polyadenylation, sequences for transcription termination, and a selectable marker gene. Shuttle vectors for replication in both yeast and *E. coli* are also included herein.

Alternatively, insect cells may be used as host cells. In one embodiment, the polypeptides of the invention are expressed using a baculovirus expression system (see, Luckow et al., *Bio/Technology,* 1988, 6, 47, BACULOVIRUS EXPRESSION VECTORS: A LABORATORY MANUAL, O'Rielly et al. (Eds.), W.H. Freeman and Company, New York, 1992, and U.S. Pat. No. 4,879,236, each of which is incorporated herein by reference in its entirety). In addition, the MAXBAC™ complete baculovirus expression system (Invitrogen) can, for example, be used for production in insect cells.

In still another related embodiment, the invention provides methods for producing a DmGPCR polypeptide (or fragment thereof) comprising the steps of growing a host cell of the invention in a nutrient medium and isolating the polypeptide or variant thereof from the cell or the medium. Because DmGPCR is a seven transmembrane receptor, it will be appreciated that, for some applications, such as certain activity assays, isolation may involve isolation of cell membranes containing the polypeptide embedded therein, whereas for other applications a more complete isolation may be desired.

Host cells of the invention are a valuable source of immunogen for development of antibodies specifically immunoreactive with DmGPCR. Host cells of the invention are also useful in methods for the large-scale production of DmGPCR polypeptides wherein the cells are grown in a suitable culture medium and the desired polypeptide products are isolated from the cells, or from the medium in which the cells are grown, by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those methods wherein the desired protein is expressed and purified as a fusion protein having a specific tag, label, or chelating moiety that is recognized by a specific binding partner or agent. The purified protein can be cleaved to yield the desired protein, or can be left as an intact fusion protein. Cleavage of the fusion component may produce a form of the desired protein having additional amino acid residues as a result of the cleavage process.

Knowledge of DmGPCR DNA sequences allows for modification of cells to permit, or increase, expression of endogenous DmGPCR. Cells can be modified (e.g., by homologous recombination) to provide increased expression by replacing, in whole or in part, the naturally occurring DmGPCR promoter with all or part of a heterologous promoter so that the cells express DmGPCR at higher levels. The heterologous promoter is inserted in such a manner that it is operatively linked to endogenous DmGPCR encoding sequences. (See, e.g., PCT International Publication No. WO 94/12650, PCT International Publication No. WO 92/20808, and PCT International Publication No. WO 91/09955.) It is also contemplated that, in addition to heterologous promoter DNA, amplifiable marker DNA (e.g., ada, dhfr, and the multifunctional CAD gene which encodes carbamoyl phosphate synthase, aspartate transcarbamylase, and dihydroorotase), and/or intron DNA may be inserted along with the heterologous promoter DNA. If linked to the DmGPCR coding sequence, amplification of the marker DNA by standard selection methods results in co-amplification of the DmGPCR coding sequences in the cells.

Knock-Outs

The DNA sequence information provided by the present invention also makes possible the development (e.g., by homologous recombination or "knock-out" strategies; see Capecchi, Science, 1989, 244, 1288-1292) of subjects that fail to express functional DmGPCR or that express a variant of DmGPCR. Such subjects (especially including insects and worms) are useful as models for studying the in vivo activities of DmGPCR and modulators of DmGPCR and are also useful for further elucidating the role of DmGPCRs in insects or worms.

Antisense

Also made available by the invention are antisense polynucleotides which recognize and hybridize to polynucleotides encoding DmGPCR. Full-length and fragment antisense polynucleotides are provided. Fragment antisense molecules of the invention include those which specifically recognize and hybridize to DmGPCR expression control sequences or DmGPCR RNA (as determined by sequence comparison of DNA encoding DmGPCR to DNA encoding other known molecules). Identification of sequences unique to DmGPCR-encoding polynucleotides, can be deduced through use of any publicly available sequence database, and/or through use of commercially available sequence comparison programs. After identification of the desired sequences, isolation through restriction digestion or amplification using any of the various polymerase chain reaction techniques well-known in the art can be performed. Antisense polynucleotides are particularly relevant to regulating expression of DmGPCR by those cells expressing DmGPCR mRNA.

Antisense nucleic acids (preferably 10 to 20 base-pair oligonucleotides) capable of specifically binding to DmGPCR expression control sequences or DmGPCR RNA are introduced into cells (e.g., by a viral vector or colloidal dispersion system such as a liposome). The antisense nucleic acid binds to the DmGPCR target nucleotide sequence in the cell and prevents transcription and/or translation of the target sequence. Phosphorothioate and methylphosphonate antisense oligonucleotides are specifically contemplated for therapeutic use by the invention. The antisense oligonucleotides may be further modified by poly-L-lysine, transferrin polylysine, or cholesterol moieties at their 5' end. Suppression of DmGPCR expression at either the transcriptional or translational level is useful to generate cellular or animal models for studying the biological role of DmGPCRs.

Antisense oligonucleotides, or fragments of a nucleotide sequence selected from the group consisting of SEQ ID NOs: 1, 3, 5, 7, 9, 11, 13, 15, 17, 19, 21, or 23, or sequences complementary or homologous thereto, derived from the nucleotide sequences of the present invention encoding DmGPCR are useful for probing gene expression in various tissues. For example, tissue can be probed in situ with oligonucleotide probes carrying detectable groups by conventional autoradiography techniques. Antisense oligonucleotides directed to regulatory regions of a nucleotide sequence may be selected from the group consisting of SEQ ID NOs: 1, 3, 5, 7, 9, 11, 13, 15, 17, 19, 21, or 23, or mRNA corresponding thereto, including, but not limited to, the initiation codon, TATA box, enhancer sequences, and the like.

Transcription Factors

The DmGPCR sequences taught in the present invention facilitate the design of novel transcription factors for modulating DmGPCR expression in native cells and subjects, and cells transformed or transfected with DmGPCR polynucleotides. For example, the $Cys_2$-$His_2$ zinc finger proteins, which bind DNA via their zinc finger domains, have been shown to be amenable to structural changes that lead to the recognition of different target sequences. These artificial zinc finger proteins recognize specific target sites with high affinity and low dissociation constants, and are able to act as gene switches to modulate gene expression. Knowledge of the particular DmGPCR target sequence of the present invention facilitates the engineering of zinc finger proteins specific for the target sequence using known methods such as a combination of structure-based modeling and screening of phage display libraries (Segal et al., Proc. Natl. Acad. Sci. USA, 1999, 96, 2758-2763; Liu et al., Proc. Natl. Acad. Sci. USA, 1997, 94, 5525-5530 (1997); Greisman et al., Science, 1997, 275, 657-661; Choo et al., J. Mol. Biol., 1997, 273, 525-532). Each zinc finger domain usually recognizes three or more base pairs. Since a recognition sequence of 18 base pairs is generally sufficient in length to render it unique in any known genome, a zinc finger protein consisting of 6 tandem repeats of zinc fingers would be expected to ensure specificity for a particular sequence (Segal et al.). The artificial zinc finger repeats, designed based on DmGPCR sequences, are fused to activation or repression domains to promote or suppress DmGPCR expression (Liu et al.). Alternatively, the zinc finger domains can be fused to the TATA box-binding factor (TBP) with varying lengths of linker region between the zinc finger peptide and the TBP to create either transcriptional activators or repressors (Kim et al., Proc. Natl. Acad. Sci. USA, 1997, 94, 3616-3620). Such proteins, and polynucleotides that encode them, have utility for modulating DmGPCR expression in vivo. The novel transcription factor can be delivered to the target cells by transfecting constructs that express the transcription factor (gene therapy), or by introducing the protein. Engineered zinc finger proteins can also be designed to bind RNA sequences for use in therapeutics as alternatives to antisense or catalytic RNA methods (McColl et al., Proc. Natl. Acad. Sci. USA, 1997, 96, 9521-9526; Wu et al., Proc. Natl. Acad. Sci. USA, 1995, 92, 344-348). The present invention contemplates methods of designing such transcription factors based on the gene sequence of the invention, as well as customized zinc finger proteins, that are useful to modulate DmGPCR expression in cells (native or transformed) whose genetic complement includes these sequences.

Polypeptides

The invention also provides purified and isolated DmG-PCR polypeptides encoded by a polynucleotide of the invention including a DmGPCR polypeptide comprising the amino acid sequence set out in any of SEQ ID NOs: 2, 4, 6, 8, 10, 12, 14, 16, 18, 20, 22, or 24.

It will be appreciated that extracellular epitopes are particularly useful for generating and screening for antibodies and other binding compounds that bind to receptors such as DmGPCR. Thus, in another embodiment, the invention provides purified and isolated polypeptides comprising at least one extracellular domain (e.g., the N-terminal extracellular domain or one of the three extracellular loops) of DmGPCR, such as the N-terminal extracellular domain of DmGPCR. Also included within the scope of the invention are purified and isolated polypeptides comprising a DmG-PCR fragment selected from the group consisting of transmembrane domains of DmGPCR, an extracellular loop connecting transmembrane domains of DmGPCR, an intracellular loop connecting transmembrane domains of DmG-PCR, the C-terminal cytoplasmic region of DmGPCR, and fusions thereof. Such fragments may be continuous portions of the native receptor. However, it will also be appreciated that knowledge of the DmGPCR gene and protein sequences as provided herein permits recombining of various domains that are not contiguous in the native protein. Using a FORTRAN computer program called "tmtrest.all" (Parodi et al., *Comput. Appl. Biosci.*, 1994, 5, 527-535), DmGPCR was shown to contain transmembrane-spanning domains.

The invention also embraces polypeptides that have at least 99%, at least 95%, at least 90%, at least 85%, at least 80%, at least 75%, at least 70%, at least 65%, at least 60%, at least 55%, or at least 50% identity and/or homology to the reference polypeptide of the invention. Percent amino acid sequence "identity" with respect to the reference polypeptide of the invention is defined herein as the percentage of amino acid residues in the candidate sequence that are identical with the residues in the DmGPCR sequence after aligning both sequences and introducing gaps, if necessary, to achieve the maximum percent sequence identity, and not considering any conservative substitutions as part of the sequence identity. Percent sequence "homology" with respect to the reference polypeptide of the invention is defined herein as the percentage of amino acid residues in the candidate sequence that are identical with the residues in the DmGPCR sequence after aligning the sequences and introducing gaps, if necessary, to achieve the maximum percent sequence identity, and also considering any conservative substitutions as part of the sequence identity.

In one aspect, percent homology is calculated as the percentage of amino acid residues in the smaller of two sequences which align with identical amino acid residue in the sequence being compared, when four gaps in a length of 100 amino acids may be introduced to maximize alignment (Dayhoff, in ATLAS OF PROTEIN SEQUENCE AND STRUCTURE, vol. 5, National Biochemical Research Foundation, Washington, D.C., 1972, p. 124, incorporated herein by reference).

Polypeptides of the invention may be isolated from natural cell sources or may be chemically synthesized, and may be produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention. Glycosylated and non-glycosylated forms of DmGPCR polypeptides are embraced by the invention.

The invention also embraces variant (or analog) DmG-PCR polypeptides. In one example, insertion variants are provided wherein one or more amino acid residues supplement a DmGPCR amino acid sequence. Insertions may be located at either or both termini of the protein, or may be positioned within internal regions of the DmGPCR amino acid sequence. Insertional variants with additional residues at either or both termini can include, for example, fusion proteins and proteins including amino acid tags or labels.

Insertion variants include DmGPCR polypeptides wherein one or more amino acid residues are added to a DmGPCR acid sequence, or to a biologically active fragment thereof.

Variant products of the invention also include mature DmGPCR products, i.e., DmGPCR products wherein leader or signal sequences are removed, with additional amino terminal residues. The additional amino terminal residues may be derived from another protein, or may include one or more residues that are not identifiable as being derived from specific proteins. DmGPCR products with an additional methionine residue at position −1 (Met$^{-1}$-DmGPCR) are contemplated, as are variants with additional methionine and lysine residues at positions −2 and −1 (Met$^{-2}$-Lys$^{-1}$-1-DmGPCR). Variants of DmGPCR with additional Met, Met-Lys, Lys residues (or one or more basic residues in general) are particularly useful for enhanced recombinant protein production in bacterial host cells.

The invention also embraces DmGPCR variants having additional amino acid residues which result from use of specific expression systems. For example, use of commercially available vectors that express a desired polypeptide as part of a glutathione-S-transferase (GST) fusion product provides the desired polypeptide having an additional glycine residue at position −1 after cleavage of the GST component from the desired polypeptide. Variants which result from expression in other vector systems are also contemplated.

Insertional variants also include fusion proteins wherein the amino terminus and/or the carboxy terminus of DmG-PCR is/are fused to another polypeptide.

In another aspect, the invention provides deletion variants wherein one or more amino acid residues in a DmGPCR polypeptide are removed. Deletions can be effected at one or both termini of the DmGPCR polypeptide, or with removal of one or more non-terminal amino acid residues of DmG-PCR. Deletion variants, therefore, include all fragments of a DmGPCR polypeptide.

The invention also embraces polypeptide fragments of the sequence set out in any of SEQ ID NOs: 2, 4, 6, 8, 10, 12, 14, 16, 18, 20, 22, or 24 wherein the fragments maintain biological (e.g., ligand binding and/or intracellular signaling) and immunological properties of a DmGPCR polypeptide. Fragments comprising at least 5, 10, 15, 20, 25, 30, 35, or 40 consecutive amino acids of any of the polypeptides described herein are comprehended by the invention. Polypeptide fragments may display antigenic properties unique to, or specific for, DmGPCR and its allelic and species homologs. Fragments of the invention having the desired biological and immunological properties can be prepared by any of the methods well-known and routinely practiced in the art.

In still another aspect, the invention provides substitution variants of DmGPCR polypeptides. Substitution variants include those polypeptides wherein one or more amino acid residues of a DmGPCR polypeptide are removed and replaced with alternative residues. In one aspect, the substitutions are conservative in nature; however, the invention embraces substitutions that are also non-conservative. Conservative substitutions for this purpose may be defined as set out in Tables 1, 2, or 3 below.

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table 1 (from WO 97/09433, page 10, published Mar. 13, 1997 (PCT/GB96/02197, filed Sep. 6, 1996)), immediately below.

TABLE 1

Conservative Substitutions I

| SIDE CHAIN CHARACTERISTIC | AMINO ACID |
|---|---|
| Aliphatic | |
| Non-polar | G A P |
| | I L V |
| Polar - uncharged | C S T M |
| | N Q |
| Polar - charged | D E |
| | K R |
| Aromatic | H F W Y |
| Other | N Q D E |

Alternatively, conservative amino acids can be grouped as described in Lehninger, (BIOCHEMISTRY, Second Edition; Worth Publishers, Inc. NY, N.Y., 1975, pp.71-77) as set out in Table 2, immediately below.

TABLE 2

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table 3, below.

TABLE 3

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |

TABLE 3-continued

Conservative Substitutions III

| Original Residue | Exemplary Substitution |
|---|---|
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

It should be understood that the definition of polypeptides of the invention is intended to include polypeptides bearing modifications other than insertion, deletion, or substitution of amino acid residues. By way of example, the modifications may be covalent in nature, and include for example, chemical bonding with polymers, lipids, other organic, and inorganic moieties. Such derivatives may be prepared to increase circulating half-life of a polypeptide, or may be designed to improve the targeting capacity of the polypeptide for desired cells, tissues, or organs. Similarly, the invention further embraces DmGPCR polypeptides that have been covalently modified to include one or more water-soluble polymer attachments such as polyethylene glycol, polyoxyethylene glycol, or polypropylene glycol.

Variants that display ligand binding properties of native DmGPCR and are expressed at higher levels, as well as variants that provide for constitutively active receptors, are particularly useful in assays of the invention; the variants are also useful in assays of the invention and in providing cellular, tissue and animal models for studying aberrant DmGPCR activity.

Antibodies

Also comprehended by the present invention are antibodies (e.g., monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR sequences which specifically recognize a polypeptide of the invention) specific for DmGPCR or fragments thereof. Antibody fragments, including Fab, Fab', F(ab')$_2$, and F$_v$, are also provided by the invention. The term "specific for," when used to describe antibodies of the invention, indicates that the variable regions of the antibodies of the invention recognize and bind DmGPCR polypeptides exclusively (i.e., are able to distinguish DmGPCR polypeptides from other known GPCR polypeptides by virtue of measurable differences in binding affinity, despite the possible existence of localized sequence identity, homology, or similarity between DmG-PCR and such polypeptides). It will be understood that specific antibodies may also interact with other proteins (for example, S. aureus protein A or other antibodies in ELISA techniques) through interactions with sequences outside the variable region of the antibodies, and, in particular, in the constant region of the molecule. Screening assays to determine binding specificity of an antibody of the invention are well-known and routinely practiced in the art. For a comprehensive discussion of such assays, see Harlow et al. (Eds.), ANTIBODIES A LABORATORY MANUAL, Cold Spring Harbor Laboratory, Cold Spring Harbor, N.Y., 1988, Chapter 6. Antibodies that recognize and bind fragments of the DmGPCR polypeptides of the invention are also contemplated, provided that the antibodies are specific for DmGPCR polypeptides. Antibodies of the invention can be produced using any method well-known and routinely practiced in the art.

The invention provides antibodies that are specific for the DmGPCR of the invention. Antibody specificity is described in greater detail below. However, it should be emphasized that antibodies that can be generated from polypeptides that have previously been described in the literature and that are capable of fortuitously cross-reacting with DmGPCR (e.g., due to the fortuitous existence of a similar epitope in both polypeptides) are considered "cross-reactive" antibodies. Such cross-reactive antibodies are not antibodies that are "specific" for DmGPCR. The determination of whether an antibody is specific for DmGPCR or is cross-reactive with another known receptor is made using any of several assays, such as Western blotting assays, that are well-known in the art. For identifying cells that express DmGPCR and also for modulating DmGPCR-ligand binding activity, antibodies that specifically bind to an extracellular epitope of the DmGPCR are useful.

In one variation, the invention provides monoclonal antibodies. Hybridomas that produce such antibodies also are intended as aspects of the invention. In yet another variation, the invention provides a humanized antibody. Humanized antibodies are useful for in vivo therapeutic indications for treatment of diseases or conditions caused by ectoparasites.

In another variation, the invention provides a cell-free composition comprising polyclonal antibodies, wherein at least one of the antibodies is an antibody of the invention specific for DmGPCR. Antisera isolated from an animal is an exemplary composition, as is a composition comprising an antibody fraction of an antisera that has been resuspended in water or in another diluent, excipient, or carrier.

In still another related embodiment, the invention provides anti-idiotypic antibodies specific for an antibody that is specific for DmGPCR.

It is well-known that antibodies contain relatively small antigen binding domains that can be isolated chemically or by recombinant techniques. Such domains are useful DmGPCR binding molecules themselves, and also may be fused to toxins or other polypeptides. Thus, in still another embodiment, the invention provides a polypeptide comprising a fragment of a DmGPCR-specific antibody, wherein the fragment and the polypeptide bind to the DmGPCR. By way of non-limiting example, the invention provides polypeptides that are single chain antibodies, CDR-grafted antibodies, and humanized antibodies.

Non-human antibodies may be humanized by any of the methods known in the art. In one method, the non-human CDRs are inserted into a human antibody or consensus antibody framework sequence. Further changes can then be introduced into the antibody framework to modulate affinity or immunogenicity.

Antibodies of the invention are useful for, e.g., therapeutic purposes (by modulating activity of ectoparasitic DmGPCR), diagnostic purposes to detect or quantitate ectoparasitic DmGPCR, and purification of DmGPCR. Kits comprising an antibody of the invention for any of the purposes described herein are also comprehended. In general, a kit of the invention also includes a control antigen for which the antibody is immunospecific.

The invention also provides methods of using antibodies of the invention. For example, the invention provides methods for modulating ligand binding of a DmGPCR comprising the step of contacting the DmGPCR with an antibody specific for the DmGPCR, under conditions wherein the antibody binds the receptor. The antibodies of the invention may be used to control an insect population by administering an anti-DmGPCR antibody to an insect to modulate ligand binding of the DmGPCR. For example, the insects may be selected from flies, fruitflies, ticks, lice, fleas, cockroaches, and mites.

Gene Manipulation

Gene manipulation using DmGPCR is also useful in subjects such as insects. Gene manipulation includes restoration of DmGPCR activity, DmGPCR overexpression, and negative regulation of DmGPCR. The present invention also comprehends gene manipulation to restore DmGPCR activity lost due to a loss of function mutation. Delivery of a functional DmGPCR gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, e.g., Anderson, Nature, 1998, suppl. 392 (6679), 25-20. For additional reviews of gene therapy technology see Friedmann, Science, 1989, 244, 1275-1281; Verma, Scientific American, 1990, 68-84; and Miller, Nature, 1992, 357, 455-460. It is also contemplated that gene manipulation, for example antisense treatment, could be applied to negatively regulate the expression of DmGPCR. As a non-limiting example, gene manipulation may be useful for controlling an insect population by knocking-out or downregulating one or more DmGPCR genes or fragments thereof (see supra and infra).

Compositions

Another aspect of the present invention is directed to compositions, including insecticidal and pharmaceutical compositions, comprising any of the nucleic acid molecules or recombinant expression vectors described above and an acceptable carrier or diluent. The carrier or diluent may be pharmaceutically acceptable. Suitable carriers are described in the most recent edition of REMINGTON'S PHARMACEUTICAL SCIENCES, A. Osol, a standard reference text in this field, which is incorporated herein by reference in its entirety. Examples of such carriers or diluents include, but are not limited to, water, saline, Ringer's solution, dextrose solution, and 5% human serum albumin. Liposomes and non-aqueous vehicles such as fixed oils may also be used. The formulations are sterilized by commonly used techniques.

Also within the scope of the invention are compositions comprising polypeptides, polynucleotides, or antibodies of the invention that have been formulated with, e.g., a pharmaceutically acceptable carrier.

The invention provides insecticidal compositions comprising a DmGPCR polynucleotide, a DmGPCR polypeptide, an anti-DmGPCR antibody, fragments or portions thereof having DmGPCR-binding activity, a DmGPCR binding partner, or a DmGPCR modulator.

Kits and Methods

The present invention is also directed to kits, including pharmaceutical and insecticidal kits. The kits can comprise any of the nucleic acid molecules described above, any of the polypeptides described above, or any antibody which binds to a polypeptide of the invention as described above, as well as a negative control. The kit may comprise additional components, such as, for example, instructions, solid support, reagents helpful for quantification, and the like.

Kits may be designed to detect either expression of polynucleotides or the encoded proteins. For example, oligonucleotide hybridization kits can be provided which include a container having an oligonucleotide probe specific for the DmGPCR-specific DNA and optionally, containers with positive and negative controls and/or instructions. Similarly, PCR kits can be provided which include a container having primers specific for the DmGPCR-specific sequences, DNA and optionally, containers with size markers, positive and negative controls and/or instructions.

Hybridization conditions should be such that hybridization occurs only with the genes in the presence of other nucleic acid molecules. Under stringent hybridization conditions only highly complementary nucleic acid sequences hybridize. Such conditions may prevent hybridization of nucleic acids having 1 or 2 mismatches out of 20 contiguous nucleotides. Such conditions are defined supra.

The test samples suitable for nucleic acid probing methods of the present invention include, for example, cells or nucleic acid extracts of cells, or biological fluids. The samples used in the above-described methods will vary based on the assay format, the detection method and the nature of the tissues, cells or extracts to be assayed. Methods for preparing nucleic acid extracts of cells are well-known in the art and can be readily adapted in order to obtain a sample that is compatible with the method utilized.

In another aspect, the invention provides methods for detection of a polynucleotide in a sample as a diagnostic tool for diseases or disorders caused by an ectoparasite, wherein the methods comprise the steps of: (a) contacting the sample with a nucleic acid probe which hybridizes under hybridization assay conditions to a nucleic acid target region encoding a polypeptide having a sequence selected from SEQ ID NO: 2, 4, 6, 8, 10, 12, 14, 16, 18, 20, 22, and 24, said probe comprising the nucleic acid sequence encoding the polypeptide, fragments thereof, and the complements of the sequences and fragments; and (b) detecting the presence or amount of the probe:target region hybrid as an indication of the disease.

Alternatively, immunoassay kits can be provided which have containers having antibodies specific for the DmGPCR protein and optionally, containers with positive and negative controls and/or instructions.

Kits are also provided that are useful in the identification of DmGPCR binding partners, such as natural ligands or modulators (agonists or antagonists). Substances useful for treatment of disorders or diseases may show positive results in one or more in vitro assays for an activity corresponding to treatment of the disease or disorder in question. Substances that modulate the activity of the polypeptides include, but are not limited to, antisense oligonucleotides, agonists and antagonists, and antibodies.

The invention also provides methods for modulating ligand binding of a DmGPCR comprising the step of contacting the DmGPCR with an antibody specific for the DmGPCR, under conditions wherein the antibody binds the receptor.

Methods of Inducing Immune Response

Another aspect of the present invention is directed to methods of inducing an immune response in a subject against a polypeptide of the invention by administering to the subject an amount of the polypeptide sufficient to induce an immune response. The amount will be dependent on the species of the subject, size of the subject, and the like but can be determined by those skilled in the art.

Methods of Identifying Ligands

Another aspect of the present invention is directed to methods of identifying compounds that bind to either DmG-PCR or nucleic acid molecules encoding DmGPCR, comprising contacting DmGPCR, or a nucleic acid molecule encoding the same, with a compound, and determining whether the compound binds DmGPCR or a nucleic acid molecule encoding the same. Binding can be determined by binding assays which are well-known to the skilled artisan, including, but not limited to, gel-shift assays, Western blots, radiolabeled competition assay, phage-based expression cloning, co-fractionation by chromatography, co-precipitation, cross linking, interaction trap/two-hybrid analysis, southwestern analysis, ELISA, and the like, which are described in, for example, CURRENT PROTOCOLS IN MOLECULAR BIOLOGY, John Wiley & Sons, NY, 1999, which is incorporated herein by reference in its entirety. The compounds to be screened include (which may include compounds which are suspected to bind DmGPCR, or a nucleic acid molecule encoding the same), but are not limited to, compounds of extracellular, intracellular, biological, or chemical origin.

The invention also provides assays to identify compounds that bind a DmGPCR. One such assay comprises contacting a composition comprising a DmGPCR with a compound suspected of binding DmGPCR and measuring binding between the compound and DmGPCR. In some embodiments, the composition comprises a cell expressing DmG-PCR on its surface. In another variation, isolated DmGPCR or cell membranes comprising DmGPCR are employed. The binding may be measured directly, e.g., by using a labeled compound, or may be measured indirectly by several techniques, including measuring intracellular signaling of DmG-PCR induced by the compound (or measuring changes in the level of DmGPCR signaling).

Specific binding molecules, including natural ligands and synthetic compounds, can be identified or developed using isolated or recombinant DmGPCR products, DmGPCR variants, or cells expressing such products. Binding partners are useful for purifying DmGPCR products and detection or quantification of DmGPCR products in fluid and tissue samples using known immunological procedures. Binding molecules are also manifestly useful in modulating (i.e., blocking, inhibiting, or stimulating) biological activities of DmGPCR, especially those activities involved in signal transduction.

The DNA and amino acid sequence information provided by the present invention also makes possible identification of binding partner compounds with which a DmGPCR polypeptide or polynucleotide will interact. Methods to identify binding partner compounds include solution assays, in vitro assays wherein DmGPCR polypeptides are immobilized, and cell-based assays. Identification of binding partner compounds of DmGPCR polypeptides provides candidates for therapeutic or prophylactic intervention in pathologies associated with ectoparasites expressing DmG-PCR and candidates for insecticides.

The invention includes several assay systems for identifying DmGPCR binding partners. In solution assays, methods of the invention comprise the steps of (a) contacting a DmGPCR polypeptide with one or more candidate binding partner compounds and (b) identifying the compounds that bind to the DmGPCR polypeptide. Identification of the compounds that bind the DmGPCR polypeptide can be achieved by isolating the DmGPCR polypeptide/binding partner complex, and separating the binding partner compound from the DmGPCR polypeptide. An additional step of characterizing the physical, biological, and/or biochemical properties of the binding partner compound is also comprehended in another embodiment of the invention. In one aspect, the DmGPCR polypeptide/binding partner complex is isolated using an antibody immunospecific for either the DmGPCR polypeptide or the candidate binding partner compound.

In still other embodiments, either the DmGPCR polypeptide or the candidate binding partner compound comprises a label or tag that facilitates its isolation, and methods of the invention to identify binding partner compounds include a step of isolating the DmGPCR polypeptide/binding partner complex through interaction with the label or tag. An exemplary tag of this type is a poly-histidine sequence, generally around six histidine residues, that permits isolation of a compound so labeled using nickel chelation. Other labels and tags, such as the FLAG® tag (Eastman Kodak, Rochester, N.Y.), well-known and routinely used in the art, are embraced by the invention. Labels of the invention also include but are not limited to, a radiolabel (e.g., $^{125}$I, $^{35}$S, $^{32}$P, $^{33}$P, $^{3}$H), a fluorescence label, a chemiluminescent label, an enzymic label, and an immunogenic label.

In some embodiments of in vitro assays, the invention provides methods comprising the steps of (a) contacting an immobilized DmGPCR polypeptide with a candidate binding partner compound and (b) detecting binding of the candidate compound to the DmGPCR polypeptide. In an alternative embodiment, the candidate binding partner compound is immobilized and binding of DmGPCR is detected. Immobilization is accomplished using any of the methods well-known in the art, including covalent bonding to a support, a bead, or a chromatographic resin, as well as non-covalent, high affinity interactions such as antibody binding, or use of streptavidin/biotin binding wherein the immobilized compound includes a biotin moiety. Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well-known and routinely practiced in the art.

The invention also provides cell-based assays to identify binding partner compounds of a DmGPCR polypeptide. In one embodiment, the invention provides methods comprising the steps of contacting a DmGPCR polypeptide expressed on the surface of a cell with a candidate binding partner compound and detecting binding of the candidate binding partner compound to the DmGPCR polypeptide. In another embodiment, the detection comprises detecting a calcium flux or other physiological event in the cell caused by the binding of the molecule.

In another embodiment of the invention, high throughput screening for compounds having suitable binding affinity to DmGPCR is employed. Briefly, large numbers of different small peptide test compounds are synthesized on a solid support or as free compounds dissolved in appropriate buffers. The peptide test compounds are contacted with DmGPCR and washed. Bound DmGPCR is then detected by methods well-known in the art. Purified polypeptides of the invention can also be coated directly onto plates for use in the aforementioned binding assays. In addition, non-neutralizing antibodies can be used to capture the protein and immobilize it on the solid support.

Generally, an expressed DmGPCR can be used for HTS binding assays in conjunction with its defined ligand. The identified peptide is labeled with a suitable radioisotope, including, but not limited to, $^{125}$I, $^{3}$H, $^{35}$S or $^{32}$P, by methods that are well-known to those skilled in the art. Alternatively, the peptides may be labeled by well-known methods with a suitable fluorescent derivative (Baindur et al., *Drug Dev. Res.*, 1994, 33, 373-398; Rogers, *Drug Discovery Today*, 1997, 2, 156-160). Radioactive ligand specifically bound to the receptor in membrane preparations made from the cell line expressing the recombinant protein can be detected in HTS assays in one of several standard ways, including filtration of the receptor-ligand complex to separate bound ligand from unbound ligand (Williams, *Med. Res. Rev.*, 1991, 11, 147-184; Sweetnam et al., *J Natural Products*, 1993, 56, 441-455). Alternative methods include a scintillation proximity assay (SPA) or a FlashPlate format in which such separation is unnecessary (Nakayama, *Curr. Opinion Drug Disc. Dev.*, 1998, 1, 85-91 Bossé et al., *J. Biomolecular Screening*, 1998, 3, 285-292). Binding of fluorescent ligands can be detected in various ways, including fluorescence energy transfer (FRET), direct spectrophotofluorometric analysis of bound ligand, or fluorescence polarization (Rogers, *Drug Discovery Today*, 1997, 2, 156-160; Hill, *Curr. Opinion Drug Disc. Dev.*, 1998, 1, 92-97).

Other assays may be used to identify specific ligands of a DmGPCR, including assays that identify ligands of the target protein through measuring direct binding of test ligands to the target protein, as well as assays that identify ligands of target proteins through affinity ultrafiltration with ion spray mass spectroscopy/HPLC methods or other physical and analytical methods. Alternatively, such binding interactions are evaluated indirectly using the yeast two-hybrid system described in Fields et al. (*Nature*, 1989, 340, 245-246) and Fields et al. (*Trends in Genetics*, 1994, 10, 286-292), both of which are incorporated herein by reference. The two-hybrid system is a genetic assay for detecting interactions between two proteins or polypeptides. It can be used to identify proteins that bind to a known protein of interest, or to delineate domains or residues critical for an interaction. Variations on this methodology have been developed to clone genes that encode DNA binding proteins, to identify peptides that bind to a protein, and to screen for drugs. The two-hybrid system exploits the ability of a pair of interacting proteins to bring a transcription activation domain into close proximity with a DNA binding domain that binds to an upstream activation sequence (UAS) of a reporter gene, and is generally performed in yeast. The assay requires the construction of two hybrid genes encoding (1) a DNA-binding domain that is fused to a first protein and (2) an activation domain fused to a second protein. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of the first and second proteins tethers the activation domain to the UAS, activating transcription of the reporter gene. For example, when the first protein is a DmGPCR gene product, or fragment thereof, that is known to interact with another protein or nucleic acid, this assay can be used to detect agents that interfere with the binding interaction. Expression of the reporter gene is monitored as different test agents are added to the system. The presence of an inhibitory agent results in lack of a reporter signal.

When the function of the DmGPCR gene product is unknown and no ligands are known to bind the gene product, the yeast two-hybrid assay can also be used to identify proteins that bind to the gene product. In an assay to identify proteins that bind to a DmGPCR receptor, or fragment thereof, a fusion polynucleotide encoding both a DmGPCR receptor (or fragment) and a UAS binding domain (i.e., a first protein) may be used. In addition, a large number of hybrid genes each encoding a different second protein fused to an activation domain are produced and screened in the assay. Typically, the second protein is encoded by one or more members of a total cDNA or genomic DNA fusion library, with each second protein coding region being fused to the activation domain. This system is applicable to a wide variety of proteins, and it is not even necessary to know the identity or function of the second binding protein. The system is highly sensitive and can detect interactions not revealed by other methods; even transient interactions may trigger transcription to produce a stable mRNA that can be repeatedly translated to yield the reporter protein.

Other assays may be used to search for agents that bind to the target protein. One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method that distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides, and small organic molecules.

Another method for identifying ligands of a target protein is described in Wieboldt et al. (*Anal. Chem.*, 1997, 69, 1683-1691), incorporated herein by reference. This technique screens combinatorial libraries of 20-30 agents at a time in solution phase for binding to the target protein. Agents that bind to the target protein are separated from other library components by simple membrane washing. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

Other embodiments of the invention comprise using competitive screening assays in which neutralizing antibodies capable of binding a polypeptide of the invention specifically compete with a test compound for binding to the polypeptide. In this manner, the antibodies can be used to detect the presence of any peptide that shares one or more antigenic determinants with DmGPCR. Radiolabeled competitive binding studies are described in A. H. Lin et al. (*Antimicrobial Agents and Chemotherapy*, 1997, 41(10), 2127-2131), the disclosure of which is incorporated herein by reference in its entirety.

Methods for Identifying Modulating Agents

The invention also provides methods for identifying a modulator of binding between a DmGPCR and a DmGPCR binding partner, comprising the steps of: (a) contacting a DmGPCR binding partner and a composition comprising a DmGPCR in the presence and in the absence of a putative modulator compound; (b) detecting binding between the binding partner and the DmGPCR; and (c) identifying a putative modulator compound or a modulator compound in view of decreased or increased binding between the binding partner and the DmGPCR in the presence of the putative modulator, as compared to binding in the absence of the putative modulator.

DmGPCR binding partners that stimulate DmGPCR activity are useful as agonists in conditions characterized by insufficient DmGPCR signaling (e.g., as a result of insufficient activity of a DmGPCR ligand). DmGPCR binding partners that block ligand-mediated DmGPCR signaling are useful as DmGPCR antagonists in conditions characterized by excessive DmGPCR signaling. In addition, DmGPCR modulators in general, as well as DmGPCR polynucleotides and polypeptides, are useful in diagnostic assays for diseases caused by ectoparasites or conditions in which DmGPCR activity is enhanced or impaired.

In another aspect, the invention provides methods for treating a disease or condition by administering to a subject in need of such treatment a substance that modulates the activity or expression of a polypeptide having a sequence selected from SEQ ID NOs: 2, 4, 6, 8, 10, 12, 14, 16, 18, 20, 22, and 24.

In another aspect, the invention provides methods for controlling an insect population by administering to an insect population a binding partner or modulator that modifies expression or activity of a DmGPCR.

Agents that modulate (i.e., increase, decrease, or block) DmGPCR activity or expression may be identified by incubating a putative modulator with a cell containing a DmGPCR polypeptide or polynucleotide and determining the effect of the putative modulator on DmGPCR activity or expression. The selectivity of a compound that modulates the activity of DmGPCR can be evaluated by comparing its effects on DmGPCR to its effect on other GPCR compounds. Selective modulators may include, for example, antibodies and other proteins, peptides, or organic molecules which specifically bind to a DmGPCR polypeptide or a DmGPCR-encoding nucleic acid. Modulators of DmGPCR activity will be therapeutically useful in treatment of diseases and physiological conditions in which normal or aberrant DmGPCR activity is involved.

DmGPCR polynucleotides and polypeptides, as well as DmGPCR modulators, may also be used in diagnostic assays for diseases caused by ectoparasites or conditions characterized by enhanced or impaired DmGPCR activity.

Methods of the invention to identify modulators include variations on any of the methods described above to identify binding partner compounds, the variations including techniques wherein a binding partner compound has been identified and the binding assay is carried out in the presence and absence of a candidate modulator. A modulator is identified in those instances where binding between the DmGPCR polypeptide and the binding partner compound changes in the presence of the candidate modulator compared to binding in the absence of the candidate modulator compound. A modulator that increases binding between the DmGPCR polypeptide and the binding partner compound is described as an enhancer or activator, and a modulator that decreases binding between the DmGPCR polypeptide and the binding partner compound is described as an inhibitor.

The invention also comprehends high-throughput screening (HTS) assays to identify compounds that interact with or inhibit biological activity (i.e., affect enzymatic activity, binding activity, etc.) of a DmGPCR polypeptide. HTS assays permit screening of large numbers of compounds in an efficient manner. Cell-based HTS systems are contemplated to investigate DmGPCR receptor-ligand interaction. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and the DmGPCR polypeptide.

Modulators falling within the scope of the invention include, but are not limited to, non-peptide molecules such as non-peptide mimetics, non-peptide allosteric effectors, and peptides. The DmGPCR polypeptide or polynucleotide employed in such a test may either be free in solution, attached to a solid support, borne on a cell surface or located intracellularly, or associated with a portion of a cell. One skilled in the art can, for example, measure the formation of complexes between DmGPCR and the compound being tested. Alternatively, one skilled in the art can examine the diminution in complex formation between DmGPCR and its substrate caused by the compound being tested.

Another aspect of the present invention is directed to methods of identifying compounds which modulate (i.e., increase or decrease) activity of DmGPCR comprising contacting DmGPCR with a compound, and determining whether the compound modifies activity of DmGPCR. The activity in the presence of the test compound is compared to the activity in the absence of the test compound. Where the activity of the sample containing the test compound is higher than the activity in the sample lacking the test compound, the compound will have increased activity. Similarly, where the activity of the sample containing the test compound is lower than the activity in the sample lacking the test compound, the compound will have inhibited activity.

The present invention is particularly useful for screening compounds by using DmGPCR in any of a variety of activity assays. The compounds to be screened include (which may include compounds which are suspected to modulate DmGPCR activity), but are not limited to, compounds of extracellular, intracellular, biological, or chemical origin. The DmGPCR polypeptide employed in such a test may be in any form, such as free in solution, attached to a solid support, borne on a cell surface, or located intracellularly. One skilled in the art can, for example, measure the formation of complexes between DmGPCR and the compound being tested. Alternatively, one skilled in the art can examine the diminution in complex formation between DmGPCR and its substrate caused by the compound being tested.

The activity of DmGPCR polypeptides of the invention can be determined by, for example, examining the ability to bind or be activated by chemically synthesized peptide ligands. Alternatively, the activity of the DmGPCRs can be assayed by examining their ability to bind calcium ions, hormones, chemokines, neuropeptides, neurotransmitters, nucleotides, lipids, odorants, and photons. Alternatively, the activity of the DmGPCRs can be determined by examining the activity of effector molecules including, but not limited to, adenylate cyclase, phospholipases, and ion channels.

Thus, modulators of DmGPCR activity may alter a DmGPCR receptor function, such as a binding property of a receptor or an activity such as G protein-mediated signal transduction or membrane localization. In various embodiments of the methods, the assay may take the form of an ion flux assay, a yeast growth assay, a non-hydrolyzable GTP assay such as a [$^{35}$S]GTPγS assay, a cAMP assay, an inositol triphosphate assay, a diacylglycerol assay, an Aequorin assay, a Luciferase assay, a FLIPR assay for intracellular $Ca^{2+}$ concentration, a mitogenesis assay, a MAP Kinase activity assay, an arachidonic acid release assay (e.g., using [$^3$H]-arachidonic acid), and an assay for extracellular acidification rates, as well as other binding or function-based assays of DmGPCR activity that are generally known in the art. In several of these embodiments, the invention comprehends the inclusion of any of the G proteins known in the art, such as $G_{16}$, $G_{15}$, or chimeric $G_{qi5}$, $G_{qs5}$, $G_{qo5}$, $G_{qz5}$, and the like. DmGPCR activity can be determined by methodologies that are used to assay for FaRP activity, which is well-known to those skilled in the art. Biological activities of DmGPCR receptors according to the invention include, but are not limited to, the binding of a natural or an unnatural ligand, as well as any one of the functional activities of GPCRs known in the art. Non-limiting examples of GPCR activities include transmembrane signaling of various forms, which may involve G protein association and/or the exertion of an influence over G protein binding of various guanidylate nucleotides; another exemplary activity of GPCRs is the binding of accessory proteins or polypeptides that differ from known G proteins.

The modulators of the invention exhibit a variety of chemical structures, which can be generally grouped into non-peptide mimetics of natural DmGPCR receptor ligands, peptide, and non-peptide allosteric effectors of DmGPCR receptors, and peptides that may function as activators or inhibitors (competitive, uncompetitive and non-competitive) (e.g., antibody products) of DmGPCR receptors. The invention does not restrict the sources for suitable modulators, which may be obtained from natural sources such as plant, animal or mineral extracts, or non-natural sources such as small molecule libraries, including the products of combinatorial chemical approaches to library construction, and peptide libraries. Examples of peptide modulators of DmGPCR receptors exhibit the following primary structures: GLGPRPLRFamide (SEQ ID NO: 49), GNSFLRFamide (SEQ ID NO: 136), GGPQGPLRFamide (SEQ ID NO: 102), GPSGPLRFamide (SEQ ID NO: 103), PDVDHVFL-RFamide (SEQ ID NO: 150), and pyro-EDVDHVFLRFamide (SEQ ID NO: 167).

Other assays can be used to examine enzymatic activity including, but not limited to, photometric, radiometric, HPLC, electrochemical, and the like, which are described in, for example, ENZYME ASSAYS: A PRACTICAL APPROACH, eds. R. Eisenthal and M. J. Danson, 1992, Oxford University Press, which is incorporated herein by reference in its entirety.

The use of cDNAs encoding GPCRs in activity assays is well-known; assays capable of testing thousands of unknown compounds per day in high-throughput screens (HTSs) are thoroughly documented. The literature is replete with examples of the use of radiolabelled ligands in HTS binding assays for drug discovery (see Williams, *Medicinal Research Reviews*, 1991, 11, 147-184; Sweetnam, et al., *J. Natural Products*, 1993, 56, 441-455 for review). Recombinant receptors are preferred for binding assay HTS because they allow for better specificity (higher relative purity), provide the ability to generate large amounts of receptor material, and can be used in a broad variety of formats (see Hodgson, *Bio/Technology*, 1992, 10, 973-980, incorporated herein by reference in its entirety).

A variety of heterologous systems are available for functional expression of recombinant receptors that are well-known to those skilled in the art. Such systems include bacteria (Strosberg, et al., *Trends in Pharmacological Sciences*, 1992, 13, 95-98), yeast (Pausch, *Trends in Biotechnology*, 1997, 15, 487-494), several kinds of insect cells (Vanden Broeck, *Int. Rev. Cytology*, 1996, 164, 189-268), amphibian cells (Jayawickreme et al., *Curr. Opin. Biotechnol.*, 1997, 8, 629-634) and several mammalian cell lines (CHO, HEK293, COS, etc.; see Gerhardt, et al., *Eur. J. Pharmacology*, 1997, 334, 1-23). These examples do not preclude the use of other possible cell expression systems, including cell lines obtained from nematodes (PCT application WO 98/37177).

In some embodiments of the invention, methods of screening for compounds which modulate DmGPCR activity comprise contacting test compounds with DmGPCR and assaying for the presence of a complex between the compound and DmGPCR. In such assays, the ligand is typically labeled. After suitable incubation, free ligand is separated from that present in bound form, and the amount of free or uncomplexed label is a measure of the ability of the particular compound to bind to DmGPCR.

It is well-known that activation of heterologous receptors expressed in recombinant systems results in a variety of biological responses, which are mediated by G proteins expressed in the host cells. Occupation of a GPCR by an agonist results in exchange of bound GDP for GTP at a binding site on the $G_\alpha$ subunit; one can use a radioactive, non-hydrolyzable derivative of GTP, [$^{35}$S]GTPγS, to measure binding of an agonist to the receptor (Sim et al., *Neuroreport*, 1996, 7, 729-733). One can also use this binding to measure the ability of antagonists to bind to the receptor by decreasing binding of [$^{35}$S]GTPγS in the presence of a known agonist. One could therefore construct a HTS assay based on [$^{35}$S]GTPγS binding.

The G proteins required for functional expression of heterologous GPCRs can be native constituents of the host cell or can be introduced through well-known recombinant technology. The G proteins can be intact or chimeric. Often, a nearly universally competent G protein (e.g., $G_{\alpha 16}$) is used to couple any given receptor to a detectable response pathway. G protein activation results in the stimulation or inhibition of other native proteins, events that can be linked to a measurable response.

Examples of such biological responses include, but are not limited to, the following: the ability to survive in the absence of a limiting nutrient in specifically engineered yeast cells (Pausch, *Trends in Biotechnology*, 1997, 15, 487-494); changes in intracellular $Ca^{2+}$ concentration as measured by fluorescent dyes (Murphy, et al., *Curr. Opin. Drug Disc. Dev.*, 1998, 1, 192-199). Fluorescence changes can also be used to monitor ligand-induced changes in membrane potential or intracellular pH; an automated system suitable for HTS has been described for these purposes (Schroeder, et al., *J. Biomolecular Screening*, 1996, 1, 75-80). Melanophores prepared from *Xenopus laevis* show a ligand-dependent change in pigment organization in response to heterologous GPCR activation; this response is adaptable to HTS formats (Jayawickreme, et al., *Curr. Opin. Biotechnol.*, 1997, 8, 629-634). Assays are also available for the measurement of common second messengers, including cAMP, phosphoinositides, and arachidonic acid.

Methods of HTS employing these receptors include permanently transfected CHO cells, in which agonists and antagonists can be identified by the ability to specifically alter the binding of [$^{35}$S]GTPγS in membranes prepared from these cells. In another embodiment of the invention, permanently transfected CHO cells could be used for the preparation of membranes which contain significant amounts of the recombinant receptor proteins; these membrane preparations would then be used in receptor binding assays, employing the radiolabelled ligand specific for the particular receptor. Alternatively, a functional assay, such as fluorescent monitoring of ligand-induced changes in internal $Ca^{2+}$ concentration or membrane potential in permanently transfected CHO cells containing each of these receptors individually or in combination would be useful for HTS. Equally useful would be an alternative type of mammalian cell, such as HEK293 or COS cells, in similar formats. Permanently transfected insect cell lines, such as *Drosophila* S2 cells, and recombinant yeast cells expressing the *Drosophila melanogaster* receptors in HTS formats well-known to those skilled in the art (e.g., Pausch, *Trends in Biotechnology*, 1997, 15, 487-494), would also be useful in the invention.

The invention contemplates a multitude of assays to screen and identify inhibitors of ligand binding to DmGPCR receptors. In one example, the DmGPCR receptor is immobilized and interaction with a binding partner is assessed in the presence and absence of a candidate modulator such as an inhibitor compound. In another example, interaction between the DmGPCR receptor and its binding partner is assessed in a solution assay, both in the presence and absence of a candidate inhibitor compound. In either assay, an inhibitor is identified as a compound that decreases binding between the DmGPCR receptor and its binding partner. Another contemplated assay involves a variation of the di-hybrid assay wherein an inhibitor of protein/protein interactions is identified by detection of a positive signal in a transformed or transfected host cell, as described in PCT publication number WO 95/20652, published Aug. 3, 1995.

Candidate modulators contemplated by the invention include compounds selected from libraries of either potential activators or potential inhibitors. There are a number of different libraries used for the identification of small molecule modulators, including: (1) chemical libraries, (2) natural product libraries, and (3) combinatorial libraries comprised of random peptides, oligonucleotides, or organic molecules. Chemical libraries consist of random chemical structures, some of which are analogs of known compounds or analogs of compounds that have been identified as "hits" or "leads" in other drug discovery screens, some of which are derived from natural products, and some of which arise from non-directed synthetic organic chemistry. Natural product libraries are collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. For a review, see *Science*, 1998, 282, 63-68. Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.*, 1997, 8, 701-707. Identification of modulators through use of the various libraries described herein permits modification of the candidate "hit" (or "lead") to optimize the capacity of the "hit" to modulate activity.

Still other candidate inhibitors contemplated by the invention can be designed and include soluble forms of binding partners, as well as such binding partners as chimeric, or fusion, proteins. A "binding partner" as used herein broadly encompasses non-peptide modulators, as well as such peptide modulators as neuropeptides other than natural ligands, antibodies, antibody fragments, and modified compounds comprising antibody domains that are immunospecific for the expression product of the identified DmGPCR gene.

In other embodiments of the invention, the polypeptides of the invention are employed as a research tool for identification, characterization and purification of interacting, regulatory proteins. Appropriate labels are incorporated into the polypeptides of the invention by various methods known in the art and the polypeptides are used to capture interacting molecules. For example, molecules are incubated with the labeled polypeptides, washed to remove unbound polypeptides, and the polypeptide complex is quantified. Data obtained using different concentrations of polypeptide are used to calculate values for the number, affinity, and association of polypeptide with the protein complex.

Labeled polypeptides are also useful as reagents for the purification of molecules with which the polypeptide interacts including, but not limited to, inhibitors. In one embodiment of affinity purification, a polypeptide is covalently coupled to a chromatography column. Cells and their membranes are extracted, and various cellular subcomponents are passed over the column. Molecules bind to the column by virtue of their affinity to the polypeptide. The polypeptide-complex is recovered from the column, dissociated and the recovered molecule is subjected to protein sequencing. This amino acid sequence is then used to identify the captured molecule or to design degenerate oligonucleotides for cloning the corresponding gene from an appropriate cDNA library.

Alternatively, compounds may be identified which exhibit similar properties to the ligand for the DmGPCR of the invention, but which are smaller and exhibit a longer half-life than the endogenous ligand in a human or animal body. When an organic compound is designed, a molecule according to the invention is used as a "lead" compound. The design of mimetics to known pharmaceutically active compounds is a well-known approach in the development of pharmaceuticals based on such "lead" compounds. Mimetic design, synthesis, and testing are generally used to avoid randomly screening a large number of molecules for a target property. Furthermore, structural data deriving from the analysis of the deduced amino acid sequences encoded by the DNAs of the present invention are useful to design new drugs which are more specific and, therefore, have a higher pharmacological potency.

Comparison of the protein sequences of the present invention with the sequences present in all the available databases showed a significant homology with the transmembrane portion of G protein coupled receptors. Accordingly, computer modelling can be used to develop a putative tertiary structure of the proteins of the invention based on the available information of the transmembrane domain of other proteins. Thus, novel ligands based on the predicted structure of DmGPCR can be designed.

In a particular embodiment, the novel molecules identified by the screening methods according to the invention are low molecular weight organic molecules, in which case a composition or pharmaceutical composition can be prepared thereof for oral intake, such as in tablets. The compositions, or pharmaceutical compositions, comprising the nucleic acid molecules, vectors, polypeptides, antibodies and compounds identified by the screening methods described herein, may be prepared for any route of administration including, but not limited to, oral, intravenous, cutaneous, subcutaneous, nasal, intramuscular, or intraperitoneal. The nature of the carrier or other ingredients will depend on the specific route of administration and particular embodiment of the invention to be administered. Examples of techniques and protocols that are useful in this context are, inter alia, found in REMINGTON'S PHARMACEUTICAL SCIENCES, Osol, A (ed.), 1980, which is incorporated herein by reference in its entirety.

The dosage of these low molecular weight compounds will depend on the disease state or condition to be treated and other clinical factors, such as weight and condition of the subject to be treated and the route of administration of the compound. For treating animals, between approximately 0.5 mg/kg of body weight to 500 mg/kg of body weight of the compound can be administered. Therapy is typically administered at lower dosages and is continued until the desired therapeutic outcome is observed.

Methods of determining the dosages of compounds to be administered to a subject and modes of administering compounds to an organism are disclosed in U.S. application Ser. No. 08/702,282, filed Aug. 23, 1996 and International patent publication number WO 96/22976, published Aug. 1, 1996, both of which are incorporated herein by reference in their entirety, including any drawings, figures or tables. Those skilled in the art will appreciate that such descriptions are applicable to the present invention and can be easily adapted to it.

The proper dosage depends on various factors such as the type of disease being treated, the particular composition being used, and the size and physiological condition of the subject. Therapeutically effective doses for the compounds described herein can be estimated initially from cell culture and animal models. For example, a dose can be formulated in animal models to achieve a circulating concentration range that initially takes into account the $IC_{50}$ as determined in cell culture assays.

Plasma half-life and biodistribution of the drug and metabolites in the plasma, tumors, and major organs can also be determined to facilitate the selection of drugs most appropriate to inhibit a disorder. Such measurements can be carried out. For example, HPLC analysis can be performed on the plasma of animals treated with the drug and the location of radiolabeled compounds can be determined using detection methods such as X-ray, CAT scan and MRI. Compounds that show potent inhibitory activity in the screening assays, but have poor pharmacokinetic characteristics, can be optimized by altering the chemical structure and retesting. In this regard, compounds displaying good pharmacokinetic characteristics can be used as a model.

Toxicity studies can also be carried out by measuring the blood cell composition. For example, toxicity studies can be carried out in a suitable animal model as follows: 1) the compound is administered to mice (an untreated control mouse should also be used); 2) blood samples are periodically obtained via the tail vein from one mouse in each treatment group; and 3) the samples are analyzed for red and white blood cell counts, blood cell composition and the percent of lymphocytes versus polymorphonuclear cells. A comparison of results for each dosing regime with the controls indicates if toxicity is present.

At the termination of each toxicity study, further studies can be carried out by sacrificing the animals (preferably, in accordance with the American Veterinary Medical Association guidelines Report of the American Veterinary Medical Assoc. Panel on Euthanasia, *J. Amer. Vet. Med. Assoc.*, 1993, 202, 229-249). Representative animals from each treatment group can then be examined by gross necropsy for immediate evidence of metastasis, unusual illness, or toxicity. Gross abnormalities in tissue are noted and tissues are examined histologically.

The present compounds and methods, including nucleic acid molecules, polypeptides, antibodies, compounds identified by the screening methods described herein, have a variety of pharmaceutical and agricultural (e.g., insecticidal) applications and may be used, for example, to treat or prevent conditions caused by ectoparasites or to control an insect population.

The present invention also encompasses methods of agonizing (stimulating) or antagonizing a DmGPCR natural binding partner associated activity in a subject comprising administering to said subject an agonist or antagonist to one of the above disclosed polypeptides in an amount sufficient to effect said agonism or antagonism. One embodiment of the present invention, then, is a method of treating diseases or conditions in a subject caused by an ectoparasite with an agonist or antagonist of the protein of the present invention comprising administering the agonist or antagonist to a subject in an amount sufficient to agonize or antagonize the ectoparasitic DmGPCR-associated functions.

The following Table 4 contains the sequences of the polynucleotides and polypeptides of the invention.

TABLE 4

The following DNA sequence for DmGPCR1 (SEQ ID NO:1) was identified in
D. melanogaster:

ATGGCCAACTTAAGCTGGCTGAGCACCATCACCACCACCTCCTCCTCCATCAGCACCAGC

CAGCTGCCATTGGTCAGCACAACCAACTGGAGCCTAACGTCGCCGGGAACTACTAGCGCT

ATCTTGGCGGATGTGGCTGCATCGGATGAGGATAGGAGCGGCGGGATCATTCACAACCAG

TTCGTGCAAATCTTCTTCTACGTCCTGTACGCCACGGTCTTTGTCCTGGGTGTCTTCGGA

AATGTCCTGGTTTGCTACGTAGTTCTGAGGAATCGGGCCATGCAGACTGTGACCAATATA

TTCATCACGAATCTGGCCCTGTCGGACATATTGCTCTGCGTCCTGGCGGTGCCATTTACT

CCGCTTTACACGTTCATGGGTCGCTGGGCCTTCGGCAGGAGTCTGTGCCATCTGGTGTCC

TTTGCCCAGGGATGCAGCATCTACATATCCACGCTGACCCTCACCTCGATTGCCATCGAT

CGGTACTTCGTTATCATATACCCCTTCCATCCGCGCATGAAGCTCTCCACCTGCATCGGG

ATCATAGTGAGCATCTGGGTGATAGCCCTGCTGGCCACCGTTCCCTACGGCATGTACATG

AAGATGACCAACGAGCTGGTGAACGGAACGCAGACAGGCAACGAGACCCTGGTGGAGGCC

ACTCTAATGCTAAACGGAAGCTTTGTGGCCCAGGGATCAGGATTCATCGAGGCGCCGGAC

TCTACCTCGGCCACCCAGGCCTATATGCAGGTGATGACCGCCGGATCAACGGGACCGGAG

ATGCCCTATGTGCGGGTGTACTGCGAGGAGAACTGGCCATCGGAGCAGTACCGGAAGGTG

TTCGGTGCCATCACAACCACTCTGCAGTTTGTGCTGCCCTTCTTCATCATCTCGATTTGC

TACGTGTGGATATCGGTGAAGCTAAACCAGCGGGCCAGGGCCAAGCCGGGATCGAAATCC

TCGAGACGGGAGGAGGCGGATCGGGATCGCAAGAAGCGCACCAACCGCATGCTCATCGCC

ATGGTGGCGGTATTCGGACTCAGCTGGCTGCCCATCAATGTGGTCAACATATTCGATGAC

TTCGATGACAAGTCCAACGAGTGGCGCTTCTACATCCTATTCTTCTTTGTGGCCCACTCT

ATTGCCATGAGCTCCACCTGCTACAATCCCTTCCTGTACGCCTGGCTGAACGAGAACTTC

CGCAAGGAGTTCAAGCACGTGCTGCCCTGCTTTAATCCCTCGAACAACAACATCATCAAC

ATCACCAGGGGCTATAATCGGAGTGATCGGAACACCTGTGGTCCGCGACTGCATCATGGC

AAGGGGATGGTGGCATGGGCGGTGGCAGTCTGGACGCCGACGACCAGGACGAGAACGGC

ATCACCCAGGAGACCTGTCTGCCCAAGGAGAAGCTGCTGATTATCCCCAGGGAGCCGACT

TACGGCAATGGCACGGGTGCCGTGTCGCCAATCCTTAGCGGGCGCGGCATTAACGCCGCC

CTGGTGCACGGTGGCGACCATCAGATGCACCAGCTGCAGCCGTCACACCATCAACAGGTG

GAGCTGACGAGGCGAATCCGCCGGCGGACAGACGAGACGGACGGGGATTACCTGGACTCC

TABLE 4-continued

```
GGCGACGAGCAGACCGTGGAGGTGCGCTTCAGCGAGACGCCGTTCGTCAGCACGGATAAT

ACCACCGGGATCAGCATTCTGGAGACGAGTACGAGTCACTGCCAGGACTCGGATGTGATG

GTCGAGCTGGGCGAGGCAATCGGCGCCGGTGGTGGGGCAGAGCTGGGGAGGCGAATCAAC

TGA
```

The following amino acid sequence (SEQ ID NO:2) is the amino acid sequence for the protein encoded by the DNA sequence of SEQ ID NO:1:

```
MANLSWLSTITTTSSSISTSQLPLVSTTNWSLTSPGTTSAILADVAASDEURSGGIIHNQ

FVQIFFYVLYATVFVLGVFGNVLVCYVVLRNRAMQTVTNIFITNLALSDILLCVLAVPFT

PLYTFMGRWAFGRSLCHLVSFAQGCSIYISTLTLTSIATDRYFVIIYPFHPRMKLSTCIG

IIVSIWVIALLATVPYGMYMKMTNELVNGTQTGNETLVEATLMLNGSFVAQGSGFIEAPD

STSATQAYMQVMTAGSTGPEMPYVRVYCEENWPSEQYRKVFGAITTTLQFVLPFFIISIC

YVWISVKLNQRARAKPGSKSSRREEADRDRKKRTNRMLIAMVAVFGLSWLPINVVNIFDD

FDDKSNEWRFYILFFFVAHSIAMSSTCYNPFLYAWLNENFRKEFKHVLPCFNPSNNNIIN

ITRGYNRSDRNTCGPRLHHGKGDGGMGGGSLDADDQDENCITQETCLPKEKLLIIPREPT

YGNCTGAVSPILSGRGINAALVHGGDHQMHQLQPSHHQQVELTRRIRRRTDETDGDYLDS

GDEQTVEVRFSETPFVSTDNTTGISILETSTSHCQDSDVNVELGEAICAGGGAELGRRIN
```

The following DNA sequence for DmGPCR2a (SEQ ID NO:3) was identified in D. melanogaster:

```
ATGAATCAGACGGAGCCCCCCCAGCTCGCAGATGGGGAGCATCTGAGTGC

ATACGCCAGCAGCAGCAACAGCGTGCGCTATCTGGACGACCGGCATCCGC

TGGACTACCTTGACCTCGGCACGGTGCACGCCCTCAACACCACTGCCATC

AACACCTCGCATCTGAATGAGACTGGGAGCAGGCCGCTGGACCCCGTCCT

TATCGATAGGTTCCTCAGCAACAGGGCGGTGGACAGCCCCTCGTACCACA

TGCTCATCAGCATGTACGGCGTGCTAATCGTCTTCGGCGCCCTACGCAAC

ACCCTGGTTGTTATAGCCCTCATCCGGAAGCCCATCATGCGCACTGCTCG

CAATCTGTTCATCCTCAACCTGGCCATATCGGACCTACTTTTATGCCTAC

TCACCATGCCGCTGACCTTGATGGACATCCTGTCCAAGTACTGGCCCTAC

GGCTCCTGCTCCATCCTGTGCAAAACGATTCCCATGCTCCACGCACTTTG

TATTTTCGTGTCGACAATATCCATAACGCCCATTGCCTTCGACAGATATC

AGGTGATCGTGTACCCCACGCGGGACAGCCTGCAGTTCGTGGGCCCGGTG

ACGATCCTGGCCCGGATCTGGGCACTCGCACTGCTGCTGGCCTCGCCGCT

GTTCGTCTACAAGGACCTGATCAACACAGACACGCCGGCACTCCTGCAGC

AGATCGGCCTCCAGGACACGATCCCGTACTGCATTGAGGACTGGCCAAGT

CCCAACGGGCGCTTCTACTACTCGATCTTCTCGCTGTCCGTACAATACCT

GGTGCCCATCCTGATCGTCTCGGTGGCATACTTCCGGATCTACAACAAGC

TGAAGAGCCGCATCACCCTGGTGGCTGTGCAGGCGTCCTCCGCTCAGCGG

AAGGTGGAGCGGGGCCGCGGATGAAGCGCACCAACTGCCTACTGATCAG

CATCGCCATCATCTTTGGCGTTTCTTGGCTGCCGCTCAACTTTTTCAACC

TGTACGCGGACATGGAGCCCTCGCCGGTCACTCAGAGCATGCTAGTCCGC

TACCCCATCTCCCACATCATCGCCATGAGCTCCGCCTGCTCCAACCCGTT

GCTCTACGGCTGGCTCAACGACAACTTCCGTAAAGAATTTCAAGAACTGC
```

TABLE 4-continued

TCTGCCGTTGCTCAGACACTAATGTTGCTCTTAACGGTCACACGACAGGC

TGCAACCTCCACCCGCCGGCGCGCAAGCGTCGCAAGTTGGGCGCCGAACT

CTCCAAAGGCGAACTCAAGCTGCTGGGGCCAGGCGGCGCCCAGAGCGGTA

CCGCCGGCGCGGAAGCCGGTCTGGCGGCCACCGACTTCATGACCGGCCAC

CACCAGGCCCGACTGCCCAGCGCCATAACCGAGTCGGTGGCCCTCACGGA

CCACAACCCCGTGCCCTCGGAGGTCACCAAGCTGATGCCGCCGTA

The following amino acid sequence (SEQ ID NO:4) is the amino acid sequence for the protein encoded by the DNA sequence of SEQ ID NO:3:

MENTTMLANISLNATRNEENITSFFTDEEWLAINGTLPWIVGFFFGVIAITGFFGNLLVILVVVFNNNMRS

TTNLMTVNLAAADLMFVILCIPFTATDYMVYYWPYGRFWCRSVQYLIVVTAFASIYTLVLMSIDRFLAVVH

PIRSRMMRTENITLIAIVTLWIVVLVVSVPVAETHDVVVDYDAKKNITYGMCTFTTNDFLGPRTYQVTFFI

SSYLLPLMIISGLYMRMIMRLWRQGTGVRMSKESQRGRKRVTRLVVVVVIAFASLWLPVQLILLLKSLDVI

ETNTLTKLVIQVTAQTLAYSSSCIHPLLYAFLSENFRKAFYKAVNCSSRYQNYTSDLPPPRKTSCARTSTT

GL

The following DNA sequence for DmGPCR2b (SEQ ID NO:5) was identified in *D. melanogaster*:

ATGAATCAGACGGAGCCCGCCCAGCTGGCAGATGGGGAGCATCTGAGTGG

ATACGCCAGCAGCAGCAACAGCGTGCGCTATCTGGACGACCCGCATCCGC

TGGACTACCTTGACCTGGGCACGGTGCACGCCCTCAACACCACTGCCATC

AACACCTCGGATCTGAATGAGACTGGGAGCAGGCCGCTGGACCCGGTGCT

TATCGATAGGTTCCTGAGCAACAGGGCGGTGGACAGCCCCTCGTACCACA

TGCTCATCAGCATGTACGGCGTGCTAATCGTCTTCGGCGCCCTAGGCAAC

ACCCTGGTTGTTATAGCCGTCATCCGGAAGCCCATCATGCGCACTGCTCG

CAATCTGTTCATCCTCAACCTGGCCATATCGGACCTACTTTTATGCCTAG

TCACCATGCCGCTGACCTTGATGGAGATCCTGTCCAAGTACTGGCCCTAC

GGCTCCTGCTCCATCCTGTGCAAAACGATTGCCATGCTGCAGGCACTTTG

TATTTTCGTGTCGACAATATCCATAACGGCCATTGCCTTCGACAGATATC

AGGTGATCGTGTACCCCACGCGGGACAGCCTGCAGTTCGTGGGCGCGGTG

ACGATCCTGGCGGGGATCTGGGCACTGGCACTGCTGCTGGCCTCGCCGCT

GTTCGTCTACAAGGAGCTGATCAACACAGACACGCCGGCACTCCTGCAGC

AGATCGGCCTGCAGGACACGATCCCGTACTGCATTGAGGACTGGCCAAGT

CGCAACGGGCGCTTCTACTACTCGATCTTCTCGCTGTGCGTACAATACCT

GGTGCCCATCCTGATCGTCTCGGTGGCATACTTCGGGATCTACAACAAGC

TGAAGAGCCGCATCACCGTGGTGGCTGTGCAGGCGTCCTCCGCTCAGCGG

AAGGTGGAGCGGGGCGGCGGATGAAGCGCACCAACTGCCTACTGATCAG

CATCGCCATCATCTTTGGCGTTTCTTGGCTGCCGCTGAACTTTTTCAACC

TGTACGCGGACATGGAGCGCTCGCCGGTCACTCAGAGCATGCTAGTCCGC

TACGCCATCTGCCACATGATCGGCATGAGCTCCGCCTGCTCCAACCCGTT

GCTCTACGGCTGGCTCAACGACAACTTCCGCTGCAACGTCCAGGCGGCGG

CGCGCAAGCGTCGCAAGTTGGGCGCCGAACTCTCCAAAGGCGAACTCAAG

TABLE 4-continued

CTGCTGGGGCCAGGCGGCGCCCAGAGCGGTACCGCCGGCGGGGAAGGCGG

TCTGGCGGCCACCGACTTCATGACCGGCCACCACGAGGGCGGACTGCGCA

GCGCCATAACCGAGTCGGTGGCCCTCACGGACCACAACCCCGTGCCCTCG

GAGGTCACCAAGCTGATGCCGCGGTA

The following amino acid sequence (SEQ ID NO:6) is the amino acid sequence for the protein encoded by the DNA sequence of SEQ ID NO:5:

MNQTEPAQLADGEHLSGYASSSNSVRYLDDRHPLDYLDLGTVHALNTTAINTSDLNETGSRPLDPVLIDRE

LSNRAVDSPWYHMLISMYGVLIVFGALGNTLVVIAVIRKPIMRTARNLFILNLAISDLLLCLVTMPLTLME

ILSKYWPYGSCSJLCKTIAMLQALCIFVSTISITAIAFDRYQVIVYPTRDSLQFVGAVTILAGIWALALLE

ASPLFVYKELINTDTPALLQQIGLQDTIPYCIEDWPSRNGRPYYSIFSLCVQYLVPILIVSVAYFGIYNKL

KSRITVVAVQASSAQRKVERGRRMKRTNCLLISIAIIFGVSWLPLNFFNLYADMERSPVTQSMLVRYAICH

MIGMSSACSNPLLYGWLNDNFRCNVQAAARKRRKLGAELSKGELKLLGPGGAQSGTAGGEGGLAATDFMTG

HHEGGLRSAITESVALTDHNPVPSEVTKLMPR

The following DNA sequence for DmGPCR4 (SEQ ID NO:7) was identified in *D. melanogaster*:

ATGGAGAACACCACAATGCTGGCTAATATTAGCCTAAATGCAACCAGAAA

TGAGGAGAATATCACCTCATTCTTCACCGACGAAGAGTGGCTGGCCATCA

ATGGCACTTTGCCGTGGATAGTGGGATTCTTCTTCGGCGTCATCCCCATC

ACGGGATTCTTCCGCAACCTGCTGGTCATCCTGGTGGTGGTCTTCAACAA

CAACATGCGCTCCACCACCAACCTGATGATTGTCAATCTGGCTGCCGCTG

ATCTGATCTTCGTAATCCTCTGCATTCCCTTCACGGCCACCGATTACATG

GTGTACTACTGGCCATATGGAAGGTTCTGGTGCCGCAGTGTCCAGTACCT

GATTGTGGTGACCGCCTTCGCCTCCATCTACACGCTGGTGCTAATGTCCA

TCGATCGGTTCCTCGCGGTGGTTCATCCCATTCGCTCGCGGATGATGAGG

ACGGAGAACATTACCCTGATTGCCATCGTGACTCTGTGGATCGTGGTGCT

GGTCGTTTCGGTGCCACTGGCCTTCACCCACGACGTGGTGGTGGACTACG

ATGCAAAGAAGAACATCACCTACGGCATGTGCACCTTCACGACGAACGAC

TTCCTTGGTCCGCGCACCTACCAGGTCACCTTCTTCATCAGCTCCTACCT

GCTGCCCCTGATGATCATCAGCGGTCTCTACATGCGCATGATCATGCGGC

TCTGGCGCCAGGGAACCGGCGTCCGCATGTCCAAGCAGTCGCAGCGCCCT

CGCAAGCGGGTCACCCGACTCGTCGTCGTGGTGGTCATCGCCTTCGCCTC

GCTCTGGCTGCCTGTCCAGCTCATCCTGCTGCTCAAGTCACTGGATGTCA

TCGAGACCAACACCCTCACCAAGCTAGTCATCCAGGTCACCGCCCACACT

CTGGCCTACAGCAGCTCGTGTATCAATCCGCTGCTCTACGCCTTCCTCTC

CGAGAATTTCCGGAAGGCCTTCTATAAGGCCGTTAACTGCTCCTCTCGAT

ACCAGAACTACACATCTGATTTGCCGCCCCCCCGCAACACCTCCTGTCCC

AGGACCTCCACCACTGGACTCTA

The following amino acid sequence (SEQ ID NO:8) is the amino acid sequence for the protein encoded by the DNA sequence of SEQ ID NO:7:

MENTTMLANISLNATRNEENITSFFTDEEWLAINGTLPWIVCFFFGVIAITGFFGNLLVILVVVFNNNMRS

TTNLMIVNLAAADLMFVILCIPFTATDYMVYYWPYGRFWCRSVQYLTVVTAFASTYTLVLMSIDRFLAVVH

TABLE 4-continued

PIRSRMMRTENITLIAIVTLWIVVLVVSVPVAFTHDVVVDYDAKKNITYGMCTFTTNDFLGPRTYQVTFFI

SSYLLPLMIISGLYMRMIMRLWRQGTGVRMSKESQRGRKRVTRLVVVVVIAFASLWLPVQLILLLKSLDVI

ETNTLTKLVIQVTAQTLAYSSSCINPLLYAFLSENFRKAFYKAVNCSSRYQNYTSDLPPPRKTSCARTSTT

GL

The following DNA sequence for DmGPCR5a (SEQ ID NO:9) was identified
in D. melanogaster:

ATGCAGAATCGCAGTCACTTCGAGGCGGATCACTACGGCGACATCAGTTG

GAGCAATTGGAGCAACTGGAGCACCCCCCCGGCGTCCTTTTCTCGGCCA

TGAGCACCGTGCTCTCGGCCACCAACCATACGCCCCTGCCGGACTTTGGC

CAGGACCTCGCCCTATCCACCAGCTCCTTCAATCACAGCCAGACCCTATC

CACCGACCAGCCCGCCGTCGGGGACGTGGAAGACGCCGCCGAGGATGCGG

CGGCGTCCATGGACACGGGCTCGTTTGCATTTGTCCTCCCCTGGTGGCGT

CAGGTCCTCTGCAGCATCCTCTTCGGCGGCATCGTCATTGTCGCGACGGG

CGGTAACCTCATTGTTGTCTGGATCGTGATGACGACCAAGCGGATGCGCA

CGGTAACCAACTATTTCATAGTGAATCTCTCCATCCCGCACGCCATGGTG

TCCAGCCTAAACGTCACCTTCAACTACTACTATATCCTGGATACCGACTG

GCCCTTCGGCGAGTTCTACTGCAAGTTGTCCCAGTTCATCGCGATGCTAA

GCATCTGCGCCTCAGTGTTCACCCTAATGGCCATCTCCATCGACAGATAC

GTGGCCATCATCCGGCCACTGCAGCCGCGGATGAGCAAGCGGTGCAACCT

GGCCATCGCGGCGGTCATCTGGCTGGCCTCCACGCTCATCTCCTGCCCCA

TGATGATCATCTACCGCACGGAGGAGGTGCCGGTCCGCGGGCTCAGCAAC

CGCACGGTCTGCTACCCGGAGTGGCCCGATGGGCCCACCAATCACTCCAC

GATGGAGTCCCTCTACAACATCCTCATCATCATYCTAACCTACTTCCTGC

CCATCGTCTCCATGACGGTCACCTACTCGCGCGTGGGCATCGAGCTCTGG

GGATCCAAGACCATCGGCGAGTGCACGCCCCGCCAGGTGGARAAYGTGCG

GAGTAAGCCAAGGGTGGTGAAGATGATGATTGTGGTCGTCCTGATATTCG

CCATCTGCTGGCTGCCGTTCCACAGCTACTTCATAATCACATCCTGCTAC

CCGGCCATCACGGAGGCGCCCTTCATCCAGGAACTCTACCTGGCCATCTA

CTGGCTGGCCATGAGCAACTCCATGTACAATCCCATTATATACTGCTGGA

TGAATTCGCGCTTTCGCTATGGTTTCAAGATGGTCTTCCGCTGGTGCCTG

TTTGTGCGCGTGGGCACTGAACCCTTTAGTCGGCGGGAGAACCTGACATC

CCGGTACTCCTGCTCCGGTTCCCCGGATCACAATCGCATCAAGCGCAATG

ATACCCAGAAATCGATACTTTATACCTGTCCCAGCTCACCCAAGTCGCAT

CGAATTTCGCACAGCGGAACAGGTCGCAGTGCGACGCTGCGGAACAGTCT

GCCGGCGGAGTCACTGTCGTCCGGCGGATCTGGTGGTGGAGGGCACAGGA

AACGGTTGTCCTACCAGCAGGAAATGCAGCAGCGTTGGTCAGGACCCAAT

AGTGCCACCGCAGTGACCAATTCCAGCAGTACGGCCAACACCACCCAACT

GCTCTCCTG

The following amino acid sequence (SEQ ID NO:10) is the amino acid
sequence for the protein encoded by the DNA sequence of SEQ ID NO:9:

MENRSDFEADDYGDISWSNWSNWSTPAGVLFSAMSSVLSASNHTPLPDFGQELALSTSSFNHSQTLSTDQP

TABLE 4-continued

AVGDVEDAAEDAAASMETGSFAFVVPWWRQVLWSILFGGMVIVATGGNLIVVWIVMTTKRMRTVTNYFTVN

LSIADAMVSSLNVTFNYYYMLDSDWPFGEFYCKLSQFIAMLSICASVFTLMAISIDRYVAIIRPLQPRMSK

RCNLAIAAVIWLASTLISCPMMIIYRTEEVPVRGLSNRTVCYPEWPDGPTNHSTMESLYNILIIILTYFEP

IVSMTVTYSRVGIELWGSKTIGECTPRQVENVRSKRRVVKMMTVVVLIFAICWLPFHSYFIITSCYPAITE

APFIQELYLAIYWLAMSNSMYNPIIYCWMNSRFRYGFKMVFRWCLFVRVGTEPFSRRENLTSRYSCSGSPD

HNRIKRNDTQKSILYTCPSSPKSHRISHSGTGRSATLRNSLPAESLSSGGSGGGGHRKRLSYQQEMQQRWS

GPNSATAVTNSSSTANTTQLLS

The following DNA sequence for DmGPCR5b (SEQ ID NO:11) was identified
in D melanogaster:

ATGGAGAATCGCAGTGACTTCGAGGCGGATGACTACGGCGACATCAGTTG

GAGCAATTGGAGCAATTGGAGCAACTGGAGCACCCCCGCCGGCGTCCTTT

TCTCGGCCATGAGCAGCGTGCTCTCGGCCAGCAACCATACGCCTCTGCCG

GACTTTGGCCAGGAGCTCGCCCTATCCACCAGCTCCTTCAATCACAGCCA

GACCCTATCCACCGACCTGCCCGCCGTCGGGGACGTGGAAGACGCGGCCG

AGGATGCGGCGGCGTCCATGGAGACGGGCTCGTTTGCATTTGTGGTCCCG

TGGTGGCGTCAGGTGCTCTGGAGCATCCTCTTCGGCGGCATGGTCATTGT

GGCGACGGCCGGTAACCTGATTGTTGTCTGGATCGTGATGACGACCAAGC

GGATGCGGACGGTAACCAACTATTTCATAGTAAATCTCTCCATCGCGGAC

GCCATGGTGTCCAGCCTGAACGTCACCTTCAACTACTACTACATGCTGGA

TAGCGACTGGCCCTTCGGCGAGTTCTACTGCAAGTTGTCCCAGTTCATCG

CGATGCTAAGCATCTGCGCCTCAGTGTTCACCCTAATGGCCATCTCCATC

GACAGATACGTGGCCATCATCCGGCCACTGCAGCCGCGGATGAGCAAGCG

GTGCAACCTGGCCATCGCGGCGGTCATCTGGCTGGCCTCCACGCTCATCT

CCTGCCCCATCATGATCATCTACCGCACGGAGGAGGTGCCGGTCCCCGGG

CTCAGCAACCGCACGGTCTGCTACCCGGAGTGGCCCGATGGGCCCACCAA

TCACTCCACGATGGAGTCCCTCTACAACATCCTCATCATCATTCTAACCT

ACTTCCTGCCCATCGTCTCCATGACGGTCACCTACTCGCGCGTGGGCATC

GAGCTCTGGGGATCCAAGACCATCGGCGAGTGCACGCCCCGCCAGGTGGA

GAATGTGCGGAGTAAGCGAAGGGTGGTGAAGATGATGATTGTGGTCGTCC

TGATATTCGCCATCTGCTGGCTGCCGTTCCACAGCTACTTCATAATCACA

TCCTGCTACCCGGCCATCACGGAGGCGCCCTTCATCCAGGAACTTTACCT

GGCCATCTACTGGCTGGCCATGAGCAACTCCATGTACAATCCCATTATAT

ACTGCTGGATGAATTCGCGCTTTCGCTATGGTTTCAAGATGGTCTTCCGC

TGGTGCCTGTTTGTGCGCGTGGGCACTGAACCCTTTAGTCGGCGGGAGAA

CCTGACATCCCGGTACTCCTGCTCCGGTTCCCCGGATCACAATCGCATCA

AGCGCAATGATACCCAGAAATCGATACTTTATACCTGTCCCAGCTCACCC

AAGTCGCATCGAATTTCGCACAGCGGAACAGGTCGCAGTGCGACGCTGAG

GAACAGTCTGCCGGCGGAGTCATTGTCGTCCGGTGGATCTGGAGGTGGAG

GACACAGGAAACGGTTGTCCTACCAGCAGGAAATGCAGCAGCGGTGGTCA

GGACCCAATAGTGCCACCGCAGTGACCAATTCCAGCAGTACGGCCAACAC

TABLE 4-continued

```
CACCCAACTGCTCTCCTG
```

The following amino acid sequence (SEQ ID NO:12) is the amino acid
sequence for the protein encoded by the DNA sequence of SEQ ID NO:11:

```
MENRSDFEADDYGDISWSNWSNWSNWSTPAGVLFSAMSSVLSASNHTPLPDFGQELALSTSSFNHSQTLST

DLRAVGDVEDAAEDAAASMETGSFAFVVPWWRQVLWSILFGGMVIVATGGNLIVVWIVNTTKRMRTVTNYF

IVNLSIADAMVSSLNVTFNYYYMLDSDWPFGEFYCKLSQFIAMLSICASVFTLMAISIDRYVAIIRPLQPR

MSKRCNLAIAAVIWLASTLISCEMMIIYRTEEVPVRGLSNRTVCYPEWPDGPTNHSTMESLYNILIIILTY

FLPIVSMTVTYSRVGIELWGSKTIGECTFRQVENVRSKRRVVKMMIVVVLIFAICWLPFHSYFIITSCYPA

ITEAPFIQELYLAIYWLAMSNSMYNPIIYCWMNSRFRYGFKMVFRWCLFVRVGTEPPFSRRENLTSRYSCSG

SPDHNRTKRNDTQKSILYTCPSSPKSHRISHSGTGRSATLRNSLPAESLSSGGSGGGGHRKRLSYQQEMQQ

RWSGENSATAVTNSSSTANTTQLLS
```

The following DNA sequence for DmGPCR6aL (SEQ ID NO:13) was identified
in *D. melanogaster*:

```
ATGGACCACCACAATAGCCATCTCTTGCCTGGTGCCACCGAGAAGATGTA

CTACATAGCTCACCAGCAGCCGATGCTGCCGAACGAGGATGATAACTACC

AGGAGGGGTACTTCATCAGGCCGGACCCTGCATCCTTACTTTACAATACC

ACCGCACTGCCAGCGCACGATGAAGGGTCCAACTATGGATATGGCTCCAC

CACAACGCTCAGTGGCCTCCAGTTCGAGACCTATAATATCACTGTGATGA

TCAACTTTACCTGTGACGACTATGACCTTCTATCGGAGGACATGTGGTCT

AGTGCCTACTTTAAGATCATCGTCTACATGCTCTACATTCCCATCTTTAT

CTTCGCCCTGATCGGCAACGGAACGGTCTGCTATATCGTCTATTCCACAC

CTCGCATGCCCACGGTCACCAATTACTTTATAGCCAGCTTGGCCATCGGC

GACATCCTGATGTCCTTCTTCTGCGTTCCGTCGTCCTTCATCTCGCTGTT

CATCCTGAACTACTGGCCTTTTGGCCTGCCCCTCTGTCACTTTGTGAACT

ACTCGCAGGCGGTCTCAGTTCTGGTCAGCGCCTATACTTTGGTGGCAATT

AGCATTGACCGCTACATAGCCATTATGTGGCCATTAAAGCCACGCATCAC

AAAACGCTATGCCACCTTCATCATCGCCGGCGTTTGCTTTATTGCACTTG

CCACCGCACTTCCCATACCCATCGTCTCTCGACTCGACATCCCAATGTCG

CCGTGGCACACGAAATCCGAGAAATACATTTGCCGCGAAATGTGGCCGTC

GCGGACCCAGGAGTACTACTACACCCTGTCCCTCTTCGCGCTGCAGTTCC

TCGTGCCGCTGGGCGTGCTCATCTTCACCTACGCCCGGATCACCATTCGC

GTCTGGGCGAAACCACCGCCACCCCAGGCGGAAACCAACCGCGACCAGCG

CATGGCACGCTCCAAACGCAAGATGGTCAAAATGATGCTCACGGTTGTGA

TTGTGTTCACCTGCTGTTGGCTGCCCTTCAATATTTTCCAGCTTTTACTG

AACGACGAGGAGTTCCCCCACTGCGATCCTCTGCCCTATGTATGCTTCGC

GTTTCACTCCCTGGCCATGTCGCACTGCTGCTACAATCCGATCATCTACT

GCTACATGAACGCCCGTTTCAGGAGCCGATTCGTCCAGCTGATGCACCGT

ATGCCCGGCCTGCGTCGCTGGTGCTGCCTGCGGAGCGTCGGTGATCGCAT

GAACGCAACTTCCGGAACGGGTCCAGCACTTCCTCTCAATCGAATGAACA

CATCCACCACCTACATCACCGCTCGTCGAAAGCCACGAGCGACATCTTTG
```

TABLE 4-continued

CGAGCGAACCCATTATCATGCGGCGAGACGTCACCACTGCGGTA

The following amino acid sequence (SEQ ID NO:14) is the amino acid sequence for the protein encoded by the DNA sequence of SEQ ID NO:13:

MEHHNSHLLPGGSEKMYYIAHQQPMLRNEDDNYQEGYFIRPDPASLLYNTTALPADDEGSNYCYCSTTTLS

GLQFETYNITVMMNFSCDDYDLLSEDMWSSAYFKITVYMLYIPIFIFALIGNGTVCYIVYSTPRMRTVTNY

FIASLAIGDILMSFFCVPSSFISLFILNYWPFGLALCHFVNYSQAVSVLVSAYTLVAISTDRYIAIMWPLK

PRITKRYATFITAGVWFIALATALPIPIVSGLDIPMSPWHTKCEKYICREMWPSRTQEYYYTLSLFALQFV

VPLCVLIFTYARITIRVWAKRPPGEAETNRDQRMARSKRKMVKMMLTVVIVFTCCWLPFNILQLLLNDEEF

AHWDPLPYVWFAFHWLAMSHCCYNPIIYCYMNARFRSCPVQLMHRMPGLRRWCCLRSVGDRMNATSCTGPA

LPLNPMNTSTTYISARRKPRATSLPANPLSCGETSPLR

The following DNA sequence for DmGPCR6bL (SEQ ID NO:15) was identified in *D. melanogaster*:

ATGGAGCACCACAATAGCCATCTGTTGCCTGGTGGCAGCCACAACATGTA

CTACATACCTCACCAGCAGCCGATGCTGCGGAACGAGGATGATAACTACC

AGCAGGGGTACTTCATCACGCCGGACCCTGCATCCTTACTTTACAATACC

ACCGCACTGCCAGCGGACCATGAACGGTCCAACTATGGATATCCCTCCAC

CACAACGCTCAGTGGCCTCCAGTTCGAGACCTATAATATCACTGTGATGA

TCAACTTTACCTCTGACGACTATGACCTTCTATCGGAGCACATGTGCTCT

AGTGCCTACTTTAAGATCATCGTCTACATGCTCTACATTCCCATCTTTAT

CTTCGCCCTGATCGGCAACGGAACGGTCTGCTATATCGTCTATTCCACAC

CTCGCATCCCCACGGTCACCAATTACTTTATACCCAGCTTGCCCATCGGC

GACATCCTGATGTCCTTCTTCTGCGTTCCGTCGTCCTTCATCTCGCTGTT

CATCCTGAACTACTGCCCTTTTGGCCTGGCCCTCTGTCACTTTGTGAACT

ACTCGCAGGCCGTCTCAGTTCTGCTCACCGCCTATACTTTGGTGCCAATT

ACCATTGACCCCTACATACCCATTATGTGGCCATTAAAGCCACGCATCAC

AAAACGCTATGCCACCTTCATCATCGCCCGCGTTTCGTTTATTGCACTTG

CCACCGCACTTCCCATACCCATCGTCTCTGGACTCCACATCCCAATGTCG

CCGTGGCACACCAAATGCGAGAAATACATTTGCCGCGAAATGTGCCCCTC

GCGGACGCAGGAGTACTACTACACCCTGTCCCTCTTCGCGCTCCAGTTCG

TCGTGCCCCTGCGCGTCCTCATCTTCACCTACGCCCGCATCACCATTCGC

GTCTGGGCCAAACCACCGCCACGCGAGCCGGAAACCAACCCCCACCAGCG

GATGGCACGCTCCAAACCCAAGATCCTCAAAATGATGCTGACGGTTCTCA

TTGTGTTCACCTCCTGTTGGCTGCCCTTCAATATTTTGCAGCTTTTACTG

AACCACGACCACTTCCCCCACTCGGATCCTCTGCCCTATCTCTCCTTCGC

GTTTCACTCGCTGGCCATCTCCCACTGCTGCTACAATCCGATCATCTACT

GCTACATCAACGCCCCCTTTCACGAGCGCATTCGTCCAGCTGATCCACCGT

ATGCCCCGCCTGCGTCGCTCGTGCTCCCTGCGCACCCTCGGTCATCGCAT

GAACGCAACTTCCGCTGACATGACTACGAAGTACCATCCCCATGTCGGCC

ATGCCCTATTCCGGAAACCCAAAATATGCATTAGCAACCCGTCCACCACT

TCCTCTCAATCGAATGAACACATCCACCACCTACATCACCGCTCGTCCAA

AGCCACCACCGACATCTTTCCCAGCGAACCCATTATCATCCGGCCAGACG

TABLE 4-continued

```
TCACCACTGCCGTAGCTGTCATATCAAAAAATAAAACTCATTCACCGCTC

CGCCGATCGGGAAGCTCAGGTGGAACAGAAGCAAACATAAGAAGCACCGA

GTTTTG
```

The following amino acid sequence (SEQ ID NO:16) is the amino acid sequence for the protein encoded by the DNA sequence of SEQ ID NO:15:

```
MEHHNSHLLPGGSEKMYYIAHQQPMLRNEDDNYQEGYFIRPDPASLLYNTTALPADDEGSNYGYGSTTTLS

GLQFETYNITVMMNFSCDDYDLLSEDMWSSAYFKTIVYMLYIPIFIFALIGNGTVCYIVYSTPRMRTVTWY

FIASLAIGDILMSFFCVPSSFISLFTLNYWPFGLALCHFVNYSQAVSVLVSAYTLVAISIDRYIAIMWPLK

PRITKRYATFIIAGVWFTALATALPIPIVSGLDIPMSPWHTKCEKYICREMWPSRTQEYYYTLSLFALQFV

VPLGVLIFTYARITIRVWAKRPPGEAFTNRDQRMARSKRKMVKMMLTVVIVFTCCWLPFNILQLLLNDEEF

AHWDPLPYVWFAFHWLAMSHCCYNPIIYCYMNARFRSGFVQLNHRNPGLRRWCCLRSVGDRMNATSGEMTT

KYHRHVGDALFRKPKICIRNGSSTSSQSNEHIHHLHQRSSKATSDIFASEPIIMRRDVTTAVAVISKNKTD

SPVRRSGSSGGTEANIRSTEF
```

The following DNA sequence for DmGPCR7 (SEQ ID NO:17) was identified in *D. melanogaster*:

```
ATGGCAATGGACTTAATCGAGCAGGAGTCCCGCCTGGAATTCCTGCCCGG

AGCCGAGGAGGAAGCAGAATTTGAGCGTCTATACGCGGCTCCCGCTGAGA

TTGTGGCCCTGTTGTCCATTTTCTATGGGGGAATCAGTATCGTGGCCGTC

ATTGGCAACACTTTGGTCATCTGGGTGGTGGCCACGACCAGGCAAATGCG

GACCGTGACAAATATGTATATCGCTAATTTGGCTTTTGCCGATGTGATTA

TTGGCCTCTTCTGCATACCATTTCAGTTCCAGGCTGCCCTGCTGCAGAGT

TGGAACCTGCCGTGGTTCATGTGCAGCTTCTGCCCCTTCGTCCAGGCCCT

GAGTGTAAATGTCTCGGTATTCACGCTGACCGCCATTGCAATCGATCGGC

ATAGGGCCATCATTAATCCACTTAGGGCACGTCCCACCAAGTTCGTATCG

AACTTCATAATTGGTGGAATTTGGATGCTGGCCCTGCTATTTGCGGTGCC

CTTTGCCATTGCCTTTCGTGTGGAGGAGTTGACCGAAAGATTTCGCGAGA

ACAATGAGACCTACAATGTGACGCGGCCATTCTGCATGAACAAGAACCTA

TCCGATGATCAATTGCAATCCTTTCGCTACACCCTGGTTTTTGTGCAGTA

TCTGGTTCCATTCTGTGTCATCAGCTTTGTCTACATCCAGATGGCGGTAC

GATTGTGGGGCACACGTGCTCCTGGTAACGCACAGGATTCACGGGACATA

ACGCTGTTGAAAAACAAGAAGAAGGTCATCAAAATGCTGATTATCGTGGT

CATTATCTTTGGACTCTGCTGGCTGCCACTGCAGCTCTATAATATTCTGT

ATCTCACGATACCGGAAATCAACGACTACCACTTCATTAGCATCGTCTGG

TTTTGCTGCGATTGGCTGGCCATGAGCAATAGCTGCTACAATCCCTTTAT

TTATGGCATCTACAATGAAAAATTTAAGCGGGAATTCAACAAGCGATTTG

CGGCCTGTTTCTGCAAGTTCAAGACGAGCATGGACGCCCACGAAAGGACC

TTTTCGATGCACACCCGCGCCAGCTCCATAAGGTCAACCTACGCCAACTC

CTCGATGCGAATCCGGAGTAATCTCTTTGGTCCGGCGCGTGGTGGTGTCA

ACAATGGGAAGCCGGGCTTGCATATGCCGCGGGTGCATGGATCCGGTGCT

AACAGCGGCATTTACAACGGAAGTAGTGGGCAGAACAACAATGTCAATGG
```

TABLE 4-continued

CCAACATCATCAGCATCAAAGCGTGGTTACCTTTGCGGCCACTCCGGGTG

TTTCGGCACCAGGTGTTGGCGTTGCAATGCCGCCGTGGCGGCGAAACAAC

TTCAAACCTCTGCATCCGAACGTAATCGAATGCGAGGACGACGTGGCACT

CATGGAGCTGCCATCAACCACGCCCCCCAGCGAGGAGTTGGCATCCGGGG

CCGGAGTCCAGTTGGCCCTGCTAAGCAGGGAGAGCTCCAGCTGCATTTGC

GAACAGGAATTTGGCAGCCAAACCGAATGCGATGGCACCTGCATACTCAG

CGAGGTGTCGCGAGTCCACCTGCCCGGCTCGCAGGCGAAGGACAAGGATG

CGGGCAAGTCCTTGTGGCCAACCACTTTA

The following amino acid sequence (SEQ ID NO:18) is the amino acid sequence for the protein encoded by the DNA sequence of SEQ ID NO:17:

MAMDLIEQESRLEFLPGAEEEAEFERLYAAPAEIVALLSIFYGGISIVAVIGNTLVIWVVATTRQMRTVTN

MYIANLAFADVTIGLPCIPFQFQAALLQSWNLPWFMCSFCPFVQALSVNVSVFTLTAIAIDRHRAIINPLR

ARPTKFVSKFIIGGIWMLALLFAVPFAIAFRVEELTERFRENNETYNVTRPFCMNKNLSDDQLQSFRYTLV

FVQYLVPFCVISFVYIQMAVRLWGTRAPGNAQDSRDITLLKNKKKVIKMLIIVVIIFGLCWLPLQLYNILY

VTIPEINDYRFISIVWFCCDWLAMSNSCYNPFIYGIYNEKFKREFNKRFAACFCKFKTSMDAHERTFSMHT

RASSTRSTYANSSMRIRSNLFGPARGGVNNGKPGLHMPRVHGSGANSGIYNGSSGQNNNVNGQHHQHQSVV

TFAATPGVSAPGVGVAMPPWRRNNFKPLHPNVIECEDDVALMELPSTTPPSEELASGAGVQLALLSRESSS

CICEQEFGSQTECDGTCTLSEVSRVHLPGSQAKDKDAGKSLWQPL

The following DNA sequence for DmGPCR8 (SEQ ID NO:19) was identified in *D. melanogaster*:

ATGTTTACGTGGCTGATGATGGATGTCCTCCAGTTTGTGAAAGGGGAAAT

GACAGCCGATTCAGAGGCAAATGCCACAAATTGGTATAACACGAACGAGA

GCTTATATACCACGGAACTGAACCATAGATGGATTAGTGGTAGTTCCACA

ATTCAGCCAGAGGAGTCCCTTTATGGCACTGATTTGCCCACCTATCAACA

TTGCATAGCCACGCGGAATTCCTTTGCTGACTTGTTCACTGTGGTGCTCT

ACGGATTTGTGTGCATTATCGGATTATTTGGCAACACCCTGGTGATCTAC

GTCCTGTTGCGCTTTTCCAAAATGCAAACGGTCACGAATATATATATCCT

GAATCTGGCGGTGGCAGACGAGTGCTTCCTGATTGGAATACCCTTTCTGC

TGTACACAATGCGAATTTGCAGCTGCCCATTCGGGGAGTTTATGTGCAAA

GCCTACATGGTGACCACATCCATCACCTCCTTCACCTCGTCGATTTTTCT

GCTCATCATCTCCGCGGATCCATATATAGCGGTATGCCACCCGATTTCCT

CGCCACGATATCGAACTCTGCATATTGCCAAAGTGCTCTCAGCGATTGCC

TGGTCAACTTCACCGGTCCTCATGCTGCCCGTGATCCTTTATGCCAGCAC

TGTGGAGCAGGAGGATGGCATCAATTACTCGTGCAACATAATGTGGCCAG

ATGCGTACAAGAAGCATTCGGGCACCACCTTCATACTGTACACATTTTTC

CTAGGATTCGCCACACCGCTGTGCTTTATCCTGAGTTTCTACTACTTGGT

TATAAGGAAACTGCGATCCCTGGGTCCCAAACCAGCAACCAAGTCCAACG

AGAAGAGGCGGGCTCACAGGAAGGTCACTCCACTGGTACTGACGGTCATA

AGTGTATACATTCTATGTTGGCTCCCTCACTGGATTTCTCAGGTGGCCCT

GATTCACTCGAATCCCGCGCAAACGGACCTCTCCCGACTCCAAATACTCA

TTTTCCTACTTCTGGCGCCACTGGTTTACTCGAATTCGGCGGTGAATCCC

TABLE 4-continued

```
ATACTTTATGCCTTCCTAAGTGAGAACTTCCGCAAGAGCTTCTTCAAGGC

CTTTACCTGTATGAATAAGCAGGATATCAACCCTCAACTCCAGCTGGAGC

CCAGTGTTTTCACCAAACAGCGCAGTAAAAAGAGGGGTGGCTCCAAGCGC

CTGTTGACCAGCAATCCGCAGATTCCTCCACTGCTGCCACTGAATGCGGG

TAACAACAATTCATCGACCACCACATCCTCGACCACGACAGCGGAAAAGA

CCGGAACCACGGGGACACAGAAATCATGCAATTCCAATCGCAAAGTGACA

GCTCCGCCGGAGAATTTCATTATATGTTTGAGCCAGCAGCAGGAGGCATT

TTGCACCACCGCGAGAAGAGGATCGCGCCCAGTGCAGCACACAGATTTGT

A
```

The following amino acid sequence (SEQ ID NO:20) is the amino acid sequence for the protein encoded by the DNA sequence of SEQ ID NO:19:

```
MFTWLMMDVLQFVKDEMTADSEANATNWYNTNESLYTTELNHRWISDSSTIQPEESLYCTDLPTYQHCIAT

RNSFADLFTVVLYGFVCIIGLFGNTLVIYVVLRFSKMQTVTNIYILNLAVADECFLICIPFLLYTMRICSW

RFGEFMCKAYMVSTSITSFTSSIFLLIMSADRYIAVCHPISSPRYRTLHIAKVVSAIAWSTSAVLMLPVTL

YASTVEQEDGINYSCNIMWPDAYKKHSGTTFILYTFFLGFATPLCFILSFYYLVIRKLRSVGPKPGTKSKE

KRRAHRKVTRLVLTVISVYILCWLPHWISQVALIHSNPAQRDLSRLETLTFLLLGALVYSNSAVNPILYAF

LSENFRKSFFKAFTCMNKQDINAQLQLEPSVFTKQGSKKRGGSKRLLTSNPQIPPLLPLNAGNNNSSTTTS

STTTAEKTGTTCTQKSCNSNGKVTAPPENLIICLSEQQEAFCTTARRGSGAVQQTDL
```

The following DNA sequence for DmGPCR9 (SEQ ID NO:21) was identified in *D. melanogaster*:

```
ATGTTCAACTACGAGGAGGCGGATGCCGACCAGGCGGCCATGGCTGCAGC

GGCTGCCTATAGGCCACTGCTCGACTACTATGCCAATCCGCCAAGTGCGG

CGGCTCACATAGTGTCCCTCAACGTGGCACCCTACAATGGAACTGGAAAC

GGAGGCACTGTCTCCTTGGCGGGCAATCCCACAACCAGCTATGGCGATGA

TGATAGGCATGCCTATATGGACACCGACCCCAGTGACCTGGTCACCGAAC

TGGCCTTCTCCCTGGGCACCACTTCAAGTCCAAGTCCCAGTTCCACACCC

GCTTCCAGCTCCAGTACTTCCACTGGCATGCCCGTCTGCCTGATACCCAG

CTATAGCATGATTCTGCTGTTCGCCGTGCTGGGCAACCTGCTGGTCATCT

CGACGCTGGTGCAGAATCGCCGGATGCCTACCATAACCAACGTGTTCCTG

CTCAACCTCGCCATATCGGACATCCTGCTCGGCGTGCTCTGCATGCCCGT

CACCCTGCTGGGCACCCTGCTGCGAAACTTCATCTTTCGCGAGTTCCTCT

GCAAGCTCTTTCAGTTCTCGCAAGCCGCCTCCGTGCCCGTTTCGTCCTGG

ACCTTGGTGGCCATATCCTGTGAGCGCTACTACGCGATATGCCATCCACT

GCGCTCGCGATCCTGGCAGACAATCACTCACCCCTACAAGATCATCGGCT

TCATCTCGCTGGGCGGCATCCTCTGCATGACGCCCATAGCGGTCTTTAGT

CAATTGATACCCACCACTCGACCGGGCTACTGCAACTCCCCTCAGTTTTG

GCCCGACCACCGATACGAGCTCTTCTACAACATCCTGCTGGACTTCCTGC

TGCTCGTCCTGCCGCTTCTCGTCCTCTGCGTGGCCTACATCCTCATCACG

CCTACCCTGTACGTAGGCATCCCCAAGGACAGCGGACCCATCCTCCACCA

ATCGCTGCCTGTTTCCCCTACAACGGCCGGCCGAACCCCACCCAATCCGG
```

TABLE 4-continued

```
GCACCAGCACCAGTAGTAACTGCATCCTCCTCCTGACCGCCACCGCAGTC

TATAATCAAAATAGTAACAATAATAATGGAAATTCAGAGGGATCCCCACC

CCCAGGATCAACCAATATCGCAACGACCACCTTGACAACCACACCAACGG

CTCCAACTGTGATCACCACCACCACGACGACCACCCTCACCCTGGCCAAG

ACCTCCTCGCCCACCATTCGCGTCCACGATGCGGCACTTCGCAGGTCCAA

CGAGGCCAAGACCCTGGAGAGCAAGAACCCTCTGCTCAAGATGCTGTTCG

TCCTGGTCCTGGAGTTTTTCATCTCCTGGACTCCGCTGTACGTGATCAAC

ACGATCCTCATGCTGATCGGACCCGTGGTGTACGAGTATGTCCACTACAC

CCCCATCAGTTTCCTCCACCTGCTGGCCTACTCATCCACCTGCTGCAATC

CCATCACCTACTCCTTCATGAACGCCAGCTTCCCCCGCCCCTTTGTCGAC

ACCTTCAAGCCTCTGCCCTGGCGTCGTGCACCAGCTGCCAGCGGAGGCGT

CGGTCCTCCTGCTGGTGGAGCACTCTCCGCCAGCCAGGCGGGCGCAGCCC

CGGGCCCCTATGCGAGTGCCAACACCAACATTAGTCTCAATCCCGGCCTA

CCCATGGGTATGGGCACCTCCCGCAGTCGCTCACGCCACCAGTTTCTCAA

TGCGGTGGTGACCACCAATAGTGCCGCCGCCGCCGTCAACACTCCTCAGC

TCTA
```

The following amino acid sequence (SEQ ID NO:22) is the amino acid sequence for the protein encoded by the DNA sequence of SEQ ID NO:21:

```
MFNYEEGDADQAAMAAAAAYRALLDYYANAPSAAGHIVSLNVAPYNGTGNGGTVSLAGNATSSYGDDDRDG

YMDTEPSDLVTELAFSLGTSSSPSPSSTPASSSSTSTCMPVWLIPSYSMILLFAVLGNLLVISTLVQNRRM

RTITNVFLLNLAISDMLLGVLCMPVTLVGTLLRNFIFGEFLCKLFQFSQAASVAVSSWTLVAISCERYYAI

CHPLRSRSWQTISHAYKIIGFIWLGGILCMTPIAVFSQLIPTSRPGYCKCREFWPDQGYELFYNILLDFLL

LVLPLLVLCVAYILITRTLYVGMAKDSGRILQQSLPVSATTAGGSAPNPGTSSSSNCILVLTATAVYNENS

NNNNGNSEGSAGGGSTNMATTTLTTRPTAPTVITTTTTTVTLAKTSSPSIRVHDAALRRSNEAKTLESKK

RVVKMLFVLVLEFFICWTPLYVINTMVMLIGPVVYEYVDYTAISFLQLLAYSSSCCNPITYCFMNASFRRA

FVDTFKGLPWRRGAGASGGVGGAAGGGLSASQAGAGPGAYASANTNTSLNPGLAMGMGTWRSRSRHEFLNA

VVTTNSAAAAVNSPQL
```

The following DNA sequence for DmGPCR10 (SEQ ID NO:23) was identified in *D. melanogaster*:

```
ATGTACGCCTCCTTGATGGACGTTGGCCAGACGTTGGCAGCCAGGCTGGCGGATAGCGAC

GGCAACGGGGCCAATGACAGCGGACTCCTGGCAACCGGACAAGGTCTGGAGCAGGAGCAG

GAGGGTCTGGCACTGCATATGGGCCACAATGCCAGCGCCGACGGCGGAATAGTACCGTAT

GTGCCCGTGCTGGACCGCCGGAGACGTACATTGTCACCGTGCTGTACACGCTCATCTTC

ATTGTGGGAGTTTTGGGCAACGGCACGCTGGTCATCATCTTCTTTCGCCACCGCTCCATG

CGCAACATACCCAACACATACATTCTTTCACTGGCCCTGGCTGATCTGTTGGTTATATTG

GTGTGTGTACCTGTGGCCACGATTGTCTACACGCAGGAAAGCTGGCCCTTTGAGCGGAAC

ATGTGCCGCATCAGCGAGTTCTTTAAGGACATATCCATCGGGGTGTCCGTGTTTACACTG

ACCGCCCTTTCCGGCGAGCGGTACTGCGCCATTGTAAATCCCCTACGCAAGCTTCAGACC

AAGCCGCTCACTGTCTTTACTGCGGTGATGATCTGGATCCTGGCCATCCTACTGGGCATG

CCTTCGCTTCTTTTCTCCGACATCAAGTCCTACCCTGTGTTCACAGCCACCGGTAACATG

ACCATTGAAGTGTGCTCCCCATTTCGCGACCCGGAGTATGCAAAGTTCATGGTGGCGGGC
```

TABLE 4-continued

```
AAGGCACTGGTGTACTACCTGTTGCCGCTGTCCATCATTGGGGCGCTATACATCATGATG

GCCAAGCGGCTCCATATGAGCGCCCGCAACATGCCCGGCGAACAGCAGAGCATGCAGAGC

CGCACCCAGGCTAGGGCCCGACTCCATGTGGCGCGCATGGTGGTAGCATTCGTGGTGGTG

TTCTTCATCTGCTTCTTCCCGTACCACGTGTTTGACCTGTGGTACCACTTCTACCCAACG

GCTGAGGAGGACTTCGATGAGTTCTGGAACGTGCTGCGCATCCTTCCTAAACTCGTGCGT

CAACCCCGTGGCCTCTACTGCGTGTCCGGGGTGTTTCGGCAGCACTTTAATCGCTACCTC

TGCTGCATCTGCGTCAAGCGGCAGCCGCACCTGCGGCAGCACTCAACGGCCACTGGAATG

ATGGACAATACCAGTGTGATGTCCATGCGCCGCTCCACGTACGTGGGTGGAACCGCTGGC

AATCTGCGGGCCTCGCTGCACCGGAACAGCAATCACGGAGTTGGTCGAGCTGGAGGTGGA

GTAGGAGGAGGAGTAGCGTCAGGTCGTGTGGGCAGCTTTCATCGGCAGGACTCGATGCCC

CTGCAGCACGGAAATGCCCACGGAGGTGGTGCGGCGGGGGATCCTCCGGACTTGGAGCC

GGCGGGCGGACGGCGGCAGTGAGCGAAAAGAGCTTTATAAATCGTTACGAAAGTGGCGTA

ATGCGCTACTAA
```

The following amino acid sequence (SEQ ID NO:24) is the amino acid sequence for the protein encoded by the DNA sequence of SEQ ID NO:23:

```
MYASLMDVGQTLAARLADSDGNGANDSGLLATGQGLEQEQEGLALDMGHNASADGGIVPYVPVLDRPETYI

VTVLYTLIFIVGVLGNCTLVIIFFRHRSMRNIPNTYILSLALADLLVILVCVPVATIVYTQESWPFERNMC

RISEFFKDISIGVSVFTLTALSCERYCAIVNPLRKLQTKPLTVFTAVMIWILAILLGMPSVLFSDIKSYPV

FTATGNMTIEVCSPFRDPEYAKFMVAGKALVYYLLPLSIIGALYIMMAKRLHMSARNMPGEQQSMQSRTQA

RARLHVARMVVAFWVVFFICFFPYHVFELWYHFYPTAEEDFDEFWNVLRILPKLVRQPRGLYCVSGVFRQH

FNRYLCCICVKRQPHLRQHSTATGMMDNTSVMSMRRSTYVGGTAGNLRASLHRNSNHGVGGAGGGVGGGVG

SCRVGSFHRQDSMPLQHGNAHGGGAGGGSSGLGAGGRTAAVSEKSFINRYESGVMRY
```

In accordance with the Budapest Treaty, clones of the present invention have been deposited at the Agricultural Research Culture Collection (NRRL) International Depository Authority, 1815 N. University Street, Peoria, Ill. 61604, U.S.A. Accession numbers and deposit dates are provided below in Table 5.

TABLE 5

| Clone | NRRL Accession No. | Date of Deposit |
|---|---|---|
| DmGPCR1 (SEQ ID NO:1) | NRRL B-30347 | 19 Oct. 2000 |
| DmGPCR2a (SEQ ID NO:3) | NRRL B-30348 | 19 Oct. 2000 |
| DmGPCR4 (SEQ ID NO:7) | NRRL B-30349 | 19 Oct. 2000 |
| DmGPCR5a (SEQ ID NO:9) | NRRL B-30350 | 19 Oct. 2000 |
| DmGPCR6aL (SEQ ID NO:13) | NRRL B-30351 | 19 Oct. 2000 |
| DmGPCR6bL (SEQ ID NO:15) | NRRL B-30352 | 19 Oct. 2000 |
| DmGPCR7 (SEQ ID NO:17) | NRRL B-30353 | 19 Oct. 2000 |
| DmGPCR8 (SEQ ID NO:19) | NRRL B-30354 | 19 Oct. 2000 |
| DmGPCR9 (SEQ ID NO:21) | NRRL B-30355 | 19 Oct. 2000 |

The invention is further illustrated by way of the following examples which are intended to elucidate the invention. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

It is intended that each of the patents, applications, and printed publications mentioned in this patent document be hereby incorporated by reference in their entirety.

EXAMPLES

Example 1

Identification of DmGPCRs

A Celera genomic *D. melanogaster* database was converted to a database of predicted proteins and a mRNA database using a variety of gene finding software tools to predict the mRNAs that would be generated (the "PnuFly-Pep" database). Procedures for analyzing genomic databases using gene-finding software tools are known to those skilled in the art.

The nucleotide sequences of several *C. elegans* FaRP GPCRs were used as query sequences against the mRNA database described above. This database was searched for regions of similarity using a variety of tools, including FASTA and Gapped BLAST (Altschul et al., *Nuc. Acids Res.*, 1997, 25, 3389, which is incorporated herein by reference in its entirety).

Briefly, the BLAST algorithm, which stands for Basic Local Alignment Search Tool is suitable for determining sequence similarity (Altschul et al., *J. Mol. Biol.*, 1990, 215, 403-410, which is incorporated herein by reference in its entirety). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T, and X determine the sensitivity and speed of the alignment. The Blast program uses as defaults a word length (W) of 11, the BLOSUM62 scoring matrix (see Henikoff et al., *Proc. Natl. Acad. Sci. USA,* 1992, 89, 10915-10919, which is incorporated herein by reference in its entirety) alignments (B) of 50, expectation (E) of 10, M=5, N=4, and a comparison of both strands.

The BLAST algorithm (Karlin et al., *Proc. Natl. Acad. Sci. USA,* 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a DmGPCR gene or cDNA if the smallest sum probability in comparison of the test nucleic acid to a DmGPCR nucleic acid is less than about 1, preferably less than about 0.1, more preferably less than about 0.01, and most preferably less than about 0.001.

The mRNAs corresponding to the predicted proteins were retrieved from the database of predicted mRNAs used to prepare the PnuFlyPep database. These are identified as the following nucleotide sequences: SEQ ID NOs: 1, 3, 5, 7, 9, 11, 13, 15, 17, 19, 21, and 23, each having a statistically significant overlapping homology to the query sequence. The nucleotide sequences SEQ ID NOs: 3, 5, 9, 11, 13, and 15 (corresponding to DmGPCRs 2a, 2b, 5a, 5b, 6a, and 6b) were obtained from PCR cloning and sequencing of another identified sequence (not shown). Each of these sequences represents a splice variant of a DmGPCR gene.

Example 2

Cloning of DmGPCRs cDNA Preparation cDNA was prepared from either adult *Drosophila melanogaster* poly A⁺ RNA (Clontech Laboratories, Palo Alto, Calif.) or adult *Drosophila melanogaster* total RNA (below). To obtain total RNA, parent stocks of *Drosophila melanogaster* (Biological Supply Company, Burlington, N.C.) were anesthetized by chilling, and 5 to 6 adults were added to a culture vessel containing 10 ml $H_2O$, 10 ml Formula 4-24 Instant *Drosophila* Medium, and 6 to 10 grains of active dry yeast (Biological Supply Company). A polyurethane foam plug was placed at end of each vessel, and flies were incubated at room temperature (RT) for 4 to 6 weeks. At maturity, the vessels were chilled, and the anesthetized flies were poured into a 50 ml polypropylene tube held in liquid $N_2$. The frozen flies were stored at −70° C. until they were ground with a mortar and pestle in the presence of liquid $N_2$. The powdered tissue along with some liquid $N_2$ was decanted into 50 ml polypropylene tubes on dry ice. Following evaporation of the liquid $N_2$, the powdered tissue was stored at −70° C.

To prepare RNA, 300 mg of powdered tissue was placed into polypropylene tubes on dry ice, and 5 ml of 6 M guanidine hydrochloride in 0.1 M NaOAc, pH 5.2 was added. All solutions were either treated with DEPC, or prepared with DEPC-treated $dH_2O$, and all glassware was baked, or virgin plastic labware was used, to reduce problems with RNase contamination. Tubes were vortex-mixed then placed on ice. The powdered tissue was homogenized by successive passage through 20, 21, and 22 gauge needles. The tubes were centrifuged (1000×g for 10 min), then 2.5 to 3 ml of supernatant was layered on top of 8 ml 5.7 M cesium chloride in 0.1 M NaOAc contained in 14×95 mm Ultra-Clear centrifuge tubes (Beckman Instruments, Inc., Palo Alto, Calif.). The samples were centrifuged at 25000 rpm for 18 h at 18° C. in an L8-70 ultracentrifuge (Beckman Instruments, Inc.,). The supernatant was decanted, and the tube was inverted and allowed to drain. The RNA pellet was suspended in 200 µl of RNase-free $dH_2O$ (Qiagen Inc., Valencia, Calif.), then rinsed twice with 100 µl RNase-free $dH_2O$ (total, 400 µl). The RNA was precipitated by the addition of 44 µl of 3M NaOAc, pH 5.2, and 1 ml cold 100% ethanol. Following overnight storage at −70° C., the tube was centrifuged at 14000 rpm for 1 h (Eppendorf microfuge 5402), rinsed with 75% ethanol (prepared with DEPC-treated $dH_2O$), then the pellet was dissolved in RNase-free $dH_2O$. Absorbances at 260 or 280 nm determined in 10 mM Tris-HCl, pH 7.5 were used to estimate RNA concentration and purity.

First-strand cDNA was prepared according to the procedure supplied with the Superscript II enzyme (GIBCO BRL, Rockville, Md.). Either 500 ng (2 µl) of poly A⁺ RNA or 3 µg (4 µl) of total RNA was added to microfuge tubes containing RNase-free $dH_2O$ and 250 ng (2.5 µl) random primers. The tubes (12 µl) were incubated at 70° C. for 10 min, chilled on ice, then 4 µl of 5× first strand buffer, 2 µl of 0.1 M DTT, and 1 µl of 10 mM dNTP mix were added. Following incubation at 25° C. for 10 min, then at 42° C. for 2 min, 1 µl (200 units) of Superscript II was added, and incubation continued at 42° C. for 50 min. The enzyme was inactivated by incubation at 70° C. for 15 min. To remove RNA complimentary to the cDNA, 2 µl (2 units) of RNase H (Boehringer Mannheim, Indianapolis, Ind.) was added, followed by incubation at 37° C. for 20 min. The cDNA was stored at −20° C.

PCR Reactions

Either a standard 50/100 µl PCR reaction or Hot Start PCR Reaction, using Ampliwax beads (Perkin Elmer Cetus, Norwalk, Conn.) was used to amplify the *Drosophila melanogaster* G protein-coupled receptors (DmGPCRs). Distilled $H_2O$ was used to dissolve the primers (Genosys Biotechnologies, Inc., The Woodlands, Tex.): 5'- and 3'-primers at 10 µM concentrations, internal primers at 1 µM. Each PCR reaction contained 2 to 4 units of rTth XL DNA polymerase, 1.2 to 1.5 mM $Mg(OAc)_2$, 200 µM each dNTP, and 200 or 400 nM each primer. For Hot Start PCR, 32 or 36 µl 'lower' cocktail (dH$_2$O, 3.3× XL-buffer, dNTP and Mg(OAc)$_2$ was added to 2 or 4 µl of each primer (total volume, 40 µl). An Ampliwax bead (Perkin Elmer Cetus) was added, tubes incubated at 75° C. for 5 min, cooled at room temperature (RT), then 60 µl 'upper' cocktail (dH$_2$O, 3.3× XL-buffer, rTth and template) was added. PCR amplifications were performed in a Perkin Elmer Series 9600 thermal cycler. The typical program for the thermal cycler included: 1 min at 94° C., followed by 30 cycles of amplification (0.5 min at 94° C., 0.5 min at 60° C., 2 min at 72° C.), followed by 6 min at 60° C. In order to create 3' A-overhangs on the PCR product ('tailing'), 1 µl Taq polymerase (Invitrogen, Carlsbad, Calif.) was added at the end of the PCR amplification, and tubes incubated at 72° C. for 10 min. The reaction mixtures were analyzed on 1% agarose gel prepared in TAE buffer (5). PCR products were typically purified using QIAquick spun columns (QIAGEN).

Ligation and Transformation

Ligation of all PCR products into PCR 3.1 vector (Invitrogen) and transformation of the ligated products into One Shot™ TOP10F' competent cells (Invitrogen) were done according to the manufacturer's directions. Transformants to be screened for inserts were propagated in LB broth containing 50 µg ampicillin/ml. Colonies with inserts were identified either by a boiling-lysis plasmid mini-prep procedure (5) or by a 'colony PCR' procedure that directly amplified the plasmid DNA from the transformed bacteria (6).

DNA Sequencing

DNA for sequencing was prepared using Qiagen anion-exchange plasmid kits (QIAGEN-tip 20) to isolate the DNA from 5 ml LB cultures grown at 37° C. overnight as per the manufacturer's directions. Four primers (T7, M13 reverse, 'sense' and 'antisense') were typically used for sequencing each DNA (Table 6). Dye-terminator sequencing chemistry was used, either the BigDye™ Terminator reagents (Applied Biosystems, Foster City, Calif.) or DYEnamic™ ET terminator kit (Amersham Pharmacia Biotech, Inc., Piscataway, N.J.). Manufacturer's recommendations were followed for preparation of the sequencing reactions. Primers and unincorporated nucleotides were removed using Centri-Sep spun columns (Princeton Separations, Adelphia, N.J.). Sequencing reactions were analyzed on an Applied Biosystems 377 automated DNA sequencer. DNA sequences were assembled and analyzed using Sequencher (Gene Codes, Ann Arbor, Mich.), the GCG group of sequence analysis programs (Wisconsin Package Version 10.1, Genetics Computer Group (GCG), Madison, Wis.), and functions available through the Vector NTI 5.5 suite of programs (Informax, Bethesda, Md.).

TABLE 6

DNA Sequencing Primers

| | DmGP | | Internal Primers | |
|---|---|---|---|---|
| CR | 5'Primer | 3'Primer | Sense | Antisense |
| 1 | VGS28-gtagccgccATGGCC AACTTAAGCTGGCTGA GCAC (SEQ ID NO 184) | VGS29-gtaTCAGTTGATT CGCCTCCCCAGCTCT (SEQ ID NO 185) | VGS49-TGCAGCATCTAC ATATCCACGCTGA (SEQ ID NO:186) | VGS50-GATTGGCG ACACGGCACCCGT GCCA (SEQ ID NO:187) |
| 2 | VGS30-gtagccgccATGTCA CTACCCAGCTGGCTAAC AGA (SEQ ID NO 188) DEL1937-gccgccATGAAT CAGACGGAGCCCGCCC AGC (SEQ ID NO 189) | VGS31gtaTTACCGCGG ATCAGCTTGGTGACC (SEQ ID NO:190) | VGS59-GTACGGCGTGCT AATCGTCTTCGGC (SEQ ID NO:191) | VGS60-ATTGCGAG CAGTGCGCATGAT GGGC (SEQ ID NO:192) |
| 3 | DEL1840-gccgccATGTCG GAGATTGTCGACACCG AGC (SEQ ID NO 193) | DEL1860-TTCCAGTGGC AGGACAGATCGGGAT (SEQ ID NO:194) | VGS65-ATGTGGCCAGAT GGACGATATCCCA (SEQ ID NO:195) | VGS66-CAATCATG GGAATGCCCGTAG TCAG (SEQ ID NO:196) |
| 4 | DEL1933-gccgccATGGAG AACACCACAATGCTGG CTA (SEQ ID NO:197) | DEL1934-TTAGAGTCCA GTGGTGGAGGTCCTG (SEQ ID NO:198) | VGS47-GCCATCATCCGG CCACTGCAGCCGC (SEQ ID NO 199) | VGS48-AATGGGAT TGTACATGGAGTT GCTC (SEQ ID NO 200) |
| 5 | DEL1844-gccgccATGGAG AATCGCAGTGACTTCG AGGC (SEQ ID NO:201) | DEL1845-tctagaTCAGGAG AGCAGTTGGGTGGTGTT GGC (SEQ ID NO 202) | DEL1891-ATCTCCATCG ACAGATACGT (SEQ ID NO:203) | DEL1892-GCCGCGA TGGCCAGGTTGCA (SEQ ID NO:204) |
| 6 | DEL1842-gccgccATGTAC TACATAGCTCACCAGC AGCCG (SEQ ID NO:205) | DEL1862-CGATCGGCGC ACCGGAGAATCAGTT (SEQ ID NO:207) | VGS51-GTCACCAATTAC TTTATAGCCAGCT (SEQ ID NO 209) | VGS52-GGGCAGCC AACAGCAGGTGAA CACA (SEQ ID NO:210) |
| | DEL1990-gccgccATGGAG CACCACAATAGCCATCT GTT (SEQ ID NO:206) | DEL1989-TCAAAACTCG GTGCTTCTTATGTTTG (SEQ ID NO 208) | | DEL1991-GTGAGAT GACTACGAAGTAC CATC (SEQ ID NO.211) |

TABLE 6-continued

DNA Sequencing Primers

| CR | DmGP 5'Primer | 3'Primer | Internal Primers Sense | Antisense |
|---|---|---|---|---|
| 7 | VGS69-gtagccgccATGGCAATGGACTTAATCGAGCA (SEQ ID NO:212) | VGS70-TTAAAGTGGTTGCCACAAGGACT (SEQ ID NO:213) | VGS74-GGGCACACGTGCTCCTGGTAACG (SEQ ID NO 214) | VGS73-ATAGAGCTGCAGTGGCAGCCAGC (SEQ ID NO 215) |
| 8 | VGS38-gtagccgccATGTTTACGTGGCTGATGATGGATGT (SEQ ID NO 216) | VGS39-gtaATTACAAATCTGTCTGCTGCACTGCG (SEQ ID NO 217) | VGS55-GTGCAAAGCCTACATGGTGAGCACA (SEQ ID NO.218) | VGS56-TGAGTATTTCCAGTCGGGAGAGGTC (SEQ ID NO 219) |
| 9 | VGS40-gtagccgccATGTTCAACTACGAGGAGGGGGATGC (SEQ ID NO 220) | VGS41-gtaTTAGAGCTGAGGACTGTTGACGGCG (SEQ ID NO 221) | VGS53-GTGCTCTGCATGCCCGTCACCCTGG (SEQ ID NO 220) | VGS54-GACGAACAGCATCTTGACCACACGC (SEQ ID NO 223) |
| 11 | DEL1905-gccgccATGGCTGGCCATCAGTCGCTGGCAC (SEQ ID NO 224) | DEL1906-TTAGAGCATTTCAATATTGGACGTT (SEQ ID NO 225) | VGS57-CCCGTGACTAGCATGTCCCTCCGAA (SEQ ID NO 226) | VGS58-ACCGGAATCGCAGTCGTCACAATCG (SEQ ID NO.227) |

The results of cloning and sequencing of the DmGPCRs of the present invention are as follows:

DmGPCR1

PCR primers designed to the cDNA corresponding to PnuFlyPep34651 were used to successfully amplify a PCR product from a cDNA preparation prepared from *Drosophila* polyA$^+$ mRNA. The resulting product was cloned and sequenced. The experimentally obtained sequence was identical to the predicted sequence. An intact clone was obtained and designated 'DmGPCR1.'

DmGPCR2

Initial attempts to amplify a PCR product using primers designed to the cDNA corresponding to PnuFlyPep67585 were unsuccessful. Alignment of the predicted sequence to the existing *C. elegans* receptors, and to other neuropeptide receptors, showed that the 5' end of the predicted sequence was unusually long, and suggested that there may have been an error in gene prediction on that side. Using the genomic sequence as a guide, a variety of alternative 5' PCR primers were designed and tested. One of these primer combinations, using cDNA prepared from total RNA, was successful in giving a product of the right size. Sequencing of clones derived from the PCR reaction showed that the amplified product contained the anticipated 5' and 3' ends, and was identical to the predicted sequence with the exception that the predicted sequence was missing a small stretch of 6 amino acids. Comparison of the clones also revealed that two splicing isoforms were present, one similar to the predicted sequence (designated 'DmGPCR2a'), and the other missing a stretch of 23 amino acids located just past TM VII into the intracellular C-terminus of the molecule (designated DmGPCR2b').

DmGPCR3

A gene corresponding to the DmGPCR3 predicted protein had already been reported in the literature. This gene (GenBank accession M77168) was described as NKD, "a developmentally regulated tachykinin receptor". Monnier D, et al., *J. Biol. Chem.* 1992, 267(2), 1298-302. Comparison of the M77168 and PnuFlyPep68505 sequences showed that the predicted sequences were significantly different from the cDNA. The cDNA had a longer 5' end, was missing an exon encoding 51 amino acids, and was significantly shorter on the 3' end. PCR primers were designed to the published sequence, and a PCR product was obtained using cDNA prepared from total RNA. This product was identical in structure to the reported NKD sequence.

DmGPCR4

The cDNA corresponding to PnuFlyPep 67393 was used to design PCR primers for the amplification of DmGPCR4. Using a cDNA library prepared from total *Drosophila* mRNA, a PCR product was obtained and cloned. Comparison of the clones with the sequence predicted by PnuFlyPep revealed that the sequences were identical with the exception that one exon predicted by HMMGene was not present in any of the cloned PCR products. DmGPCR4 has been recently cloned by Lenz et al., *Biochem. Biophys. Res. Comm.*, 2000, 273, 571-577, and was classified as a second putative allatostatin receptor.

DmGPCR5

DmGPCR5 (FlyPepCG7887) incorrectly contains a frameshift mutation. The PnuFlyPep version, PnuFlyPep67522, which has been described in the literature as a '*Drosophila* receptor for tachykinin-related peptides' (M77168) (Li XJ, et al., *EMBO Journal*, 1991, 10(11), 3221-3229), corrects that mistake but incorrectly predicts some internal sequences and the C-terminus. At first appearance, the predicted cDNA corresponding to the PnuFlyPep protein was identical to the published sequence. PCR primers were used to successfully amplify a PCR product of the appropriate size from a cDNA mixture prepared from *Drosophila melanogaster* poly A$^+$ mRNA. Sequencing of the cloned PCR products revealed that, although the overall splicing pattern was the same, two sequencing errors were present in the PnuFlyPep sequence. These errors resulted in a frameshift mutation followed by a compensatory frameshift mutation, resulting in a difference of 13 amino acids between the experimentally determined and reported sequences, starting at amino acid position 46. This cloned gene was designated 'DmGPCR5a.'

Additionally, a splicing isoform was found for DmG-PCR5. This variant encoded an extra three amino acids in the N-terminal extracellular domain. This variant was designated 'DmGPCR5b'.

DmGPCR6

The GPCR corresponding to PnuFlyPep15731 had already been described in the literature as a 'Neuropeptide Y' receptor (M81490. Li XJ, et al., *J. Biol. Chem.*, 1992, 267(1), 9-12). The PnuFlyPep-predicted sequence was different from M81490 at both ends of the molecule. PnuFlyPep15731 contained an extra 15 amino acids on the N-terminus as compared to M81490. The 3' end of PnuFlyPep 15731 was also different from M81490, being truncated and not containing conserved TM VI and TM VII residues.

The initial PCR primers were designed using the sequence of M81490. Using these primers, and a template derived from total mRNA, a PCR product was obtained. Examination of the cloned PCR product revealed that it used an identical processing pattern to M81490. This clone was designated 'DmGPCR6a'.

During the cloning of DmGPCR6a an additional splicing isoform was discovered. This isoform was generated by use of an alternative splice acceptor site to generate an alternative 3' end of the molecule using much of the same sequence as the '6a' form but in a different reading frame. Additionally, the open reading frame for this clone extended past the original 3' PCR primer. Examination of the genomic sequence on the 3' end revealed a number of likely candidate exons. PCR primers corresponding to a number of these possible exons were tested until one was found that would amplify a PCR product. This product was designated '6b'. Examination of the genomic sequence also predicted that the initiator ATG predicted by PnuFlyPep15731 was in-frame with the M81490 initiation codon containing an extra 15 amino acids, and that it was likely that the PnuFlyPep15731 start codon was the authentic start codon. A new 5' PCR primer was designed that incorporated the PnuFlyPep15731 start codon and was used in conjunction with the two 3' PCR primers to amplify and clone 'DmGPCR6aL' and 'DmGPCR6bL' ('long').

DmGPCR7

Initial attempts to amplify the DmGPCR7 gene product were unsuccessful. Alignment of the predicted sequence (PnuFlyPep67863) with other GPCRs suggested that the error was probably in the prediction of the 3' end of the molecule. The predicted sequence had a 3' end that was far longer than that of most other GPCRs. Examination of the genomic sequence suggested that the likely error was in the prediction of a splicing event that removed an in-frame stop codon that would have resulted in a molecule of the appropriate size. A 3' PCR primer was designed within that intron. Additionally, a new 5' PCR primer was designed to utilize an in-frame ATG just upstream of the predicted start codon. PCR amplification of cDNA derived from total mRNA resulted in a product of the expected size.

The PnuFlyPep and WO 01/70980 versions of DmGPCR7 are both missing two amino acids on the N-terminus. As previously noted, the PnuFlyPep and FlyPep CG10626 versions are also incorrect at the C-terminus. The incorrect versions of the DmGPCR7 gene product were predicted to be putative *Drosophila* leucokinin receptors (e.g., Hewes & Taghert, *Genome Res.*, 2001, 11, 1126-1142; Holmes et al., *Insect Mol. Biol.*, 2000, 9, 457-465); however, no experimental evidence prior to this invention has confirmed this prediction.

DmGPCR8

DmGPCR8 was successfully amplified using PCR primers designed to the PnuFlyPep predicted sequence. cDNA derived from poly $A^+$ RNA was used as template for the PCR reaction. All six of the sequenced clones were identical in structure to the PnuFlyPep-predicted sequence. A polymorphism was noted at position #68 (DNA sequence), with half of the clones having a "C" at this position, and half an "A." This change does result in an amino acid change, Asp or Glu, respectively. The Celera sequence noted an "A," so an "A" clone (Glu) was arbitrarily chosen for further study. No "A" clones were obtained in the correct orientation, thus a subcloning step, utilizing Pme I to remove the insert from the original pCR3.1 clone and a Pme I-digested pCR3.1 vector, was used to reverse the orientation.

The PnuFlyPep version is correct. The WO 01/70980 version, however, is missing approximately 17 N-terminal amino acids and approximately 15 internal amino acids. This receptor was classified as a putative somatostatin-like receptor (e.g., Hewes & Taghert, *Genome Res.*, 2001, 11, 1126-1142). No experimental evidence prior to this invention has confirmed this prediction.

DmGPCR9

DmGPCR9 was cloned using PCR primers designed to the PnuFlyPep predicted sequence and a cDNA template prep prepared from poly $A^+$ RNA. The genomic structure was correctly predicted in PnuFlyPep.

DmGPCR10

Initial attempts to generate a PCR product with primers designed for DmGPCR10 (PnuFlyPep70325) were unsuccessful. Examination of the predicted cDNA showed that the predicted sequence was unusual in that it did not contain the highly conserved "WXP" motif in TM VI, nor the "NPXXF" motif in TM VII, though several other conserved residues were present. Examination of genomic sequences up to 80 kb downstream of the last exon did not reveal any other potential exons. Attempts to obtain an intact clone for DmGPCR10 were not undertaken.

DmGPCR11 (Allatostatin-Like Peptide Receptor)

PCR primers for the 'allatostatin-like peptide receptor were designed using the published sequence. Birgul et al., *EMBO Journal*, 1999, 18(21), 5892-5900. A PCR product was obtained using cDNA derived from a total mRNA prep, and was cloned and sequenced. The final cDNA coded for a protein identical to that described in publication.

Example 3

Northern Blot Analysis

Northern blots may be performed to examine the expression of mRNA. The sense orientation oligonucleotide and the antisense-orientation oligonucleotide, described above, are used as primers to amplify a portion of the GPCR cDNA sequence of a nucleotide sequence selected from the group consisting of SEQ ID NO: 1, 3, 5, 7, 9, 11, 13, 15, 17, 19, 21, and 23.

Multiple human tissue northern blot from Clontech (Human II # 7767-1) are hybridized with the probe. Pre-hybridization is carried out at 42° C. for 4 hours in 5×SSC, 1× Denhardt's reagent, 0.1% SDS, 50% formamide, 250 mg/ml salmon sperm DNA. Hybridization is performed overnight at 42° C. in the same mixture with the addition of about 1.5×106 cpm/ml of labeled probe.

The probe is labeled with α-32P-dCTP by Rediprime DNA labelling system (Amersham Pharmacia), purified on Nick Column (Amersham Pharmacia), and added to the hybridization solution. The filters are washed several times at 42° C. in 0.2×SSC, 0.1% SDS. Filters are exposed to Kodak XAR film (Eastman Kodak Company, Rochester, N.Y., USA) with intensifying screen at −80° C.

Example 4

Recombinant Expression of DmGPCR in Eukaryotic Cells

Expression of DmGPCR in Mammalian Cells

To produce DmGPCR protein, a DmGPCR-encoding polynucleotide is expressed in a suitable host cell using a suitable expression vector and standard genetic engineering techniques. For example, the DmGPCR-encoding sequence described in Example 1 is subcloned into the commercial expression vector pzeoSV2 (Invitrogen, San Diego, Calif.) and transfected into Chinese Hamster Ovary (CHO) cells using the transfection reagent FuGENE 6 (Boehringer-Mannheim) and the transfection protocol provided in the product insert. Other eukaryotic cell lines, including human embryonic kidney (HEK 293) and COS cells, for example, are suitable as well. Cells stably expressing DmGPCR are selected by growth in the presence of 100 µg/ml zeocin (Stratagene, LaJolla, Calif.). Optionally, DmGPCR may be purified from the cells using standard chromatographic techniques. To facilitate purification, antisera is raised against one or more synthetic peptide sequences that correspond to portions of the DmGPCR amino acid sequence, and the antisera is, used to affinity purify DmGPCR. The DmG-PCR also may be expressed in-frame with a tag sequence (e.g., polyhistidine, hemagluttinin, FLAG) to facilitate purification. Moreover, it will be appreciated that many of the uses for DmGPCR polypeptides, such as assays described below, do not require purification of DmGPCR from the host cell.

Expression of DmGPCR in 293 Cells

For expression of DmGPCR in 293 cells, a plasmid bearing the relevant DmGPCR coding sequence is prepared, using vector pSecTag2A (Invitrogen). Vector pSecTag2A contains the murine IgK chain leader sequence for secretion, the c-myc epitope for detection of the recombinant protein with the anti-myc antibody, a C-terminal polyhistidine for purification with nickel chelate chromatography, and a Zeocin resistant gene for selection of stable transfectants. The forward primer for amplification of this GPCR cDNA is determined by routine procedures and preferably contains a 5' extension of nucleotides to introduce the HindIII cloning site and nucleotides matching the GPCR sequence. The reverse primer is also determined by routine procedures and preferably contains a 5' extension of nucleotides to introduce an XhoI restriction site for cloning and nucleotides corresponding to the reverse complement of the DmGPCR sequence. The PCR conditions are 55° C. as the annealing temperature. The PCR product is gel purified and cloned into the HindIII-XhoI sites of the vector.

The DNA is purified using Qiagen chromatography columns and transfected into 293 cells using DOTAP transfection media (Boehringer Mannheim, Indianapolis, Ind.). Transiently transfected cells are tested for expression after 24 hours of transfection, using western blots probed with antiHis and anti-DmGPCR peptide antibodies. Permanently transfected cells are selected with Zeocin and propagated. Production of the recombinant protein is detected from both cells and media by western blots probed with anti-His, anti-Myc, or anti-GPCR peptide antibodies.

Expression of DmGPCR in COS Cells

For expression of the DmGPCR in COS7 cells, a polynucleotide molecule having a nucleotide sequence selected from the group consisting of SEQ ID NOs: 1, 3, 5, 7, 9, 11, 13, 15, 17, 19, 21, or 23 can be cloned into vector p3-CI. This vector is a pUC18-derived plasmid that contains the HCMV (human cytomegalovirus) promoter-intron located upstream from the bGH (bovine growth hormone) polyadenylation sequence and a multiple cloning site. In addition, the plasmid contains the dhfr (dihydrofolate reductase) gene which provides selection in the presence of the drug methotrexane (MTX) for selection of stable transformants.

The forward primer is determined by routine procedures and preferably contains a 5' extension which introduces an XbaI restriction site for cloning, followed by nucleotides which correspond to a nucleotide sequence selected from the group consisting of SEQ ID NOs: 1, 3, 5, 7, 9, 11, 13, 15, 17, 19, 21, or 23. The reverse primer is also determined by routine procedures and preferably contains 5'-extension of nucleotides which introduces a SalI cloning site followed by nucleotides which correspond to the reverse complement of a nucleotide sequence selected from the group consisting of SEQ ID NOs: 1, 3, 5, 7, 9, 11, 13, 15, 17, 19, 21, or 23.

The PCR consists of an initial denaturation step of 5 min at 95° C., 30 cycles of 30 sec denaturation at 95° C., 30 sec annealing at 58° C., and 30 sec extension at 72° C., followed by 5 min extension at 72° C. The PCR product is gel purified and ligated into the XbaI and SalI sites of vector p3-CI. This construct is transformed into E. coli cells for amplification and DNA purification. The DNA is purified with Qiagen chromatography columns and transfected into COS7 cells using Lipofectamine reagent from BRL, following the manufacturer's protocols. Forty eight and 72 hours after transfection, the media and the cells are tested for recombinant protein expression.

DmGPCR expressed from a COS cell culture can be purified by concentrating the cell-growth media to about 10 mg of protein/ml, and purifying the protein by, for example, chromatography. Purified DmGPCR is concentrated to 0.5 mg/ml in an Amicon concentrator fitted with a YM-10 membrane and stored at −80° C.

Expression of DmGPCR in Insect Cells

For expression of DmGPCR in a baculovirus system, a polynucleotide molecule having a nucleotide sequence selected from the group consisting of SEQ ID NOs: 1, 3, 5, 7, 9, 11, 13, 15, 17, 19, 21, or 23 can be amplified by PCR. The forward primer is determined by routine procedures and preferably contains a 5' extension which adds the NdeI cloning site, followed by nucleotides which correspond to a nucleotide sequence selected from the group consisting of SEQ ID NOs: 1, 3, 5, 7, 9, 11, 13, 15, 17, 19, 21, or 23. The reverse primer is also determined by routine procedures and preferably contains a 5' extension which introduces the KpnI cloning site, followed by nucleotides which correspond to the reverse complement of a nucleotide sequence selected from the group consisting of SEQ ID NOs: 1, 3, 5, 7, 9, 11, 13, 15, 17, 19, 21, or 23.

The PCR product is gel purified, digested with NdeI and KpnI, and cloned into the corresponding sites of vector pAcHTL-A (Pharmingen, San Diego, Calif.). The pAcHTL expression vector contains the strong polyhedrin promoter of the *Autographa californica* nuclear polyhedrosis virus (AcMNPV), and a 6XHis tag upstream from the multiple cloning site. A protein kinase site for phosphorylation and a thrombin site for excision of the recombinant protein precedes the multiple cloning site is also present. Of course, many other baculovirus vectors could be used in place of pAcHTL-A, such as pAc373, pVL941 and pAcIM1. Other suitable vectors for the expression of GPCR polypeptides can be used, provided that the vector construct includes appropriately located signals for transcription, translation, and trafficking, such as an in-frame AUG and a signal peptide, as required. Such vectors are described in Luckow et al., Virology 170:31-39, among others.

The virus is grown and isolated using standard baculovirus expression methods, such as those described in Summers et al. (A MANUAL OF METHODS FOR BACULOVIRUS VECTORS AND INSECT CELL CULTURE PROCEDURES, Texas Agricultural Experimental Station Bulletin No. 1555 (1987)).

In one embodiment, pAcHLT-A containing DmGPCR gene is introduced into baculovirus using the "BaculoGold" transfection kit (Pharmingen, San Diego, Calif.) using methods established by the manufacturer. Individual virus isolates are analyzed for protein production by radiolabeling infected cells with $^{35}$S-methionine at 24 hours post infection. Infected cells are harvested at 48 hours post infection, and the labeled proteins are visualized by SDS-PAGE. Viruses exhibiting high expression levels can be isolated and used for scaled up expression.

For expression of a DmGPCR polypeptide in Sf9 cells, a polynucleotide molecule having a nucleotide sequence selected from the group consisting of SEQ ID NOs: 1, 3, 5, 7, 9, 11, 13, 15, 17, 19, 21, or 23, can be amplified by PCR using the primers and methods described above for baculovirus expression. The DmGPCR cDNA is cloned into vector pAcHLT-A (Pharmingen) for expression in Sf9 insect cells. The insert is cloned into the NdeI and KpnI sites, after elimination of an internal NdeI site (using the same primers described above for expression in baculovirus). DNA is purified with Qiagen chromatography columns and expressed in Sf9 cells. Preliminary Western blot experiments from non-purified plaques are tested for the presence of the recombinant protein of the expected size which reacted with the GPCR-specific antibody. These results are confirmed after further purification and expression optimization in HiG5 cells.

Example 5

Interaction Trap/Two-Hybrid System

In order to assay for DmGPCR-interacting proteins, the interaction trap/two-hybrid library screening method can be used. This assay was first described in Fields, et al., Nature, 1989, 340, 245, which is incorporated herein by reference in its entirety. A protocol is published in CURRENT PROTOCOLS IN MOLECULAR BIOLOGY, John Wiley & Sons, NY, 1999, and Ausubel et al., SHORT PROTOCOLS IN MOLECULAR BIOLOGY, fourth edition, Greene and Wiley-interscience, NY, 1992, which are incorporated herein by reference in their entireties. Kits are available from Clontech, Palo Alto, Calif. (Matchmaker Two-Hybrid System 3).

A fusion of the nucleotide sequences encoding all or partial DmGPCR and the yeast transcription factor GAL4 DNA-binding domain (DNA-BD) is constructed in an appropriate plasmid (i.e., pGBKT7) using standard subcloning techniques. Similarly, a GAL4 active domain (AD) fusion library is constructed in a second plasmid (i.e., pGADT7) from cDNA of potential GPCR-binding proteins (for protocols on forming cDNA libraries, see Sambrook et al., MOLECULAR CLONING: A LABORATORY MANUAL, second edition, Cold Spring Harbor Press, Cold Spring Harbor, N.Y., 1989), which is incorporated herein by reference in its entirety. The DNA-BD/GPCR fusion construct is verified by sequencing, and tested for autonomous reporter gene activation and cell toxicity, both of which would prevent a successful two-hybrid analysis. Similar controls are performed with the AD/library fusion construct to ensure expression in host cells and lack of transcriptional activity. Yeast cells are transformed (ca. 105 transformants/mg DNA) with both the GPCR and library fusion plasmids according to standard procedure (Ausubel et al., SHORT PROTOCOLS IN MOLECULAR BIOLOGY, fourth edition, Greene and Wiley-interscience, NY, 1992, which is incorporated herein by reference in its entirety). In vivo binding of DNA-BD/GPCR with AD/library proteins results in transcription of specific yeast plasmid reporter genes (i.e., lacZ, HIS3, ADE2, LEU2). Yeast cells are plated on nutrient-deficient media to screen for expression of reporter genes. Colonies are dually assayed for β-galactosidase activity upon growth in Xgal (5-bromo-4-chloro-3-indolyl-β-D-galactoside) supplemented media (filter assay for β-galactosidase activity is described in Breeden et al., Cold Spring Harb. Symp. Quant. Biol., 1985, 50, 643, which is incorporated herein by reference in its entirety). Positive AD-library plasmids are rescued from transformants and reintroduced into the original yeast strain as well as other strains containing unrelated DNA-BD fusion proteins to confirm specific DmGPCR/library protein interactions. Insert DNA is sequenced to verify the presence of an open reading frame fused to GAL4 AD and to determine the identity of the DmGPCR-binding protein.

Example 6

Mobility Shift DNA-Binding Assay Using Gel Electrophoresis

A gel electrophoresis mobility shift assay can rapidly detect specific protein-DNA interactions. Protocols are widely available in such manuals as Sambrook et al., MOLECULAR CLONING: A LABORATORY MANUAL, second edition, Cold Spring Harbor Press, Cold Spring Harbor, N.Y., 1989, and Ausubel et al., SHORT PROTOCOLS IN MOLECULAR BIOLOGY, fourth edition, Greene and Wiley-interscience, NY, 1992, each of which is incorporated herein by reference in its entirety.

Probe DNA(<300 bp) is obtained from synthetic oligonucleotides, restriction endonuclease fragments, or PCR fragments and end-labeled with $^{32}$P An aliquot of purified DmGPCR (ca. 15 μg) or crude DmGPCR extract (ca. 15 ng) is incubated at constant temperature (in the range 22-37° C.) for at least 30 minutes in 10-15 μl of buffer (i.e., TAE or TBE, pH 8.0-8.5) containing radiolabeled probe DNA, non-specific carrier DNA (ca. 1 μg), BSA (300 μg/ml), and 10% (v/v) glycerol. The reaction mixture is then loaded onto a polyacrylamide gel and run at 30-35 mA until good separation of free probe DNA from protein-DNA complexes occurs. The gel is then dried and bands corresponding to free DNA and protein-DNA complexes are detected by autoradiography.

Example 7

Antibodies to DmGPCR

Standard techniques are employed to generate polyclonal or monoclonal antibodies to the DmGPCR and to generate useful antigen-binding fragments thereof or variants thereof, including "humanized" variants. Such protocols can be found, for example, in Sambrook et al. (1989), supra, and Harlow et al. (Eds.), ANTIBODIES: A LABORATORY MANUAL, Cold Spring Harbor Laboratory, Cold Spring Harbor, N.Y., 1988. In one embodiment, recombinant DmGPCR polypeptides (or cells or cell membranes containing such polypeptides) are used as antigen to generate the antibodies. In another embodiment, one or more peptides having amino acid sequences corresponding to an immunogenic portion of DmGPCR (e.g., 6, 7, 8, 9, 10, 11, 12, 13, 14, 15, 16, 17, 18, 19, 20, or more amino acids) are used as antigen. Peptides corresponding to extracellular portions of DmGPCR, especially hydrophilic extracellular portions, are included in the invention. The antigen may be mixed with an adjuvant or linked to a hapten to increase antibody production.

Polyclonal or Monoclonal Antibodies

As one exemplary protocol, recombinant DmGPCR or a synthetic fragment thereof is used to immunize a mouse for generation of monoclonal antibodies (or larger mammal, such as a rabbit, for polyclonal antibodies). To increase antigenicity, peptides are conjugated to Keyhole Lympet Hemocyanin (Pierce), according to the manufacturer's recommendations. For an initial injection, the antigen is emulsified with Freund's Complete Adjuvant and injected subcutaneously. At intervals of two to three weeks, additional aliquots of DmGPCR antigen are emulsified with Freund's Incomplete Adjuvant and injected subcutaneously. Prior to the final booster injection, a serum sample is taken from the immunized mice and assayed by western blot to confirm the presence of antibodies that immunoreact with DmGPCR. Serum from the immunized animals may be used as a polyclonal antisera or used to isolate polyclonal antibodies that recognize DmGPCR. Alternatively, the mice are sacrificed and their spleen removed for generation of monoclonal antibodies.

To generate monoclonal antibodies, the spleens are placed in 10 ml serum-free RPMI 1640, and single cell suspensions are formed by grinding the spleens in serum-free RPMI 1640, supplemented with 2 mM L-glutamine, 1 mM sodium pyruvate, 100 units/ml penicillin, and 100 µg/ml streptomycin (RPMI) (Gibco, Canada). The cell suspensions are filtered and washed by centrifugation and resuspended in serum-free RPMI. Thymocytes taken from three naive Balb/c mice are prepared in a similar manner and used as a Feeder Layer. NS-1 myeloma cells, kept in log phase in RPMI with 10% fetal bovine serum (FBS) (Hyclone Laboratories, Inc., Logan, Utah) for three days prior to fusion, are centrifuged and washed as well.

To produce hybridoma fusions, spleen cells from the immunized mice are combined with NS-1 cells and centrifuged, and the supernatant is aspirated. The cell pellet is dislodged by tapping the tube, and 2 ml of 37° C. PEG 1500 (50% in 75 mM HEPES, pH 8.0) (Boehringer-Mannheim) is stirred into the pellet, followed by the addition of serum-free RPMI. Thereafter, the cells are centrifuged, resuspended in RPMI containing 15% FBS, 100 µM sodium hypoxanthine, 0.4 µM aminopterin, 16 µM thymidine (HAT) (Gibco), 25 units/ml IL-6 (Boehringer-Mannheim), and $1.5 \times 10^6$ thymocytes/ml, and plated into 10 Coming flat-bottom 96-well tissue culture plates (Coming, Corning N.Y.).

On days 2, 4, and 6 after the fusion, 100 µl of medium is removed from the wells of the fusion plates and replaced with fresh medium. On day 8, the fusions are screened by ELISA, testing for the presence of mouse IgG that binds to DmGPCR. Selected fusion wells are further cloned by dilution until monoclonal cultures producing anti-DmGPCR antibodies are obtained.

Humanization of Anti-DmGPCR Monoclonal Antibodies

The expression pattern of DmGPCR as reported herein and the proven track record of GPCRs as targets for therapeutic intervention suggest therapeutic indications for DmGPCR inhibitors (antagonists). DmGPCR-neutralizing antibodies comprise one class of therapeutics useful as DmGPCR antagonists. Following are protocols to humanize the monoclonal antibodies of the invention.

The principles of humanization have been described in the literature and are facilitated by the modular arrangement of antibody proteins. To minimize the possibility of binding complement, a humanized antibody of the IgG4 isotype may be used.

For example, a level of humanization is achieved by generating chimeric antibodies comprising the variable domains of non-human antibody proteins of interest with the constant domains of human antibody molecules. (See, e.g., Morrison et al., *Adv. Immunol.,* 1989, 44, 65-92). The variable domains of DmGPCR-neutralizing anti-DmGPCR antibodies are cloned from the genomic DNA of a B-cell hybridoma or from cDNA generated from mRNA isolated from the hybridoma of interest. The V region gene fragments are linked to exons encoding human antibody constant domains, and the resultant construct is expressed in suitable mammalian host cells (e.g., myeloma or CHO cells).

To achieve an even greater level of humanization, only those portions of the variable region gene fragments that encode antigen-binding complementarity determining regions ("CDR") of the non-human monoclonal antibody genes are cloned into human antibody sequences. (See, e.g., Jones et al., *Nature,* 1986, 321, 522-525; Riechmann et al., *Nature,* 1988, 332, 323-327; Verhoeyen et al., *Science,* 1988, 239, 1534-36; and Tempest et al., *Bio/Technology,* 1991, 9, 266-71). If necessary, the β-sheet framework of the human antibody surrounding the CDR3 regions also is modified to more closely mirror the three dimensional structure of the antigen-binding domain of the original monoclonal antibody. (See Kettleborough et al., *Protein Engin.,* 1991, 4, 773-783; and Foote et al., *J. Mol. Biol.,* 1992, 224, 487-499).

In an alternative approach, the surface of a non-human monoclonal antibody of interest is humanized by altering selected surface residues of the non-human antibody, e.g., by site-directed mutagenesis, while retaining all of the interior and contacting residues of the non-human antibody. See Padlan, *Molecular Immunol.,* 1991, 28(4/5), 489-98.

The foregoing approaches are employed using DmGPCR-neutralizing anti-DmGPCR monoclonal antibodies and the hybridomas that produce them to generate humanized DmGPCR-neutralizing antibodies useful as therapeutics to treat or palliate conditions wherein DmGPCR expression or ligand-mediated DmGPCR signaling is detrimental.

Example 8

Assays to Identify Modulators of DmGPCR Activity

Set forth below are several nonlimiting assays for identifying modulators (agonists and antagonists) of DmGPCR activity. Among the modulators that can be identified by these assays are natural ligand compounds of the receptor; synthetic analogs and derivatives of natural ligands; antibodies, antibody fragments, and/or antibody-like compounds derived from natural antibodies or from antibody-like combinatorial libraries; and/or synthetic compounds identified by high-throughput screening of libraries; and the like. All modulators that bind DmGPCR are useful for identifying DmGPCR in tissue samples (e.g., for diagnostic purposes, pathological purposes, and the like). Agonist and antagonist modulators are useful for up-regulating and down-regulating DmGPCR activity, respectively, to treat disease states characterized by abnormal levels of DmGPCR activity. The assays may be performed using single putative modulators, and/or may be performed using a known agonist in combination with candidate antagonists (or visa versa).

cAMP Assays

In one type of assay, levels of cyclic adenosine monophosphate (cAMP) are measured in DmGPCR-transfected cells that have been exposed to candidate modulator compounds. Protocols for cAMP assays have been described in the literature. (See, e.g., Sutherland et al., Circulation, 1968, 37, 279; Frandsen et al., Life Sciences, 1976, 18, 529-541; Dooley et al., *J. Pharm. and Exper. Ther.*, 1997, 283(2), 735-41; and George et al., *J. Biomolecular Screening*, 1997, 2(4), 235-40). An exemplary protocol for such an assay, using an Adenylyl Cyclase Activation FlashPlate® Assay from NEN™ Life Science Products, is set forth below.

Briefly, the DmGPCR coding sequence (e.g., a cDNA or intronless genomic DNA) is subcloned into a commercial expression vector, such as pzeoSV2 (Invitrogen), and transiently transfected into Chinese Hamster Ovary (CHO) cells using known methods, such as the transfection protocol provided by Boehringer-Mannheim when supplying the FuGENE 6 transfection reagent. Transfected CHO cells are seeded into 96-well microplates from the FlashPlate® assay kit, which are coated with solid scintillant to which antisera to cAMP has been bound. For a control, some wells are seeded with wild type (untransfected) CHO cells. Other wells in the plate receive various amounts of a cAMP standard solution for use in creating a standard curve.

One or more test compounds (i.e., candidate modulators) are added to the cells in each well, with water and/or compound-free medium/diluent serving as a control or controls. After treatment, cAMP is allowed to accumulate in the cells for exactly 15 minutes at room temperature. The assay is terminated by the addition of lysis buffer containing [$^{125}$I]-labeled cAMP, and the plate is counted using a Packard Topcount™ 96-well microplate scintillation counter. Unlabeled cAMP from the lysed cells (or from standards) and fixed amounts of [$^{125}$I]-cAMP compete for antibody bound to the plate. A standard curve is constructed, and cAMP values for the unknowns are obtained by interpolation. Changes in intracellular cAMP levels of cells in response to exposure to a test compound are indicative of DmGPCR modulating activity. Modulators that act as agonists of receptors which couple to the $G_s$ subtype of G proteins will stimulate production of cAMP, leading to a measurable 3-10 fold increase in cAMP levels. Agonists of receptors which couple to the $G_{I/O}$ subtype of G proteins will inhibit forskolin-stimulated cAMP production, leading to a measurable decrease in cAMP levels of 50-100%. Modulators that act as inverse agonists will reverse these effects at receptors that are either constitutively active or activated by known agonists.

Aequorin Assays

In another assay, cells (e.g., CHO cells) are transiently co-transfected with both a DmGPCR expression construct and a construct that encodes the photoprotein apoaquorin. In the presence of the cofactor coelenterazine, apoaquorin will emit a measurable luminescence that is proportional to the amount of intracellular (cytoplasmic) free calcium. (See generally, Cobbold, et al., "Aequorin measurements of cytoplasmic free calcium," in CELLULAR CALCIUM: A PRACTICAL APPROACH, McCormack J. G. and Cobbold P. H., eds., Oxford: IRL Press, 1991; Stables et al., *Anal. Biochem.*, 1997, 252, 115-26; and Haugland, HANDBOOK OF FLUORESCENT PROBES AND RESEARCH CHEMICALS, sixth edition, Eugene, Oreg., Molecular Probes, 1996).

In one exemplary assay, DmGPCR is subcloned into the commercial expression vector pzeoSV2 (Invitrogen) and transiently co-transfected along with a construct that encodes the photoprotein apoaquorin (Molecular Probes, Eugene, Oreg.) into CHO cells using the transfection reagent FuGENE 6 (Boehringer-Mannheim) and the transfection protocol provided in the product insert.

The cells are cultured for 24 hours at 37° C. in MEM (Gibco/BRL, Gaithersburg, Md.) supplemented with 10% fetal bovine serum, 2 mM glutamine, 10 U/ml penicillin, and 10 µg/ml streptomycin, at which time the medium is changed to serum-free MEM containing 5 µM coelenterazine (Molecular Probes, Eugene, Oreg.). Culturing is then continued for two additional hours at 37° C. Subsequently, cells are detached from the plate using VERSEN (Gibco/BRL), washed, and resuspended at 200,000 cells/ml in serum-free MEM.

Dilutions of candidate DmGPCR modulator compounds are prepared in serum-free MEM and dispensed into wells of an opaque 96-well assay plate at 50 µl/well. Plates are then loaded onto an MLX microtiter plate luminometer (Dynex Technologies, Inc., Chantilly, Va.). The instrument is programmed to dispense 50 µl cell suspensions into each well, one well at a time, and immediately read luminescence for 15 seconds. Dose-response curves for the candidate modulators are constructed using the area under the curve for each light signal peak. Data are analyzed with SlideWrite, using the equation for a one-site ligand, and $EC_{50}$ values are obtained. Changes in luminescence caused by the compounds are considered indicative of modulatory activity. Modulators that act as agonists at receptors which couple to the $G_q$ subtype of G proteins give an increase in luminescence of up to 100-fold. Modulators that act as inverse agonists will reverse this effect at receptors that are either constitutively active or activated by known agonists.

Luciferase Reporter Gene Assay

The photoprotein luciferase provides another useful tool for assaying for modulators of DmGPCR activity. Cells (e.g., CHO cells or COS7 cells) are transiently co-transfected with both a DmGPCR expression construct (e.g., DmGPCR in pzeoSV2) and a reporter construct which includes a gene for the luciferase protein downstream from a transcription factor binding site, such as the cAMP-response element (CRE), AP-1, or NF-kappa B. Agonist binding to receptors coupled to the $G_s$ subtype of G proteins leads to increases in cAMP, thereby activating the CRE transcription factor and resulting in expression of the luciferase gene. Agonist binding to receptors coupled to the $G_q$ subtype of G protein leads to production of diacylglycerol that activates protein kinase C, which activates the AP-1 or NF-kappa B transcription factors, in turn resulting in expression of the luciferase gene. Expression levels of luciferase reflect the activation status of the signaling events. See generally, George et al., *J. Biomolecular Screening*, 1997, 2(4), 235-240; and Stratowa et al., *Curr. Opin. Biotechnol.*, 1995, 6, 574-581. Luciferase activity may be quantitatively measured using, e.g., luciferase assay reagents that are commercially available from Promega (Madison, Wis.).

In one exemplary assay, CHO cells are plated in 24-well culture dishes at a density of 100,000 cells/well one day prior to transfection and cultured at 37° C. in MEM (Gibco/BRL) supplemented with 10% fetal bovine serum, 2 mM glutamine, 10 µg/ml penicillin, and 10 µg/ml streptomycin. Cells are transiently co-transfected with both a DmGPCR expression construct and a reporter construct containing the luciferase gene. The reporter plasmids CRE-luciferase, AP-1-luciferase, and NF-kappaB-luciferase may be purchased from Stratagene (LaJolla, Calif.). Transfections are performed using the FuGENE 6 transfection reagent (Boehringer-Mannheim) according to the supplier's instructions. Cells transfected with the reporter construct alone are used as a control. Twenty-four hours after transfection, cells are washed once with PBS pre-warmed to 37° C. Serum-free MEM is then added to the cells either alone (control) or with one or more candidate modulators and the cells are incubated at 37° C. for five hours. Thereafter, cells are washed once with ice-cold PBS and lysed by the addition of 100 µl of lysis buffer per well from the luciferase assay kit supplied by Promega. After incubation for 15 minutes at room temperature, 15 µl of the lysate is mixed with 50 µl of substrate solution (Promega) in an opaque-white, 96-well plate, and the luminescence is read immediately on a Wallace model 1450 MicroBeta scintillation and luminescence counter (Wallace Instruments, Gaithersburg, Md.).

Differences in luminescence in the presence versus the absence of a candidate modulator compound are indicative of modulatory activity. Receptors that are either constitutively active or activated by agonists typically give a 3-20-fold stimulation of luminescence compared to cells transfected with the reporter gene alone. Modulators that act as inverse agonists will reverse this effect.

Intracellular Calcium Measurement using FLIPR

Changes in intracellular calcium levels are another recognized indicator of G protein-coupled receptor activity, and such assays can be employed to screen for modulators of DmGPCR activity. For example, CHO cells stably transfected with a DmGPCR expression vector are plated at a density of $4 \times 10^4$ cells/well in Packard black-walled, 96-well plates specially designed to discriminate fluorescence signals emanating from the various wells on the plate. The cells are incubated for 60 minutes at 37° C. in modified Dulbecco's PBS (D-PBS) containing 36 mg/L pyruvate and 1 g/L glucose and one of four calcium indicator dyes (Fluo-3™ AM, Fluo-4™ AM, Calcium Green™-1 AM, or Oregon Green™ 488 BAPTA-1 AM), each at a concentration of 4 µM. Plates are washed once with modified D-PBS and incubated for 10 minutes at 37° C. to remove residual dye from the cellular membrane. In addition, a series of washes with modified D-PBS is performed immediately prior to activation of the calcium response.

A calcium response is initiated by the addition of one or more candidate receptor agonist compounds, calcium ionophore A23187 (10 µM; positive control), or ATP (4 µM; positive control). Fluorescence is measured by Molecular Device's FLIPR with an argon laser (excitation at 488 nm). (See, e.g., Kuntzweiler et al., *Drug Dev. Res.*, 1998, 44(1), 14-20). The F-stop for the detector camera was set at 2.5, and the length of exposure was 0.4 milliseconds. Basal fluorescence of cells was measured for 20 seconds prior to addition of candidate agonist, ATP, or A23187, and the basal fluorescence level was subtracted from the response signal. The calcium signal is measured for approximately 200 seconds, taking readings every two seconds. Calcium ionophore A23187 and ATP increase the calcium signal 200% above baseline levels. In general, activated GPCRs increase the calcium signal approximately 10-15% above baseline signal.

Mitogenesis Assay

In a mitogenesis assay, the ability of candidate modulators to induce or inhibit DmGPCR-mediated cell division is determined. (See, e.g., Lajiness et al., *J. Pharm. and Exper.*

*Ther.*, 1993, 267(3), 1573-1581). For example, CHO cells stably expressing DmGPCR are seeded into 96-well plates at a density of 5000 cells/well and grown at 37° C. in MEM with 10% fetal calf serum for 48 hours, at which time the cells are rinsed twice with serum-free MEM. After rinsing, 80 µl of fresh MEM, or MEM containing a known mitogen, is added along with 20 µl MEM containing varying concentrations of one or more candidate modulators or test compounds diluted in serum-free medium. As controls, some wells on each plate receive serum-free medium alone, and some receive medium containing 10% fetal bovine serum. Untransfected cells or cells transfected with vector alone also may serve as controls.

After culture for 16-18 hours, 1 µCi of [$^3$H]-thymidine (2 Ci/mmol) is added to the wells and cells are incubated for an additional 2 hours at 37° C. The cells are trypsinized and collected on filter mats with a cell harvester (Tomtec); the filters are then counted in a Betaplate counter. The incorporation of [$^3$H]-thymidine in serum-free test wells is compared to the results achieved in cells stimulated with serum (positive control). Use of multiple concentrations of test compounds permits creation and analysis of dose-response curves using the non-linear, least squares fit equation: $A = B \times [C/(D+C)] + G$, where A is the percent of serum stimulation; B is the maximal effect minus baseline; C is the $EC_{50}$; D is the concentration of the compound; and G is the maximal effect. Parameters B, C and G are determined by Simplex optimization.

Agonists that bind to the receptor are expected to increase [$^3$H]-thymidine incorporation into cells, showing up to 80% of the response to serum. Antagonists that bind to the receptor will inhibit the stimulation seen with a known agonist by up to 100%.

[$^{35}$S]GTPγS Binding Assay

Because G protein-coupled receptors signal through intracellular G proteins whose activity involves GTP binding and hydrolysis to yield bound GDP, measurement of binding of the non-hydrolyzable GTP analog [$^{35}$S]GTPγS in the presence and absence of candidate modulators provides another assay for modulator activity. See, e.g., Kowal et al., *Neuropharmacology*, 1998, 37, 179-187.

In one exemplary assay, cells stably transfected with a DmGPCR expression vector are grown in 10 cm tissue culture dishes to subconfluence, rinsed once with 5 ml of ice-cold $Ca^{2+}/Mg^{2+}$-free phosphate-buffered saline, and scraped into 5 ml of the same buffer. Cells are pelleted by centrifugation (500×g, 5 minutes), resuspended in TEE buffer (25 mM Tris, pH 7.5, 5 mM EDTA, 5 mM EGTA), and frozen in liquid nitrogen. After thawing, the cells are homogenized using a Dounce homogenizer (one ml TEE per plate of cells), and centrifuged at 1,000×g for 5 minutes to remove nuclei and unbroken cells.

The homogenate supernatant is centrifuged at 20,000×g for 20 minutes to isolate the membrane fraction, and the membrane pellet is washed once with TEE and resuspended in binding buffer (20 mM HEPES, pH 7.5, 150 mM NaCl, 10 mM $MgCl_2$, 1 mM EDTA). The resuspended membranes can be frozen in liquid nitrogen and stored at −70° C. until use.

Aliquots of cell membranes prepared as described above and stored at −70° C. are thawed, homogenized, and diluted into buffer containing 20 mM HEPES, 10 mM $MgCl_2$, 1 mM EDTA, 120 mM NaCl, 10 µM GDP, and 0.2 mM ascorbate, at a concentration of 10-50 µg/ml. In a final volume of 90 µl, homogenates are incubated with varying concentrations of candidate modulator compounds or 100 µM GTP for 30 minutes at 30° C. and then placed on ice. To each sample, 10

μl guanosine 5'-O-(3[$^{35}$S]thio) triphosphate (NEN, 1200 Ci/mmol; [$^{35}$S]-GTPγS), was added to a final concentration of 100-200 pM. Samples are incubated at 30° C. for an additional 30 minutes, 1 ml of 10 mM HEPES, pH 7.4, 10 mM MgCl$_2$, at 4° C. is added and the reaction is stopped by filtration.

Samples are filtered over Whatman GF/B filters and the filters are washed with 20 ml ice-cold 10 mM HEPES, pH 7.4, 10 mM MgCl$_2$. Filters are counted by liquid scintillation spectroscopy. Nonspecific binding of [$^{35}$S]-GTPγS is measured in the presence of 100 μM GTP and subtracted from the total. Compounds are selected that modulate the amount of [$^{35}$S]GTPγS binding in the cells, compared to untransfected control cells. Activation of receptors by agonists gives up to a five-fold increase in [$^{35}$S]GTPγS binding. This response is blocked by antagonists.

MAP Kinase Activity Assay

Evaluation of MAP kinase activity in cells expressing a GPCR provides another assay to identify modulators of DmGPCR activity. See, e.g., Lajiness et al., *J. Pharm. and Exper. Ther.*, 1993, 267(3), 1573-1581 and Boulton et al., *Cell*, 1991, 65, 663-675.

In one embodiment, CHO cells stably transfected with DmGPCR are seeded into 6-well plates at a density of 70,000 cells/well 48 hours prior to the assay. During this 48-hour period, the cells are cultured at 37° C. in MEM medium supplemented with 10% fetal bovine serum, 2 mM glutamine, 10 U/ml penicillin, and 10 μg/ml streptomycin. The cells are serum-starved for 1-2 hours prior to the addition of stimulants.

For the assay, the cells are treated with medium alone or medium containing either a candidate agonist or 200 nM Phorbol ester-myristoyl acetate (i.e., PMA, a positive control), and the cells are incubated at 37° C. for varying times. To stop the reaction, the plates are placed on ice, the medium is aspirated, and the cells are rinsed with 1 ml of ice-cold PBS containing 1 mM EDTA. Thereafter, 200 μl of cell lysis buffer (12.5 mM MOPS, pH 7.3, 12.5 mM glycerophosphate, 7.5 mM MgCl$_2$, 0.5 mM EGTA, 0.5 mM sodium vanadate, 1 mM benzamidine, 1 mM dithiothreitol, 10 μg/ml leupeptin, 10 μg/ml aprotinin, 2 μg/ml pepstatin A, and 1 μM okadaic acid) is added to the cells. The cells are scraped from the plates and homogenized by 10 passages through a 23 ¾ G needle, and the cytosol fraction is prepared by centrifugation at 20,000×g for 15 minutes.

Aliquots (5-10 μl containing 1-5 μg protein) of cytosol are mixed with 1 mM MAPK Substrate Peptide (APRTPGGRR (SEQ ID NO: 168), Upstate Biotechnology, Inc., N.Y.) and 50 μM [γ-$^{32}$P]ATP (NEN, 3000 Ci/mmol), diluted to a final specific activity of ~2000 cpm/pmol, in a total volume of 25 μl. The samples are incubated for 5 minutes at 30° C., and reactions are stopped by spotting 20 μl on 2 cm$^2$ squares of Whatman P81 phosphocellulose paper. The filter squares are washed in 4 changes of 1% H$_3$PO$_4$, and the squares are subjected to liquid scintillation spectroscopy to quantitate bound label. Equivalent cytosolic extracts are incubated without MAPK substrate peptide, and the bound label from these samples are subtracted from the matched samples with the substrate peptide. The cytosolic extract from each well is used as a separate point. Protein concentrations are determined by a dye binding protein assay (Bio-Rad Laboratories). Agonist activation of the receptor is expected to result in up to a five-fold increase in MAPK enzyme activity. This increase is blocked by antagonists.

[$^3$H]Arachidonic Acid Release

The activation of GPCRs also has been observed to potentiate arachidonic acid release in cells, providing yet another useful assay for modulators of GPCR activity. See, e.g., Kanterman et al., *Molecular Pharmacology*, 1991, 39, 364-369. For example, CHO cells that are stably transfected with a DmGPCR expression vector are plated in 24-well plates at a density of 15,000 cells/well and grown in MEM medium supplemented with 10% fetal bovine serum, 2 mM glutamine, 10 U/ml penicillin, and 10 μg/ml streptomycin for 48 hours at 37° C. before use. Cells of each well are labeled by incubation with [$^3$H]-arachidonic acid (Amersham Corp., 210 Ci/mmol) at 0.5 μCi/ml in 1 ml MEM supplemented with 10 mM HEPES, pH 7.5, and 0.5% fatty-acid-free bovine serum albumin for 2 hours at 37° C. The cells are then washed twice with 1 ml of the same buffer.

Candidate modulator compounds are added in 1 ml of the same buffer, either alone or with 10 μM ATP, and the cells are incubated at 37° C. for 30 minutes. Buffer alone and mock-transfected cells are used as controls. Samples (0.5 ml) from each well are counted by liquid scintillation spectroscopy. Agonists which activate the receptor will lead to potentiation of the ATP-stimulated release of [$^3$H]-arachidonic acid. This potentiation is blocked by antagonists.

Extracellular Acidification Rate

In yet another assay, the effects of candidate modulators of DmGPCR activity are assayed by monitoring extracellular changes in pH induced by the test compounds. See, e.g., Dunlop et al., *J. Pharmacological and Toxicological Methods*, 1998, 40(1), 47-55. In one embodiment, CHO cells transfected with a DmGPCR expression vector are seeded into 12 mm capsule cups (Molecular Devices Corp.) at 4×10$^5$ cells/cup in MEM supplemented with 10% fetal bovine serum, 2 mM L-glutamine, 10 U/ml penicillin, and 10 μg/ml streptomycin. The cells are incubated in this medium at 37° C. in 5% CO$_2$ for 24 hours.

Extracellular acidification rates are measured using a Cytosensor microphysiometer (Molecular Devices Corp.). The capsule cups are loaded into the sensor chambers of the microphysiometer and the chambers are perfused with running buffer (bicarbonate-free MEM supplemented with 4 mM L-glutamine, 10 units/ml penicillin, 10 μg/ml streptomycin, 26 mM NaCl) at a flow rate of 100 μl/minute. Candidate agonists or other agents are diluted into the running buffer and perfused through a second fluid path. During each 60-second pump cycle, the pump is run for 38 seconds and is off for the remaining 22 seconds. The pH of the running buffer in the sensor chamber is recorded during the cycle from 43-58 seconds, and the pump is re-started at 60 seconds to start the next cycle. The rate of acidification of the running buffer during the recording time is calculated by the Cytosoft program. Changes in the rate of acidification are calculated by subtracting the baseline value (the average of 4 rate measurements immediately before addition of a modulator candidate) from the highest rate measurement obtained after addition of a modulator candidate. The selected instrument detects 61 mV/pH unit. Modulators that act as agonists of the receptor result in an increase in the rate of extracellular acidification compared to the rate in the absence of agonist. This response is blocked by modulators which act as antagonists of the receptor.

Example 9

Matching DmGPCRs with Peptide Ligands

Cell Cultures and Transfections

Wild type Chinese hamster ovary (CHO-K1) cells (from the American Type Culture Collection, Rockville, Md.) or CHO-10001A cells were cultured at 37° C. in a humidified atmosphere of 5% $CO_2$ in air in DMEM media supplemented with 10% heat-inactivated FBS, 10 µg/ml gentamicin, 0.1 mM nonessential amino acids to give complete DMEM media. Cells were transfected with orphan GPCR DNAs in the pCR3.1 vector, using LipofectAMINE PLUS™, essentially according to the manufacturer's instructions. Briefly, CHO cells were plated on 10 cm sterile tissue culture dishes (Corning Glass Works, Corning, N.Y.), and they were about 50-60% confluent the day of transfection. In a plastic tube, PLUS (20 µl/plate) was added to cDNA plasmid (5 µg/plate) which was earlier diluted into 0.75 ml OptiMEM, mixed and incubated at room temp for 15 min. Separately, LipofectAMINE (30 µl/plate) was mixed with 0.75 ml OptiMEM and added to the pre-complexed DNA/PLUS mixture and incubated at room temp. for 15 minutes. Medium on the cells was replaced with serum-free transfection medium (plain DMEM, 5 ml/plate), and the DNA-PLUS-LipofectAMINE complex was added (1.5 ml per plate) and mixed gently into the medium followed by a 3 hr incubation at 37° C./5% $CO_2$. Then the medium was supplemented with the complete DMEM medium containing 20% FBS (6.5 ml ml/plate) and the incubation continued at 37° C./5% $CO_2$ for 24 to 48 hrs. A plasmid for Green Fluorescent Protein (GFP, 4 µg/plate) was used for transient GFP expression in CHO cells to estimate the transfection yields under the same conditions also used for GPCRs.

Membrane Preparation

The transfected cells were washed once with ice-cold Dulbecco's phosphate buffered saline (PBS), 5 ml per 10 cm plate, and scraped into 5 ml of the same buffer. Cell suspensions from multiple plates were combined and centrifuged at 500×g for 10 min at 4° C. The cell pellet was reconstituted in ice-cold TEE (25 mM TRIS, 5 mM EGTA, 5 mM EDTA). Convenient aliquots were snap-frozen in liquid nitrogen and stored at −70° C. After thawing, the cells were homogenized and centrifuged at 4° C., 500×g for 5 minutes to pellet nuclei and unbroken cells. The supernatant was centrifuged at 47,000×g for 30 minutes at 4° C. The membrane pellet was washed once with TEE, resuspended in 20 mM HEPES, pH 7.4, 100 mM NaCl, 10 mM $MgCl_2$, 1 mM EDTA (assay buffer), aliquoted and frozen in liquid nitrogen. Membrane aliquots were stored at −70° C. Membrane protein concentration was determined using the BCA Protein Assay Reagent from Pierce (Rockford, Ill.) and BSA as standard.

[$^{35}$S]GTPγS Binding Assay

Aliquots of cell membranes were thawed, homogenized, and diluted into buffer containing 20 mM HEPES, pH 7.4, 100 mM NaCl, 10 mM $MgCl_2$, 1 mM EDTA (assay buffer). Initially, reaction mixtures were prepared in 96-well polypropylene plates (Nunc). In each well, peptide aqueous solution (20 µl, 10×), or water controls (20 µl), 18.2 µM GDP in assay buffer (0.11 ml, 10 µM final), and membranes suspended in assay buffer (50 µl, 10 µg membrane protein) were mixed and placed on ice. The ligand-GDP-membrane mixtures were incubated for 20 min. at room temperature on a shaking platform and then placed on ice. To each sample, 20 µl guanosine-5'-O-(3-[$^{35}$S]thio)-triphosphate ([$^{35}$S]GTPγS) (600-1,200 Ci/mmol from New England Nuclear, Boston, Mass.) was added to ~40,000 cpm/0.2 ml, or a final concentration of 0.1 nM. Plates with the incubation mixtures (0.2 ml/well total) were incubated at room temperature for 45 minutes. Reaction mixture aliquots, 0.175 ml each, were then transferred into wash buffer pretreated (100 µl/well) 96-well FB MultiScreen filter plates (Millipore) and vacuum filtered using a MultiScreen Vacuum manifold (Millipore). Then the membranes were washed 3 times with 0.25 ml ice-cold wash buffer/well (10 mM HEPES, 10 mM $MgCl_2$, pH 7.4) and vacuum filtered. After the last wash, Supermix Opti-phase scintillation fluid (25 µl/well, Wallac) was added and the plates were sealed and counted in a Trilux 1450 Microbeta counter (Wallac) for 1 minute/well. As positive controls, membranes from CHO cells stably expressing a dopamine type 2 ($rD_2$) receptor were treated with 1 mM dopamine in 0.025% ascorbic acid (100 µM dopamine final) or vehicle (0.0025% ascorbic acid final). Non-specific binding was measured in the presence of 100 µM cold GTPγS and was subtracted from the total. Each treatment was carried out in triplicates.

Data Analysis

Ligand-induced stimulation of [$^{35}$S]GTPγS binding was expressed as fold increase over the basal activity with no ligand added. Each treatment was run either in triplicate, or, on occasion, in duplicate, and the binding (cpm) was calculated as means +/− standard deviations. Dose-response curves for the receptor/ligand systems were analyzed using a non-linear least square SAS model, $y=B_{max} X/(K_d+X)$. Other dose-response curves were analyzed using Prism (GraphPad Software, Inc. San Diego, Calif.) and the following equation $y=\text{Bottom}+(\text{Top}-\text{Bottom})/(1+10^{LogEC50-X})$.

Results

Originally, we have chosen the GTPγS assay as a functional assay because agonist-driven stimulation of GTPγS reflects early events in the DmGPCR activation cascade, regardless of further activation pathways of various downstream signaling events. This appears especially useful for the assessment of possible activation of orphan DmGPCRs with unknown functions and unknown signaling pathways. The GTPγS assay was carried out with membranes prepared from CHO cells transiently transfected with DNA encoding *Drosophila* GPCRs using a 96-well MultiScreen G/FB filter plates and a MultiScreen vacuum manifold (Millipore) for filtration. Since the GTPγS assay is known to poorly recognize GPCRs coupled to the Gq class of G-proteins, a $Ca^{+2}$ mobilization assay based on a FLIPR readout was used as well to evaluate Gq-coupled orphan GPCRs in CHO cells transiently transfected with DNA encoding *Drosophila* GPCRs.

Using GTPγS assay, DmGPCR1 (PnuFlyPep34651) was found to be best activated by two peptides, DPKQDFMRF-$NH_2$ (SEQ ID NO: 26) and PDNFMRF-$NH_2$ (SEQ ID NO: 27) ($EC_{50}$'s range 370 nM to 500 nM). As reported by Nambu et al. (*Neuron*, 1988, 1, 55-61), these two peptides are encoded on the same precursor gene together with nine other FaRPs. Additional FaRPs and other neuropeptides which also stimulated GTPγS binding, although less effectively ($EC_{50}$'s in the range of 5 to 10 µM), included the following peptides: TDVDHVFLRF-$NH_2$ (SEQ ID NO: 25), TPAEDFMRF-$NH_2$ (SEQ ID NO: 28), SLKQDFMHF-$NH_2$ (SEQ ID NO: 29), SVKQDFMHF-$NH_2$ (SEQ ID NO: 30), AAMDRY-$NH_2$ (SEQ ID NO: 31), and SVQDNFMHF-$NH_2$ (SEQ ID NO: 32). In addition, the FLIPR assay identified a Colorado potato beetle peptide, ARGPQLRLRF-$NH_2$ (SEQ ID NO: 33), matched to DmGPCR1 receptor with an $EC_{50}$ of 100-200 nM.

As shown by the GTPγS responses, DmGPCR4 (PnuFlyPep 67393) was activated by a *Drosophila melanogaster* allatostatin, drostatin-3 (SRPYSFGL-$NH_2$ (SEQ ID NO: 165)) with an $EC_{50}$ in the low nanomolar range, as well as by various *Diplotera punctata* (cockroach) allatostatins, namely: GDGRLYAFGL-$NH_2$ (SEQ ID NO: 34), DRLYSFGL-$NH_2$ (SEQ ID NO: 35), APSGAQRLYGFGL-$NH_2$ (SEQ ID NO: 36), and GGSLYSFGL-$NH_2$ (SEQ ID NO: 37) ($EC_{50}$s in the range of ca. 20-280 nM). The same peptides elicited a very strong calcium signal when tested at 10 μM by FLIPR. DmGPCR4 has been recently cloned by Lenz et al., supra, and classified as a second putative allatostatin receptor (DARII). However, no pharmacological data on receptor activation have been reported to date. To our knowledge this is the very first experimental evidence that various allatostatins do activate this receptor.

As shown by the GTPγS responses, DmGPCR5 (GenBank Accession No. AX128628) when transiently expressed in CHO-1000A cells, was activated by drotachykinins (DTKs), namely DTK-1 (APTSSFIGMR-NH$_2$) (SEQ ID NO: 169), Met8-DTK-2 (APLAFYGMR-NH$_2$) (SEQ ID NO: 170), DTK-2 (APLAFYGLR-NH$_2$) (SEQ ID NO: 171, DTK-3 (APTGFTGMR-NH$_2$) (SEQ ID NO: 172), DTK-4 (APVNSFVGMR-NH$_2$) (SEQ ID NO: 173), and DTK-5 (APNGFLGMR-NH$_2$) (SEQ ID NO: 174). In a dose-response experiment, DTK-1, Met8-DTK-2, DTK-3, and DTK-5 stimulated GTPγS binding with $EC_{50}$'s in the 250-500 nM range and the maximal stimulation ca. 1.5-fold above basal level. DTK-2 and DTK-4 were less potent as judged by their EC50's in the low micromolar range. In the calcium mobilization assay (FLIPR), DmGPCR5 showed Ca$^{+2}$ responses to the same DTKs with the $EC_{50}$'s in the 1-20 nM range. Additionally, DTK-5, DTK-2 and Met8-DTK-2 were tested in a cAMP (reporter-gene-based) assay and stimulated cAMP release in a dose-response fashion with $EC_{50}$'s of 197 nM, 1.06 μM, and 583 nM, respectively. These data indicate that DmGPCR5 couples to both Gs (cAMP) and Gq (Ca$^{+2}$)-mediated signaling pathways which is analogous to the signaling pathways reported for vertebrate tachykinin receptors.

DmGPCR6a (M811490) was reported as a PYY receptor by Li et al. (*J. Biol. Chem.*, 1992, 267, 9-12). Using the GTPγS assay, the peptides listed in Table 7, tested at 5 μM, stimulated GTPγS binding (1.7 to 4 fold increase above the basal) to membranes from CHO cells transfected with a DNA encoding DmGPCR6a. It is noteworthy that, in addition to a battery of insect and *C. elegans* peptides that activated this receptor, also human NPFF (FLFQPQRF-NH$_2$ (SEQ ID NO: 59)) was found to be a ligand for DmGPCR6 (4-fold increase in GTPγS binding by 5 μM NPFF).

Dmgpcr6aL and Dmgpcr6bL are two splice variants of DmGPCR6a (M811490). The latter was reported as a PYY receptor by Li et al. (*J. Biol. Chem.*, 1992, 267, 9-12). We name both DmGPCR6aL and DmGPCR6bL, RF-amide receptors since they recognize only peptides that have an Arg-Phe-NH$_2$ (RFa) sequence at the C-terminus. The peptides that these DmGPCRs did not "see" have different than RFa sequences at the C-end (e.g., SFa, QFa, YFa, RLa, DWa, RPa, HFa, LQa, SNa etc.). In the calcium mobilization assay (FLIPR), Dmgpcr6a$_L$ and Dmgpcr6b$_L$ showed very strong Ca$^{+2}$ responses to a battery of FaRPs tested at 10 μM. The sequences shown below in Table 7 represent all the identified active FaRPs belonging to various species including *Drosophila, C. elegans, A. suum, Mollusca, P. redivivus, Trematoda*, lobster, human, and leech: The only exception to the C-end "RFamide rule" was the peptide pGluDRDYR-PLQF-NH$_2$ (SEQ ID NO: 120), whose C-terminus ends with an Gln-Phe-NH$_2$ (QFa) sequence. Interestingly, both Dmgpcr6a$_L$ and Dmgpcr6b$_L$ also recognized NPFF (FLFQPQRF-NH$_2$ (SEQ ID NO: 152)), a mammalian peptide with the RFamide sequence at the C-terminus. (Note in the results above that p-Glu or pQ refers to pyroglutamic acid.)

As shown by FLIPR analysis, DmGPCR7 (GenBank Accession No. AX128636) transiently expressed in CHO-10001A cells, was activated by the leucokinins (LKs) and related peptides, namely LK-I (DPAFNSWGa) (SEQ ID NO: 175), LK-V (GSGFSSWGa) (SEQ ID NO: 176), LK-VI (pGlu-SSFHSWGa) (SEQ ID NO: 177), LK-VIII (GSAFYSWGa) (SEQ ID NO: 178), Culekinin (NPFH-SWGa) (SEQ ID NO: 179), mollusc lymnokinin (PSFH-SWSa) (SEQ ID NO: 180), and *Drosophila* leucokinin-like peptides DLK-1 (NSVVLGKKQRFHSWGa) (SEQ ID NO: 181), DLK-2 (pGlu-RFHSWGa) (SEQ ID NO: 182) and DLK-2A (QRFHSWGa) (SEQ ID NO: 183). DmGPCR7 was best activated by the LK peptides having a common C-terminal tetrapeptide sequence, HSWGa. Treatments with this group of peptides, which included DLK-1, DLK-2, DLK-2a, LK-VI and Culekinin, resulted in a very potent intracellular calcium release ($EC_{50}$'s in the picomoloar to subnanomolar range). In contrast other locust LK's with the C-terminal S/NSWGa (LK-I, LK-V) as well the Lymnaea LK (SEQ ID NO: 180), showed lower potency ($EC_{50}$'s 15-30 nM) and the LK-VIII with its YSWGa C-terminal sequence was the least potent in the series ($EC_{50}$'s in the 100-200 nM range). No GTPγS responses to these peptides could be detected in membranes prepared from DmGPCR7/CHO cells, which is indicative of a $G_{q/11}$-coupled receptor. Therefore, DmGPCR7 was identified as a calcium-signaling leucokinin receptor (most likely $G_{q/11}$-coupled) and matched with the drolucokinins as its cognate ligands.

As shown by the GTPγS responses, DmGPCR8 (GenBank Accession No. AX128638) transiently expressed in CHO-10001A cells was activated by the *Manduca sexta* allatostatin-C (AST-C, or Manse-AC), (pGlu-VRFRQCYFNPISCF-OH)      (SEQ ID NO: 184)

or drostatin-C (DST-C), also called flatline peptide (FLT)

(pGlu-VRFRQCYFNPISCF-OH).      (SEQ ID NO: 185)

In a dose response GTPγS-binding experiment, a high potency AST-C and DST-C responses were detected ($EC_{50}$'s in a low nanomolar range). These activities were completely abolished by cell pretreatment with pertussin toxin indicating Gi/Go involvement in receptor activation. In a direct calcium mobilization assay (FLIPR), DmGPCR8 did not show any activity when challenged with AST-C or DST-C. However, strong calcium releasing activity to DST-C was detected in CHO-10001A cells co-transfected with DmGPCR8 and chimeric G-proteins Gqi5 or Gqo5 ($EC_{50}$'s ca 30 nM). On the other hand, coupling to Gqz5 was less efficient ($EC_{50}$ 244 nM) and no calcium mobilization was observed in cells co-transfected with DmGPCR8 and Gqs5. These results indicate that DmGPCR8 is an inhibitory receptor in CHO cells that preferably couples to the Gi/Go type G-proteins. The presented results unequivocally identify DmGPCR8 as a DST-C/FLT receptor.

DmGPCR9 has been matched with FDDY(SO$_3$H) GHLRF-NH$_2$ (SEQ ID NO: 157), based on its very strong signal in the calcium mobilization assay ($EC_{50}$ in the low nanomolar range). The fact that no GTPγS responses to this peptide were detected with membranes prepared from CHO cells transfected with a DNA encoding DmGPCR9, indicates that DmGPCR9 is most likely coupled to Gq signaling pathways. FDDY(SO$_3$H)GHLRF-NH$_2$ (SEQ ID NO: 157)

represents a Met7→Leu7 analog of the naturally occurring drosulfakinin-1 (DSK-1), FDDY(SO$_3$H)GHMRF-NH$_2$ (SEQ ID NO: 159). Therefore we assign the DmGPCR9 receptor as a sulfakinin receptor. This match is very specific since even FDDYGHLRF-NH$_2$ (SEQ ID NO:158), which is an unsulfated counterpart of FDDY(SO$_3$H)GHLRF-NH$_2$ (SEQ ID NO: 157), showed only a very weak calcium signal when tested at 10 μM and none of the other 117 tested FaRPs and related peptides showed any activity either in FLIPR or in the GTPγS assay at the DmGPCR9 receptor.

A table matching the ligands with their associated receptors is shown below in Table 7.

TABLE 7

| GPCR | SEQ ID NO | Peptide Matching Sequence |
|---|---|---|
| dmgpcr1 | SEQ ID NO:25 | TDVDHVFLRF-NH$_2$ |
| | SEQ ID NO:26 | DPKQDFMRF-NH$_2$ |
| | SEQ ID NO 27 | PDNFMRF-NH$_2$ |
| | SEQ ID NO:28 | TPAEDFMRF-NH$_2$ |
| | SEQ ID NO:29 | SLKQDFMHF-NH$_2$ |
| | SEQ ID NO:30 | SVKQDFMHF-NH$_2$ |
| | SEQ ID NO:31 | AAMDRY-NH$_2$ |
| | SEQ ID NO:32 | SVQDNFMHF-NH$_2$ |
| | SEQ ID NO:33 | ARGPQLRLRF-NH$_2$ |
| dmgpcr4 | SEQ ID NO:34 | GDGRLYAFGL-NH$_2$ |
| | SEQ ID NO:35 | DRLYSFGL-NH$_2$ |
| | SEQ ID NO:36 | APSGAQRLYGFGL-NH$_2$ |
| | SEQ ID NO:37 | GGSLYSFGL-NH$_2$ |
| dmgpcr6 (6a) | SEQ ID NO:38 | FIRF-NH$_2$ |
| | SEQ ID NO:39 | KNEFIRF-NH$_2$ |
| | SEQ ID NO:40 | FMRF-NH$_2$ |
| | SEQ ID NO:41 | KSAFMRF-NH$_2$ |
| | SEQ ID NO:42 | KPNFLRF-NH$_2$ |
| | SEQ ID NO:43 | FLRF-NH$_2$ |
| | SEQ ID NO:44 | YLRF-NH$_2$ |
| | SEQ ID NO:45 | KPNFLRY-NH$_2$ |
| | SEQ ID NO:46 | TNRNFLRF-NH$_2$ |
| | SEQ ID NO:47 | RNKFEFIRF-NH$_2$ |
| | SEQ ID NO:48 | AGPRFIRF-NH$_2$ |
| | SEQ ID NO:49 | GLGPRPLRF-NH$_2$ |
| | SEQ ID NO:50 | IL-Nle-RF-NH$_2$ |
| | SEQ ID NO:51 | AGAKFIRF-NH$_2$ |
| | SEQ ID NO:52 | APKPKFIRF-NH$_2$ |
| | SEQ ID NO:53 | KSAFVLRF-NH$_2$ |
| | SEQ ID NO:54 | TKEQDFLRF-NH$_2$ |
| | SEQ ID NO:55 | SAEPFGTMRF-NH$_2$ |
| | SEQ ID NO:56 | ASEDALFGTMRF-NH$_2$ |
| | SEQ ID NO:57 | SADDSAPFGTMRF-NH$_2$ |
| | SEQ ID NO:58 | EDGNAPFGTMRF-NH$_2$ |
| | SEQ ID NO:59 | FLFQPQRF-NH$_2$ |
| dmgpcr6 6aL and 6bL | SEQ ID NO:60 | SADPNFLRF-NH$_2$ |
| | SEQ ID NO:61 | SQPNFLRF-NH$_2$ |
| | SEQ ID NO:62 | ASGDPNFLRF-NH$_2$ |
| | SEQ ID NO:63 | SDPNFLRF-NH$_2$ |
| | SEQ ID NO:64 | AAADPNFLRF-NH$_2$ |
| | SEQ ID NO:65 | PNFLRF-NH$_2$ |
| | SEQ ID NO:66 | KPNFLRF-NH$_2$ |
| | SEQ ID NO:67 | AGSDPNFLRF-NH$_2$ |
| | SEQ ID NO:68 | KPNFLRY-NH$_2$ |
| | SEQ ID NO:69 | SPREPIRF-NH$_2$ |
| | SEQ ID NO:70 | LRGEPIRF-NH$_2$ |
| | SEQ ID NO:71 | SPLGTMRF-NH$_2$ |
| | SEQ ID NO:72 | EAEEPLGTMRF-NH$_2$ |
| | SEQ ID NO:73 | ASEDALFGTMRF-NH$_2$ |
| | SEQ ID NO:74 | EDGNAPFGTMRF-NH$_2$ |
| | SEQ ID NO:75 | SAEPFGTMRF-NH$_2$ |
| | SEQ ID NO:76 | SADDSAPFGTMRF-NH$_2$ |
| | SEQ ID NO:77 | KPTFIRF-NH$_2$ |
| | SEQ ID NO:78 | ASPSFIRF-NH$_2$ |
| | SEQ ID NO:79 | GAKFIRF-NH$_2$ |
| | SEQ ID NO:80 | AGAKFIRF-NH$_2$ |
| | SEQ ID NO:81 | APKPKFIRF-NH$_2$ |
| | SEQ ID NO:82 | KSAYMRF-NH$_2$ |
| | SEQ ID NO:83 | SPMQRSSMVRF-NH$_2$ |
| | SEQ ID NO:84 | SPMERSAMVRF-NH$_2$ |
| | SEQ ID NO:85 | SPMDRSKMVRF-NH$_2$ |
| | SEQ ID NO:86 | KNEFIRF-NH$_2$ |

TABLE 7-continued

| GPCR | SEQ ID NO | Peptide Matching Sequence |
|---|---|---|
| | SEQ ID NO:87 | KPSFVRF-NH$_2$ |
| | SEQ ID NO:88 | pQPKARSGYIRF-NH$_2$ |
| | SEQ ID NO:89 | AMRNALVRF-NH$_2$ |
| | SEQ ID NO:90 | ASGGMRNALVRF-NH$_2$ |
| | SEQ ID NO:91 | NGAPQPFVRF-NH$_2$ |
| | SEQ ID NO:92 | RNKFEFIRF-NH$_2$ |
| | SEQ ID NO:93 | SDRPTRAMDSPLIRF-NH$_2$ |
| | SEQ ID NO:94 | AADGAPLIRF-NH$_2$ |
| | SEQ ID NO:95 | APEASPFIRF-NH$_2$ |
| | SEQ ID NO:96 | ASPSAPLIRF-NH$_2$ |
| | SEQ ID NO:97 | SPSAVPLIRF-NH$_2$ |
| | SEQ ID NO:98 | ASSAPLIRF-NH$_2$ |
| | SEQ ID NO:99 | KHEYLRF-NH$_2$ |
| | SEQ ID NO:100 | SLLDYRF-NH$_2$ |
| | SEQ ID NO:101 | EIVFHQISPIFFRF-NH$_2$ |
| | SEQ ID NO:102 | GGPQGPLRF-NH$_2$ |
| | SEQ ID NO:103 | GPSGPLRF-NH$_2$ |
| | SEQ ID NO:104 | AQTFVRF-NH$_2$ |
| | SEQ ID NO:105 | GQTFVRF-NH$_2$ |
| | SEQ ID NO:106 | KSAFVRF-NH$_2$ |
| | SEQ ID NO:107 | KSQYIRF-NH$_2$ |
| | SEQ ID NO:108 | DVPGVLRF-NH$_2$ |
| | SEQ ID NO:109 | KSVPGVLRF-NH$_2$ |
| | SEQ ID NO:110 | SEVPGVLRF-NH$_2$ |
| | SEQ ID NO:111 | SVPGVLRF-NH$_2$ |
| | SEQ ID NO:112 | DFDGAMPGVLRF-NH$_2$ |
| | SEQ ID NO:113 | EIPGVLRF-NH$_2$ |
| | SEQ ID NO:114 | WANQVRF-NH$_2$ |
| | SEQ ID NO:115 | ASWASSVRF-NH$_2$ |
| | SEQ ID NO:116 | AMMRF-NH$_2$ |
| | SEQ ID NO:117 | GLGPRPLRF-NH$_2$ |
| | SEQ ID NO:118 | SPSAKWMRF-NH$_2$ |
| | SEQ ID NO:119 | TKFQDFLRF-NH$_2$ |
| | SEQ ID NO:120 | pQDRDYRPLQF-NH$_2$ |
| | SEQ ID NO:121 | FIRF-NH$_2$ |
| | SEQ ID NO:122 | AVPGVLRF-NH$_2$ |
| | SEQ ID NO:123 | GDVPGVLRF-NH$_2$ |
| | SEQ ID NO:124 | SDIGISEPNFLRF-NH$_2$ |
| | SEQ ID NO:125 | SGKPTFIRF-NH$_2$ |
| | SEQ ID NO:126 | AEGLSSPLIRF-NH$_2$ |
| | SEQ ID NO:127 | FDRDFMRF-NH$_2$ |
| | SEQ ID NO:128 | AGPRFIRF-NH$_2$ |
| | SEQ ID NO:129 | GMPGVLRF-NH$_2$ |
| | SEQ ID NO:130 | IL-Nle-RF-NH$_2$ |
| | SEQ ID NO:131 | LQPNFLRF-NH$_2$ |
| | SEQ ID NO:132 | KPNFIRF-NH$_2$ |
| | SEQ ID NO:133 | FMRF-NH$_2$ |
| | SEQ ID NO:134 | FLRF-NH$_2$ |
| | SEQ ID NO:135 | YIRF-NH$_2$ |
| | SEQ ID NO:136 | GNSFLRF-NH$_2$ |
| | SEQ ID NO:137 | DPSFLRF-NH$_2$ |
| | SEQ ID NO:138 | pQDFMRF-NH$_2$ |
| | SEQ ID NO:139 | KPNQDFMRF-NH$_2$ |
| | SEQ ID NO:140 | TDVDHVFLRF-NH$_2$ |
| | SEQ ID NO:141 | AAMDRY-NH$_2$ |
| | SEQ ID NO:142 | SPKQDFMRF-NH$_2$ |
| | SEQ ID NO:143 | PDNFMRF-NH$_2$ |
| | SEQ ID NO:144 | DPKQDFMRF-NH$_2$ |
| | SEQ ID NO:145 | TPAEDFMRF-NH$_2$ |
| | SEQ ID NO:146 | SDNFMRF-NH$_2$ |
| | SEQ ID NO:147 | YLRF-NH$_2$ |
| | SEQ ID NO:148 | SDRNFLRF-NH$_2$ |
| | SEQ ID NO:149 | TNRNFLRF-NH$_2$ |
| | SEQ ID NO:150 | PDVDHVFLRF-NH$_2$ |
| | SEQ ID NO:151 | pQDVDHVFLRF-NH$_2$ |
| | SEQ ID NO:152 | FLFQPQRF-NH$_2$ |
| | SEQ ID NO:153 | ARGPQLRLRF-NH$_2$ |
| | SEQ ID NO:154 | FDDY(SO$_3$H)GHLRF-NH$_2$ |
| | SEQ ID NO:155 | FDDYGHLRF-NH$_2$ |
| | SEQ ID NO:156 | MDSNFIRF-NH$_2$ |
| dmgpcr9 | SEQ ID NO:157 | FDDY(SO$_3$H)GHLRF-NH$_2$ |
| dmgpcr5 | SEQ ID NO:169 | APTSSFIGMR-NH$_2$ |
| | SEQ ID NO:170 | APLAFYGMR-NH$_2$ |
| | SEQ ID NO:171 | APLAFYGLR-NH$_2$ |
| | SEQ ID NO:172 | APTGFTGMR-NH$_2$ |
| | SEQ ID NO:173 | APVNSFVGMR-NH$_2$ |
| | SEQ ID NO:174 | APNGFLGMR-NH$_2$ |

TABLE 7-continued

| GPCR | SEQ ID NO | Peptide Matching Sequence |
|---|---|---|
| dmgpcr7 | SEQ ID NO:175 | DPAFNSWG-NH$_2$ |
| | SEQ ID NO:176 | GSGFSSWG-NH$_2$ |
| | SEQ ID NO:177 | pGlu-SSFHSWG-NH$_2$ |
| | SEQ ID NO:178 | GASFYSWG-NH$_2$ |
| | SEQ ID NO:179 | NPFHSWG-NH$_2$ |
| | SEQ ID NO:180 | PSFHSWS-NH$_2$ |
| | SEQ ID NO:181 | NSVVLGKKQRFHSWG-NH$_2$ |
| | SEQ ID NO:182 | pGlu-RFHSWG-NH$_2$ |
| | SEQ ID NO:183 | QRFHSWG-NH$_2$ |
| dmgpcr8 | SEQ ID NO:184 | pGlu-VRFRQCYFNPISCF-OH |
| | SEQ ID NO:185 | pGlu-VRYRQCYFNPISCF-OH |

Example 10

Competition Assay

Preparation of Mono-Iodinated Peptide

The peptide is iodinated via a typical chloramine T procedure. Added to a 2 ml glass vial are 10 μl of a 1 mM water solution of peptide, 10 μl of 0.1M (pH 7.99) sodium phosphate buffer, 1.0 mCi [$^{125}$I] sodium iodide, and 5 μl of a 2 mg/ml chloramine T solution (in the phosphate buffer). The mixture is vortexed for 60 seconds and the reaction stopped by the addition of 25 μl of a 5 mg/ml solution of sodium metabisulfite in phosphate buffer. The mixture then undergoes HPLC by injecting it onto a Vydac C18 (0.45×15 cm) column and subjecting it to gradient separation. The gradient used is 70% A and 30% B at time zero to 20% A and 80% B at time 25 minutes (A=0.1M NH$_4$ acetate in water. B=0.1M NH$_4$ acetate in water 40%: CH$_3$CN 60%, v:v.). Flow rate is 1.0 ml/minute. Samples are collected into 0.25 ml capture buffer (0.1M sodium phosphate buffer with 0.5% bovine serum albumin, 0.1% Triton X100 and 0.05% Tween 20) at 30 second intervals from t=8 to t=20 minutes. Monoiodo peptide typically elutes at t=11 minutes and the yield is approximately 100 μCi in 0.75 ml.

Binding Assay 96-well plates used are Millipore Multiscreen® filtration plates (FB opaque 1.0 μM glass fiber type B, cat. # MAF-BNOB50). A Millipore Multiscreen® solvent resistant manifold (cat. # MAVMO960R) is used in conjunction with the plates to filter the assay at termination. Each replicate is one well and has a volume of 100 ul containing 5 ug protein (preparation described above). Each test group contains two replicates. For each test compound, one group is run with [$^{125}$I]peptide only (for total binding) and one with 1 μM (or as designated) concentration of the test compound and [$^{125}$I]peptide (for non-specific binding). The order of adding reagents for each replicate is: assay buffer (20 mM HEPES, 10 mM MgCl$_2$, 1% bovine serum albumin, pH 7.4) test compound (made up in assay buffer), [$^{125}$I]peptide (in assay buffer) and membrane suspension (in assay buffer). The addition of the membrane suspension initiates the binding reaction which is run for 30 minutes at room temperature (22° C.). Following the 30 minute incubation each plate is place on the filtration manifold and vacuum is applied, pulling the liquid through the filter (discarded) and catching the protein on the filters in each well. For washing, the vacuum is released and 200 μl assay buffer is added to each well followed by reapplication of the vacuum. This washing is repeated twice more (total of 3× washes for each replicate). Following washing, the plastic covering on the underside of each plate is removed and the plate placed in a bottom sealed Microbeta® scintillation counting cassette (cat # 1450-105). 25 μl of scintillant is added to each well and the plate is placed on a rotary shaker at 80 rpm for one hour and then allowed to sit overnight. The following day the plate is counted in a Microbeta® scintillation counter. The mean non-specific binding is subtracted from the mean total binding to yield specific binding for both the standard (peptideamide) and the unknowns.

As those skilled in the art will appreciate, numerous changes and modifications may be made to the embodiments of the invention described above without departing from the spirit of the invention. It is intended that all such variations fall within the scope of the invention.

The entire disclosure of each publication cited herein is hereby incorporated by reference.

What is claimed is:

1. A method for identifying a modulator of binding and/or function of the bound complex between a DmGPCR and a drotachykinin, comprising the steps of:
   - contacting a drotachykinin and a composition comprising a DmGPCR encoded by the nucleotide sequence consisting of SEQ ID NO:9 in the presence or in the absence of a putative modulator compound;
   - detecting binding between the drotachykinin and the DmGPCR; and
   - determining whether binding in the presence of said putative modulator compound is increased or decreased compared to binding in the absence of said putative modulator compound, and/or
   - determining whether function in the presence of said putative modulator compound is increased or decreased compared to function in the absence of said putative modulator compound,
   - wherein said DmGPCR binds to a drotachykinin.

2. The method according to claim 1, wherein said drotachykinin is selected from the group consisting of DTK-1 (SEQ ID NO: 169), Met8-DTK-2 (SEQ ID NO: 170), DTK-2 (SEQ ID NO: 171), DTK-3 (SEQ ID NO: 172), DTK-4 (SEQ ID NO: 173), and DTK-5 (SEQ ID NO: 174).

3. The method according to claim 2 wherein said drotachykinin is DTK-1 (SEQ ID NO: 169).

4. The method according to claim 1 wherein said DmGPCR has the amino acid sequence of SEQ ID NO: 10.

5. The method according to claim 2 wherein said DmGPCR has the amino acid sequence of SEQ ID NO: 10.

* * * * *

SEQUENCE LISTING

<160> NUMBER OF SEQ ID NOS: 185

<210> SEQ ID NO 1
<211> LENGTH: 1803
<212> TYPE: DNA
<213> ORGANISM: D. melanogaster

<400> SEQUENCE: 1

```
atggccaact taagctggct gagcaccatc accaccacct cctcctccat cagcaccagc       60
cagctgccat tggtcagcac aaccaactgg agcctaacgt cgccgggaac tactagcgct      120
atcttggcgg atgtggctgc atcggatgag gataggagcg gcgggatcat tcacaaccag      180
ttcgtgcaaa tcttcttcta cgtcctgtac gccacggtct ttgtcctggg tgtcttcgga      240
aatgtcctgg tttgctacgt agttctgagg aatcgggcca tgcagactgt gaccaatata      300
ttcatcacga atctggccct gtcggacata ttgctctgcg tcctggcggt gccatttact      360
ccgctttaca cgttcatggg tcgctgggcc ttcggcagga gtctgtgcca tctggtgtcc      420
```

```
tttgcccagg gatgcagcat ctacatatcc acgctgaccc tcacctcgat tgccatcgat      480
cggtacttcg ttatcatata ccccttccat ccgcgcatga agctctccac ctgcatcggg      540
atcatagtga gcatctgggt gatagccctg ctggccaccg ttccctacgg catgtacatg      600
aagatgacca acgagctggt gaacggaacg cagacaggca acgagaccct ggtggaggcc      660
actctaatgc taaacggaag ctttgtggcc cagggatcag gattcatcga ggcgccggac      720
tctacctcgg ccacccaggc ctatatgcag gtgatgaccg ccggatcaac gggaccggag      780
atgccctatg tgcgggtgta ctgcgaggag aactggccat cggagcagta ccggaaggtg      840
ttcggtgcca tcacaaccac tctgcagttt gtgctgccct tcttcatcat ctcgatttgc      900
tacgtgtgga tatcggtgaa gctaaaccag cgggccaggg ccaagccggg atcgaaatcc      960
tcgagacggg aggaggcgga tcgggatcgc aagaagcgca ccaaccgcat gctcatcgcc     1020
atggtggcgg tattcggact cagctggctg cccatcaatg tggtcaacat attcgatgac     1080
ttcgatgaca agtccaacga gtggcgcttc tacatcctat tcttctttgt ggcccactct     1140
attgccatga gctccacctg ctacaatccc ttcctgtacg cctggctgaa cgagaacttc     1200
cgcaaggagt tcaagcacgt gctgccctgc tttaatccct cgaacaacaa catcatcaac     1260
atcaccaggg gctataatcg gagtgatcgg aacacctgtg gtccgcgact gcatcatggc     1320 aaggggatg gtggcatggg cggtggcagt ctggacgccg acgaccagga cgagaacggc     1380
atcacccagg agacctgtct gcccaaggag aagctgctga ttatcccag ggagccgact     1440 tacggcaatg cacgggtgc cgtgtcgcca atccttagcg ggcgcggcat taacgccgcc     1500
ctggtgcacg gtggcgacca tcagatgcac cagctgcagc cgtcacacca tcaacaggtg     1560
gagctgacga ggcgaatccg ccggcggaca gacgagacgg acggggatta cctggactcc     1620
ggcgacgagc agaccgtgga ggtgcgcttc agcgagacgc cgttcgtcag cacggataat     1680
accaccggga tcagcattct ggagacgagt acgagtcact gccaggactc ggatgtgatg     1740
gtcgagctgg gcgaggcaat cggcgccggt ggtggggcag agctggggag gcgaatcaac     1800
tga                                                                   1803
```

<210> SEQ ID NO 2
<211> LENGTH: 600
<212> TYPE: PRT
<213> ORGANISM: D. melanogaster

<400> SEQUENCE: 2

```
Met Ala Asn Leu Ser Trp Leu Ser Thr Ile Thr Thr Ser Ser Ser
1               5                  10                  15

Ile Ser Thr Ser Gln Leu Pro Leu Val Ser Thr Asn Trp Ser Leu
                20                  25                  30

Thr Ser Pro Gly Thr Thr Ser Ala Ile Leu Ala Asp Val Ala Ser
            35                  40                  45

Asp Glu Asp Arg Ser Gly Gly Ile Ile His Asn Gln Phe Val Gln Ile
    50                  55                  60

Phe Phe Tyr Val Leu Tyr Ala Thr Val Phe Leu Gly Val Phe Gly
65                  70                  75                  80

Asn Val Leu Val Cys Tyr Val Val Leu Arg Asn Arg Ala Met Gln Thr
                85                  90                  95

Val Thr Asn Ile Phe Ile Thr Asn Leu Ala Leu Ser Asp Ile Leu Leu
            100                 105                 110

Cys Val Leu Ala Val Pro Phe Thr Pro Leu Tyr Thr Phe Met Gly Arg
```

-continued

```
            115                 120                 125
Trp Ala Phe Gly Arg Ser Leu Cys His Leu Val Ser Phe Ala Gln Gly
        130                 135                 140

Cys Ser Ile Tyr Ile Ser Thr Leu Thr Leu Thr Ser Ile Ala Ile Asp
145                 150                 155                 160

Arg Tyr Phe Val Ile Ile Tyr Pro Phe His Pro Arg Met Lys Leu Ser
                165                 170                 175

Thr Cys Ile Gly Ile Ile Val Ser Ile Trp Val Ile Ala Leu Leu Ala
                180                 185                 190

Thr Val Pro Tyr Gly Met Tyr Met Lys Met Thr Asn Glu Leu Val Asn
                195                 200                 205

Gly Thr Gln Thr Gly Asn Glu Thr Leu Val Glu Ala Thr Leu Met Leu
            210                 215                 220

Asn Gly Ser Phe Val Ala Gln Gly Ser Gly Phe Ile Glu Ala Pro Asp
225                 230                 235                 240

Ser Thr Ser Ala Thr Gln Ala Tyr Met Gln Val Met Thr Ala Gly Ser
                245                 250                 255

Thr Gly Pro Glu Met Pro Tyr Val Arg Val Tyr Cys Glu Glu Asn Trp
                260                 265                 270

Pro Ser Glu Gln Tyr Arg Lys Val Phe Gly Ala Ile Thr Thr Thr Leu
            275                 280                 285

Gln Phe Val Leu Pro Phe Phe Ile Ile Ser Ile Cys Tyr Val Trp Ile
            290                 295                 300

Ser Val Lys Leu Asn Gln Arg Ala Arg Ala Lys Pro Gly Ser Lys Ser
305                 310                 315                 320

Ser Arg Arg Glu Glu Ala Asp Arg Asp Arg Lys Lys Arg Thr Asn Arg
                325                 330                 335

Met Leu Ile Ala Met Val Ala Val Phe Gly Leu Ser Trp Leu Pro Ile
                340                 345                 350

Asn Val Val Asn Ile Phe Asp Asp Phe Asp Lys Ser Asn Glu Trp
            355                 360                 365

Arg Phe Tyr Ile Leu Phe Phe Phe Val Ala His Ser Ile Ala Met Ser
        370                 375                 380

Ser Thr Cys Tyr Asn Pro Phe Leu Tyr Ala Trp Leu Asn Glu Asn Phe
385                 390                 395                 400

Arg Lys Glu Phe Lys His Val Leu Pro Cys Phe Asn Pro Ser Asn Asn
                405                 410                 415

Asn Ile Ile Asn Ile Thr Arg Gly Tyr Asn Arg Ser Asp Arg Asn Thr
                420                 425                 430

Cys Gly Pro Arg Leu His His Gly Lys Gly Asp Gly Met Gly Gly
            435                 440                 445

Gly Ser Leu Asp Ala Asp Asp Gln Asp Glu Asn Gly Ile Thr Gln Glu
        450                 455                 460

Thr Cys Leu Pro Lys Glu Lys Leu Leu Ile Ile Pro Arg Glu Pro Thr
465                 470                 475                 480

Tyr Gly Asn Gly Thr Gly Ala Val Ser Pro Ile Leu Ser Gly Arg Gly
                485                 490                 495

Ile Asn Ala Ala Leu Val His Gly Gly Asp His Gln Met His Gln Leu
            500                 505                 510

Gln Pro Ser His His Gln Val Glu Leu Thr Arg Arg Ile Arg Arg
            515                 520                 525

Arg Thr Asp Glu Thr Asp Gly Asp Tyr Leu Asp Ser Gly Asp Glu Gln
        530                 535                 540
```

Thr Val Glu Val Arg Phe Ser Glu Thr Pro Phe Val Ser Thr Asp Asn
545                 550                 555                 560

Thr Thr Gly Ile Ser Ile Leu Glu Thr Ser Thr Ser His Cys Gln Asp
            565                 570                 575

Ser Asp Val Met Val Glu Leu Gly Glu Ala Ile Gly Ala Gly Gly
        580                 585                 590

Ala Glu Leu Gly Arg Arg Ile Asn
        595                 600

<210> SEQ ID NO 3
<211> LENGTH: 1445
<212> TYPE: DNA
<213> ORGANISM: D. melanogaster

<400> SEQUENCE: 3

```
atgaatcaga cggagcccgc ccagctggca gatggggagc atctgagtgg atacgccagc      60
agcagcaaca gcgtgcgcta tctggacgac cggcatccgc tggactacct tgacctgggc     120
acggtgcacg ccctcaacac cactgccatc aacacctcgg atctgaatga actgggagc      180
aggccgctgg acccggtgct tatcgatagg ttcctgagca cagggcggt ggacagcccc      240
tggtaccaca tgctcatcag catgtacggc gtgctaatcg tcttcggcgc cctaggcaac     300
accctggttg ttatagccgt catccggaag cccatcatgc gcactgctcg caatctgttc     360
atcctcaacc tggccatatc ggacctactt ttatgcctag tcaccatgcc gctgaccttg     420
atggagatcc tgtccaagta ctggccctac ggctcctgct ccatcctgtg caaaacgatt     480
gccatgctgc aggcactttg tattttcgtg tcgacaatat ccataacggc cattgccttc     540
gacagatatc aggtgatcgt gtaccccacg cgggacagcc tgcagttcgt gggcgcggtg     600
acgatcctgg cggggatctg ggcactggca ctgctgctgg cctcgccgct gttcgtctac     660
aaggagctga tcaacacaga cacgccggca ctcctgcagc agatcggcct gcaggacacg     720
atcccgtact gcattgagga ctggccaagt cgcaacgggc gcttctacta ctcgatcttc     780
tcgctgtgcg tacaataccct ggtgccatc ctgatcgtct cggtggcata cttcgggatc     840
tacaacaagc tgaagagccg catcaccgtg gtggctgtgc aggcgtcctc cgctcagcgg     900
aaggtggagc gggggcggcg gatgaagcgc accaactgcc tactgatcag catcgccatc     960
atctttggcg tttcttggct gccgctgaac ttttttcaacc tgtacgcgga catggagcgc    1020
tcgccggtca ctcagagcat gctagtccgc tacgccatct gccacatgat cggcatgagc    1080
tccgcctgct ccaacccgtt gctctacggc tggctcaacg acaacttccg taaagaattt    1140
caagaactgc tctgccgttg ctcagacact aatgttgctc ttaacggtca cacgacaggc    1200
tgcaacgtcc aggcggcggc gcgcaagcgt cgcaagttgg gcgccgaact ctccaaaggc    1260
gaactcaagc tgctggggcc aggcggcgcc cagagcggta ccgccggcgg ggaaggcggt    1320
ctggcggcca ccgacttcat gaccggccac cacgagggcg gactgcgcag cgccataacc    1380
gagtcggtgg ccctcacgga ccacaacccc gtgccctcgg aggtcaccaa gctgatgccg    1440
cggta                                                                1445
```

<210> SEQ ID NO 4
<211> LENGTH: 357
<212> TYPE: PRT
<213> ORGANISM: D. melanogaster

<400> SEQUENCE: 4

```
Met Glu Asn Thr Thr Met Leu Ala Asn Ile Ser Leu Asn Ala Thr Arg
1               5                   10                  15

Asn Glu Glu Asn Ile Thr Ser Phe Phe Thr Asp Glu Glu Trp Leu Ala
                20                  25                  30

Ile Asn Gly Thr Leu Pro Trp Ile Val Gly Phe Phe Gly Val Ile
            35                  40                  45

Ala Ile Thr Gly Phe Phe Gly Asn Leu Leu Val Ile Leu Val Val Val
50                      55                  60

Phe Asn Asn Asn Met Arg Ser Thr Thr Asn Leu Met Ile Val Asn Leu
65                  70                  75                  80

Ala Ala Ala Asp Leu Met Phe Val Ile Leu Cys Ile Pro Phe Thr Ala
                85                  90                  95

Thr Asp Tyr Met Val Tyr Tyr Trp Pro Tyr Gly Arg Phe Trp Cys Arg
            100                 105                 110

Ser Val Gln Tyr Leu Ile Val Val Thr Ala Phe Ala Ser Ile Tyr Thr
                115                 120                 125

Leu Val Leu Met Ser Ile Asp Arg Phe Leu Ala Val Val His Pro Ile
    130                 135                 140

Arg Ser Arg Met Met Arg Thr Glu Asn Ile Thr Leu Ile Ala Ile Val
145                 150                 155                 160

Thr Leu Trp Ile Val Val Leu Val Val Ser Val Pro Val Ala Phe Thr
                165                 170                 175

His Asp Val Val Val Asp Tyr Asp Ala Lys Lys Asn Ile Thr Tyr Gly
            180                 185                 190

Met Cys Thr Phe Thr Thr Asn Asp Phe Leu Gly Pro Arg Thr Tyr Gln
            195                 200                 205

Val Thr Phe Phe Ile Ser Ser Tyr Leu Leu Pro Leu Met Ile Ile Ser
    210                 215                 220

Gly Leu Tyr Met Arg Met Ile Met Arg Leu Trp Arg Gln Gly Thr Gly
225                 230                 235                 240

Val Arg Met Ser Lys Glu Ser Gln Arg Gly Arg Lys Arg Val Thr Arg
                245                 250                 255

Leu Val Val Val Val Ile Ala Phe Ala Ser Leu Trp Leu Pro Val
                260                 265                 270

Gln Leu Ile Leu Leu Lys Ser Leu Asp Val Ile Glu Thr Asn Thr
    275                 280                 285

Leu Thr Lys Leu Val Ile Gln Val Thr Ala Gln Thr Leu Ala Tyr Ser
    290                 295                 300

Ser Ser Cys Ile Asn Pro Leu Leu Tyr Ala Phe Leu Ser Glu Asn Phe
305                 310                 315                 320

Arg Lys Ala Phe Tyr Lys Ala Val Asn Cys Ser Ser Arg Tyr Gln Asn
                325                 330                 335

Tyr Thr Ser Asp Leu Pro Pro Pro Arg Lys Thr Ser Cys Ala Arg Thr
            340                 345                 350

Ser Thr Thr Gly Leu
        355
```

<210> SEQ ID NO 5
<211> LENGTH: 1376
<212> TYPE: DNA
<213> ORGANISM: D. melanogaster

<400> SEQUENCE: 5
atgaatcaga cggagcccgc ccagctggca gatggggagc atctgagtgg atacgccagc    60

```
agcagcaaca gcgtgcgcta tctggacgac cggcatccgc tggactacct tgacctgggc    120
acggtgcacg ccctcaacac cactgccatc aacacctcgg atctgaatga gactgggagc    180
aggccgctgg acccggtgct tatcgatagg ttcctgagca cagggcggt ggacagcccc     240
tggtaccaca tgctcatcag catgtacggc gtgctaatcg tcttcggcgc cctaggcaac    300
accctggttg ttatagccgt catccggaag cccatcatgc gcactgctcg caatctgttc    360
atcctcaacc tggccatatc ggacctactt ttatgcctag tcaccatgcc gctgaccttg    420
atggagatcc tgtccaagta ctggccctac ggctcctgct ccatcctgtg caaaacgatt    480
gccatgctgc aggcactttg tattttcgtg tcgacaatat ccataacggc cattgccttc    540
gacagatatc aggtgatcgt gtaccccacg cgggacagcc tgcagttcgt gggcgcggtg    600
acgatcctgg cggggatctg ggcactggca ctgctgctgg cctcgccgct gttcgtctac    660
aaggagctga tcaacacaga cacgccggca ctcctgcagc agatcggcct gcaggacacg    720
atcccgtact gcattgagga ctggccaagt cgcaacgggc gcttctacta ctcgatcttc    780
tcgctgtgcg tacaatacct ggtgcccatc ctgatcgtct cggtggcata cttcgggatc    840
tacaacaagc tgaagagccg catcaccgtg gtggctgtgc aggcgtcctc cgctcagcgg    900
aaggtggagc gggggcggcg gatgaagcgc accaactgcc tactgatcag catcgccatc    960
atctttggcg tttcttggct gccgctgaac tttttcaacc tgtacgcgga catggagcgc   1020
tcgccggtca ctcagagcat gctagtccgc tacgccatct gccacatgat cggcatgagc   1080
tccgcctgct ccaacccgtt gctctacggc tggctcaacg acaacttccg ctgcaacgtc   1140
caggcggcgg cgcgcaagcg tcgcaagttg ggcgccgaac tctccaaagg cgaactcaag   1200
ctgctggggc caggcggcgc ccagagcggt accgccggcg gggaaggcgg tctggcggcc   1260
accgacttca tgaccggcca ccacgagggc ggactgcgca gcgccataac cgagtcggtg   1320
gccctcacgg accacaaccc cgtgccctcg gaggtcacca agctgatgcc gcggta        1376
```

<210> SEQ ID NO 6
<211> LENGTH: 458
<212> TYPE: PRT
<213> ORGANISM: D. melanogaster

<400> SEQUENCE: 6

```
Met Asn Gln Thr Glu Pro Ala Gln Leu Ala Asp Gly Glu His Leu Ser
1               5                   10                  15

Gly Tyr Ala Ser Ser Ser Asn Ser Val Arg Tyr Leu Asp Asp Arg His
            20                  25                  30

Pro Leu Asp Tyr Leu Asp Leu Gly Thr Val His Ala Leu Asn Thr Thr
        35                  40                  45

Ala Ile Asn Thr Ser Asp Leu Asn Glu Thr Gly Ser Arg Pro Leu Asp
    50                  55                  60

Pro Val Leu Ile Asp Arg Phe Leu Ser Asn Arg Ala Val Asp Ser Pro
65                  70                  75                  80

Trp Tyr His Met Leu Ile Ser Met Tyr Gly Val Leu Ile Val Phe Gly
                85                  90                  95

Ala Leu Gly Asn Thr Leu Val Val Ile Ala Val Ile Arg Lys Pro Ile
            100                 105                 110

Met Arg Thr Ala Arg Asn Leu Phe Ile Leu Asn Leu Ala Ile Ser Asp
        115                 120                 125

Leu Leu Leu Cys Leu Val Thr Met Pro Leu Thr Leu Met Glu Ile Leu
    130                 135                 140
```

-continued

```
Ser Lys Tyr Trp Pro Tyr Gly Ser Cys Ser Ile Leu Cys Lys Thr Ile
145                 150                 155                 160
Ala Met Leu Gln Ala Leu Cys Ile Phe Val Ser Thr Ile Ser Ile Thr
            165                 170                 175
Ala Ile Ala Phe Asp Arg Tyr Gln Val Ile Val Tyr Pro Thr Arg Asp
        180                 185                 190
Ser Leu Gln Phe Val Gly Ala Val Thr Ile Leu Ala Gly Ile Trp Ala
    195                 200                 205
Leu Ala Leu Leu Leu Ala Ser Pro Leu Phe Val Tyr Lys Glu Leu Ile
210                 215                 220
Asn Thr Asp Thr Pro Ala Leu Leu Gln Gln Ile Gly Leu Gln Asp Thr
225                 230                 235                 240
Ile Pro Tyr Cys Ile Glu Asp Trp Pro Ser Arg Asn Gly Arg Phe Tyr
                245                 250                 255
Tyr Ser Ile Phe Ser Leu Cys Val Gln Tyr Leu Val Pro Ile Leu Ile
            260                 265                 270
Val Ser Val Ala Tyr Phe Gly Ile Tyr Asn Lys Leu Lys Ser Arg Ile
        275                 280                 285
Thr Val Val Ala Val Gln Ala Ser Ser Ala Gln Arg Lys Val Glu Arg
    290                 295                 300
Gly Arg Arg Met Lys Arg Thr Asn Cys Leu Leu Ile Ser Ile Ala Ile
305                 310                 315                 320
Ile Phe Gly Val Ser Trp Leu Pro Leu Asn Phe Phe Asn Leu Tyr Ala
                325                 330                 335
Asp Met Glu Arg Ser Pro Val Thr Gln Ser Met Leu Val Arg Tyr Ala
            340                 345                 350
Ile Cys His Met Ile Gly Met Ser Ser Ala Cys Ser Asn Pro Leu Leu
        355                 360                 365
Tyr Gly Trp Leu Asn Asp Asn Phe Arg Cys Asn Val Gln Ala Ala Ala
    370                 375                 380
Arg Lys Arg Lys Leu Gly Ala Glu Leu Ser Lys Gly Glu Leu Lys
385                 390                 395                 400
Leu Leu Gly Pro Gly Gly Ala Gln Ser Gly Thr Ala Gly Gly Glu Gly
                405                 410                 415
Gly Leu Ala Ala Thr Asp Phe Met Thr Gly His His Glu Gly Gly Leu
            420                 425                 430
Arg Ser Ala Ile Thr Glu Ser Val Ala Leu Thr Asp His Asn Pro Val
        435                 440                 445
Pro Ser Glu Val Thr Lys Leu Met Pro Arg
    450                 455
```

<210> SEQ ID NO 7
<211> LENGTH: 1073
<212> TYPE: DNA
<213> ORGANISM: D. melanogaster

<400> SEQUENCE: 7

```
atggagaaca ccacaatgct ggctaatatt agcctaaatg caaccagaaa tgaggagaat      60
atcacctcat tcttcaccga cgaagagtgg ctggccatca atggcacttt gccgtggata     120
gtgggattct tcttcggcgt catcgccatc acgggattct tcggcaacct gctggtcatc     180
ctggtggtgg tcttcaacaa caacatgcgc tccaccacca acctgatgat tgtcaatctg     240
gctgccgctg atcgatgtt cgtaatcctc tgcattccct tcacggccac cgattacatg      300
gtgtactact ggccatatgg aaggttctgg tgccgcagtg tccagtacct gattgtggtg     360
```

-continued

```
accgccttcg cctccatcta cacgctggtg ctaatgtcca tcgatcggtt cctggcggtg    420
gttcatccca ttcgctcgcg gatgatgagg acggagaaca ttaccctgat tgccatcgtg    480
actctgtgga tcgtggtgct ggtcgtttcg gtgccagtgg ccttcaccca cgacgtggtg    540
gtggactacg atgcaaagaa gaacatcacc tacggcatgt gcaccttcac gacgaacgac    600
ttccttggtc cgcgcaccta ccaggtcacc ttcttcatca gctcctacct gctgcccctg    660
atgatcatca gcggtctcta catgcgcatg atcatgcggc tctggcgcca gggaaccggc    720
gtccgcatgt ccaaggagtc gcagcgcggt cgcaagcggg tcacccgact cgtcgtcgtg    780
gtggtcatcg ccttcgcctc gctctggctg cctgtccagc tcatcctgct gctcaagtca    840
ctggatgtca tcgagacgaa caccctcacc aagctagtca tccaggtcac cgcccagact    900
ctggcctaca gcagctcgtg tatcaatccg ctgctctacg ccttcctctc cgagaatttc    960
cggaaggcct tctataaggc cgttaactgc tcctctcgat accagaacta cacatctgat   1020
ttgccgccgc cgcgcaagac gtcctgtgcc aggacctcca ccactggact cta           1073
```

<210> SEQ ID NO 8
<211> LENGTH: 357
<212> TYPE: PRT
<213> ORGANISM: D. melanogaster

<400> SEQUENCE: 8

```
Met Glu Asn Thr Thr Met Leu Ala Asn Ile Ser Leu Asn Ala Thr Arg
1               5                   10                  15

Asn Glu Glu Asn Ile Thr Ser Phe Phe Thr Asp Glu Glu Trp Leu Ala
                20                  25                  30

Ile Asn Gly Thr Leu Pro Trp Ile Val Gly Phe Phe Gly Val Ile
            35                  40                  45

Ala Ile Thr Gly Phe Phe Gly Asn Leu Leu Val Ile Leu Val Val Val
        50                  55                  60

Phe Asn Asn Asn Met Arg Ser Thr Thr Asn Leu Met Ile Val Asn Leu
65                  70                  75                  80

Ala Ala Ala Asp Leu Met Phe Val Ile Leu Cys Ile Pro Phe Thr Ala
                85                  90                  95

Thr Asp Tyr Met Val Tyr Tyr Trp Pro Tyr Gly Arg Phe Trp Cys Arg
            100                 105                 110

Ser Val Gln Tyr Leu Ile Val Val Thr Ala Phe Ala Ser Ile Tyr Thr
        115                 120                 125

Leu Val Leu Met Ser Ile Asp Arg Phe Leu Ala Val Val His Pro Ile
    130                 135                 140

Arg Ser Arg Met Met Arg Thr Glu Asn Ile Thr Leu Ile Ala Ile Val
145                 150                 155                 160

Thr Leu Trp Ile Val Val Leu Val Val Ser Val Pro Val Ala Phe Thr
                165                 170                 175

His Asp Val Val Val Asp Tyr Asp Ala Lys Lys Asn Ile Thr Tyr Gly
            180                 185                 190

Met Cys Thr Phe Thr Thr Asn Asp Phe Leu Gly Pro Arg Thr Tyr Gln
        195                 200                 205

Val Thr Phe Phe Ile Ser Ser Tyr Leu Leu Pro Leu Met Ile Ile Ser
    210                 215                 220

Gly Leu Tyr Met Arg Met Ile Met Arg Leu Trp Arg Gln Gly Thr Gly
225                 230                 235                 240

Val Arg Met Ser Lys Glu Ser Gln Arg Gly Arg Lys Arg Val Thr Arg
```

```
                    245                 250                 255
Leu Val Val Val Val Ile Ala Phe Ala Ser Leu Trp Leu Pro Val
            260                 265                 270

Gln Leu Ile Leu Leu Leu Lys Ser Leu Asp Val Ile Glu Thr Asn Thr
        275                 280                 285

Leu Thr Lys Leu Val Ile Gln Val Thr Ala Gln Thr Leu Ala Tyr Ser
        290                 295                 300

Ser Ser Cys Ile Asn Pro Leu Leu Tyr Ala Phe Leu Ser Glu Asn Phe
305                 310                 315                 320

Arg Lys Ala Phe Tyr Lys Ala Val Asn Cys Ser Ser Arg Tyr Gln Asn
                325                 330                 335

Tyr Thr Ser Asp Leu Pro Pro Pro Arg Lys Thr Ser Cys Ala Arg Thr
            340                 345                 350

Ser Thr Thr Gly Leu
        355

<210> SEQ ID NO 9
<211> LENGTH: 1559
<212> TYPE: DNA
<213> ORGANISM: D. melanogaster

<400> SEQUENCE: 9
atggagaatc gcagtgactt cgaggcggat gactacggcg acatcagttg gagcaattgg      60
agcaactgga gcacccccgc cggcgtcctt ttctcggcca tgagcagcgt gctctcggcc     120
agcaaccata cgccctgcc ggactttggc caggagctcg ccctatccac cagctccttc     180
aatcacagcc agaccctatc caccgaccag cccgccgtcg ggacgtgga agacgcggcc     240 gaggatgcgg cggcgtccat ggagacgggc tcgtttgcat tgtggtccc gtggtggcgt     300 caggtgctct ggagcatcct cttcggcggc atggtcattg tggcgacggg cggtaacctg     360
attgttgtct ggatcgtgat gacgaccaag cggatgcgga cggtaaccaa ctatttcata     420
gtgaatctct ccatcgcgga cgccatggtg tccagcctaa acgtcacctt caactactac     480
tatatgctgg atagcgactg gcccttcggc gagttctact gcaagttgtc ccagttcatc     540
gcgatgctaa gcatctgcgc ctcagtgttc accctaatgg ccatctccat cgacagatac     600
gtggccatca tccggccact gcagccgcgg atgagcaagc ggtgcaacct ggccatcgcg     660
gcggtcatct ggctggcctc cacgctcatc tcctgcccca tgatgatcat ctaccgcacg     720
gaggaggtgc cggtccgcgg gctcagcaac cgcacggtct gctaccccgga gtggcccgat     780 gggcccacca atcactccac gatggagtcc ctctacaaca tcctcatcat catyctaacc     840
tacttcctgc ccatcgtctc catgacggtc acctactcgc gcgtgggcat cgagctctgg     900
ggatccaaga ccatcggcga gtgcacgccc cgccaggtgg araaygtgcg gagtaagcga     960
agggtggtga agatgatgat tgtggtcgtc ctgatattcg ccatctgctg gctgccgttc    1020
cacagctact tcataatcac atcctgctac ccggccatca cggaggcgcc cttcatccag    1080
gaactctacc tggccatcta ctggctggcc atgagcaact ccatgtacaa tcccattata    1140
tactgctgga tgaattcgcg ctttcgctat ggtttcaaga tggtcttccg ctggtgcctg    1200
tttgtgcgcg tgggcactga acccttagt cggcgggaga acctgacatc ccggtactcc    1260
tgctccggtt ccccggatca caatcgcatc aagcgcaatg atacccagaa atcgatactt    1320
tatacctgtc ccagctcacc caagtcgcat cgaattcgc acagcggaac aggtcgcagt    1380
gcgacgctgc ggaacagtct gccggcggag tcactgtcgt ccggcggatc tggtggtgga    1440
```

```
gggcacagga acggttgtc ctaccagcag gaaatgcagc agcgttggtc aggacccaat    1500
agtgccaccg cagtgaccaa ttccagcagt acggccaaca ccacccaact gctctcctg    1559
```

<210> SEQ ID NO 10
<211> LENGTH: 519
<212> TYPE: PRT
<213> ORGANISM: D. melanogaster

<400> SEQUENCE: 10

```
Met Glu Asn Arg Ser Asp Phe Glu Ala Asp Tyr Gly Asp Ile Ser
1               5                   10                  15

Trp Ser Asn Trp Ser Asn Trp Ser Thr Pro Ala Gly Val Leu Phe Ser
            20                  25                  30

Ala Met Ser Ser Val Leu Ser Ala Ser Asn His Thr Pro Leu Pro Asp
        35                  40                  45

Phe Gly Gln Glu Leu Ala Leu Ser Thr Ser Ser Phe Asn His Ser Gln
    50                  55                  60

Thr Leu Ser Thr Asp Gln Pro Ala Val Gly Asp Val Glu Asp Ala Ala
65                  70                  75                  80

Glu Asp Ala Ala Ala Ser Met Glu Thr Gly Ser Phe Ala Phe Val Val
                85                  90                  95

Pro Trp Trp Arg Gln Val Leu Trp Ser Ile Leu Phe Gly Gly Met Val
            100                 105                 110

Ile Val Ala Thr Gly Gly Asn Leu Ile Val Val Trp Ile Val Met Thr
        115                 120                 125

Thr Lys Arg Met Arg Thr Val Thr Asn Tyr Phe Ile Val Asn Leu Ser
    130                 135                 140

Ile Ala Asp Ala Met Val Ser Ser Leu Asn Val Thr Phe Asn Tyr Tyr
145                 150                 155                 160

Tyr Met Leu Asp Ser Asp Trp Pro Phe Gly Glu Phe Tyr Cys Lys Leu
                165                 170                 175

Ser Gln Phe Ile Ala Met Leu Ser Ile Cys Ala Ser Val Phe Thr Leu
            180                 185                 190

Met Ala Ile Ser Ile Asp Arg Tyr Val Ala Ile Ile Arg Pro Leu Gln
        195                 200                 205

Pro Arg Met Ser Lys Arg Cys Asn Leu Ala Ile Ala Ala Val Ile Trp
    210                 215                 220

Leu Ala Ser Thr Leu Ile Ser Cys Pro Met Met Ile Ile Tyr Arg Thr
225                 230                 235                 240

Glu Glu Val Pro Val Arg Gly Leu Ser Asn Arg Thr Val Cys Tyr Pro
                245                 250                 255

Glu Trp Pro Asp Gly Pro Thr Asn His Ser Thr Met Glu Ser Leu Tyr
            260                 265                 270

Asn Ile Leu Ile Ile Leu Thr Tyr Phe Leu Pro Ile Val Ser Met
        275                 280                 285

Thr Val Thr Tyr Ser Arg Val Gly Ile Glu Leu Trp Gly Ser Lys Thr
    290                 295                 300

Ile Gly Glu Cys Thr Pro Arg Gln Val Glu Asn Val Arg Ser Lys Arg
305                 310                 315                 320

Arg Val Val Lys Met Met Ile Val Val Leu Ile Phe Ala Ile Cys
                325                 330                 335

Trp Leu Pro Phe His Ser Tyr Phe Ile Ile Thr Ser Cys Tyr Pro Ala
            340                 345                 350

Ile Thr Glu Ala Pro Phe Ile Gln Glu Leu Tyr Leu Ala Ile Tyr Trp
```

```
                355                 360                 365
Leu Ala Met Ser Asn Ser Met Tyr Asn Pro Ile Ile Tyr Cys Trp Met
    370                 375                 380

Asn Ser Arg Phe Arg Tyr Gly Phe Lys Met Val Phe Arg Trp Cys Leu
385                 390                 395                 400

Phe Val Arg Val Gly Thr Glu Pro Phe Ser Arg Arg Glu Asn Leu Thr
                405                 410                 415

Ser Arg Tyr Ser Cys Ser Gly Ser Pro Asp His Asn Arg Ile Lys Arg
            420                 425                 430

Asn Asp Thr Gln Lys Ser Ile Leu Tyr Thr Cys Pro Ser Ser Pro Lys
        435                 440                 445

Ser His Arg Ile Ser His Ser Gly Thr Gly Arg Ser Ala Thr Leu Arg
    450                 455                 460

Asn Ser Leu Pro Ala Glu Ser Leu Ser Ser Gly Ser Gly Gly Gly
465                 470                 475                 480

Gly His Arg Lys Arg Leu Ser Tyr Gln Gln Glu Met Gln Gln Arg Trp
                485                 490                 495

Ser Gly Pro Asn Ser Ala Thr Ala Val Thr Asn Ser Ser Thr Ala
            500                 505                 510

Asn Thr Thr Gln Leu Leu Ser
        515

<210> SEQ ID NO 11
<211> LENGTH: 1568
<212> TYPE: DNA
<213> ORGANISM: D. melanogaster

<400> SEQUENCE: 11
atggagaatc gcagtgactt cgaggcggat gactacggcg acatcagttg gagcaattgg      60
agcaattgga gcaactggag caccccccgcc ggcgtccttt tctcggccat gagcagcgtg     120
ctctcggcca gcaaccatac gcctctgccg gactttggcc aggagctcgc cctatccacc     180
agctccttca atcacagcca gaccctatcc accgacctgc ccgccgtcgg ggacgtggaa     240
gacgcggccg aggatgcggc ggcgtccatg gagacgggct cgtttgcatt tgtggtcccg     300
tggtggcgtc aggtgctctg gagcatcctc ttcggcggca tggtcattgt ggcgacgggc     360
ggtaacctga ttgttgtctg gatcgtgatg acgaccaagc ggatgcggac ggtaaccaac     420
tatttcatag taaatctctc catcgcggac gccatggtgt ccagcctgaa cgtcaccttc     480
aactactact acatgctgga tagcgactgg cccttcggcg agttctactg caagttgtcc     540
cagttcatcg cgatgctaag catctgcgcc tcagtgttca ccctaatggc catctccatc     600
gacagatacg tggccatcat ccggccactg cagccgcgga tgagcaagcg gtgcaacctg     660
gccatcgcgg cggtcatctg gctggcctcc acgctcatct cctgccccat gatgatcatc     720
taccgcacgg aggaggtgcc ggtccgcggg ctcagcaacc gcacggtctg ctacccggag     780
tggcccgatg ggcccaccaa tcactccacg atggagtccc tctacaacat cctcatcatc     840
attctaacct acttcctgcc catcgtctcc atgacggtca cctactcgcg cgtgggcatc     900
gagctctggg gatccaagac catcggcgag tgcacgcccc gccaggtgga gaatgtgcgg     960
agtaagcgaa gggtggtgaa gatgatgatt gtggtcgtcc tgatattcgc catctgctgg    1020
ctgccgttcc acagctactt cataatcaca tcctgctacc cggccatcac ggaggcgccc    1080
ttcatccagg aactttacct ggccatctac tggctggcca tgagcaactc catgtacaat    1140
cccattatat actgctggat gaattcgcgc tttcgctatg gtttcaagat ggtcttccgc    1200
```

-continued

```
tggtgcctgt tgtgcgcgt gggcactgaa ccctttagtc ggcgggagaa cctgacatcc    1260
cggtactcct gctccggttc cccggatcac aatcgcatca agcgcaatga tacccagaaa    1320
tcgatacttt atacctgtcc cagctcaccc aagtcgcatc gaatttcgca cagcggaaca    1380
ggtcgcagtg cgacgctgag gaacagtctg ccggcggagt cattgtcgtc cggtggatct    1440
ggaggtggag gacacaggaa acggttgtcc taccagcagg aaatgcagca gcggtggtca    1500
ggacccaata gtgccaccgc agtgaccaat tccagcagta cggccaacac cacccaactg    1560
ctctcctg                                                              1568
```

```
<210> SEQ ID NO 12
<211> LENGTH: 522
<212> TYPE: PRT
<213> ORGANISM: D. melanogaster

<400> SEQUENCE: 12

Met Glu Asn Arg Ser Asp Phe Glu Ala Asp Asp Tyr Gly Asp Ile Ser
1               5                   10                  15

Trp Ser Asn Trp Ser Asn Trp Ser Asn Trp Ser Thr Pro Ala Gly Val
                20                  25                  30

Leu Phe Ser Ala Met Ser Ser Val Leu Ser Ala Ser Asn His Thr Pro
            35                  40                  45

Leu Pro Asp Phe Gly Gln Glu Leu Ala Leu Ser Thr Ser Ser Phe Asn
        50                  55                  60

His Ser Gln Thr Leu Ser Thr Asp Leu Pro Ala Val Gly Asp Val Glu
65                  70                  75                  80

Asp Ala Ala Glu Asp Ala Ala Ala Ser Met Glu Thr Gly Ser Phe Ala
                85                  90                  95

Phe Val Val Pro Trp Trp Arg Gln Val Leu Trp Ser Ile Leu Phe Gly
            100                 105                 110

Gly Met Val Ile Val Ala Thr Gly Gly Asn Leu Ile Val Val Trp Ile
        115                 120                 125

Val Met Thr Thr Lys Arg Met Arg Thr Val Thr Asn Tyr Phe Ile Val
130                 135                 140

Asn Leu Ser Ile Ala Asp Ala Met Val Ser Ser Leu Asn Val Thr Phe
145                 150                 155                 160

Asn Tyr Tyr Tyr Met Leu Asp Ser Asp Trp Pro Phe Gly Glu Phe Tyr
                165                 170                 175

Cys Lys Leu Ser Gln Phe Ile Ala Met Leu Ser Ile Cys Ala Ser Val
            180                 185                 190

Phe Thr Leu Met Ala Ile Ser Ile Asp Arg Tyr Val Ala Ile Ile Arg
        195                 200                 205

Pro Leu Gln Pro Arg Met Ser Lys Arg Cys Asn Leu Ala Ile Ala Ala
    210                 215                 220

Val Ile Trp Leu Ala Ser Thr Leu Ile Ser Cys Pro Met Met Ile Ile
225                 230                 235                 240

Tyr Arg Thr Glu Glu Val Pro Val Arg Gly Leu Ser Asn Arg Thr Val
                245                 250                 255

Cys Tyr Pro Glu Trp Pro Asp Gly Pro Thr Asn His Ser Thr Met Glu
            260                 265                 270

Ser Leu Tyr Asn Ile Leu Ile Ile Leu Thr Tyr Phe Leu Pro Ile
        275                 280                 285

Val Ser Met Thr Val Thr Tyr Ser Arg Val Gly Ile Glu Leu Trp Gly
    290                 295                 300
```

```
Ser Lys Thr Ile Gly Glu Cys Thr Pro Arg Gln Val Glu Asn Val Arg
305                 310                 315                 320

Ser Lys Arg Arg Val Val Lys Met Met Ile Val Val Leu Ile Phe
            325                 330                 335

Ala Ile Cys Trp Leu Pro Phe His Ser Tyr Phe Ile Ile Thr Ser Cys
                340                 345                 350

Tyr Pro Ala Ile Thr Glu Ala Pro Phe Ile Gln Glu Leu Tyr Leu Ala
            355                 360                 365

Ile Tyr Trp Leu Ala Met Ser Asn Ser Met Tyr Asn Pro Ile Ile Tyr
        370                 375                 380

Cys Trp Met Asn Ser Arg Phe Arg Tyr Gly Phe Lys Met Val Phe Arg
385                 390                 395                 400

Trp Cys Leu Phe Val Arg Val Gly Thr Glu Pro Phe Ser Arg Arg Glu
                405                 410                 415

Asn Leu Thr Ser Arg Tyr Ser Cys Ser Gly Ser Pro Asp His Asn Arg
            420                 425                 430

Ile Lys Arg Asn Asp Thr Gln Lys Ser Ile Leu Tyr Thr Cys Pro Ser
        435                 440                 445

Ser Pro Lys Ser His Arg Ile Ser His Ser Gly Thr Gly Arg Ser Ala
            450                 455                 460

Thr Leu Arg Asn Ser Leu Pro Ala Glu Ser Leu Ser Ser Gly Gly Ser
465                 470                 475                 480

Gly Gly Gly Gly His Arg Lys Arg Leu Ser Tyr Gln Gln Glu Met Gln
                485                 490                 495

Gln Arg Trp Ser Gly Pro Asn Ser Ala Thr Ala Val Thr Asn Ser Ser
            500                 505                 510

Ser Thr Ala Asn Thr Thr Gln Leu Leu Ser
            515                 520

<210> SEQ ID NO 13
<211> LENGTH: 1394
<212> TYPE: DNA
<213> ORGANISM: D. melanogaster

<400> SEQUENCE: 13
atggagcacc acaatagcca tctgttgcct ggtggcagcg agaagatgta ctacatagct      60
caccagcagc cgatgctgcg gaacgaggat gataactacc aggagggta cttcatcagg     120 ccggaccctg catccttact ttacaatacc accgcactgc cagcggacga tgaagggtcc     180
aactatggat atggctccac cacaacgctc agtggcctcc agttcgagac ctataatatc     240
actgtgatga tgaactttag ctgtgacgac tatgaccttc tatcggagga catgtggtct     300
agtgcctact ttaagatcat cgtctacatg ctctacattc ccatctttat cttcgccctg     360
atcggcaacg gaacggtctg ctatatcgtc tattccacac ctcgcatgcg cacggtcacc     420
aattacttta tagccagctt ggccatcggc gacatcctga tgtccttctt ctgcgttccg     480
tcgtccttca tctcgctgtt catcctgaac tactggcctt ttggcctggc cctctgtcac     540
tttgtgaact actcgcaggc ggtctcagtt ctggtcagcg cctatacttt ggtggcaatt     600
agcattgacc gctacatagc cattatgtgg ccattaaagc cacgcatcac aaaacgctat     660
gccaccttca tcatcgccgg cgtttggttt attgcacttg ccaccgcact tcccataccc     720
atcgtctctg gactcgacat cccaatgtcc ccgtggcaca cgaaatgcga gaaatacatt     780
tgccgcgaaa tgtggccgtc gcggacgcag gagtactact acaccctgtc cctcttcgcg     840
```

-continued

```
ctgcagttcg tcgtgccgct gggcgtgctc atcttcacct acgcccggat caccattcgc    900
gtctgggcga aacgaccgcc aggcgaggcg gaaaccaacc gcgaccagcg gatggcacgc    960
tccaaacgga agatggtcaa aatgatgctg acggttgtga ttgtgttcac ctgctgttgg   1020
ctgcccttca atattttgca gcttttactg aacgacgagg agttcgccca ctgggatcct   1080
ctgccgtatg tatggttcgc gtttcactgg ctggccatgt cgcactgctg ctacaatccg   1140
atcatctact gctacatgaa cgcccgtttc aggagcggat tcgtccagct gatgcaccgt   1200
atgcccggcc tgcgtcgctg gtgctgcctg cggagcgtcg gtgatcgcat gaacgcaact   1260
tccggaacgg gtccagcact tcctctcaat cgaatgaaca catccaccac ctacatcagc   1320
gctcgtcgaa agccacgagc gacatctttg cgagcgaacc cattatcatg cggcgagacg   1380
tcaccactgc ggta                                                     1394
```

<210> SEQ ID NO 14
<211> LENGTH: 464
<212> TYPE: PRT
<213> ORGANISM: D. melanogaster

<400> SEQUENCE: 14

```
Met Glu His His Asn Ser His Leu Leu Pro Gly Gly Ser Glu Lys Met
1               5                   10                  15

Tyr Tyr Ile Ala His Gln Gln Pro Met Leu Arg Asn Glu Asp Asp Asn
            20                  25                  30

Tyr Gln Glu Gly Tyr Phe Ile Arg Pro Asp Pro Ala Ser Leu Leu Tyr
        35                  40                  45

Asn Thr Thr Ala Leu Pro Ala Asp Asp Glu Gly Ser Asn Tyr Gly Tyr
    50                  55                  60

Gly Ser Thr Thr Thr Leu Ser Gly Leu Gln Phe Glu Thr Tyr Asn Ile
65                  70                  75                  80

Thr Val Met Met Asn Phe Ser Cys Asp Asp Tyr Asp Leu Leu Ser Glu
                85                  90                  95

Asp Met Trp Ser Ser Ala Tyr Phe Lys Ile Ile Val Tyr Met Leu Tyr
            100                 105                 110

Ile Pro Ile Phe Ile Phe Ala Leu Ile Gly Asn Gly Thr Val Cys Tyr
        115                 120                 125

Ile Val Tyr Ser Thr Pro Arg Met Arg Thr Val Thr Asn Tyr Phe Ile
    130                 135                 140

Ala Ser Leu Ala Ile Gly Asp Ile Leu Met Ser Phe Phe Cys Val Pro
145                 150                 155                 160

Ser Ser Phe Ile Ser Leu Phe Ile Leu Asn Tyr Trp Pro Phe Gly Leu
                165                 170                 175

Ala Leu Cys His Phe Val Asn Tyr Ser Gln Ala Val Ser Val Leu Val
            180                 185                 190

Ser Ala Tyr Thr Leu Val Ala Ile Ser Ile Asp Arg Tyr Ile Ala Ile
        195                 200                 205

Met Trp Pro Leu Lys Pro Arg Ile Thr Lys Arg Tyr Ala Thr Phe Ile
    210                 215                 220

Ile Ala Gly Val Trp Phe Ile Ala Leu Ala Thr Ala Leu Pro Ile Pro
225                 230                 235                 240

Ile Val Ser Gly Leu Asp Ile Pro Met Ser Pro Trp His Thr Lys Cys
                245                 250                 255

Glu Lys Tyr Ile Cys Arg Glu Met Trp Pro Ser Arg Thr Gln Glu Tyr
            260                 265                 270
```

```
Tyr Tyr Thr Leu Ser Leu Phe Ala Leu Gln Phe Val Val Pro Leu Gly
        275                 280                 285

Val Leu Ile Phe Thr Tyr Ala Arg Ile Thr Ile Arg Val Trp Ala Lys
290                 295                 300

Arg Pro Pro Gly Glu Ala Glu Thr Asn Arg Asp Gln Arg Met Ala Arg
305                 310                 315                 320

Ser Lys Arg Lys Met Val Lys Met Met Leu Thr Val Val Ile Val Phe
                325                 330                 335

Thr Cys Cys Trp Leu Pro Phe Asn Ile Leu Gln Leu Leu Leu Asn Asp
            340                 345                 350

Glu Glu Phe Ala His Trp Asp Pro Leu Pro Tyr Val Trp Phe Ala Phe
        355                 360                 365

His Trp Leu Ala Met Ser His Cys Cys Tyr Asn Pro Ile Ile Tyr Cys
    370                 375                 380

Tyr Met Asn Ala Arg Phe Arg Ser Gly Phe Val Gln Leu Met His Arg
385                 390                 395                 400

Met Pro Gly Leu Arg Arg Trp Cys Cys Leu Arg Ser Val Gly Asp Arg
                405                 410                 415

Met Asn Ala Thr Ser Gly Thr Gly Pro Ala Leu Pro Leu Asn Arg Met
            420                 425                 430

Asn Thr Ser Thr Thr Tyr Ile Ser Ala Arg Arg Lys Pro Arg Ala Thr
        435                 440                 445

Ser Leu Arg Ala Asn Pro Leu Ser Cys Gly Glu Thr Ser Pro Leu Arg
    450                 455                 460

<210> SEQ ID NO 15
<211> LENGTH: 1556
<212> TYPE: DNA
<213> ORGANISM: D. melanogaster

<400> SEQUENCE: 15
atggagcacc acaatagcca tctgttgcct ggtggcagcg agaagatgta ctacatagct      60
caccagcagc cgatgctgcg aacgaggat gataactacc aggaggggta cttcatcagg      120
ccggaccctg catccttact ttacaatacc accgcactgc cagcggacga tgaagggtcc      180
aactatggat atggctccac acaacgctc agtggcctcc agttcgagac ctataatatc      240
actgtgatga tgaactttag ctgtgacgac tatgaccttc tatcggagga catgtggtct      300
agtgcctact ttaagatcat cgtctacatg ctctacattc ccatcttttat cttcgccctg      360 atcggcaacg gaacggtctg ctatatcgtc tattccacac ctcgcatgcg cacggtcacc      420
aattacttta tagccagctt ggccatcggc gacatcctga tgtccttctt ctgcgttccg      480
tcgtccttca tctcgctgtt catcctgaac tactggcctt ttggcctggc cctctgtcac      540
tttgtgaact actcgcaggc ggtctcagtt ctggtcagcg cctatacttt ggtggcaatt      600
agcattgacc gctacatagc cattatgtgg ccattaaagc cacgcatcac aaaacgctat      660
gccaccttca tcatcgccgg cgtttggttt attgcacttg ccaccgcact tcccataccc      720
atcgtctctg gactcgacat cccaatgtcg ccgtggcaca cgaaatgcga gaaatacatt      780
tgccgcgaaa tgtggccgtc gcggacgcag gagtactact acaccctgtc cctcttcgcg      840
ctgcagttcg tcgtgccgct gggcgtgctc atcttcacct acgcccggat caccattcgc      900
gtctgggcga aacgaccgcc aggcgaggcg gaaaccaacc gcgaccagcg gatggcacgc      960
tccaaacgga gatggtcaa atgatgctg acgttgtga ttgtgttcac ctgctgttgg     1020
ctgcccttca atattttgca gcttttactg aacgacgagg agttcgccca ctgggatcct     1080
```

-continued

```
ctgccgtatg tgtggttcgc gtttcactgg ctggccatgt cgcactgctg ctacaatccg      1140
atcatctact gctacatgaa cgcccgtttc aggagcggat tcgtccagct gatgcaccgt      1200
atgcccggcc tgcgtcgctg gtgctgcctg cggagcgtcg gtgatcgcat gaacgcaact      1260
tccggtgaga tgactacgaa gtaccatcgc catgtcggcg atgccctatt ccggaaaccc      1320
aaaatatgca ttaggaacgg gtccagcact tcctctcaat cgaatgaaca catccaccac      1380
ctacatcagc gctcgtcgaa agccacgagc gacatctttg cgagcgaacc cattatcatg      1440
cggcgagacg tcaccactgc ggtagctgtc atatcaaaaa ataaaactga ttcaccggtg      1500
cgccgatcgg gaagctcagg tggaacagaa gcaaacataa gaagcaccga gttttg         1556
```

<210> SEQ ID NO 16
<211> LENGTH: 518
<212> TYPE: PRT
<213> ORGANISM: D. melanogaster

<400> SEQUENCE: 16

```
Met Glu His His Asn Ser His Leu Leu Pro Gly Gly Ser Glu Lys Met
1               5                   10                  15

Tyr Tyr Ile Ala His Gln Gln Pro Met Leu Arg Asn Glu Asp Asp Asn
            20                  25                  30

Tyr Gln Glu Gly Tyr Phe Ile Arg Pro Asp Pro Ala Ser Leu Leu Tyr
        35                  40                  45

Asn Thr Thr Ala Leu Pro Ala Asp Asp Glu Gly Ser Asn Tyr Gly Tyr
    50                  55                  60

Gly Ser Thr Thr Thr Leu Ser Gly Leu Gln Phe Glu Thr Tyr Asn Ile
65                  70                  75                  80

Thr Val Met Met Asn Phe Ser Cys Asp Asp Tyr Asp Leu Leu Ser Glu
                85                  90                  95

Asp Met Trp Ser Ser Ala Tyr Phe Lys Ile Ile Val Tyr Met Leu Tyr
            100                 105                 110

Ile Pro Ile Phe Ile Phe Ala Leu Ile Gly Asn Gly Thr Val Cys Tyr
        115                 120                 125

Ile Val Tyr Ser Thr Pro Arg Met Arg Thr Val Thr Asn Tyr Phe Ile
    130                 135                 140

Ala Ser Leu Ala Ile Gly Asp Ile Leu Met Ser Phe Phe Cys Val Pro
145                 150                 155                 160

Ser Ser Phe Ile Ser Leu Phe Ile Leu Asn Tyr Trp Pro Phe Gly Leu
                165                 170                 175

Ala Leu Cys His Phe Val Asn Tyr Ser Gln Ala Val Ser Val Leu Val
            180                 185                 190

Ser Ala Tyr Thr Leu Val Ala Ile Ser Ile Asp Arg Tyr Ile Ala Ile
        195                 200                 205

Met Trp Pro Leu Lys Pro Arg Ile Thr Lys Arg Tyr Ala Thr Phe Ile
    210                 215                 220

Ile Ala Gly Val Trp Phe Ile Ala Leu Ala Thr Ala Leu Pro Ile Pro
225                 230                 235                 240

Ile Val Ser Gly Leu Asp Ile Pro Met Ser Pro Trp His Thr Lys Cys
                245                 250                 255

Glu Lys Tyr Ile Cys Arg Glu Met Trp Pro Ser Arg Thr Gln Glu Tyr
            260                 265                 270

Tyr Tyr Thr Leu Ser Leu Phe Ala Leu Gln Phe Val Val Pro Leu Gly
        275                 280                 285
```

```
Val Leu Ile Phe Thr Tyr Ala Arg Ile Thr Ile Arg Val Trp Ala Lys
    290                 295                 300

Arg Pro Pro Gly Glu Ala Glu Thr Asn Arg Asp Gln Arg Met Ala Arg
305                 310                 315                 320

Ser Lys Arg Lys Met Val Lys Met Met Leu Thr Val Val Ile Val Phe
                325                 330                 335

Thr Cys Cys Trp Leu Pro Phe Asn Ile Leu Gln Leu Leu Leu Asn Asp
            340                 345                 350

Glu Glu Phe Ala His Trp Asp Pro Leu Pro Tyr Val Trp Phe Ala Phe
        355                 360                 365

His Trp Leu Ala Met Ser His Cys Cys Tyr Asn Pro Ile Ile Tyr Cys
    370                 375                 380

Tyr Met Asn Ala Arg Phe Arg Ser Gly Phe Val Gln Leu Met His Arg
385                 390                 395                 400

Met Pro Gly Leu Arg Arg Trp Cys Cys Leu Arg Ser Val Gly Asp Arg
                405                 410                 415

Met Asn Ala Thr Ser Gly Glu Met Thr Thr Lys Tyr His Arg His Val
            420                 425                 430

Gly Asp Ala Leu Phe Arg Lys Pro Lys Ile Cys Ile Arg Asn Gly Ser
        435                 440                 445

Ser Thr Ser Ser Gln Ser Asn Glu His Ile His His Leu His Gln Arg
    450                 455                 460

Ser Ser Lys Ala Thr Ser Asp Ile Phe Ala Ser Glu Pro Ile Ile Met
465                 470                 475                 480

Arg Arg Asp Val Thr Thr Ala Val Ala Val Ile Ser Lys Asn Lys Thr
                485                 490                 495

Asp Ser Pro Val Arg Arg Ser Gly Ser Ser Gly Gly Thr Glu Ala Asn
            500                 505                 510

Ile Arg Ser Thr Glu Phe
        515

<210> SEQ ID NO 17
<211> LENGTH: 1628
<212> TYPE: DNA
<213> ORGANISM: D. melanogaster

<400> SEQUENCE: 17
atggcaatgg acttaatcga gcaggagtcc cgcctggaat tcctgcccgg agccgaggag      60
gaagcagaat tgagcgtct atacgcggct cccgctgaga ttgtggccct gttgtccatt     120
ttctatgggg gaatcagtat cgtggccgtc attggcaaca cttttggtca tctgggtggtg    180 gccacgacca ggcaaatgcg gaccgtgaca aatatgtata tcgctaattt ggcttttgcc    240
gatgtgatta ttggcctctt ctgcatacca tttcagttcc aggctgccct gctgcagagt    300
tggaacctgc cgtggttcat gtgcagcttc tgcccttcg tccaggcccct gagtgtaaat    360 gtctcggtat tcacgctgac cgccattgca atcgatcggc atagggccat cattaatcca    420
cttagggcac gtcccaccaa gttcgtatcg aagttcataa ttggtggaat ttggatgctg    480
gccctgctat ttgcggtgcc ctttgccatt gcctttcgtg tggaggagtt gaccgaaaga    540
tttcgcgaga caatgagac ctacaatgtg acgcggccat tctgcatgaa caagaaccta    600
tccgatgatc aattgcaatc ctttcgctac acctggtttt tgtgcagta tctggttcca    660 ttctgtgtca tcagctttgt ctacatccag atggcggtac gattgtgggg cacacgtgct    720
cctggtaacg cacaggattc acgggacata acgctgttga aaaacaagaa gaaggtcatc    780
```

-continued

```
aaaatgctga ttatcgtggt cattatcttt ggactctgct ggctgccact gcagctctat    840
aatattctgt atgtcacgat accggaaatc aacgactacc acttcattag catcgtctgg    900
ttttgctgcg attggctggc catgagcaat agctgctaca atccctttat ttatggcatc    960
tacaatgaaa aatttaagcg ggaattcaac aagcgatttg cggcctgttt ctgcaagttc   1020
aagacgagca tggacgccca cgaaaggacc ttttcgatgc acaccgcgc cagctccata   1080 aggtcaacct acgccaactc ctcgatgcga atccggagta atctctttgg tccggcgcgt   1140
ggtggtgtca acaatgggaa gccgggcttg catatgccgc gggtgcatgg atccggtgct   1200
aacagcggca tttacaacgg aagtagtggg cagaacaaca atgtcaatgg ccaacatcat   1260
cagcatcaaa gcgtggttac ctttgcggcc actccgggtg tttcggcacc aggtgttggc   1320
gttgcaatgc cgccgtggcg gcgaaacaac ttcaaacctc tgcatccgaa cgtaatcgaa   1380
tgcgaggacg acgtggcact catggagctg ccatcaacca cgccccccag cgaggagttg   1440
gcatccgggg ccggagtcca gttggccctg ctaagcaggg agagctccag ctgcatttgc   1500
gaacaggaat ttggcagcca aaccgaatgc gatggcacct gcatactcag cgaggtgtcg   1560
cgagtccacc tgcccggctc gcaggcgaag gacaaggatg cgggcaagtc cttgtggcaa   1620
ccactttta                                                           1628
```

<210> SEQ ID NO 18
<211> LENGTH: 542
<212> TYPE: PRT
<213> ORGANISM: D. melanogaster

<400> SEQUENCE: 18

```
Met Ala Met Asp Leu Ile Glu Gln Glu Ser Arg Leu Glu Phe Leu Pro
1               5                   10                  15

Gly Ala Glu Glu Ala Glu Phe Glu Arg Leu Tyr Ala Ala Pro Ala
            20                  25                  30

Glu Ile Val Ala Leu Leu Ser Ile Phe Tyr Gly Gly Ile Ser Ile Val
        35                  40                  45

Ala Val Ile Gly Asn Thr Leu Val Ile Trp Val Ala Thr Thr Arg
    50                  55                  60

Gln Met Arg Thr Val Thr Asn Met Tyr Ile Ala Asn Leu Ala Phe Ala
65                  70                  75                  80

Asp Val Ile Ile Gly Leu Phe Cys Ile Pro Phe Gln Phe Gln Ala Ala
                85                  90                  95

Leu Leu Gln Ser Trp Asn Leu Pro Trp Phe Met Cys Ser Phe Cys Pro
            100                 105                 110

Phe Val Gln Ala Leu Ser Val Asn Val Ser Val Phe Thr Leu Thr Ala
        115                 120                 125

Ile Ala Ile Asp Arg His Arg Ala Ile Ile Asn Pro Leu Arg Ala Arg
    130                 135                 140

Pro Thr Lys Phe Val Ser Lys Phe Ile Ile Gly Gly Ile Trp Met Leu
145                 150                 155                 160

Ala Leu Leu Phe Ala Val Pro Phe Ala Ile Ala Phe Arg Val Glu Glu
                165                 170                 175

Leu Thr Glu Arg Phe Arg Glu Asn Asn Glu Thr Tyr Asn Val Thr Arg
            180                 185                 190

Pro Phe Cys Met Asn Lys Asn Leu Ser Asp Asp Gln Leu Gln Ser Phe
        195                 200                 205

Arg Tyr Thr Leu Val Phe Val Gln Tyr Leu Val Pro Phe Cys Val Ile
    210                 215                 220
```

```
Ser Phe Val Tyr Ile Gln Met Ala Val Arg Leu Trp Gly Thr Arg Ala
225                 230                 235                 240

Pro Gly Asn Ala Gln Asp Ser Arg Asp Ile Thr Leu Leu Lys Asn Lys
            245                 250                 255

Lys Lys Val Ile Lys Met Leu Ile Ile Val Ile Ile Phe Gly Leu
            260                 265                 270

Cys Trp Leu Pro Leu Gln Leu Tyr Asn Ile Leu Tyr Val Thr Ile Pro
            275                 280                 285

Glu Ile Asn Asp Tyr His Phe Ile Ser Ile Val Trp Phe Cys Cys Asp
290                 295                 300

Trp Leu Ala Met Ser Asn Ser Cys Tyr Asn Pro Phe Ile Tyr Gly Ile
305                 310                 315                 320

Tyr Asn Glu Lys Phe Lys Arg Glu Phe Asn Lys Arg Phe Ala Ala Cys
                325                 330                 335

Phe Cys Lys Phe Lys Thr Ser Met Asp Ala His Glu Arg Thr Phe Ser
            340                 345                 350

Met His Thr Arg Ala Ser Ser Ile Arg Ser Thr Tyr Ala Asn Ser Ser
            355                 360                 365

Met Arg Ile Arg Ser Asn Leu Phe Gly Pro Ala Arg Gly Gly Val Asn
370                 375                 380

Asn Gly Lys Pro Gly Leu His Met Pro Arg Val His Gly Ser Gly Ala
385                 390                 395                 400

Asn Ser Gly Ile Tyr Asn Gly Ser Ser Gly Gln Asn Asn Val Asn
                405                 410                 415

Gly Gln His His Gln His Gln Ser Val Val Thr Phe Ala Ala Thr Pro
            420                 425                 430

Gly Val Ser Ala Pro Gly Val Gly Val Ala Met Pro Pro Trp Arg Arg
            435                 440                 445

Asn Asn Phe Lys Pro Leu His Pro Asn Val Ile Glu Cys Glu Asp Asp
            450                 455                 460

Val Ala Leu Met Glu Leu Pro Ser Thr Thr Pro Pro Ser Glu Leu
465                 470                 475                 480

Ala Ser Gly Ala Gly Val Gln Leu Ala Leu Leu Ser Arg Glu Ser Ser
                485                 490                 495

Ser Cys Ile Cys Glu Gln Glu Phe Gly Ser Gln Thr Glu Cys Asp Gly
            500                 505                 510

Thr Cys Ile Leu Ser Glu Val Ser Arg Val His Leu Pro Gly Ser Gln
            515                 520                 525

Ala Lys Asp Lys Asp Ala Gly Lys Ser Leu Trp Gln Pro Leu
530                 535                 540

<210> SEQ ID NO 19
<211> LENGTH: 1451
<212> TYPE: DNA
<213> ORGANISM: D. melanogaster

<400> SEQUENCE: 19
atgtttacgt ggctgatgat ggatgtcctc cagtttgtga aaggggaaat gacagccgat      60
tcagaggcaa atgccacaaa ttggtataac acgaacgaga gcttatatac cacggaactg     120
aaccatagat ggattagtgg tagttccaca attcagccag aggagtccct ttatggcact     180
gatttgccca cctatcaaca ttgcatagcc acgcggaatt cctttgctga cttgttcact     240
gtggtgctct acggatttgt gtgcattatc ggattatttg gcaacaccct ggtgatctac     300
```

-continued

```
gtggtgttgc gcttttccaa aatgcaaacg gtcacgaata tatatatcct gaatctggcg    360
gtggcagacg agtgcttcct gattggaata cccttctgc tgtacacaat gcgaatttgc     420
agctggcgat tcggggagtt tatgtgcaaa gcctacatgg tgagcacatc catcacctcc    480
ttcacctcgt cgattttcct gctcatcatg tccgcggatc gatatatagc ggtatgccac    540 ccgattcct cgccacgata tcgaactctg catattgcca aagtggtctc agcgattgcc     600
tggtcaactt cagcggtcct catgctgccc gtgatccttt atgccagcac tgtggagcag    660
gaggatggca tcaattactc gtcaacata atgtggccag atgcgtacaa gaagcattcg     720
ggcaccacct tcatactgta cacattttc ctaggattcg ccacaccgct gtgctttatc     780
ctgagtttct actacttggt tataaggaaa ctgcgatcgg tgggtcccaa accaggaacg    840
aagtccaagg agaagaggcg ggctcacagg aaggtcactc gactggtact gacggtgata    900
agtgtataca ttctatgttg gctccctcac tggatttctc aggtggccct gattcactcg    960
aatcccgcgc aaagggacct ctcccgactg aaatactca ttttcctact tctgggggca     1020
ctggtttact cgaattcggc ggtgaatccc atactttatg ccttcctaag tgagaacttc    1080
cggaagagct tcttcaaggc ctttacctgt atgaataagc aggatatcaa cgctcaactc    1140
cagctggagc ccagtgtttt caccaaacag ggcagtaaaa agaggggtgg ctccaagcgc    1200
ctgttgacca gcaatccgca gattcctcca ctgctgccac tgaatgcggg taacaacaat    1260
tcatcgacca ccacatcctc gaccacgaca gcggaaaaga ccggaaccac ggggacacag    1320
aaatcatgca attccaatgg caaagtgaca gctccgccgg agaatttgat tatatgtttg    1380
agcgagcagc aggaggcatt ttgcaccacc gcgagaagag gatcgggcgc agtgcagcag    1440
acagatttgt a                                                          1451
```

<210> SEQ ID NO 20
<211> LENGTH: 483
<212> TYPE: PRT
<213> ORGANISM: D. melanogaster

<400> SEQUENCE: 20

Met Phe Thr Trp Leu Met Met Asp Val Leu Gln Phe Val Lys Gly Glu
1               5                   10                  15

Met Thr Ala Asp Ser Glu Ala Asn Ala Thr Asn Trp Tyr Asn Thr Asn
            20                  25                  30

Glu Ser Leu Tyr Thr Thr Glu Leu Asn His Arg Trp Ile Ser Gly Ser
        35                  40                  45

Ser Thr Ile Gln Pro Glu Glu Ser Leu Tyr Gly Thr Asp Leu Pro Thr
    50                  55                  60

Tyr Gln His Cys Ile Ala Thr Arg Asn Ser Phe Ala Asp Leu Phe Thr
65                  70                  75                  80

Val Val Leu Tyr Gly Phe Val Cys Ile Ile Gly Leu Phe Gly Asn Thr
                85                  90                  95

Leu Val Ile Tyr Val Val Leu Arg Phe Ser Lys Met Gln Thr Val Thr
            100                 105                 110

Asn Ile Tyr Ile Leu Asn Leu Ala Val Ala Asp Glu Cys Phe Leu Ile
        115                 120                 125

Gly Ile Pro Phe Leu Leu Tyr Thr Met Arg Ile Cys Ser Trp Arg Phe
    130                 135                 140

Gly Glu Phe Met Cys Lys Ala Tyr Met Val Ser Thr Ser Ile Thr Ser
145                 150                 155                 160

Phe Thr Ser Ser Ile Phe Leu Leu Ile Met Ser Ala Asp Arg Tyr Ile

```
                    165                 170                 175
Ala Val Cys His Pro Ile Ser Ser Pro Arg Tyr Arg Thr Leu His Ile
            180                 185                 190
Ala Lys Val Val Ser Ala Ile Ala Trp Ser Thr Ser Ala Val Leu Met
            195                 200                 205
Leu Pro Val Ile Leu Tyr Ala Ser Thr Val Glu Gln Glu Asp Gly Ile
            210                 215                 220
Asn Tyr Ser Cys Asn Ile Met Trp Pro Asp Ala Tyr Lys Lys His Ser
225                 230                 235                 240
Gly Thr Thr Phe Ile Leu Tyr Thr Phe Phe Leu Gly Phe Ala Thr Pro
                245                 250                 255
Leu Cys Phe Ile Leu Ser Phe Tyr Tyr Leu Val Ile Arg Lys Leu Arg
            260                 265                 270
Ser Val Gly Pro Lys Pro Gly Thr Lys Ser Lys Glu Lys Arg Arg Ala
            275                 280                 285
His Arg Lys Val Thr Arg Leu Val Leu Thr Val Ile Ser Val Tyr Ile
        290                 295                 300
Leu Cys Trp Leu Pro His Trp Ile Ser Gln Val Ala Leu Ile His Ser
305                 310                 315                 320
Asn Pro Ala Gln Arg Asp Leu Ser Arg Leu Glu Ile Leu Ile Phe Leu
                325                 330                 335
Leu Leu Gly Ala Leu Val Tyr Ser Asn Ser Ala Val Asn Pro Ile Leu
            340                 345                 350
Tyr Ala Phe Leu Ser Glu Asn Phe Arg Lys Ser Phe Phe Lys Ala Phe
            355                 360                 365
Thr Cys Met Asn Lys Gln Asp Ile Asn Ala Gln Leu Gln Leu Glu Pro
        370                 375                 380
Ser Val Phe Thr Lys Gln Gly Ser Lys Lys Arg Gly Gly Ser Lys Arg
385                 390                 395                 400
Leu Leu Thr Ser Asn Pro Gln Ile Pro Pro Leu Leu Pro Leu Asn Ala
                405                 410                 415
Gly Asn Asn Ser Ser Thr Thr Ser Ser Thr Thr Thr Ala Glu
            420                 425                 430
Lys Thr Gly Thr Thr Gly Thr Gln Lys Ser Cys Asn Ser Asn Gly Lys
        435                 440                 445
Val Thr Ala Pro Pro Glu Asn Leu Ile Ile Cys Leu Ser Glu Gln Gln
        450                 455                 460
Glu Ala Phe Cys Thr Thr Ala Arg Arg Gly Ser Gly Ala Val Gln Gln
465                 470                 475                 480
Thr Asp Leu

<210> SEQ ID NO 21
<211> LENGTH: 1754
<212> TYPE: DNA
<213> ORGANISM: D. melanogaster

<400> SEQUENCE: 21
atgttcaact acgaggaggg ggatgccgac caggcggcca tggctgcagc ggctgcctat    60
agggcactgc tcgactacta tgccaatgcg ccaagtgcgg cgggtcacat agtgtcgctc   120
aacgtggcac cctacaatgg aactggaaac ggaggcactg tctccttggc gggcaatgcg   180
acaagcagct atggcgatga tgatagggat ggctatatgg acaccgagcc cagtgacctg   240
gtcaccgaac tggccttctc cctgggcacc agttcaagtc aagtcccag  ttccacaccc   300
```

-continued

```
gcttccagct ccagtacttc cactggcatg cccgtctggc tgatacccag ctatagcatg        360
attctgctgt tcgccgtgct gggcaacctg ctggtcatct cgacgctggt gcagaatcgc        420
cggatgcgta ccataaccaa cgtgttcctg ctcaacctgg ccatatcgga catgctgctg        480
ggcgtgctct gcatgcccgt caccctggtg ggcaccctgc tgcgaaactt catctttggc        540
gagttcctct gcaagctctt tcagttctcg caagccgcct ccgtggccgt ttcgtcctgg        600
accttggtgg ccatatcctg tgagcgctac tacgcgatat gccatccact gcgctcgcga        660
tcctggcaga caatcagtca cgcctacaag atcatcggct tcatctggct gggcggcatc        720
ctctgcatga cgcccatagc ggtctttagt caattgatac ccaccagtcg accgggctac        780
tgcaagtgcc gtgagttttg cccgaccag ggatacgagc tcttctacaa catcctgctg         840
gacttcctgc tgctcgtcct gccgcttctc gtcctctgcg tggcctacat cctcatcacg        900
cgtaccctgt acgtaggcat ggccaaggac agcggacgca tcctgcagca atcgctgcct        960
gtttccgcta caacggccgg cggaagcgca ccgaatccgg gcaccagcag cagtagtaac       1020
tgcatcctgg tcctgaccgc caccgcagtc tataatgaaa atagtaacaa taataatgga       1080
aattcagagg gatccgcagg cggaggatca accaatatgg caacgaccac cttgacaacg       1140
agaccaacgg ctccaactgt gatcaccacc accacgacga ccacggtgac gctggccaag       1200
acctcctcgc ccagcattcg cgtccacgat gcggcacttc gcaggtccaa cgaggccaag       1260
accctggaga gcaagaagcg tgtggtcaag atgctgttcg tcctggtgct ggagtttttc       1320
atctgctgga ctccgctgta cgtgatcaac acgatggtca tgctgatcgg accggtggtg       1380
tacgagtatg tcgactacac ggccatcagt ttcctccagc tgctggccta ctcatccagc       1440
tgctgcaatc cgatcaccta ctgcttcatg aacgccagct tccggcgcgc ctttgtcgac       1500
accttcaagg gtctgccctg cgtcgtgga gcaggtgcca gcggaggcgt cggtggtgct        1560
gctggtggag gactctccgc cagccaggcg ggcgcaggcc cgggcgccta tgcgagtgcc       1620
aacaccaaca ttagtctcaa tcccggccta gccatgggta tgggcacctg gcggagtcgc       1680
tcacgccacg agtttctcaa tgcggtggtg accaccaata gtgccgccgc cgccgtcaac       1740
agtcctcagc tcta                                                         1754
```

<210> SEQ ID NO 22
<211> LENGTH: 584
<212> TYPE: PRT
<213> ORGANISM: D. melanogaster

<400> SEQUENCE: 22

```
Met Phe Asn Tyr Glu Glu Gly Asp Ala Asp Gln Ala Ala Met Ala Ala
1               5                   10                  15

Ala Ala Ala Tyr Arg Ala Leu Leu Asp Tyr Tyr Ala Asn Ala Pro Ser
                20                  25                  30

Ala Ala Gly His Ile Val Ser Leu Asn Val Ala Pro Tyr Asn Gly Thr
            35                  40                  45

Gly Asn Gly Gly Thr Val Ser Leu Ala Gly Asn Ala Thr Ser Ser Tyr
        50                  55                  60

Gly Asp Asp Asp Arg Asp Gly Tyr Met Asp Thr Glu Pro Ser Asp Leu
65                  70                  75                  80

Val Thr Glu Leu Ala Phe Ser Leu Gly Thr Ser Ser Pro Ser Pro
                85                  90                  95

Ser Ser Thr Pro Ala Ser Ser Ser Thr Ser Thr Gly Met Pro Val
            100                 105                 110
```

-continued

```
Trp Leu Ile Pro Ser Tyr Ser Met Ile Leu Leu Phe Ala Val Leu Gly
            115                 120                 125

Asn Leu Leu Val Ile Ser Thr Leu Val Gln Asn Arg Arg Met Arg Thr
        130                 135                 140

Ile Thr Asn Val Phe Leu Leu Asn Leu Ala Ile Ser Asp Met Leu Leu
145                 150                 155                 160

Gly Val Leu Cys Met Pro Val Thr Leu Val Gly Thr Leu Leu Arg Asn
                165                 170                 175

Phe Ile Phe Gly Glu Phe Leu Cys Lys Leu Phe Gln Phe Ser Gln Ala
            180                 185                 190

Ala Ser Val Ala Val Ser Ser Trp Thr Leu Val Ala Ile Ser Cys Glu
        195                 200                 205

Arg Tyr Tyr Ala Ile Cys His Pro Leu Arg Ser Arg Ser Trp Gln Thr
    210                 215                 220

Ile Ser His Ala Tyr Lys Ile Gly Phe Ile Trp Leu Gly Gly Ile
225                 230                 235                 240

Leu Cys Met Thr Pro Ile Ala Val Phe Ser Gln Leu Ile Pro Thr Ser
                245                 250                 255

Arg Pro Gly Tyr Cys Lys Cys Arg Glu Phe Trp Pro Asp Gln Gly Tyr
            260                 265                 270

Glu Leu Phe Tyr Asn Ile Leu Leu Asp Phe Leu Leu Leu Val Leu Pro
        275                 280                 285

Leu Leu Val Leu Cys Val Ala Tyr Ile Leu Ile Thr Arg Thr Leu Tyr
    290                 295                 300

Val Gly Met Ala Lys Asp Ser Gly Arg Ile Leu Gln Gln Ser Leu Pro
305                 310                 315                 320

Val Ser Ala Thr Thr Ala Gly Gly Ser Ala Pro Asn Pro Gly Thr Ser
                325                 330                 335

Ser Ser Ser Asn Cys Ile Leu Val Leu Thr Ala Thr Ala Val Tyr Asn
            340                 345                 350

Glu Asn Ser Asn Asn Asn Gly Asn Ser Glu Gly Ser Ala Gly Gly
        355                 360                 365

Gly Ser Thr Asn Met Ala Thr Thr Leu Thr Thr Arg Pro Thr Ala
    370                 375                 380

Pro Thr Val Ile Thr Thr Thr Thr Thr Val Thr Leu Ala Lys
385                 390                 395                 400

Thr Ser Ser Pro Ser Ile Arg Val His Asp Ala Ala Leu Arg Ser
                405                 410                 415

Asn Glu Ala Lys Thr Leu Glu Ser Lys Lys Arg Val Val Lys Met Leu
            420                 425                 430

Phe Val Leu Val Leu Glu Phe Phe Ile Cys Trp Thr Pro Leu Tyr Val
        435                 440                 445

Ile Asn Thr Met Val Met Leu Ile Gly Pro Val Val Tyr Glu Tyr Val
    450                 455                 460

Asp Tyr Thr Ala Ile Ser Phe Leu Gln Leu Leu Ala Tyr Ser Ser Ser
465                 470                 475                 480

Cys Cys Asn Pro Ile Thr Tyr Cys Phe Met Asn Ala Ser Phe Arg Arg
                485                 490                 495

Ala Phe Val Asp Thr Phe Lys Gly Leu Pro Trp Arg Arg Gly Ala Gly
            500                 505                 510

Ala Ser Gly Gly Val Gly Gly Ala Gly Gly Leu Ser Ala Ser
        515                 520                 525

Gln Ala Gly Ala Gly Pro Gly Ala Tyr Ala Ser Ala Asn Thr Asn Ile
```

```
                530             535             540
Ser Leu Asn Pro Gly Leu Ala Met Gly Met Gly Thr Trp Arg Ser Arg
545                 550                 555                 560

Ser Arg His Glu Phe Leu Asn Ala Val Val Thr Thr Asn Ser Ala Ala
                565                 570                 575

Ala Ala Val Asn Ser Pro Gln Leu
                580

<210> SEQ ID NO 23
<211> LENGTH: 1452
<212> TYPE: DNA
<213> ORGANISM: D. melanogaster

<400> SEQUENCE: 23
atgtacgcct ccttgatgga cgttggccag acgttggcag ccaggctggc ggatagcgac      60
ggcaacgggg ccaatgacag cggactcctg caaccggac aaggtctgga gcaggagcag      120
gagggtctgg cactggatat gggccacaat gccagcgccg acggcggaat agtaccgtat     180
gtgcccgtgc tggaccgccc ggagacgtac attgtcaccg tgctgtacac gctcatcttc     240
attgtgggag ttttgggcaa cggcacgctg gtcatcatct tctttcgcca ccgctccatg     300
cgcaacatac ccaacacata cattctttca ctggccctgg ctgatctgtt ggttatattg     360
gtgtgtgtac ctgtggccac gattgtctac acgcaggaaa gctggccctt tgagcggaac     420
atgtgccgca tcagcgagtt ctttaaggac atatccatcg gggtgtccgt gtttacactg     480
accgcccttt ccggcgagcg gtactgcgcc attgtaaatc ccctacgcaa gcttcagacc     540
aagccgctca ctgtctttac tgcggtgatg atctggatcc tggccatcct actgggcatg     600
ccttcggttc ttttctccga catcaagtcc taccctgtgt tcacagccac cggtaacatg     660
accattgaag tgtgctcccc atttcgcgac ccggagtatg caaagttcat ggtggcgggc     720
aaggcactgg tgtactacct gttgccgctg tccatcattg ggcgctata catcatgatg     780 gccaagcggc tccatatgag cgcccgcaac atgcccggcg aacagcagag catgcagagc     840
cgcacccagg ctagggcccg actccatgtg gcgcgcatgg tggtagcatt cgtggtggtg     900
ttcttcatct gcttcttccc gtaccacgtg tttgagctgt ggtaccactt ctacccaacg     960
gctgaggagg acttcgatga gttctggaac gtgctgcgca tccttcctaa actcgtgcgt    1020
caaccccgtg gcctctactg cgtgtccggg gtgtttcggc agcactttaa tcgctacctc    1080
tgctgcatct gcgtcaagcg gcagccgcac ctgcggcagc actcaacggc cactggaatg    1140
atggacaata ccagtgtgat gtccatgcgc cgctccacgt acgtgggtgg aaccgctggc    1200
aatctgcggg cctcgctgca ccggaacagc aatcacggag ttggtggagc tggaggtgga    1260
gtaggaggag gagtagggtc aggtcgtgtg gcagctttc atcggcagga ctcgatgccc    1320
ctgcagcacg gaaatgccca cggaggtggt gcgggcgggg gatcctccgg acttggagcc    1380
ggcgggcgga cggcggcagt gagcgaaaag agctttataa atcgttacga aagtggcgta    1440
atgcgctact aa                                                        1452

<210> SEQ ID NO 24
<211> LENGTH: 483
<212> TYPE: PRT
<213> ORGANISM: D. melanogaster

<400> SEQUENCE: 24

Met Tyr Ala Ser Leu Met Asp Val Gly Gln Thr Leu Ala Ala Arg Leu
1               5                   10                  15
```

-continued

```
Ala Asp Ser Asp Gly Asn Gly Ala Asn Asp Ser Gly Leu Leu Ala Thr
             20                  25                  30
Gly Gln Gly Leu Glu Gln Glu Gln Glu Gly Leu Ala Leu Asp Met Gly
         35                  40                  45
His Asn Ala Ser Ala Asp Gly Gly Ile Val Pro Tyr Val Pro Val Leu
     50                  55                  60
Asp Arg Pro Glu Thr Tyr Ile Val Thr Val Leu Tyr Thr Leu Ile Phe
 65                  70                  75                  80
Ile Val Gly Val Leu Gly Asn Gly Thr Leu Val Ile Ile Phe Phe Arg
                 85                  90                  95
His Arg Ser Met Arg Asn Ile Pro Asn Thr Tyr Ile Leu Ser Leu Ala
            100                 105                 110
Leu Ala Asp Leu Leu Val Ile Leu Val Cys Val Pro Val Ala Thr Ile
            115                 120                 125
Val Tyr Thr Gln Glu Ser Trp Pro Phe Glu Arg Asn Met Cys Arg Ile
        130                 135                 140
Ser Glu Phe Phe Lys Asp Ile Ser Ile Gly Val Ser Val Phe Thr Leu
145                 150                 155                 160
Thr Ala Leu Ser Gly Glu Arg Tyr Cys Ala Ile Val Asn Pro Leu Arg
                165                 170                 175
Lys Leu Gln Thr Lys Pro Leu Thr Val Phe Thr Ala Val Met Ile Trp
            180                 185                 190
Ile Leu Ala Ile Leu Leu Gly Met Pro Ser Val Leu Phe Ser Asp Ile
        195                 200                 205
Lys Ser Tyr Pro Val Phe Thr Ala Thr Gly Asn Met Thr Ile Glu Val
    210                 215                 220
Cys Ser Pro Phe Arg Asp Pro Glu Tyr Ala Lys Phe Met Val Ala Gly
225                 230                 235                 240
Lys Ala Leu Val Tyr Tyr Leu Leu Pro Leu Ser Ile Ile Gly Ala Leu
                245                 250                 255
Tyr Ile Met Met Ala Lys Arg Leu His Met Ser Ala Arg Asn Met Pro
            260                 265                 270
Gly Glu Gln Gln Ser Met Gln Ser Arg Thr Gln Ala Arg Ala Arg Leu
        275                 280                 285
His Val Ala Arg Met Val Val Ala Phe Val Val Phe Phe Ile Cys
            290                 295                 300
Phe Phe Pro Tyr His Val Phe Glu Leu Trp Tyr His Phe Tyr Pro Thr
305                 310                 315                 320
Ala Glu Glu Asp Phe Asp Glu Phe Trp Asn Val Leu Arg Ile Leu Pro
                325                 330                 335
Lys Leu Val Arg Gln Pro Arg Gly Leu Tyr Cys Val Ser Gly Val Phe
            340                 345                 350
Arg Gln His Phe Asn Arg Tyr Leu Cys Cys Ile Cys Val Lys Arg Gln
        355                 360                 365
Pro His Leu Arg Gln His Ser Thr Ala Thr Gly Met Met Asp Asn Thr
    370                 375                 380
Ser Val Met Ser Met Arg Arg Ser Thr Tyr Val Gly Thr Ala Gly
385                 390                 395                 400
Asn Leu Arg Ala Ser Leu His Arg Asn Ser Asn His Gly Val Gly Gly
                405                 410                 415
Ala Gly Gly Gly Val Gly Gly Val Gly Ser Gly Arg Val Gly Ser
            420                 425                 430
```

```
Phe His Arg Gln Asp Ser Met Pro Leu Gln His Gly Asn Ala His Gly
        435                 440                 445

Gly Gly Ala Gly Gly Gly Ser Ser Gly Leu Gly Ala Gly Gly Arg Thr
450                 455                 460

Ala Ala Val Ser Glu Lys Ser Phe Ile Asn Arg Tyr Glu Ser Gly Val
465                 470                 475                 480

Met Arg Tyr

<210> SEQ ID NO 25
<211> LENGTH: 10
<212> TYPE: PRT
<213> ORGANISM: Artificial Sequence
<220> FEATURE:
<223> OTHER INFORMATION: Novel Sequence

<400> SEQUENCE: 25

Thr Asp Val Asp His Val Phe Leu Arg Phe
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Novel Sequence

<400> SEQUENCE: 26

Asp Pro Lys Gln Asp Phe Met Arg Phe
1               5

<210> SEQ ID NO 27
<211> LENGTH: 7
<212> TYPE: PRT
<213> ORGANISM: Artificial Sequence
<220> FEATURE:
<223> OTHER INFORMATION: Novel Sequence

<400> SEQUENCE: 27

Pro Asp Asn Phe Met Arg Phe
1               5

<210> SEQ ID NO 28
<211> LENGTH: 9
<212> TYPE: PRT
<213> ORGANISM: Artificial Sequence
<220> FEATURE:
<223> OTHER INFORMATION: Novel Sequence

<400> SEQUENCE: 28

Thr Pro Ala Glu Asp Phe Met Arg Phe
1               5

<210> SEQ ID NO 29
<211> LENGTH: 9
<212> TYPE: PRT
<213> ORGANISM: Artificial Sequence
<220> FEATURE:
<223> OTHER INFORMATION: Novel Sequence

<400> SEQUENCE: 29

Ser Leu Lys Gln Asp Phe Met His Phe
1               5

<210> SEQ ID NO 30
<211> LENGTH: 9
```

```
<212> TYPE: PRT
<213> ORGANISM: Artificial Sequence
<220> FEATURE:
<223> OTHER INFORMATION: Novel Sequence

<400> SEQUENCE: 30

Ser Val Lys Gln Asp Phe Met His Phe
1               5

<210> SEQ ID NO 31
<211> LENGTH: 6
<212> TYPE: PRT
<213> ORGANISM: Artificial Sequence
<220> FEATURE:
<223> OTHER INFORMATION: Novel Sequence

<400> SEQUENCE: 31

Ala Ala Met Asp Arg Tyr
1               5

<210> SEQ ID NO 32
<211> LENGTH: 9
<212> TYPE: PRT
<213> ORGANISM: Artificial Sequence
<220> FEATURE:
<223> OTHER INFORMATION: Novel Sequence

<400> SEQUENCE: 32

Ser Val Gln Asp Asn Phe Met His Phe
1               5

<210> SEQ ID NO 33
<211> LENGTH: 10
<212> TYPE: PRT
<213> ORGANISM: Artificial Sequence
<220> FEATURE:
<223> OTHER INFORMATION: Novel Sequence

<400> SEQUENCE: 33

Ala Arg Gly Pro Gln Leu Arg Leu Arg Phe
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Novel Sequence

<400> SEQUENCE: 34

Gly Asp Gly Arg Leu Tyr Ala Phe Gly Leu
1               5                   10

<210> SEQ ID NO 35
<211> LENGTH: 8
<212> TYPE: PRT
<213> ORGANISM: Artificial Sequence
<220> FEATURE:
<223> OTHER INFORMATION: Novel Sequence

<400> SEQUENCE: 35

Asp Arg Leu Tyr Ser Phe Gly Leu
1               5

<210> SEQ ID NO 36
<211> LENGTH: 13
<212> TYPE: PRT
```

```
<213> ORGANISM: Artificial Sequence
<220> FEATURE:
<223> OTHER INFORMATION: Novel Sequence

<400> SEQUENCE: 36

Ala Pro Ser Gly Ala Gln Arg Leu Tyr Gly Phe Gly Leu
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Novel Sequence

<400> SEQUENCE: 37

Gly Gly Ser Leu Tyr Ser Phe Gly Leu
1               5

<210> SEQ ID NO 38
<211> LENGTH: 4
<212> TYPE: PRT
<213> ORGANISM: Artificial Sequence
<220> FEATURE:
<223> OTHER INFORMATION: Novel Sequence

<400> SEQUENCE: 38

Phe Ile Arg Phe
1

<210> SEQ ID NO 39
<211> LENGTH: 7
<212> TYPE: PRT
<213> ORGANISM: Artificial Sequence
<220> FEATURE:
<223> OTHER INFORMATION: Novel Sequence

<400> SEQUENCE: 39

Lys Asn Glu Phe Ile Arg Phe
1               5

<210> SEQ ID NO 40
<211> LENGTH: 4
<212> TYPE: PRT
<213> ORGANISM: Artificial Sequence
<220> FEATURE:
<223> OTHER INFORMATION: Novel Sequence

<400> SEQUENCE: 40

Phe Met Arg Phe
1

<210> SEQ ID NO 41
<211> LENGTH: 7
<212> TYPE: PRT
<213> ORGANISM: Artificial Sequence
<220> FEATURE:
<223> OTHER INFORMATION: Novel Sequence

<400> SEQUENCE: 41

Lys Ser Ala Phe Met Arg Phe
1               5

<210> SEQ ID NO 42
<211> LENGTH: 7
<212> TYPE: PRT
<213> ORGANISM: Artificial Sequence
```

```
<220> FEATURE:
<223> OTHER INFORMATION: Novel Sequence

<400> SEQUENCE: 42

Lys Pro Asn Phe Leu Arg Phe
1               5

<210> SEQ ID NO 43
<211> LENGTH: 4
<212> TYPE: PRT
<213> ORGANISM: Artificial Sequence
<220> FEATURE:
<223> OTHER INFORMATION: Novel Sequence

<400> SEQUENCE: 43

Phe Leu Arg Phe
1

<210> SEQ ID NO 44
<211> LENGTH: 4
<212> TYPE: PRT
<213> ORGANISM: Artificial Sequence
<220> FEATURE:
<223> OTHER INFORMATION: Novel Sequence

<400> SEQUENCE: 44

Tyr Leu Arg Phe
1

<210> SEQ ID NO 45
<211> LENGTH: 7
<212> TYPE: PRT
<213> ORGANISM: Artificial Sequence
<220> FEATURE:
<223> OTHER INFORMATION: Novel Sequence

<400> SEQUENCE: 45

Lys Pro Asn Phe Leu Arg Tyr
1               5

<210> SEQ ID NO 46
<211> LENGTH: 8
<212> TYPE: PRT
<213> ORGANISM: Artificial Sequence
<220> FEATURE:
<223> OTHER INFORMATION: Novel Sequence

<400> SEQUENCE: 46

Thr Asn Arg Asn Phe Leu Arg Phe
1               5

<210> SEQ ID NO 47
<211> LENGTH: 9
<212> TYPE: PRT
<213> ORGANISM: Artificial Sequence
<220> FEATURE:
<223> OTHER INFORMATION: Novel Sequence

<400> SEQUENCE: 47

Arg Asn Lys Phe Glu Phe Ile Arg Phe
1               5

<210> SEQ ID NO 48
<211> LENGTH: 8
<212> TYPE: PRT
<213> ORGANISM: Artificial Sequence
<220> FEATURE:
```

<223> OTHER INFORMATION: Novel Sequence

<400> SEQUENCE: 48

Ala Gly Pro Arg Phe Ile Arg Phe
1               5

<210> SEQ ID NO 49
<211> LENGTH: 9
<212> TYPE: PRT
<213> ORGANISM: Artificial Sequence
<220> FEATURE:
<223> OTHER INFORMATION: Novel Sequence

<400> SEQUENCE: 49

Gly Leu Gly Pro Arg Pro Leu Arg Phe
1               5

<210> SEQ ID NO 50
<211> LENGTH: 2
<212> TYPE: PRT
<213> ORGANISM: Artificial Sequence
<220> FEATURE:
<223> OTHER INFORMATION: Novel Sequence

<400> SEQUENCE: 50

Ile Leu
1

<210> SEQ ID NO 51
<211> LENGTH: 8
<212> TYPE: PRT
<213> ORGANISM: Artificial Sequence
<220> FEATURE:
<223> OTHER INFORMATION: Novel Sequence

<400> SEQUENCE: 51

Ala Gly Ala Lys Ile Phe Arg Phe
1               5

<210> SEQ ID NO 52
<211> LENGTH: 9
<212> TYPE: PRT
<213> ORGANISM: Artificial Sequence
<220> FEATURE:
<223> OTHER INFORMATION: Novel Sequence

<400> SEQUENCE: 52

Ala Pro Lys Pro Lys Phe Ile Arg Phe
1               5

<210> SEQ ID NO 53
<211> LENGTH: 8
<212> TYPE: PRT
<213> ORGANISM: Artificial Sequence
<220> FEATURE:
<223> OTHER INFORMATION: Novel Sequence

<400> SEQUENCE: 53

Lys Ser Ala Phe Val Leu Arg Phe
1               5

<210> SEQ ID NO 54
<211> LENGTH: 9
<212> TYPE: PRT
<213> ORGANISM: Artificial Sequence
<220> FEATURE:
<223> OTHER INFORMATION: Novel Sequence

```
<400> SEQUENCE: 54

Thr Lys Phe Gln Asp Phe Leu Arg Phe
1               5

<210> SEQ ID NO 55
<211> LENGTH: 10
<212> TYPE: PRT
<213> ORGANISM: Artificial Sequence
<220> FEATURE:
<223> OTHER INFORMATION: Novel Sequence

<400> SEQUENCE: 55

Ser Ala Glu Pro Phe Gly Thr Met Arg Phe
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Novel Sequence

<400> SEQUENCE: 56

Ala Ser Glu Asp Ala Leu Phe Gly Thr Met Arg Phe
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Novel Sequence

<400> SEQUENCE: 57

Ser Ala Asp Asp Ser Ala Pro Phe Gly Thr Met Arg Phe
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Novel Sequence

<400> SEQUENCE: 58

Glu Asp Gly Asn Ala Pro Phe Gly Thr Met Arg Phe
1               5                   10

<210> SEQ ID NO 59
<211> LENGTH: 8
<212> TYPE: PRT
<213> ORGANISM: Artificial Sequence
<220> FEATURE:
<223> OTHER INFORMATION: Novel Sequence

<400> SEQUENCE: 59

Phe Leu Phe Gln Pro Gln Arg Phe
1               5

<210> SEQ ID NO 60
<211> LENGTH: 9
<212> TYPE: PRT
<213> ORGANISM: Artificial Sequence
<220> FEATURE:
<223> OTHER INFORMATION: Novel Sequence
```

```
<400> SEQUENCE: 60

Ser Ala Asp Pro Asn Phe Leu Arg Phe
1               5

<210> SEQ ID NO 61
<211> LENGTH: 8
<212> TYPE: PRT
<213> ORGANISM: Artificial Sequence
<220> FEATURE:
<223> OTHER INFORMATION: Novel Sequence

<400> SEQUENCE: 61

Ser Gln Pro Asn Phe Leu Arg Phe
1               5

<210> SEQ ID NO 62
<211> LENGTH: 10
<212> TYPE: PRT
<213> ORGANISM: Artificial Sequence
<220> FEATURE:
<223> OTHER INFORMATION: Novel Sequence

<400> SEQUENCE: 62

Ala Ser Gly Asp Pro Asn Phe Leu Arg Phe
1               5                   10

<210> SEQ ID NO 63
<211> LENGTH: 8
<212> TYPE: PRT
<213> ORGANISM: Artificial Sequence
<220> FEATURE:
<223> OTHER INFORMATION: Novel Sequence

<400> SEQUENCE: 63

Ser Asp Pro Asn Phe Leu Arg Phe
1               5

<210> SEQ ID NO 64
<211> LENGTH: 10
<212> TYPE: PRT
<213> ORGANISM: Artificial Sequence
<220> FEATURE:
<223> OTHER INFORMATION: Novel Sequence

<400> SEQUENCE: 64

Ala Ala Ala Asp Pro Asn Phe Leu Arg Phe
1               5                   10

<210> SEQ ID NO 65
<211> LENGTH: 6
<212> TYPE: PRT
<213> ORGANISM: Artificial Sequence
<220> FEATURE:
<223> OTHER INFORMATION: Novel Sequence

<400> SEQUENCE: 65

Pro Asn Phe Leu Arg Phe
1               5

<210> SEQ ID NO 66
<211> LENGTH: 6
<212> TYPE: PRT
<213> ORGANISM: Artificial Sequence
<220> FEATURE:
<223> OTHER INFORMATION: Novel Sequence

<400> SEQUENCE: 66
```

```
Lys Pro Phe Leu Arg Phe
 1               5

<210> SEQ ID NO 67
<211> LENGTH: 10
<212> TYPE: PRT
<213> ORGANISM: Artificial Sequence
<220> FEATURE:
<223> OTHER INFORMATION: Novel Sequence

<400> SEQUENCE: 67

Ala Gly Ser Asp Pro Asn Phe Leu Arg Phe
 1               5                  10

<210> SEQ ID NO 68
<211> LENGTH: 7
<212> TYPE: PRT
<213> ORGANISM: Artificial Sequence
<220> FEATURE:
<223> OTHER INFORMATION: Novel Sequence

<400> SEQUENCE: 68

Lys Pro Asn Phe Leu Arg Tyr
 1               5

<210> SEQ ID NO 69
<211> LENGTH: 8
<212> TYPE: PRT
<213> ORGANISM: Artificial Sequence
<220> FEATURE:
<223> OTHER INFORMATION: Novel Sequence

<400> SEQUENCE: 69

Ser Pro Arg Glu Pro Ile Arg Phe
 1               5

<210> SEQ ID NO 70
<211> LENGTH: 8
<212> TYPE: PRT
<213> ORGANISM: Artificial Sequence
<220> FEATURE:
<223> OTHER INFORMATION: Novel Sequence

<400> SEQUENCE: 70

Leu Arg Gly Glu Pro Ile Arg Phe
 1               5

<210> SEQ ID NO 71
<211> LENGTH: 8
<212> TYPE: PRT
<213> ORGANISM: Artificial Sequence
<220> FEATURE:
<223> OTHER INFORMATION: Novel Sequence

<400> SEQUENCE: 71

Ser Pro Leu Gly Thr Met Arg Phe
 1               5

<210> SEQ ID NO 72
<211> LENGTH: 11
<212> TYPE: PRT
<213> ORGANISM: Artificial Sequence
<220> FEATURE:
<223> OTHER INFORMATION: Novel Sequence

<400> SEQUENCE: 72
```

```
Glu Ala Glu Glu Pro Leu Gly Thr Met Arg Phe
1               5                   10
```

<210> SEQ ID NO 73
<211> LENGTH: 12
<212> TYPE: PRT
<213> ORGANISM: Artificial Sequence
<220> FEATURE:
<223> OTHER INFORMATION: Novel Sequence

<400> SEQUENCE: 73

```
Ala Ser Glu Asp Ala Leu Phe Gly Thr Met Arg Phe
1               5                   10
```

<210> SEQ ID NO 74
<211> LENGTH: 12
<212> TYPE: PRT
<213> ORGANISM: Artificial Sequence
<220> FEATURE:
<223> OTHER INFORMATION: Novel Sequence

<400> SEQUENCE: 74

```
Glu Asp Gly Asn Ala Pro Phe Gly Thr Met Arg Phe
1               5                   10
```

<210> SEQ ID NO 75
<211> LENGTH: 10
<212> TYPE: PRT
<213> ORGANISM: Artificial Sequence
<220> FEATURE:
<223> OTHER INFORMATION: Novel Sequence

<400> SEQUENCE: 75

```
Ser Ala Glu Pro Phe Gly Thr Met Arg Phe
1               5                   10
```

<210> SEQ ID NO 76
<211> LENGTH: 13
<212> TYPE: PRT
<213> ORGANISM: Artificial Sequence
<220> FEATURE:
<223> OTHER INFORMATION: Novel Sequence

<400> SEQUENCE: 76

```
Ser Ala Asp Asp Ser Ala Pro Phe Gly Thr Met Arg Phe
1               5                   10
```

<210> SEQ ID NO 77
<211> LENGTH: 7
<212> TYPE: PRT
<213> ORGANISM: Artificial Sequence
<220> FEATURE:
<223> OTHER INFORMATION: Novel Sequence

<400> SEQUENCE: 77

```
Lys Pro Thr Phe Ile Arg Phe
1               5
```

<210> SEQ ID NO 78
<211> LENGTH: 8
<212> TYPE: PRT
<213> ORGANISM: Artificial Sequence
<220> FEATURE:
<223> OTHER INFORMATION: Novel Sequence

<400> SEQUENCE: 78

```
Ala Ser Pro Ser Phe Ile Arg Phe
```

```
<210> SEQ ID NO 79
<211> LENGTH: 7
<212> TYPE: PRT
<213> ORGANISM: Artificial Sequence
<220> FEATURE:
<223> OTHER INFORMATION: Novel Sequence

<400> SEQUENCE: 79

Gly Ala Lys Phe Ile Arg Phe
1               5

<210> SEQ ID NO 80
<211> LENGTH: 8
<212> TYPE: PRT
<213> ORGANISM: Artificial Sequence
<220> FEATURE:
<223> OTHER INFORMATION: Novel Sequence

<400> SEQUENCE: 80

Ala Gly Ala Lys Phe Ile Arg Phe
1               5

<210> SEQ ID NO 81
<211> LENGTH: 9
<212> TYPE: PRT
<213> ORGANISM: Artificial Sequence
<220> FEATURE:
<223> OTHER INFORMATION: Novel Sequence

<400> SEQUENCE: 81

Ala Pro Lys Pro Lys Phe Ile Arg Phe
1               5

<210> SEQ ID NO 82
<211> LENGTH: 7
<212> TYPE: PRT
<213> ORGANISM: Artificial Sequence
<220> FEATURE:
<223> OTHER INFORMATION: Novel Sequence

<400> SEQUENCE: 82

Lys Ser Ala Tyr Met Arg Phe
1               5

<210> SEQ ID NO 83
<211> LENGTH: 11
<212> TYPE: PRT
<213> ORGANISM: Artificial Sequence
<220> FEATURE:
<223> OTHER INFORMATION: Novel Sequence

<400> SEQUENCE: 83

Ser Pro Met Gln Arg Ser Ser Met Val Arg Phe
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Novel Sequence

<400> SEQUENCE: 84

Ser Pro Met Glu Arg Ser Ala Met Val Arg Phe
1               5                   10
```

```
<210> SEQ ID NO 85
<211> LENGTH: 11
<212> TYPE: PRT
<213> ORGANISM: Artificial Sequence
<220> FEATURE:
<223> OTHER INFORMATION: Novel Sequence

<400> SEQUENCE: 85

Ser Pro Met Asp Arg Ser Lys Met Val Arg Phe
1               5                   10

<210> SEQ ID NO 86
<211> LENGTH: 7
<212> TYPE: PRT
<213> ORGANISM: Artificial Sequence
<220> FEATURE:
<223> OTHER INFORMATION: Novel Sequence

<400> SEQUENCE: 86

Lys Asn Glu Phe Ile Arg Phe
1               5

<210> SEQ ID NO 87
<211> LENGTH: 7
<212> TYPE: PRT
<213> ORGANISM: Artificial Sequence
<220> FEATURE:
<223> OTHER INFORMATION: Novel Sequence

<400> SEQUENCE: 87

Lys Pro Ser Phe Val Arg Phe
1               5

<210> SEQ ID NO 88
<211> LENGTH: 11
<212> TYPE: PRT
<213> ORGANISM: Artificial Sequence
<220> FEATURE:
<223> OTHER INFORMATION: Novel Sequence

<400> SEQUENCE: 88

Gln Pro Lys Ala Arg Ser Gly Tyr Ile Arg Phe
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Novel Sequence

<400> SEQUENCE: 89

Ala Met Arg Asn Ala Leu Val Arg Phe
1               5

<210> SEQ ID NO 90
<211> LENGTH: 12
<212> TYPE: PRT
<213> ORGANISM: Artificial Sequence
<220> FEATURE:
<223> OTHER INFORMATION: Novel Sequence

<400> SEQUENCE: 90

Ala Ser Gly Gly Met Arg Asn Ala Leu Val Arg Phe
1               5                   10
```

```
<210> SEQ ID NO 91
<211> LENGTH: 10
<212> TYPE: PRT
<213> ORGANISM: Artificial Sequence
<220> FEATURE:
<223> OTHER INFORMATION: Novel Sequence

<400> SEQUENCE: 91

Asn Gly Ala Pro Gln Pro Phe Val Arg Phe
1               5                   10

<210> SEQ ID NO 92
<211> LENGTH: 9
<212> TYPE: PRT
<213> ORGANISM: Artificial Sequence
<220> FEATURE:
<223> OTHER INFORMATION: Novel Sequence

<400> SEQUENCE: 92

Arg Asn Lys Phe Glu Phe Ile Arg Phe
1               5

<210> SEQ ID NO 93
<211> LENGTH: 14
<212> TYPE: PRT
<213> ORGANISM: Artificial Sequence
<220> FEATURE:
<223> OTHER INFORMATION: Novel Sequence

<400> SEQUENCE: 93

Ser Asp Arg Pro Thr Arg Ala Met Asp Ser Pro Ile Arg Phe
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Novel Sequence

<400> SEQUENCE: 94

Ala Ala Asp Gly Ala Pro Leu Ile Arg Phe
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Novel Sequence

<400> SEQUENCE: 95

Ala Pro Glu Ala Ser Pro Phe Ile Arg Phe
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Novel Sequence

<400> SEQUENCE: 96

Ala Ser Pro Ser Ala Pro Leu Ile Arg Phe
1               5                   10
```

```
<210> SEQ ID NO 97
<211> LENGTH: 10
<212> TYPE: PRT
<213> ORGANISM: Artificial Sequence
<220> FEATURE:
<223> OTHER INFORMATION: Novel Sequence

<400> SEQUENCE: 97

Ser Pro Ser Ala Val Pro Leu Ile Arg Phe
1               5                   10

<210> SEQ ID NO 98
<211> LENGTH: 9
<212> TYPE: PRT
<213> ORGANISM: Artificial Sequence
<220> FEATURE:
<223> OTHER INFORMATION: Novel Sequence

<400> SEQUENCE: 98

Ala Ser Ser Ala Pro Leu Ile Arg Phe
1               5

<210> SEQ ID NO 99
<211> LENGTH: 7
<212> TYPE: PRT
<213> ORGANISM: Artificial Sequence
<220> FEATURE:
<223> OTHER INFORMATION: Novel Sequence

<400> SEQUENCE: 99

Lys His Glu Tyr Leu Arg Phe
1               5

<210> SEQ ID NO 100
<211> LENGTH: 6
<212> TYPE: PRT
<213> ORGANISM: Artificial Sequence
<220> FEATURE:
<223> OTHER INFORMATION: Novel Sequence

<400> SEQUENCE: 100

Ser Leu Asp Tyr Arg Phe
1               5

<210> SEQ ID NO 101
<211> LENGTH: 14
<212> TYPE: PRT
<213> ORGANISM: Artificial Sequence
<220> FEATURE:
<223> OTHER INFORMATION: Novel Sequence

<400> SEQUENCE: 101

Glu Ile Val Phe His Gln Ile Ser Pro Ile Phe Phe Arg Phe
1               5                   10

<210> SEQ ID NO 102
<211> LENGTH: 9
<212> TYPE: PRT
<213> ORGANISM: Artificial Sequence
<220> FEATURE:
<223> OTHER INFORMATION: Novel Sequence

<400> SEQUENCE: 102

Gly Gly Pro Gln Gly Pro Leu Arg Phe
1               5

<210> SEQ ID NO 103
```

```
<211> LENGTH: 8
<212> TYPE: PRT
<213> ORGANISM: Artificial Sequence
<220> FEATURE:
<223> OTHER INFORMATION: Novel Sequence

<400> SEQUENCE: 103

Gly Pro Ser Gly Pro Leu Arg Phe
1               5

<210> SEQ ID NO 104
<211> LENGTH: 7
<212> TYPE: PRT
<213> ORGANISM: Artificial Sequence
<220> FEATURE:
<223> OTHER INFORMATION: Novel Sequence

<400> SEQUENCE: 104

Ala Gln Thr Phe Val Arg Phe
1               5

<210> SEQ ID NO 105
<211> LENGTH: 7
<212> TYPE: PRT
<213> ORGANISM: Artificial Sequence
<220> FEATURE:
<223> OTHER INFORMATION: Novel Sequence

<400> SEQUENCE: 105

Gly Gln Thr Phe Val Arg Phe
1               5

<210> SEQ ID NO 106
<211> LENGTH: 7
<212> TYPE: PRT
<213> ORGANISM: Artificial Sequence
<220> FEATURE:
<223> OTHER INFORMATION: Novel Sequence

<400> SEQUENCE: 106

Lys Ser Ala Phe Val Arg Phe
1               5

<210> SEQ ID NO 107
<211> LENGTH: 7
<212> TYPE: PRT
<213> ORGANISM: Artificial Sequence
<220> FEATURE:
<223> OTHER INFORMATION: Novel Sequence

<400> SEQUENCE: 107

Lys Ser Gln Tyr Ile Arg Phe
1               5

<210> SEQ ID NO 108
<211> LENGTH: 8
<212> TYPE: PRT
<213> ORGANISM: Artificial Sequence
<220> FEATURE:
<223> OTHER INFORMATION: Novel Sequence

<400> SEQUENCE: 108

Asp Val Pro Gly Val Leu Arg Phe
1               5

<210> SEQ ID NO 109
<211> LENGTH: 9
```

```
<212> TYPE: PRT
<213> ORGANISM: Artificial Sequence
<220> FEATURE:
<223> OTHER INFORMATION: Novel Sequence

<400> SEQUENCE: 109

Lys Ser Val Pro Gly Val Leu Arg Phe
1               5

<210> SEQ ID NO 110
<211> LENGTH: 9
<212> TYPE: PRT
<213> ORGANISM: Artificial Sequence
<220> FEATURE:
<223> OTHER INFORMATION: Novel Sequence

<400> SEQUENCE: 110

Ser Glu Val Pro Gly Val Leu Arg Phe
1               5

<210> SEQ ID NO 111
<211> LENGTH: 8
<212> TYPE: PRT
<213> ORGANISM: Artificial Sequence
<220> FEATURE:
<223> OTHER INFORMATION: Novel Sequence

<400> SEQUENCE: 111

Ser Val Pro Gly Val Leu Arg Phe
1               5

<210> SEQ ID NO 112
<211> LENGTH: 12
<212> TYPE: PRT
<213> ORGANISM: Artificial Sequence
<220> FEATURE:
<223> OTHER INFORMATION: Novel Sequence

<400> SEQUENCE: 112

Asp Phe Asp Gly Ala Met Pro Gly Val Leu Arg Phe
1               5                   10

<210> SEQ ID NO 113
<211> LENGTH: 8
<212> TYPE: PRT
<213> ORGANISM: Artificial Sequence
<220> FEATURE:
<223> OTHER INFORMATION: Novel Sequence

<400> SEQUENCE: 113

Glu Ile Pro Gly Val Leu Arg Phe
1               5

<210> SEQ ID NO 114
<211> LENGTH: 7
<212> TYPE: PRT
<213> ORGANISM: Artificial Sequence
<220> FEATURE:
<223> OTHER INFORMATION: Novel Sequence

<400> SEQUENCE: 114

Trp Ala Asn Gln Val Arg Phe
1               5

<210> SEQ ID NO 115
<211> LENGTH: 9
<212> TYPE: PRT
```

```
<213> ORGANISM: Artificial Sequence
<220> FEATURE:
<223> OTHER INFORMATION: Novel Sequence

<400> SEQUENCE: 115

Ala Ser Trp Ala Ser Ser Val Arg Phe
1               5

<210> SEQ ID NO 116
<211> LENGTH: 5
<212> TYPE: PRT
<213> ORGANISM: Artificial Sequence
<220> FEATURE:
<223> OTHER INFORMATION: Novel Sequence

<400> SEQUENCE: 116

Ala Met Met Arg Phe
1               5

<210> SEQ ID NO 117
<211> LENGTH: 9
<212> TYPE: PRT
<213> ORGANISM: Artificial Sequence
<220> FEATURE:
<223> OTHER INFORMATION: Novel Sequence

<400> SEQUENCE: 117

Gly Leu Gly Pro Arg Pro Leu Arg Phe
1               5

<210> SEQ ID NO 118
<211> LENGTH: 9
<212> TYPE: PRT
<213> ORGANISM: Artificial Sequence
<220> FEATURE:
<223> OTHER INFORMATION: Novel Sequence

<400> SEQUENCE: 118

Ser Pro Ser Ala Lys Trp Met Arg Phe
1               5

<210> SEQ ID NO 119
<211> LENGTH: 9
<212> TYPE: PRT
<213> ORGANISM: Artificial Sequence
<220> FEATURE:
<223> OTHER INFORMATION: Novel Sequence

<400> SEQUENCE: 119

Thr Lys Phe Gln Asp Phe Leu Arg Phe
1               5

<210> SEQ ID NO 120
<211> LENGTH: 10
<212> TYPE: PRT
<213> ORGANISM: Artificial Sequence
<220> FEATURE:
<223> OTHER INFORMATION: Novel Sequence

<400> SEQUENCE: 120

Glu Asp Arg Asp Tyr Arg Pro Leu Gln Phe
1               5                   10

<210> SEQ ID NO 121
<211> LENGTH: 4
<212> TYPE: PRT
<213> ORGANISM: Artificial Sequence
```

```
<220> FEATURE:
<223> OTHER INFORMATION: Novel Sequence

<400> SEQUENCE: 121

Phe Ile Arg Phe
1

<210> SEQ ID NO 122
<211> LENGTH: 8
<212> TYPE: PRT
<213> ORGANISM: Artificial Sequence
<220> FEATURE:
<223> OTHER INFORMATION: Novel Sequence

<400> SEQUENCE: 122

Ala Val Pro Gly Val Leu Arg Phe
1               5

<210> SEQ ID NO 123
<211> LENGTH: 9
<212> TYPE: PRT
<213> ORGANISM: Artificial Sequence
<220> FEATURE:
<223> OTHER INFORMATION: Novel Sequence

<400> SEQUENCE: 123

Gly Asp Val Pro Gly Val Leu Arg Phe
1               5

<210> SEQ ID NO 124
<211> LENGTH: 13
<212> TYPE: PRT
<213> ORGANISM: Artificial Sequence
<220> FEATURE:
<223> OTHER INFORMATION: Novel Sequence

<400> SEQUENCE: 124

Ser Asp Ile Gly Ile Ser Glu Pro Asn Phe Leu Arg Phe
1               5                   10

<210> SEQ ID NO 125
<211> LENGTH: 9
<212> TYPE: PRT
<213> ORGANISM: Artificial Sequence
<220> FEATURE:
<223> OTHER INFORMATION: Novel Sequence

<400> SEQUENCE: 125

Ser Gly Lys Pro Thr Phe Ile Arg Phe
1               5

<210> SEQ ID NO 126
<211> LENGTH: 11
<212> TYPE: PRT
<213> ORGANISM: Artificial Sequence
<220> FEATURE:
<223> OTHER INFORMATION: Novel Sequence

<400> SEQUENCE: 126

Ala Glu Gly Leu Ser Ser Pro Leu Ile Arg Phe
1               5                   10

<210> SEQ ID NO 127
<211> LENGTH: 8
<212> TYPE: PRT
<213> ORGANISM: Artificial Sequence
<220> FEATURE:
```

```
<223> OTHER INFORMATION: Novel Sequence

<400> SEQUENCE: 127

Phe Asp Arg Asp Phe Met Arg Phe
1               5

<210> SEQ ID NO 128
<211> LENGTH: 8
<212> TYPE: PRT
<213> ORGANISM: Artificial Sequence
<220> FEATURE:
<223> OTHER INFORMATION: Novel Sequence

<400> SEQUENCE: 128

Ala Gly Pro Arg Phe Ile Arg Phe
1               5

<210> SEQ ID NO 129
<211> LENGTH: 8
<212> TYPE: PRT
<213> ORGANISM: Artificial Sequence
<220> FEATURE:
<223> OTHER INFORMATION: Novel Sequence

<400> SEQUENCE: 129

Gly Met Pro Gly Val Leu Arg Phe
1               5

<210> SEQ ID NO 130
<211> LENGTH: 2
<212> TYPE: PRT
<213> ORGANISM: Artificial Sequence
<220> FEATURE:
<223> OTHER INFORMATION: Novel Sequence

<400> SEQUENCE: 130

Ile Leu
1

<210> SEQ ID NO 131
<211> LENGTH: 8
<212> TYPE: PRT
<213> ORGANISM: Artificial Sequence
<220> FEATURE:
<223> OTHER INFORMATION: Novel Sequence

<400> SEQUENCE: 131

Leu Gln Pro Asn Phe Leu Arg Phe
1               5

<210> SEQ ID NO 132
<211> LENGTH: 7
<212> TYPE: PRT
<213> ORGANISM: Artificial Sequence
<220> FEATURE:
<223> OTHER INFORMATION: Novel Sequence

<400> SEQUENCE: 132

Lys Pro Asn Phe Ile Arg Phe
1               5

<210> SEQ ID NO 133
<211> LENGTH: 4
<212> TYPE: PRT
<213> ORGANISM: Artificial Sequence
<220> FEATURE:
<223> OTHER INFORMATION: Novel Sequence
```

```
<400> SEQUENCE: 133

Phe Met Arg Phe
1

<210> SEQ ID NO 134
<211> LENGTH: 4
<212> TYPE: PRT
<213> ORGANISM: Artificial Sequence
<220> FEATURE:
<223> OTHER INFORMATION: Novel Sequence

<400> SEQUENCE: 134

Phe Leu Arg Phe
1

<210> SEQ ID NO 135
<211> LENGTH: 4
<212> TYPE: PRT
<213> ORGANISM: Artificial Sequence
<220> FEATURE:
<223> OTHER INFORMATION: Novel Sequence

<400> SEQUENCE: 135

Tyr Ile Arg Phe
1

<210> SEQ ID NO 136
<211> LENGTH: 7
<212> TYPE: PRT
<213> ORGANISM: Artificial Sequence
<220> FEATURE:
<223> OTHER INFORMATION: Novel Sequence

<400> SEQUENCE: 136

Gly Asn Ser Phe Leu Arg Phe
1               5

<210> SEQ ID NO 137
<211> LENGTH: 7
<212> TYPE: PRT
<213> ORGANISM: Artificial Sequence
<220> FEATURE:
<223> OTHER INFORMATION: Novel Sequence

<400> SEQUENCE: 137

Asp Pro Ser Phe Leu Arg Phe
1               5

<210> SEQ ID NO 138
<211> LENGTH: 6
<212> TYPE: PRT
<213> ORGANISM: Artificial Sequence
<220> FEATURE:
<223> OTHER INFORMATION: Novel Sequence

<400> SEQUENCE: 138

Gln Asp Phe Met Arg Phe
1               5

<210> SEQ ID NO 139
<211> LENGTH: 9
<212> TYPE: PRT
<213> ORGANISM: Artificial Sequence
<220> FEATURE:
<223> OTHER INFORMATION: Novel Sequence
```

```
<400> SEQUENCE: 139

Lys Pro Asn Gln Asp Phe Met Arg Phe
1               5

<210> SEQ ID NO 140
<211> LENGTH: 10
<212> TYPE: PRT
<213> ORGANISM: Artificial Sequence
<220> FEATURE:
<223> OTHER INFORMATION: Novel Sequence

<400> SEQUENCE: 140

Thr Asp Val Asp His Val Phe Leu Arg Phe
1               5                   10

<210> SEQ ID NO 141
<211> LENGTH: 6
<212> TYPE: PRT
<213> ORGANISM: Artificial Sequence
<220> FEATURE:
<223> OTHER INFORMATION: Novel Sequence

<400> SEQUENCE: 141

Ala Ala Met Asp Arg Tyr
1               5

<210> SEQ ID NO 142
<211> LENGTH: 9
<212> TYPE: PRT
<213> ORGANISM: Artificial Sequence
<220> FEATURE:
<223> OTHER INFORMATION: Novel Sequence

<400> SEQUENCE: 142

Ser Pro Lys Gln Asp Phe Met Arg Phe
1               5

<210> SEQ ID NO 143
<211> LENGTH: 7
<212> TYPE: PRT
<213> ORGANISM: Artificial Sequence
<220> FEATURE:
<223> OTHER INFORMATION: Novel Sequence

<400> SEQUENCE: 143

Pro Asp Asn Phe Met Arg Phe
1               5

<210> SEQ ID NO 144
<211> LENGTH: 9
<212> TYPE: PRT
<213> ORGANISM: Artificial Sequence
<220> FEATURE:
<223> OTHER INFORMATION: Novel Sequence

<400> SEQUENCE: 144

Asp Pro Lys Gln Asp Phe Met Arg Phe
1               5

<210> SEQ ID NO 145
<211> LENGTH: 9
<212> TYPE: PRT
<213> ORGANISM: Artificial Sequence
<220> FEATURE:
<223> OTHER INFORMATION: Novel Sequence

<400> SEQUENCE: 145
```

```
Thr Pro Ala Glu Asp Phe Met Arg Phe
1               5

<210> SEQ ID NO 146
<211> LENGTH: 7
<212> TYPE: PRT
<213> ORGANISM: Artificial Sequence
<220> FEATURE:
<223> OTHER INFORMATION: Novel Sequence

<400> SEQUENCE: 146

Ser Asp Asn Phe Met Arg Phe
1               5

<210> SEQ ID NO 147
<211> LENGTH: 4
<212> TYPE: PRT
<213> ORGANISM: Artificial Sequence
<220> FEATURE:
<223> OTHER INFORMATION: Novel Sequence

<400> SEQUENCE: 147

Tyr Leu Arg Phe
1

<210> SEQ ID NO 148
<211> LENGTH: 8
<212> TYPE: PRT
<213> ORGANISM: Artificial Sequence
<220> FEATURE:
<223> OTHER INFORMATION: Novel Sequence

<400> SEQUENCE: 148

Ser Asp Arg Asn Phe Leu Arg Phe
1               5

<210> SEQ ID NO 149
<211> LENGTH: 8
<212> TYPE: PRT
<213> ORGANISM: Artificial Sequence
<220> FEATURE:
<223> OTHER INFORMATION: Novel Sequence

<400> SEQUENCE: 149

Thr Asn Arg Asn Phe Leu Arg Phe
1               5

<210> SEQ ID NO 150
<211> LENGTH: 10
<212> TYPE: PRT
<213> ORGANISM: Artificial Sequence
<220> FEATURE:
<223> OTHER INFORMATION: Novel Sequence

<400> SEQUENCE: 150

Pro Asp Val Asp His Val Phe Leu Arg Phe
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Novel Sequence

<400> SEQUENCE: 151
```

```
Gln Asp Val Asp His Val Phe Leu Arg Phe
1               5                   10

<210> SEQ ID NO 152
<211> LENGTH: 8
<212> TYPE: PRT
<213> ORGANISM: Artificial Sequence
<220> FEATURE:
<223> OTHER INFORMATION: Novel Sequence

<400> SEQUENCE: 152

Phe Leu Phe Gln Pro Gln Arg Phe
1               5

<210> SEQ ID NO 153
<211> LENGTH: 10
<212> TYPE: PRT
<213> ORGANISM: Artificial Sequence
<220> FEATURE:
<223> OTHER INFORMATION: Novel Sequence

<400> SEQUENCE: 153

Ala Arg Gly Pro Gln Leu Arg Leu Arg Phe
1               5                   10

<210> SEQ ID NO 154
<211> LENGTH: 9
<212> TYPE: PRT
<213> ORGANISM: Artificial Sequence
<220> FEATURE:
<223> OTHER INFORMATION: Novel Sequence

<400> SEQUENCE: 154

Phe Asp Asp Tyr Gly His Leu Arg Phe
1               5

<210> SEQ ID NO 155
<211> LENGTH: 9
<212> TYPE: PRT
<213> ORGANISM: Artificial Sequence
<220> FEATURE:
<223> OTHER INFORMATION: Novel Sequence

<400> SEQUENCE: 155

Phe Asp Asp Tyr Gly His Leu Arg Phe
1               5

<210> SEQ ID NO 156
<211> LENGTH: 8
<212> TYPE: PRT
<213> ORGANISM: Artificial Sequence
<220> FEATURE:
<223> OTHER INFORMATION: Novel Sequence

<400> SEQUENCE: 156

Met Asp Ser Asn Phe Ile Arg Phe
1               5

<210> SEQ ID NO 157
<211> LENGTH: 9
<212> TYPE: PRT
<213> ORGANISM: Artificial Sequence
<220> FEATURE:
<223> OTHER INFORMATION: Novel Sequence

<400> SEQUENCE: 157

Phe Asp Asp Tyr Gly His Leu Arg Phe
```

```
<210> SEQ ID NO 158
<211> LENGTH: 9
<212> TYPE: PRT
<213> ORGANISM: Artificial Sequence
<220> FEATURE:
<223> OTHER INFORMATION: Novel Sequence

<400> SEQUENCE: 158

Phe Asp Asp Tyr Gly His Leu Arg Phe
1               5

<210> SEQ ID NO 159
<211> LENGTH: 9
<212> TYPE: PRT
<213> ORGANISM: Artificial Sequence
<220> FEATURE:
<223> OTHER INFORMATION: Novel Sequence

<400> SEQUENCE: 159

Phe Asp Asp Tyr Gly His Met Arg Phe
1               5

<210> SEQ ID NO 160
<211> LENGTH: 14
<212> TYPE: PRT
<213> ORGANISM: Artificial Sequence
<220> FEATURE:
<223> OTHER INFORMATION: Novel Sequence

<400> SEQUENCE: 160

Gly Gly Asp Asp Gln Phe Asp Asp Tyr Gly His Met Arg Phe
1               5                   10

<210> SEQ ID NO 161
<211> LENGTH: 8
<212> TYPE: PRT
<213> ORGANISM: Artificial Sequence
<220> FEATURE:
<223> OTHER INFORMATION: Novel Sequence

<400> SEQUENCE: 161

Ser Arg Pro Tyr Ser Phe Gly Leu
1               5

<210> SEQ ID NO 162
<211> LENGTH: 7
<212> TYPE: PRT
<213> ORGANISM: Artificial Sequence
<220> FEATURE:
<223> OTHER INFORMATION: Novel Sequence

<400> SEQUENCE: 162

Asp Tyr Gly His Met Arg Phe
1               5

<210> SEQ ID NO 163
<211> LENGTH: 9
<212> TYPE: PRT
<213> ORGANISM: Artificial Sequence
<220> FEATURE:
<223> OTHER INFORMATION: Novel Sequence

<400> SEQUENCE: 163

Ala Pro Arg Thr Pro Gly Gly Arg Arg
1               5
```

```
<210> SEQ ID NO 164
<211> LENGTH: 8
<212> TYPE: PRT
<213> ORGANISM: Artificial Sequence
<220> FEATURE:
<223> OTHER INFORMATION: Novel Sequence

<400> SEQUENCE: 164

Val Glu Arg Tyr Ala Phe Gly Leu
1               5

<210> SEQ ID NO 165
<211> LENGTH: 8
<212> TYPE: PRT
<213> ORGANISM: Artificial Sequence
<220> FEATURE:
<223> OTHER INFORMATION: Novel Sequence

<400> SEQUENCE: 165

Leu Pro Val Tyr Asn Phe Gly Leu
1               5

<210> SEQ ID NO 166
<211> LENGTH: 11
<212> TYPE: PRT
<213> ORGANISM: Artificial Sequence
<220> FEATURE:
<223> OTHER INFORMATION: Novel Sequence

<400> SEQUENCE: 166

Thr Thr Arg Pro Gln Pro Phe Asn Phe Gly Leu
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Novel Sequence

<400> SEQUENCE: 167

Glu Asp Val Asp His Val Phe Leu Arg Phe
1               5                   10

<210> SEQ ID NO 168
<211> LENGTH: 7
<212> TYPE: PRT
<213> ORGANISM: Artificial Sequence
<220> FEATURE:
<223> OTHER INFORMATION: Novel Sequence

<400> SEQUENCE: 168

Gly Asn Ser Phe Leu Arg Phe
1               5

<210> SEQ ID NO 169
<211> LENGTH: 10
<212> TYPE: PRT
<213> ORGANISM: Artificial Sequence
<220> FEATURE:
<223> OTHER INFORMATION: Novel Sequence

<400> SEQUENCE: 169

Ala Pro Thr Ser Ser Phe Ile Gly Met Arg
1               5                   10
```

```
<210> SEQ ID NO 170
<211> LENGTH: 9
<212> TYPE: PRT
<213> ORGANISM: Artificial Sequence
<220> FEATURE:
<223> OTHER INFORMATION: Novel Sequence

<400> SEQUENCE: 170

Ala Pro Leu Ala Phe Thr Gly Met Arg
1               5

<210> SEQ ID NO 171
<211> LENGTH: 9
<212> TYPE: PRT
<213> ORGANISM: Artificial Sequence
<220> FEATURE:
<223> OTHER INFORMATION: Novel Sequence

<400> SEQUENCE: 171

Ala Pro Leu Ala Phe Tyr Gly Leu Arg
1               5

<210> SEQ ID NO 172
<211> LENGTH: 9
<212> TYPE: PRT
<213> ORGANISM: Artificial Sequence
<220> FEATURE:
<223> OTHER INFORMATION: Novel Sequence

<400> SEQUENCE: 172

Ala Pro Thr Gly Phe Thr Gly Met Arg
1               5

<210> SEQ ID NO 173
<211> LENGTH: 10
<212> TYPE: PRT
<213> ORGANISM: Artificial Sequence
<220> FEATURE:
<223> OTHER INFORMATION: Novel Sequence

<400> SEQUENCE: 173

Ala Pro Val Asn Ser Phe Val Gly Met Arg
1               5                   10

<210> SEQ ID NO 174
<211> LENGTH: 9
<212> TYPE: PRT
<213> ORGANISM: Artificial Sequence
<220> FEATURE:
<223> OTHER INFORMATION: Novel Sequence

<400> SEQUENCE: 174

Ala Pro Asn Gly Phe Leu Gly Met Arg
1               5

<210> SEQ ID NO 175
<211> LENGTH: 8
<212> TYPE: PRT
<213> ORGANISM: Artificial Sequence
<220> FEATURE:
<223> OTHER INFORMATION: Novel Sequence

<400> SEQUENCE: 175

Asp Pro Ala Phe Asn Ser Trp Gly
1               5
```

```
<210> SEQ ID NO 176
<211> LENGTH: 8
<212> TYPE: PRT
<213> ORGANISM: Artificial Sequence
<220> FEATURE:
<223> OTHER INFORMATION: Novel Sequence

<400> SEQUENCE: 176

Gly Ser Gly Phe Ser Ser Trp Gly
1               5

<210> SEQ ID NO 177
<211> LENGTH: 8
<212> TYPE: PRT
<213> ORGANISM: Artificial Sequence
<220> FEATURE:
<223> OTHER INFORMATION: Novel Sequence

<400> SEQUENCE: 177

Glu Ser Ser Phe His Ser Trp Gly
1               5

<210> SEQ ID NO 178
<211> LENGTH: 8
<212> TYPE: PRT
<213> ORGANISM: Artificial Sequence
<220> FEATURE:
<223> OTHER INFORMATION: Novel Sequence

<400> SEQUENCE: 178

Gly Ala Ser Phe Tyr Ser Trp Gly
1               5

<210> SEQ ID NO 179
<211> LENGTH: 7
<212> TYPE: PRT
<213> ORGANISM: Artificial Sequence
<220> FEATURE:
<223> OTHER INFORMATION: Novel Sequence

<400> SEQUENCE: 179

Asn Pro Phe His Ser Trp Gly
1               5

<210> SEQ ID NO 180
<211> LENGTH: 7
<212> TYPE: PRT
<213> ORGANISM: Artificial Sequence
<220> FEATURE:
<223> OTHER INFORMATION: Novel Sequence

<400> SEQUENCE: 180

Pro Ser Phe His Ser Trp Ser
1               5

<210> SEQ ID NO 181
<211> LENGTH: 15
<212> TYPE: PRT
<213> ORGANISM: Artificial Sequence
<220> FEATURE:
<223> OTHER INFORMATION: Novel Sequence

<400> SEQUENCE: 181

Asn Ser Val Val Leu Gly Lys Lys Gln Arg Phe His Ser Trp Gly
1               5                   10                  15

<210> SEQ ID NO 182
```

```
<211> LENGTH: 7
<212> TYPE: PRT
<213> ORGANISM: Artificial Sequence
<220> FEATURE:
<223> OTHER INFORMATION: Novel Sequence

<400> SEQUENCE: 182

Glu Arg Phe His Ser Trp Gly
1               5

<210> SEQ ID NO 183
<211> LENGTH: 7
<212> TYPE: PRT
<213> ORGANISM: Artificial Sequence
<220> FEATURE:
<223> OTHER INFORMATION: Novel Sequence

<400> SEQUENCE: 183

Gln Arg Phe His Ser Trp Gly
1               5

<210> SEQ ID NO 184
<211> LENGTH: 15
<212> TYPE: PRT
<213> ORGANISM: Artificial Sequence
<220> FEATURE:
<223> OTHER INFORMATION: Novel Sequence

<400> SEQUENCE: 184

Glu Val Arg Phe Arg Gln Cys Tyr Phe Asn Pro Ile Ser Cys Phe
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: Novel Sequence

<400> SEQUENCE: 185

Glu Val Arg Tyr Arg Gln Cys Tyr Phe Asn Pro Ile Ser Cys Phe
1               5                   10                  15
```